United States Patent
Yeung et al.

(10) Patent No.: US 10,500,008 B2
(45) Date of Patent: Dec. 10, 2019

(54) SURGICAL ARM SYSTEM WITH INTERNALLY DRIVEN GEAR ASSEMBLIES

(71) Applicant: Bio-Medical Engineering (HK) Limited, Hong Kong (CN)

(72) Inventors: Chung Kwong Yeung, Hong Kong (CN); Wai Leung William Cheng, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 0 days.

(21) Appl. No.: 16/457,217

(22) Filed: Jun. 28, 2019

(65) Prior Publication Data

US 2019/0314100 A1    Oct. 17, 2019

Related U.S. Application Data

(63) Continuation-in-part of application No. 16/172,408, filed on Oct. 26, 2018, which is a continuation of
(Continued)

(51) Int. Cl.
*A61B 34/30*    (2016.01)
*A61B 34/37*    (2016.01)
(Continued)

(52) U.S. Cl.
CPC .......... *A61B 34/37* (2016.02); *A61B 17/3421* (2013.01); *A61B 17/3423* (2013.01);
(Continued)

(58) Field of Classification Search
CPC .......... A61B 17/00234; A61B 17/3421; A61B 1/00147; A61B 1/05; A61B 1/3132;
(Continued)

(56) References Cited

U.S. PATENT DOCUMENTS

| 2007/0287884 | A1* | 12/2007 | Schena | A61B 90/10 |
| | | | | 600/104 |
| 2013/0131695 | A1* | 5/2013 | Scarfogliero | A61B 34/30 |
| | | | | 606/130 |
| 2013/0345717 | A1* | 12/2013 | Markvicka | A61B 34/30 |
| | | | | 606/130 |

FOREIGN PATENT DOCUMENTS

WO    2007146987 A3    12/2007

OTHER PUBLICATIONS

Chinese Office Action dated Jul. 8, 2019 in connection with Chinese Application No. 201710714234.6, 13 pages.
(Continued)

*Primary Examiner* — Michael F Peffley
(74) *Attorney, Agent, or Firm* — Baker & McKenzie LLP

(57) ABSTRACT

Example embodiments relate to robotic arm assemblies. The robotic arm assembly may include forearm segment, upper arm segment, and elbow coupling joint assembly. Upper arm segment includes a motor. Elbow coupling joint assembly connects forearm and upper arm segments. Elbow coupling joint assembly includes distal and proximal elbow joint subassemblies. Distal elbow joint subassembly is connected to the forearm segment. Distal elbow joint subassembly includes gear train system having gear stages including first distal elbow gear stage, second distal elbow gear stage, third distal elbow gear stage, and fourth distal elbow gear stage. First distal elbow gear stage includes bevel gears. Second distal elbow gear stage includes spur gears. Third distal elbow gear stage includes bevel gears. Fourth distal elbow gear stage includes a planetary gear assembly. Proximal elbow joint subassembly connects the upper arm segment to the distal elbow joint subassembly.

28 Claims, 58 Drawing Sheets

Related U.S. Application Data application No. 15/864,628, filed on Jan. 8, 2018, now Pat. No. 10,172,680, which is a continuation of application No. 15/605,864, filed on May 25, 2017, now Pat. No. 9,895,200, which is a continuation-in-part of application No. 15/340,678, filed on Nov. 1, 2016, now Pat. No. 9,855,108, which is a continuation-in-part of application No. 15/044,895, filed on Feb. 16, 2016, and a continuation-in-part of application No. 15/044,889, filed on Feb. 16, 2016, now Pat. No. 9,737,372, and a continuation-in-part of application No. 14/693,207, filed on Apr. 22, 2015, application No. 16/457,217, filed on Jun. 28, 2019, which is a continuation-in-part of application No. 16/172,408, which is a continuation of application No. 15/864,628, which is a continuation of application No. 15/605,864, which is a continuation-in-part of application No. 15/340,699, filed on Nov. 1, 2016, now Pat. No. 9,827,058, application No. 16/457,217, filed on Jun. 28, 2019, which is a continuation-in-part of application No. 16/172,408, which is a continuation of application No. 15/864,628, which is a continuation of application No. 15/605,864, which is a continuation-in-part of application No. 14/693,207, application No. 16/457,217, filed on Jun. 28, 2019, which is a continuation-in-part of application No. 16/172,408, which is a continuation of application No. 15/864,628, which is a continuation of application No. 15/605,864, which is a continuation-in-part of application No. 15/044,895, which is a continuation-in-part of application No. 14/693,207, application No. 16/457,217, filed on Jun. 28, 2019, which is a continuation-in-part of application No. 16/172,408, which is a continuation of application No. 15/864,628, which is a continuation of application No. 15/605,864, which is a continuation-in-part of application No. 15/044,889, which is a continuation-in-part of application No. 14/693,207.

(60) Provisional application No. 61/982,717, filed on Apr. 22, 2014.

(51) Int. Cl.

| | | |
|---|---|---|
| *A61B 18/14* | (2006.01) | |
| *A61B 90/00* | (2016.01) | |
| *A61B 17/34* | (2006.01) | |
| *A61B 34/00* | (2016.01) | |
| *A61B 90/30* | (2016.01) | |
| *A61B 18/00* | (2006.01) | |
| *A61B 90/57* | (2016.01) | |
| *A61B 17/00* | (2006.01) | |
| *A61B 17/29* | (2006.01) | |
| *A61B 1/05* | (2006.01) | |
| *A61B 1/00* | (2006.01) | |
| *A61B 1/313* | (2006.01) | |

(52) U.S. Cl.
CPC .......... *A61B 18/1445* (2013.01); *A61B 34/30* (2016.02); *A61B 34/76* (2016.02); *A61B 90/30* (2016.02); *A61B 90/361* (2016.02); *A61B 90/37* (2016.02); *A61B 1/00147* (2013.01); *A61B 1/05* (2013.01); *A61B 1/3132* (2013.01); *A61B 18/1442* (2013.01); *A61B 2017/00283* (2013.01); *A61B 2017/2906* (2013.01); *A61B 2017/345* (2013.01); *A61B 2017/346* (2013.01); *A61B 2017/3445* (2013.01); *A61B 2017/3452* (2013.01); *A61B 2018/00589* (2013.01); *A61B 2018/00601* (2013.01); *A61B 2034/301* (2016.02); *A61B 2034/302* (2016.02); *A61B 2034/305* (2016.02); *A61B 2034/306* (2016.02); *A61B 2090/309* (2016.02); *A61B 2090/3612* (2016.02); *A61B 2090/571* (2016.02); *Y10S 901/02* (2013.01); *Y10S 901/27* (2013.01)

(58) Field of Classification Search
CPC ... A61B 2034/305; A61B 34/30; A61B 34/25; A61B 34/35; A61B 34/37; A61B 34/76; A61B 2090/309; A61B 2090/3612; Y10S 901/02; Y10S 901/27
See application file for complete search history.

(56) References Cited

OTHER PUBLICATIONS

Chinese Office Action dated Jul. 4, 2019 in connection with Chinese Application No. 201710713625.6, 10 pages.
Chinese Office Action dated Jul. 8, 2019 in connection with Chinese Application No. 201710713638.3, 13 pages.

\* cited by examiner

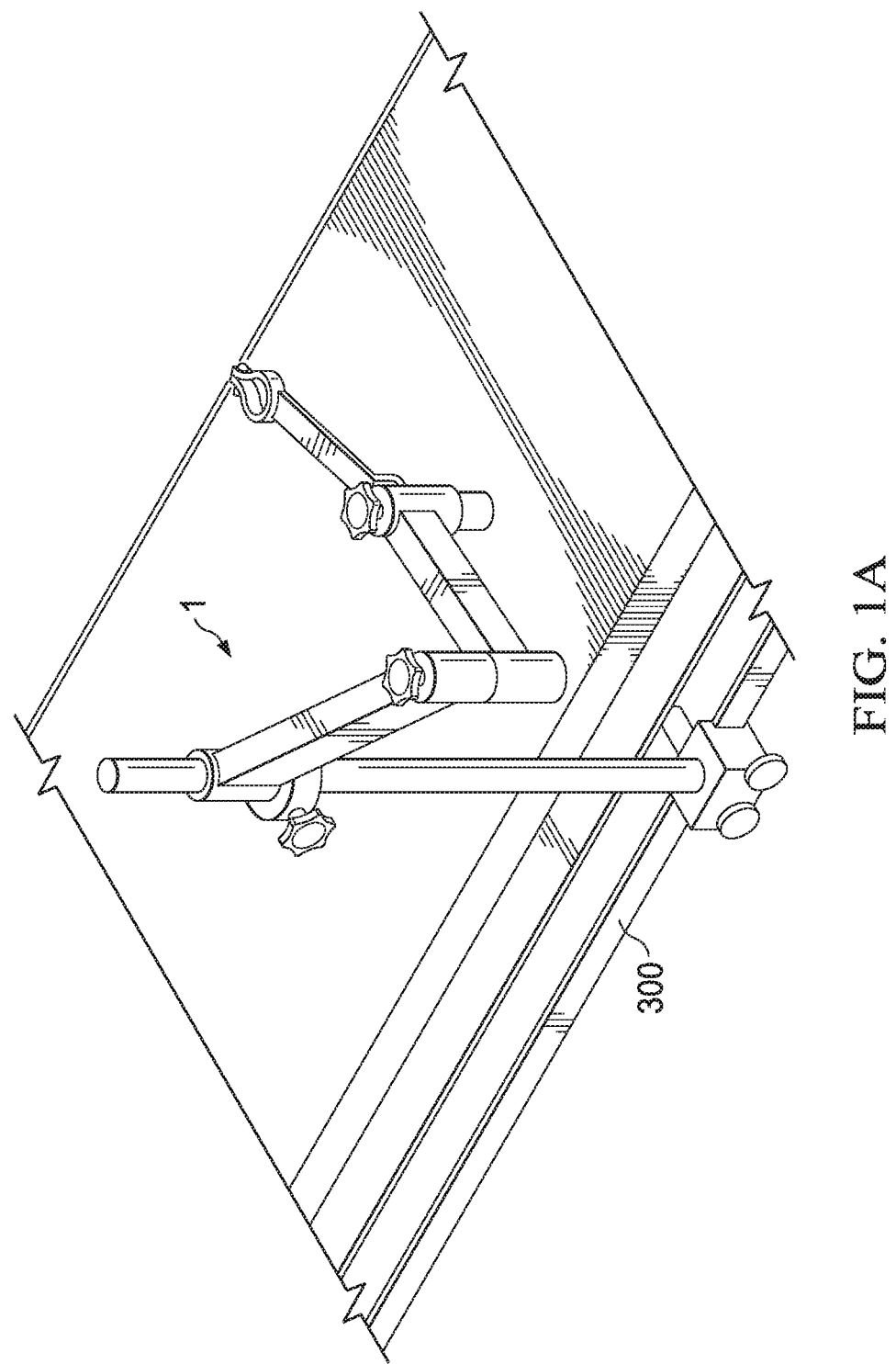

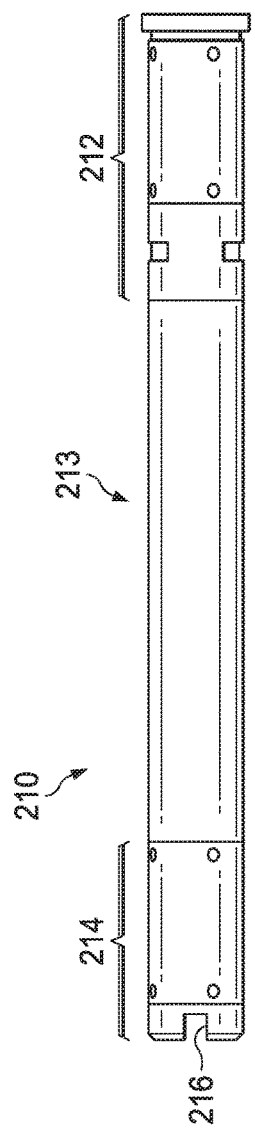
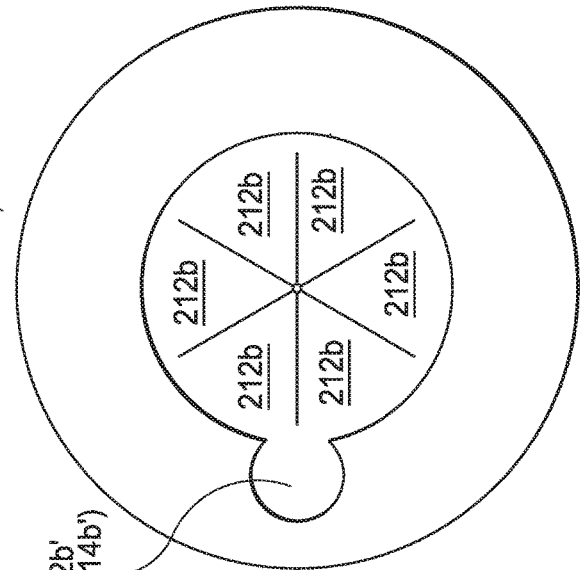
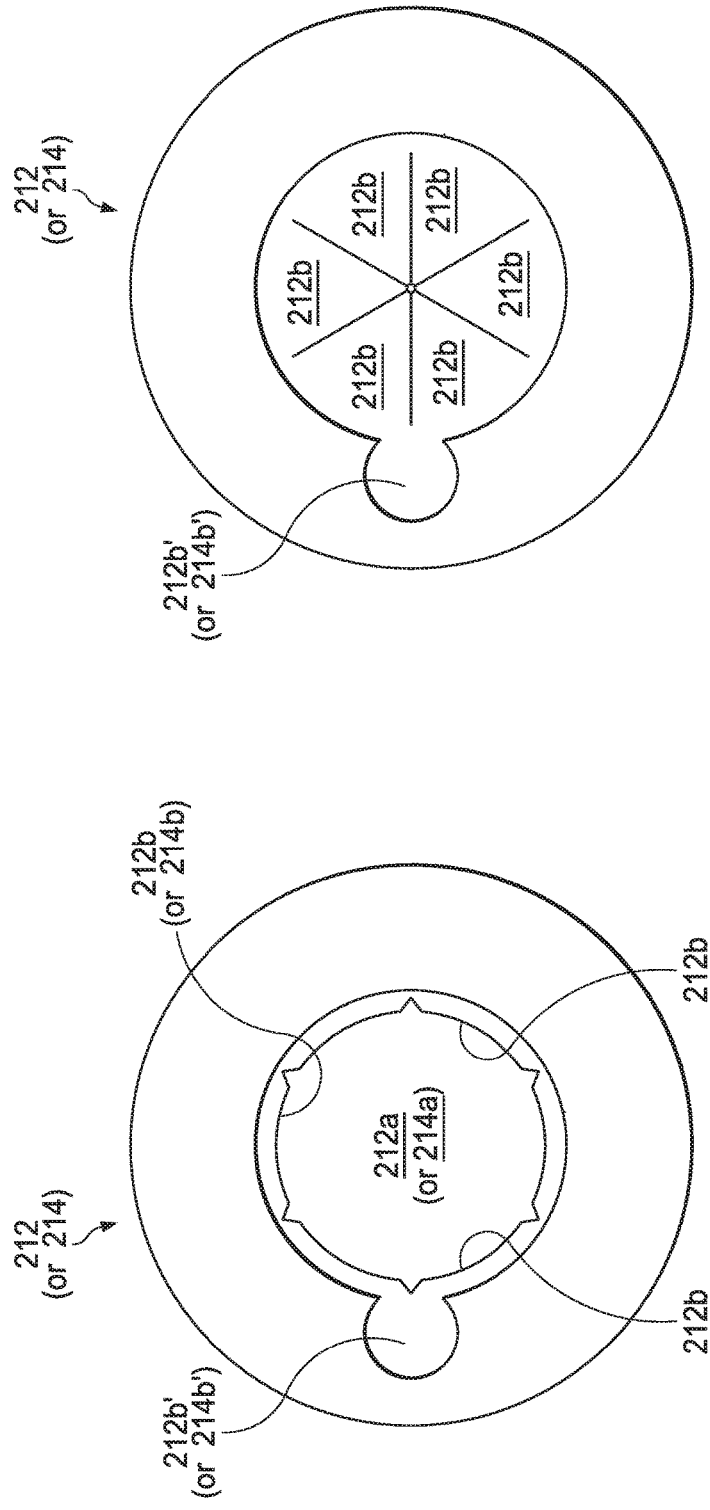
FIG. 4B
FIG. 4D
FIG. 4C

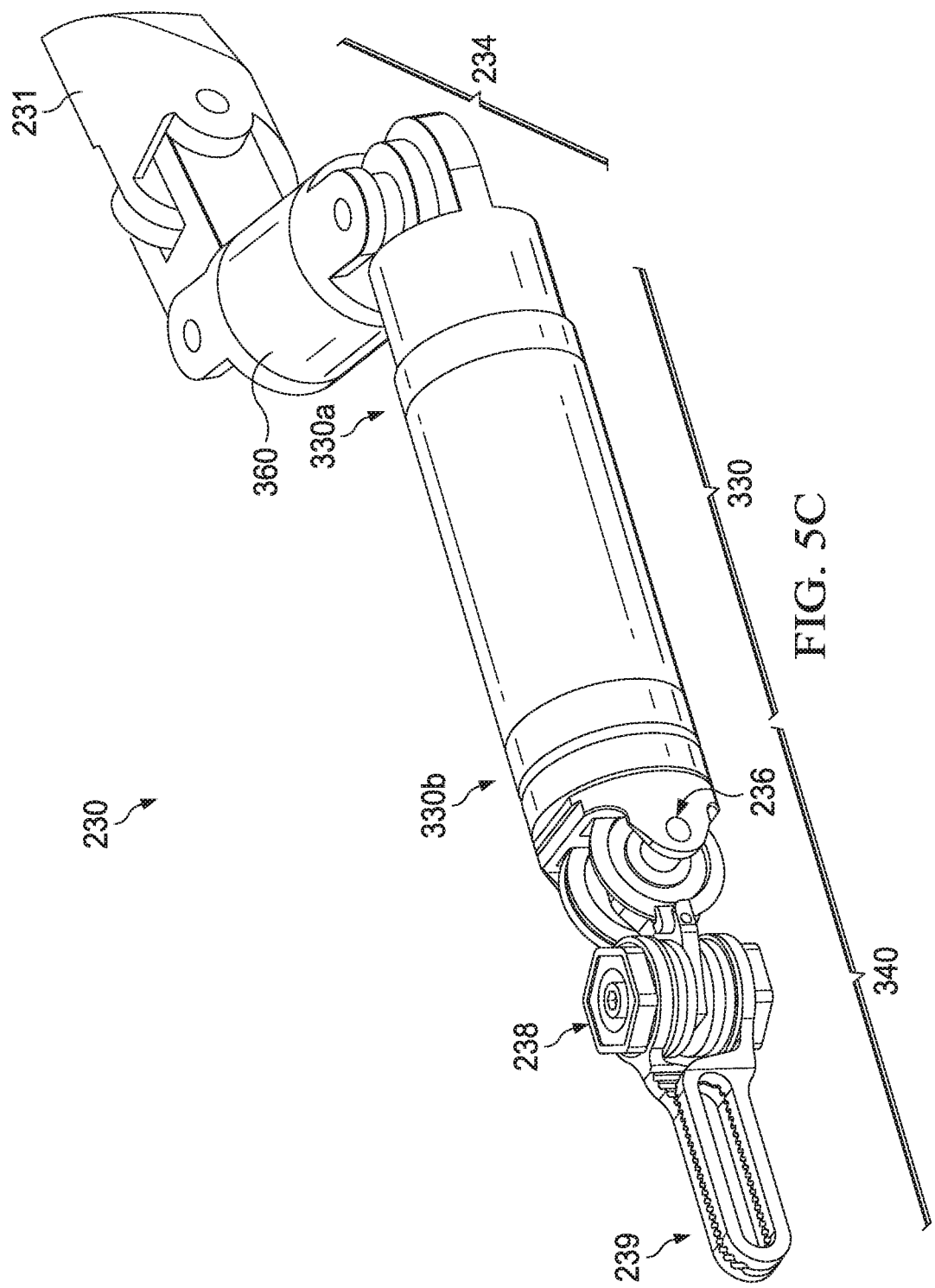

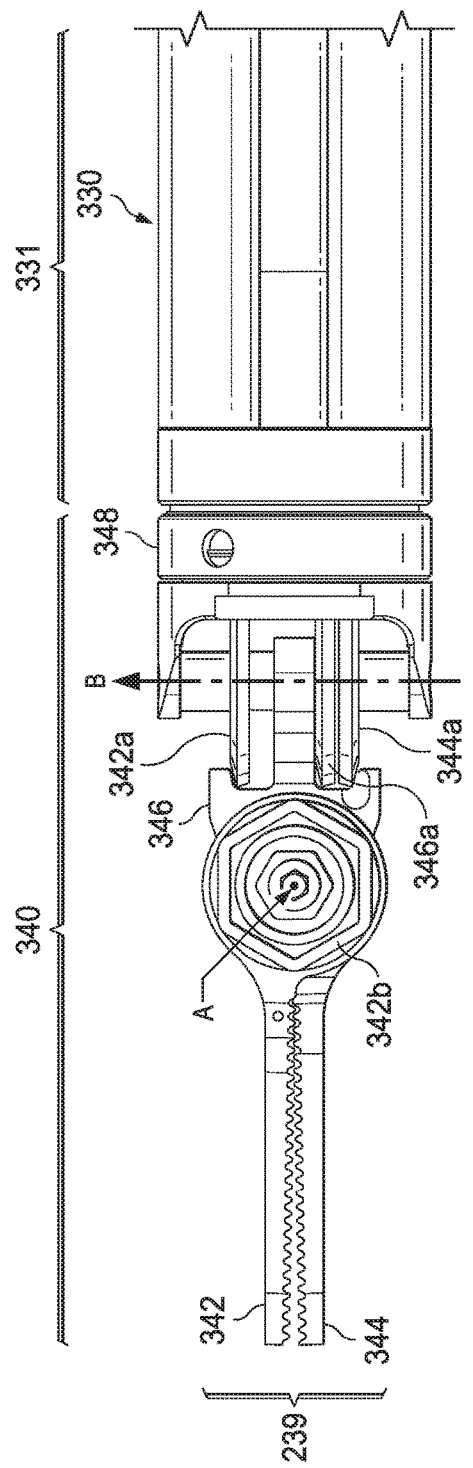
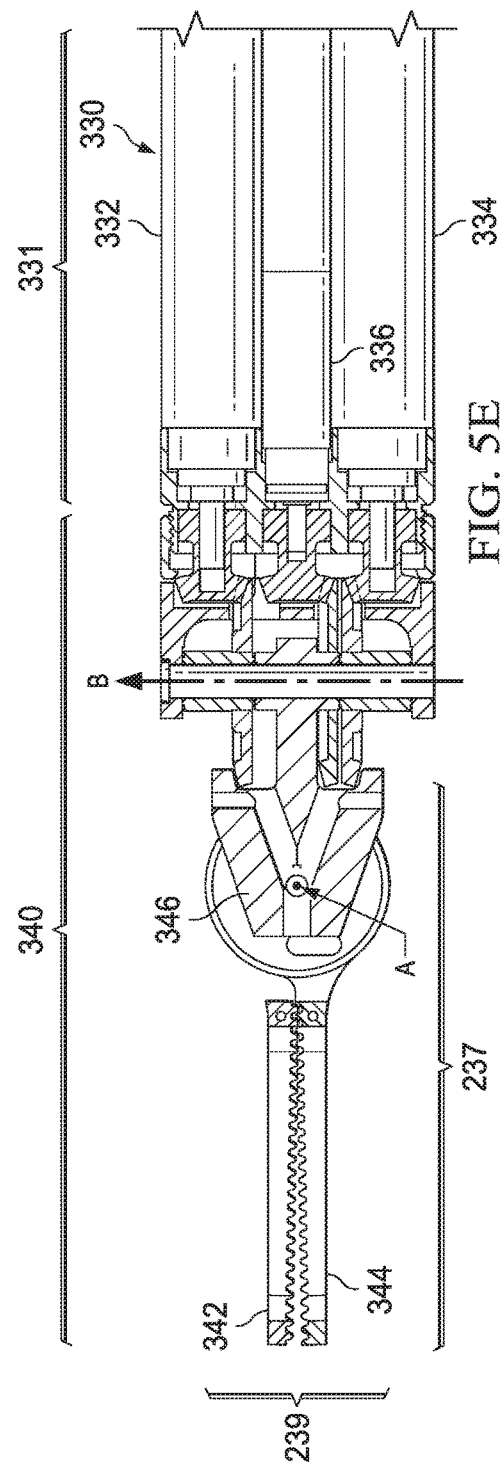
FIG. 5D
FIG. 5E

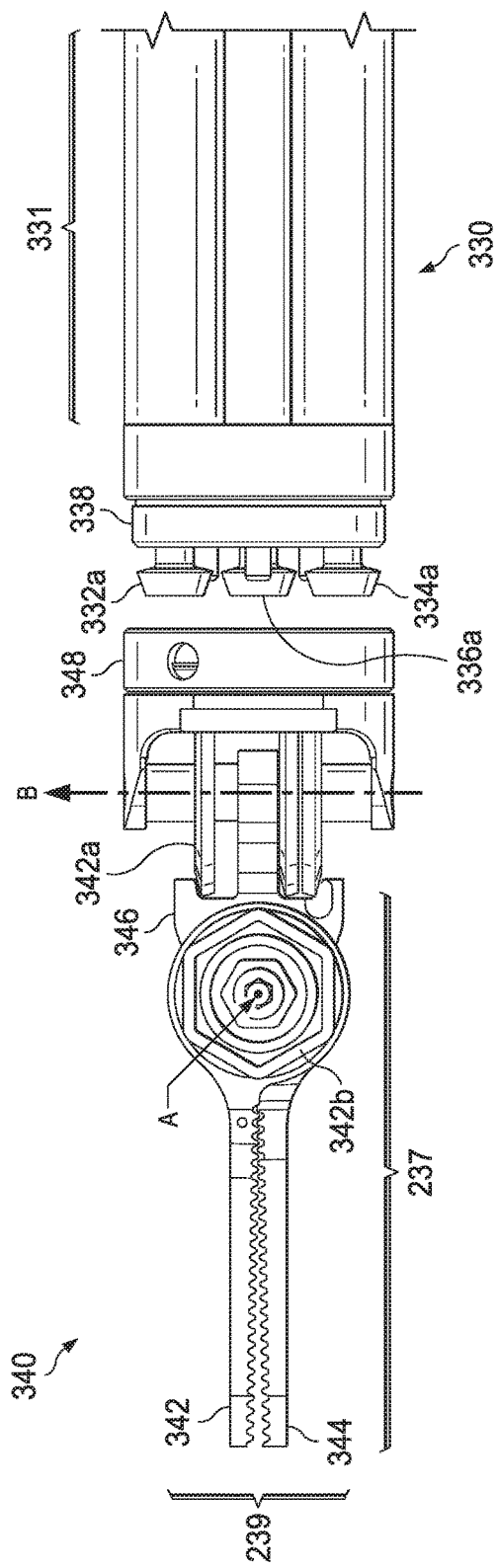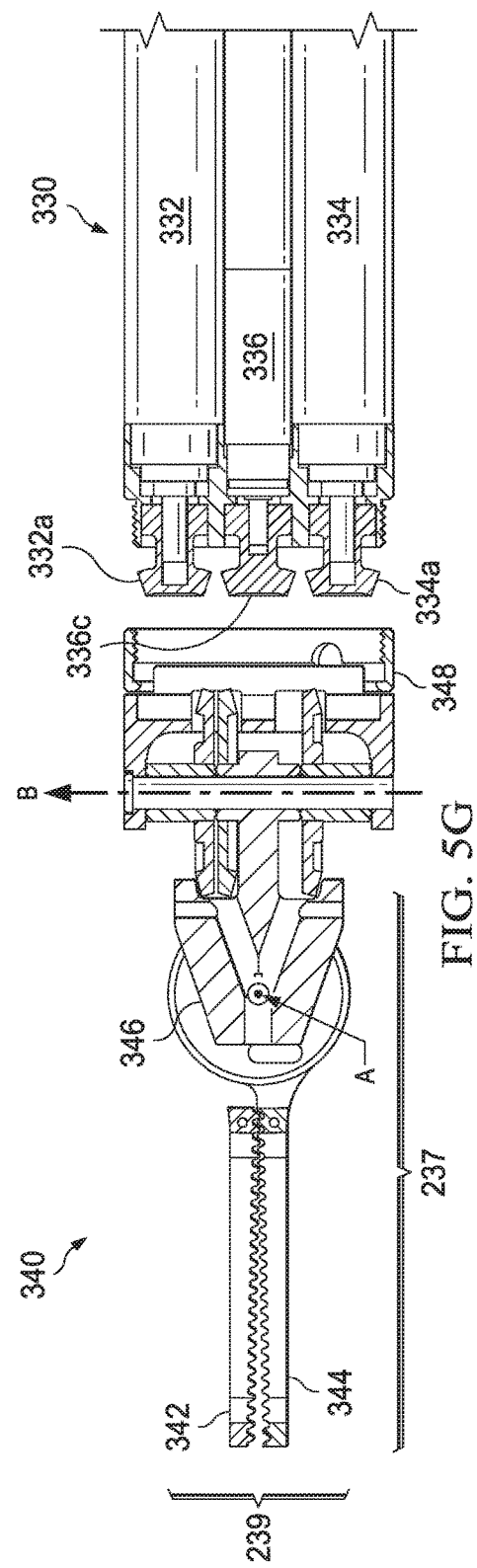

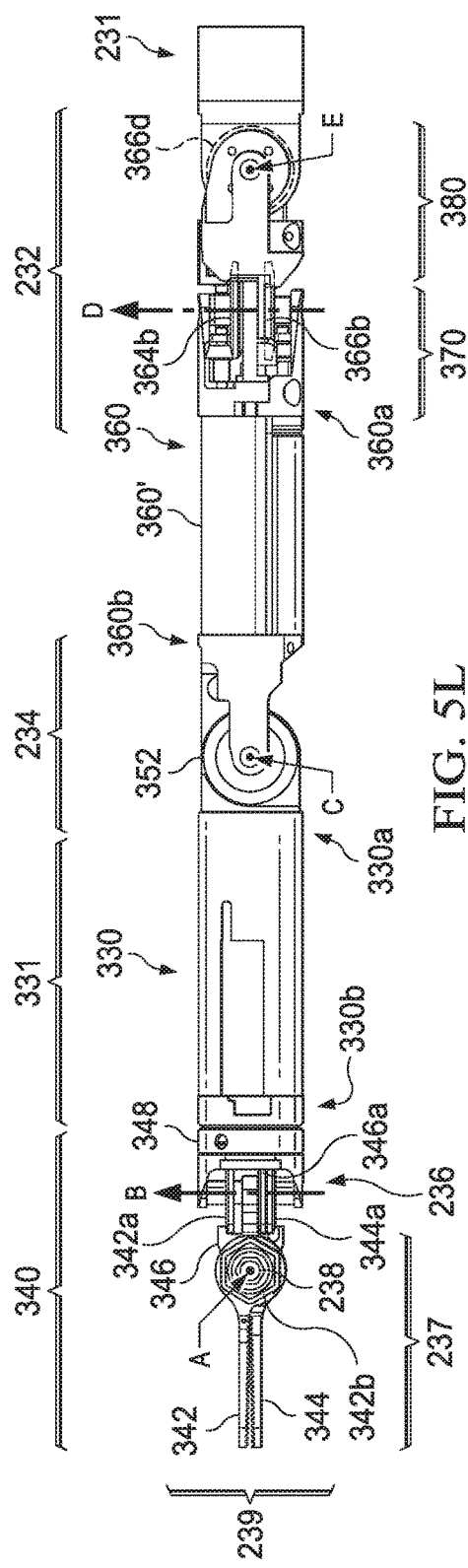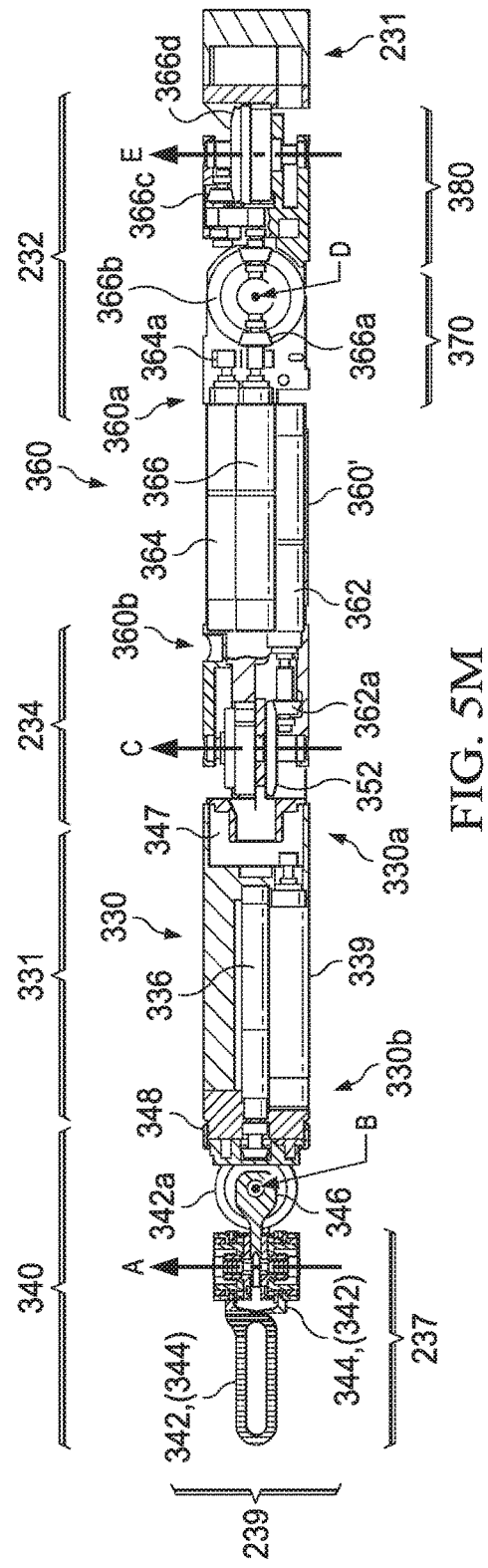
FIG. 5L
FIG. 5M

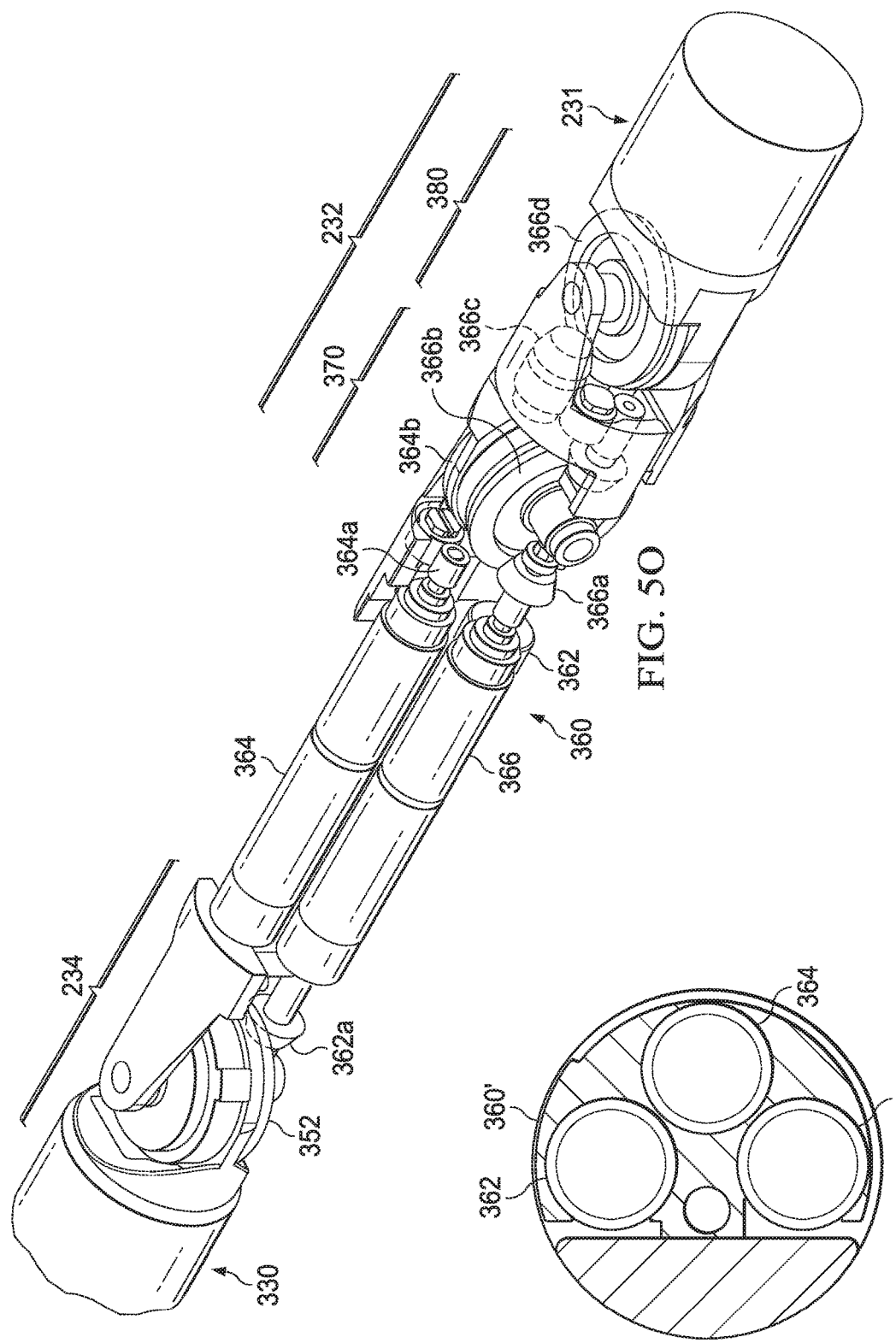

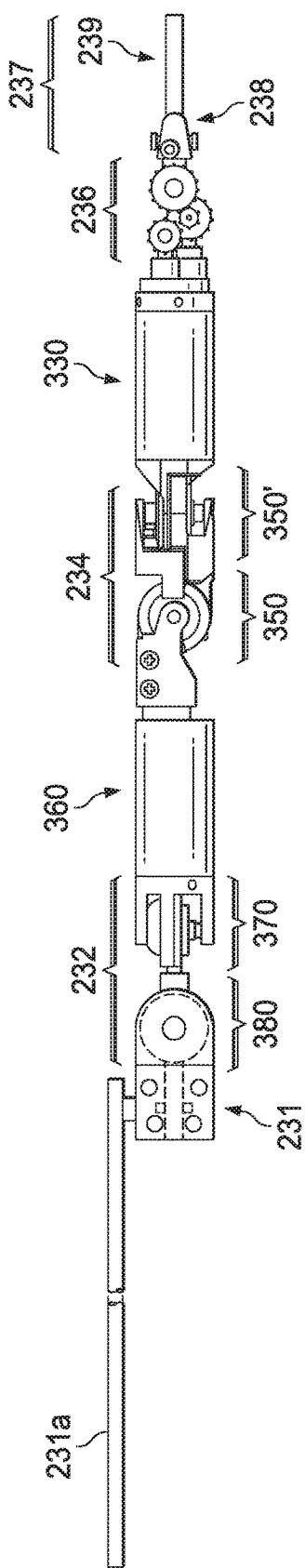
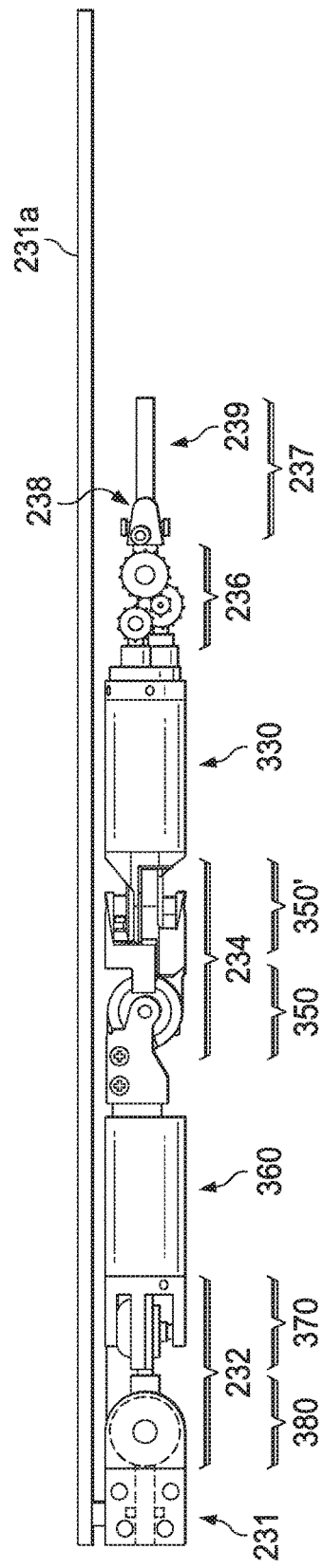
FIG. 5P
FIG. 5Q

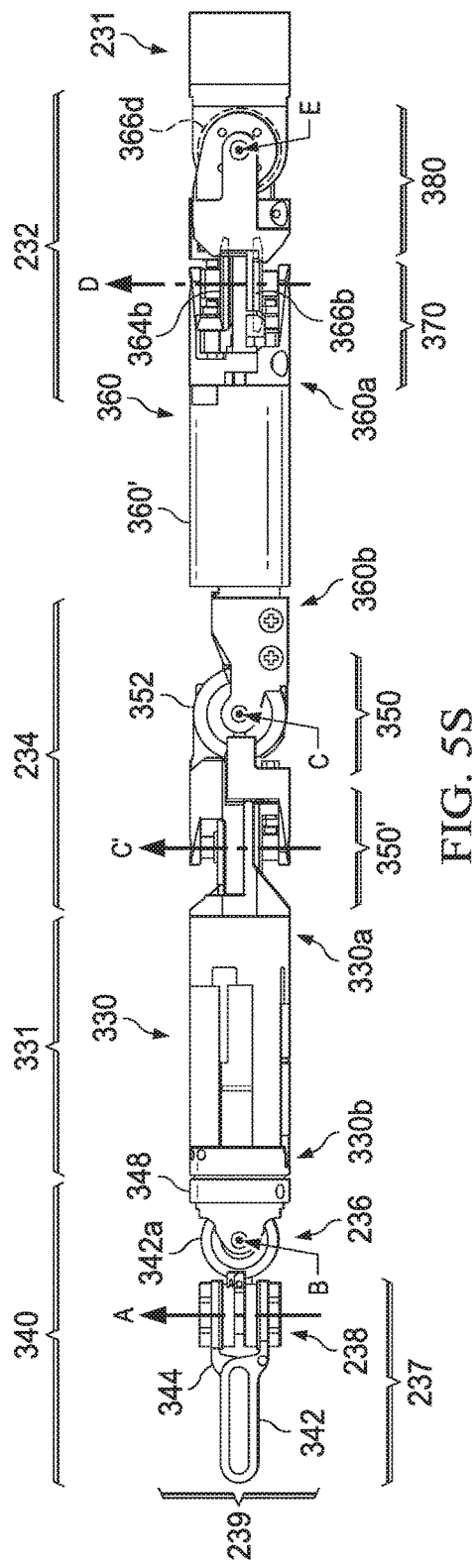
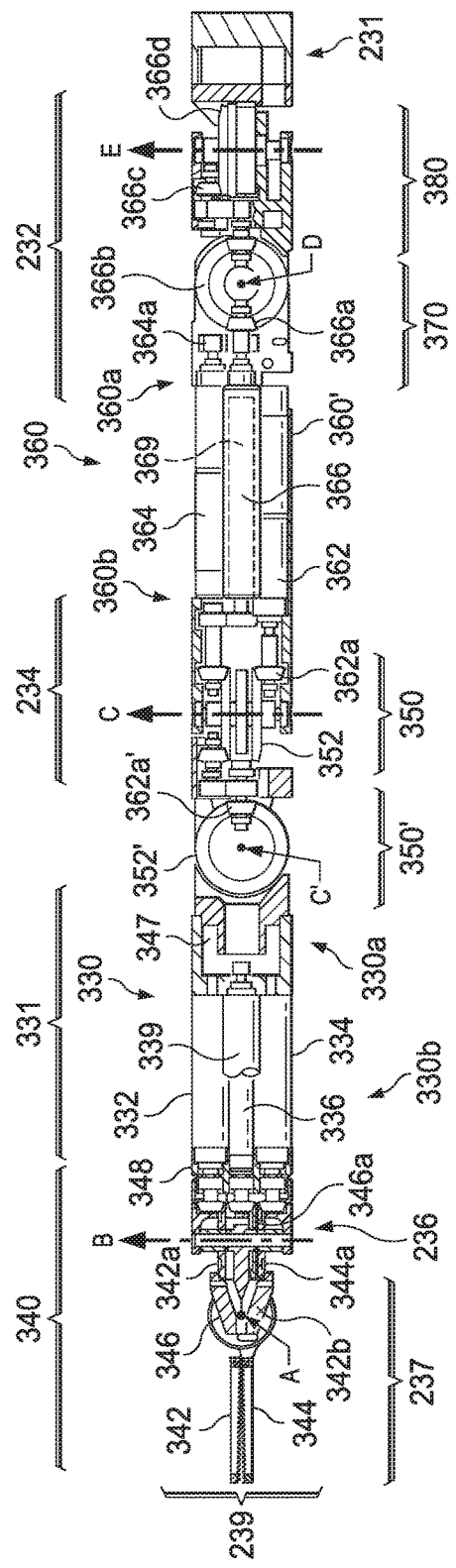
FIG. 5S
FIG. 5T

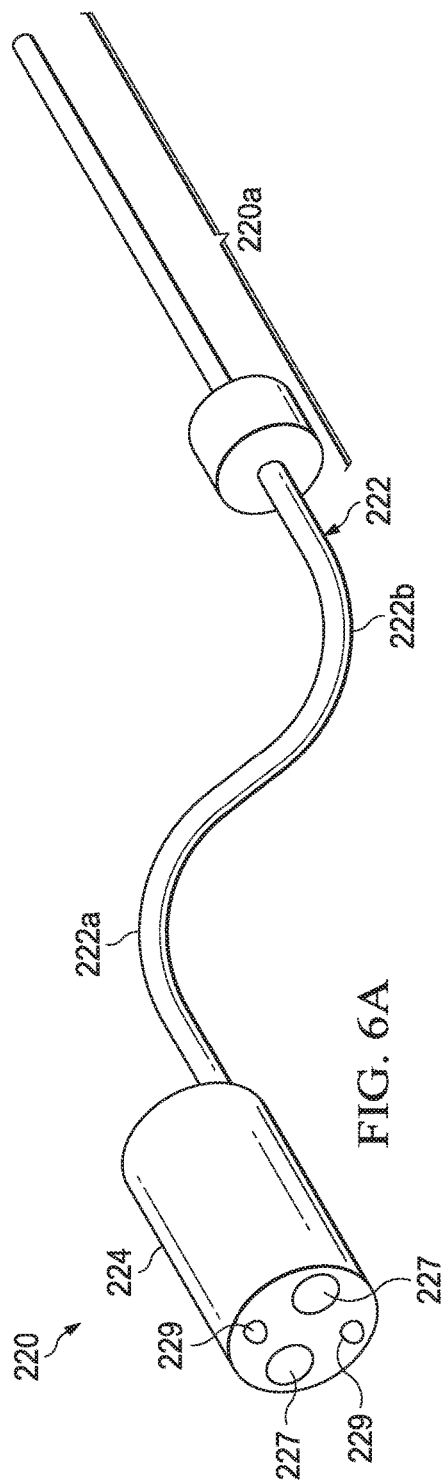
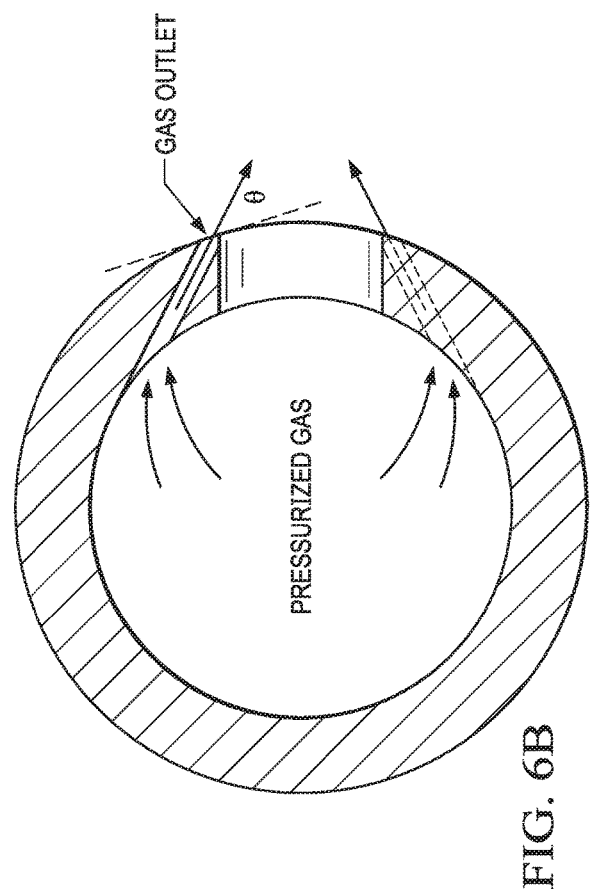
FIG. 6A
FIG. 6B

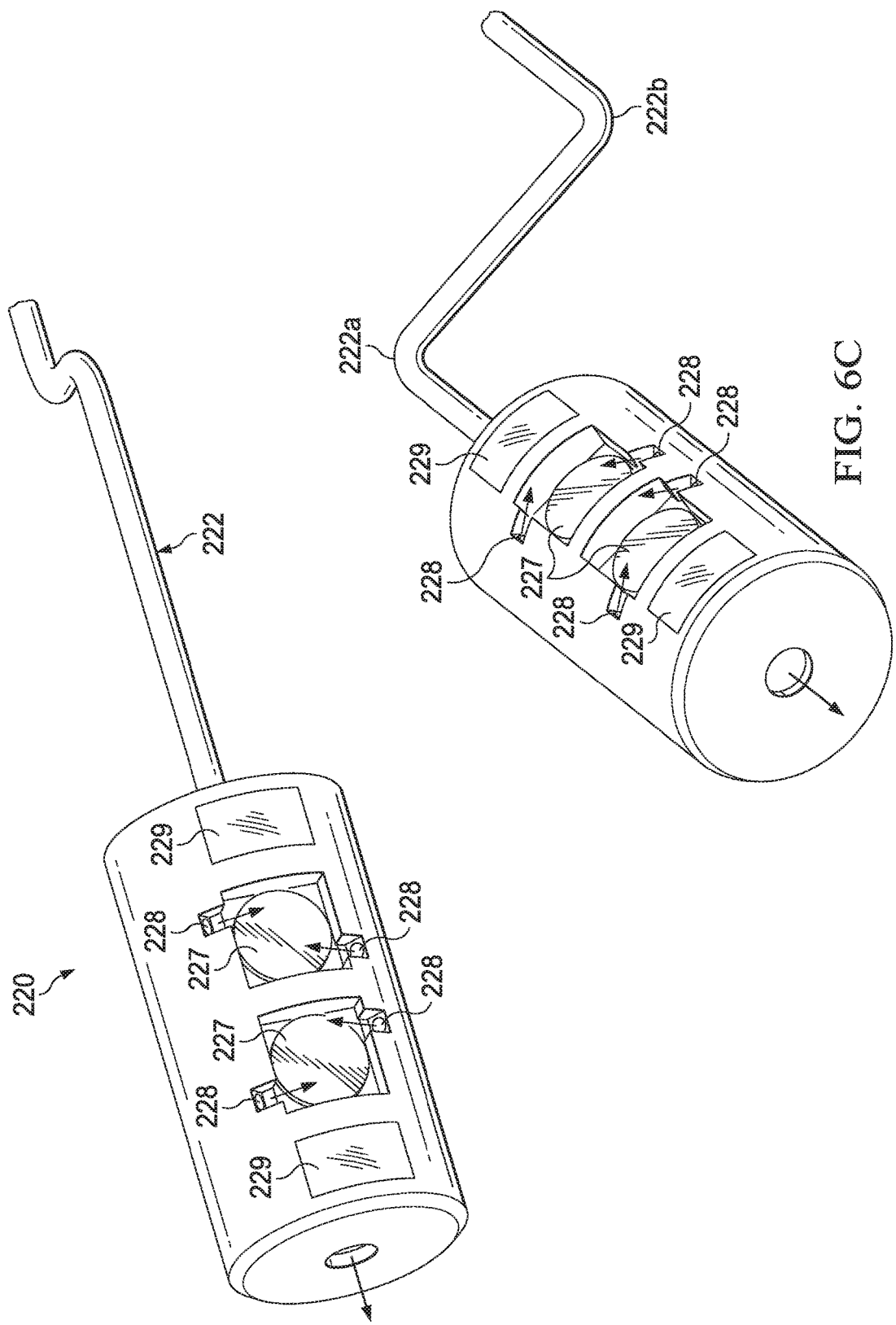

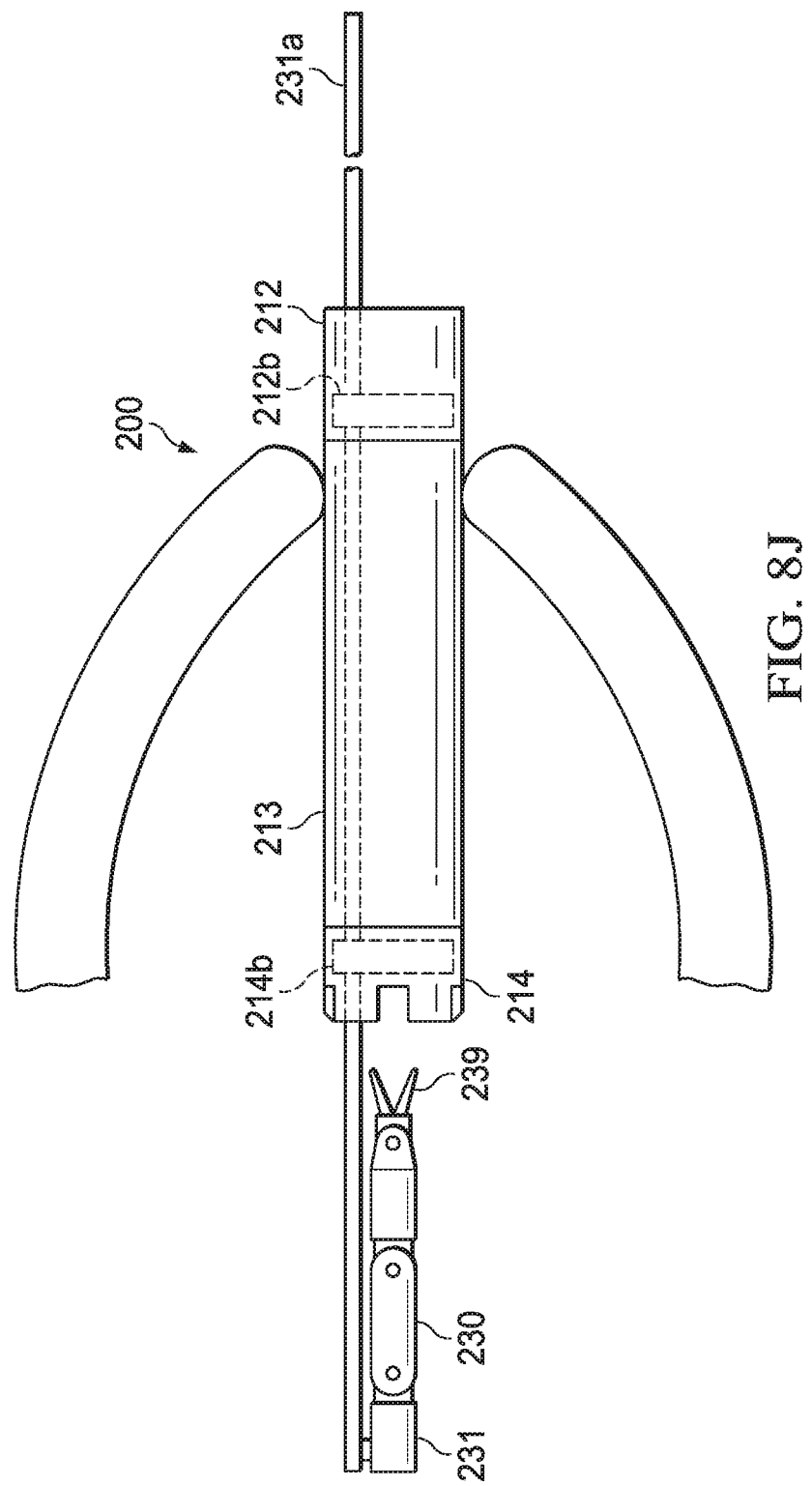

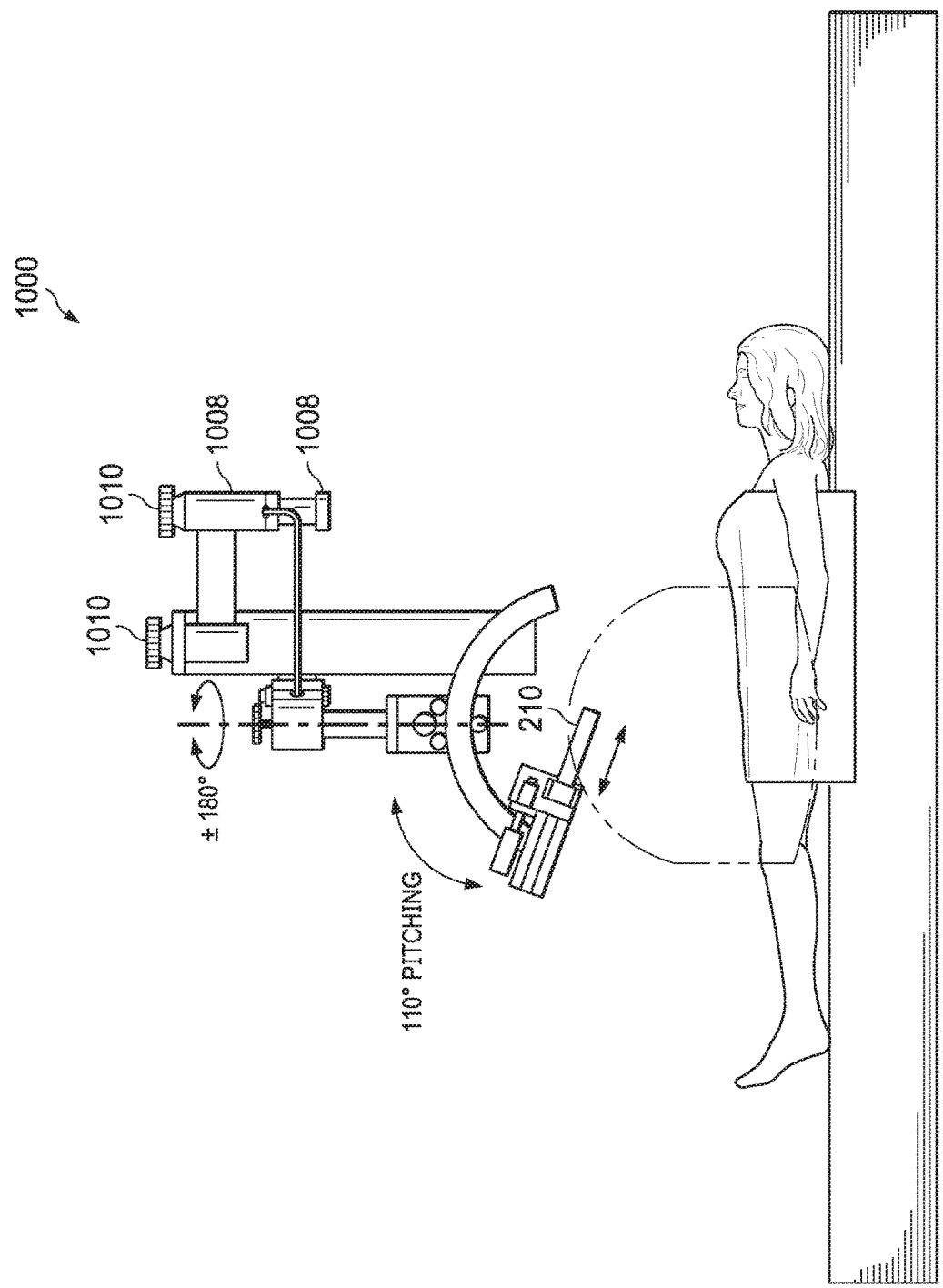

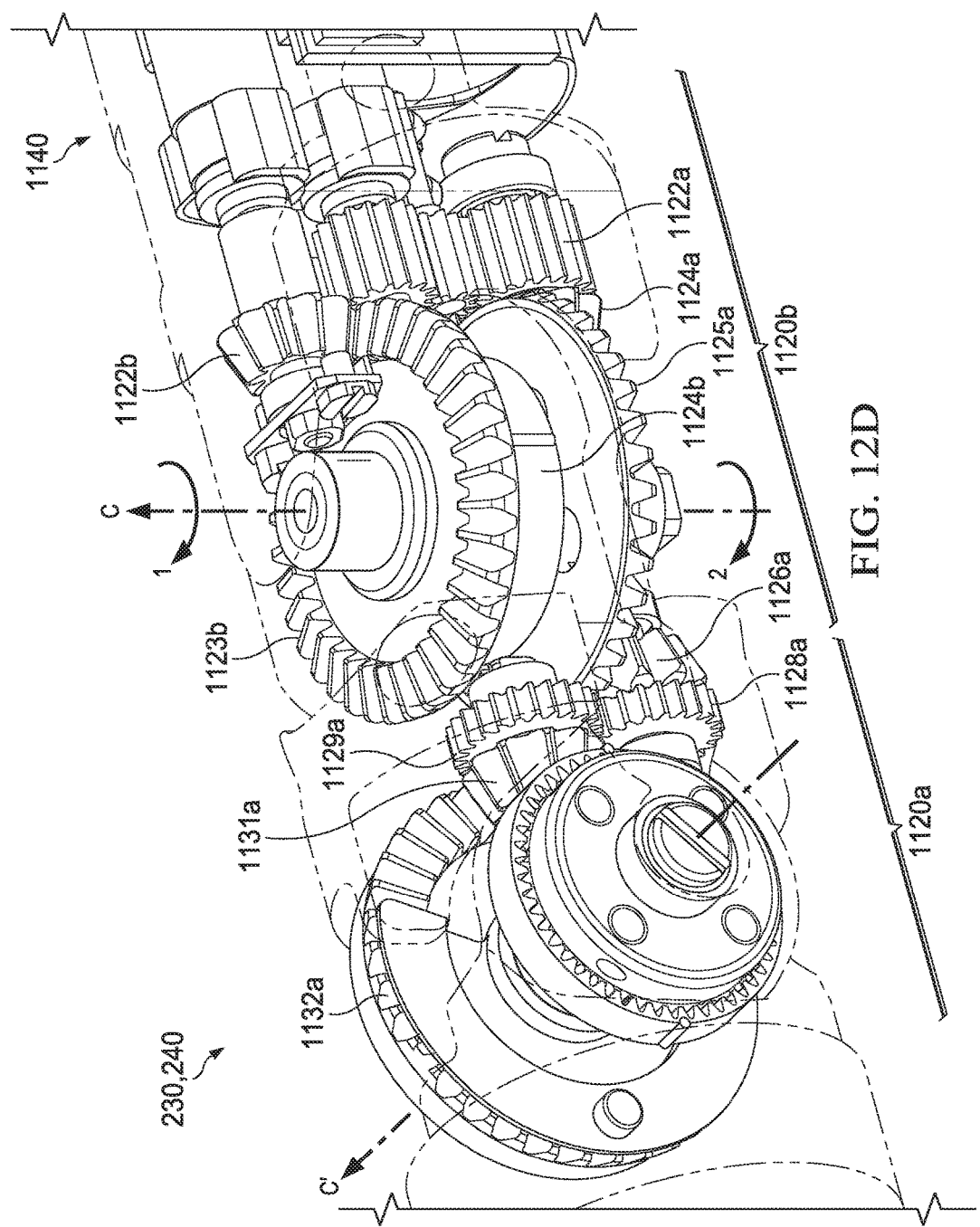

SURGICAL ARM SYSTEM WITH INTERNALLY DRIVEN GEAR ASSEMBLIES

CROSS-REFERENCE TO RELATED APPLICATIONS

This application is a continuation-in-part of U.S. application Ser. No. 16/172,408 (filed on Oct. 26, 2018), which is a continuation of U.S. application Ser. No. 15/864,628 (filed on Jan. 8, 2018), now U.S. Pat. No. 10,172,680, which is a continuation of U.S. application Ser. No. 15/605,864 (filed on May 25, 2017), now U.S. Pat. No. 9,895,200, which is a:

(A) continuation-in-part of U.S. application Ser. No. 15/340,660 (filed on Nov. 1, 2016), now U.S. Pat. No. 9,855,108, which is a continuation-in-part of U.S. application Ser. No. 15/044,889 (filed on Feb. 16, 2016), now U.S. Pat. No. 9,737,372, and a continuation-in-part of U.S. application Ser. No. 15/044,895 (filed on Feb. 16, 2016), and a continuation-in-part of U.S. application Ser. No. 14/693,207 (filed on Apr. 22, 2015), which claims priority to U.S. Provisional Application No. 61/982,717 (filed on Apr. 22, 2014);

(B) continuation-in-part of U.S. application Ser. No. 15/340,678 (filed on Nov. 1, 2016), not U.S. Pat. No. 9,855,108, which is a continuation-in-part of U.S. application Ser. No. 15/044,889, (filed on Feb. 16, 2016), now U.S. Pat. No. 9,737,372, and a continuation-in-part of U.S. application Ser. No. 15/044,895 (filed on Feb. 16, 2016), and a continuation-in-part of U.S. application Ser. No. 14/693,207 (filed on Apr. 22, 2015), which claims priority to U.S. Provisional Application No. 61/982,717 (filed on Apr. 22, 2014);

(C) continuation-in-part of U.S. application Ser. No. 15/340,699 (filed on Nov. 1, 2016, now U.S. Pat. No. 9,827,058;

(D) continuation-in-part of U.S. application Ser. No. 14/693,207 (filed on Apr. 22, 2015), which claims priority to U.S. Provisional Application No. 61/982,717, (filed on Apr. 22, 2014);

(E) continuation-in-part of U.S. application Ser. No. 15/044,895 (filed on Feb. 16, 2016, which is a continuation-in-part of U.S. application Ser. No. 14/693,207, which claims priority to U.S. Provisional Application No. 61/982,717); and (F) continuation-in-part of U.S. application Ser. No. 15/044,889 (filed on Feb. 16, 2016, now U.S. Pat. No. 9,737,372, which is a continuation-in-part of U.S. application Ser. No. 14/693,207, which claims priority to U.S. Provisional Application No. 61/982,717).

The contents of all of the aforementioned related applications are hereby expressly incorporated by reference in their entirety, including the contents and teachings of any references contained therein.

BACKGROUND

Conventionally, surgical procedures performed in a body cavity of a patient, such as the abdominal cavity, required one or more large access incisions to a patient in order for the surgical team to perform a surgical action. With advancements in medical science and technology, such conventional surgical procedures have been largely replaced by minimally invasive surgery (MIS) procedures and, where applicable, natural orifice transluminal endoscopic surgical procedures (NOTES). Recent developments in respect to computer-assisted and/or robotic surgical technology have contributed to advancements in the MIS and NOTES fields, including the ability to translate a surgeon's desired surgical actions into precise movements of surgical instruments inside a body cavity of a patient.

BRIEF SUMMARY

Despite recent developments in modern medical science and technology, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic systems oftentimes face difficulties in providing, at the same time within a patient's cavity, left and right surgical robotic arms each having a main instrument (such as a cutting or gripping instrument attached to the end of a surgical robotic arm) and one or more assistant instruments (such as a gripper, retractor, suction/irrigation, and/or image capturing device).

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example, known surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

Present example embodiments relate generally to and/or comprise systems, subsystems, processors, devices, logic, and methods for addressing conventional problems, including those described above.

In an exemplary embodiment, a robotic arm assembly is disclosed. The robotic arm assembly may include a forearm segment, an upper arm segment, and an elbow coupling joint assembly. The forearm segment may be formed as an elongated structure with a proximal end and a distal end. The upper arm segment may be formed as an elongated structure with a proximal end and a distal end. The upper arm segment may include a first distal motor. The first distal motor may include a first distal motor drive portion at the distal end of the upper arm segment. The first distal motor drive portion may be configured to rotate relative to a first axis. The first axis may be parallel to a central axis of the upper arm segment. The elbow coupling joint assembly may connect the proximal end of the forearm segment to the distal end of the upper arm segment. The elbow coupling joint assembly may include a distal elbow joint subassembly and a proximal elbow joint subassembly. The distal elbow joint subassembly may be connected at a distal end to the proximal end of the forearm segment. The distal elbow joint subassembly may include a gear train system having a plurality of gear stages including a first distal elbow gear stage, a second distal elbow gear stage, a third distal elbow gear stage, and a fourth distal elbow gear stage. The first distal elbow gear stage may include a first distal elbow bevel gear connected to the first distal motor drive portion of the first distal motor. The first distal elbow bevel gear may be configured to be driven by the first distal motor to rotate relative to the first axis. The first distal elbow gear stage may also include a second distal elbow bevel gear drivable by the first distal elbow bevel gear. The second distal elbow bevel gear may be configured to rotate relative to a first main elbow axis when driven by the first distal elbow bevel gear. The first main elbow axis may be orthogonal to the first axis. The first distal elbow gear stage may also include a third distal elbow bevel gear drivable by the second distal elbow bevel gear. The third distal elbow bevel gear may be configured to rotate relative to an axis orthogonal to the first main elbow axis when the first distal elbow bevel gear drives the second distal elbow bevel gear to rotate relative to the first main elbow axis. The second distal elbow gear stage may include a first distal elbow spur gear connected to the third distal elbow bevel gear. The first distal elbow spur gear may be configured to rotate relative to a same axis of rotation as the third distal elbow bevel gear when the third distal elbow bevel gear is driven to rotate. The second distal elbow gear stage may also include a second distal elbow spur gear drivable by the first distal elbow spur gear. The second distal elbow spur gear may be configured to rotate relative to an axis of rotation that is parallel to the axis of rotation of the first distal elbow spur gear when the second distal elbow spur gear is driven by the first distal elbow spur gear. The third distal elbow gear stage may include a fourth distal elbow bevel gear connected to the second distal elbow spur gear. The fourth distal elbow bevel gear may be configured to be driven by the second distal elbow spur gear to rotate relative to the same axis of rotation as that of the second distal elbow spur gear. The third distal elbow gear stage may also include a fifth distal elbow bevel gear drivable by the fourth distal elbow bevel gear. The fifth distal elbow bevel gear may be configured to rotate relative to a second main elbow axis when driven by the fourth distal elbow bevel gear. The second main elbow axis may be orthogonal to the first main elbow axis. The fourth distal elbow gear stage may include a distal elbow planetary gear assembly. The distal elbow planetary gear assembly may include a distal elbow sun gear configured to be driven by the fifth distal elbow bevel gear to rotate relative to the second main elbow axis. The distal elbow planetary gear assembly may also include a distal elbow ring gear configured to not rotate relative to the second main elbow axis. The distal elbow planetary gear assembly may also include a plurality of distal elbow planetary gears drivable by the distal elbow sun gear. The distal elbow planetary gear assembly may also include a distal elbow planetary gear carrier connected at one end to the plurality of distal elbow planetary gears in such a way that when the distal elbow sun gear rotates relative to the second main elbow axis, the distal elbow planetary gear carrier rotates relative to the second main elbow axis. The distal elbow planetary gear carrier may be connected at another end to the proximal end of the forearm segment in such a way that when the distal elbow sun gear is driven to rotate relative to the second main elbow axis, the distal elbow planetary gear carrier drives the forearm segment to pivotally rotate relative to the second main elbow axis. The proximal elbow joint subassembly may connect the distal end of the upper arm segment to the distal elbow joint subassembly. The proximal elbow joint subassembly may be configurable to be driven in such a way as to pivotally rotate the forearm segment relative to the first main elbow axis.

In another exemplary embodiment, a robotic arm assembly is disclosed. The robotic arm assembly may include a forearm segment, an upper arm segment, and an elbow coupling joint assembly. The forearm segment may be formed as an elongated structure with a proximal end and a distal end. The upper arm segment may be formed as an elongated structure with a proximal end and a distal end. The upper arm segment may include a first distal motor. The first distal motor may include a first distal motor drive portion at the distal end of the upper arm segment. The first distal motor drive portion may be configured to rotate relative to a first axis. The first axis may be parallel to a central axis of the upper arm segment. The elbow coupling joint assembly may connect the proximal end of the forearm segment to the distal end of the upper arm segment. The elbow coupling joint assembly may include a proximal elbow joint subassembly and a distal elbow joint subassembly. The proximal elbow joint subassembly may be connected at a proximal end to the distal end of the upper arm segment. The proximal elbow joint subassembly may include a gear train system having a plurality of gear stages including a first proximal elbow gear stage and a second proximal elbow gear stage. The first proximal elbow gear stage may include a first proximal elbow bevel gear connected to the first distal motor drive portion of the first distal motor. The first proximal elbow bevel gear may be configured to be driven by the first distal motor to rotate relative to the first axis. The first proximal elbow gear stage may also include a second proximal elbow bevel gear drivable by the first proximal elbow bevel gear. The second proximal elbow bevel gear may be configured to rotate relative to a first main elbow axis when driven by the first proximal elbow bevel gear. The first main elbow axis may be orthogonal to the first axis. The second proximal elbow gear stage may include a proximal elbow planetary gear assembly. The proximal elbow planetary gear assembly may include a proximal elbow sun gear connected to the second proximal elbow bevel gear. The proximal elbow sun gear may be configured to be driven by the second proximal elbow bevel gear to rotate relative to the first main elbow axis. The proximal elbow planetary gear assembly may also include a proximal elbow ring gear configured to not rotate relative to the first main elbow axis. The proximal elbow planetary gear assembly may also include a plurality of proximal elbow planetary gears drivable by the proximal elbow sun gear. The proximal elbow planetary gear assembly may also include a proximal elbow planetary gear carrier connected at one end to the plurality of proximal elbow planetary gears in such a way that when the proximal elbow sun gear rotates relative to the first main elbow axis, the proximal elbow planetary gear carrier rotates relative to the first main elbow axis. The distal elbow joint subassembly may be connected at a distal end to the proximal end of the forearm segment. The distal elbow joint subassembly may be configurable to be driven in such a way as to pivotally rotate the forearm segment relative to a second main elbow axis. The second main elbow axis may be orthogonal to the first main elbow axis. The proximal elbow planetary gear carrier may be connected at another end to the distal end of the upper arm segment. When the proximal elbow sun gear is driven to rotate relative to the first main elbow axis, the proximal elbow planetary gear carrier may drive the forearm segment to pivotally rotate relative to the first main elbow axis.

In another exemplary embodiment, a robotic arm assembly is disclosed. The robotic arm assembly may include a forearm segment, an upper arm segment, and an elbow coupling joint assembly. The forearm segment may be formed as an elongated structure with a proximal end and a distal end. The upper arm segment may be formed as an elongated structure with a proximal end and a distal end. The upper arm segment may include a first distal motor. The first distal motor may include a first distal motor drive portion at the distal end of the upper arm segment. The first distal motor drive portion may be configured to rotate relative to a first axis of rotation. The elbow coupling joint assembly may connect the proximal end of the forearm segment to the distal end of the upper arm segment via a serial arrangement of a distal elbow joint and a proximal elbow joint. The distal elbow joint may form a distal main elbow axis. The proximal elbow joint may form a proximal main elbow axis. The distal main elbow axis may be orthogonal to the proximal main elbow axis. The elbow coupling joint assembly may include a distal elbow joint subassembly and a proximal elbow joint subassembly. The distal elbow joint subassembly may include a first distal elbow bevel gear configured to be driven by the first distal motor drive portion of the first distal motor. The distal elbow joint subassembly may also include a first distal elbow integrated gear assembly. The first distal elbow integrated gear assembly may include a first integrated bevel gear portion. The first integrated bevel gear portion may be configured to be driven by the first distal elbow bevel gear when the first distal elbow bevel gear is driven by the first distal motor drive portion of the first distal motor. The first distal elbow integrated gear assembly may also include a first integrated spur gear portion. The first integrated spur gear portion may be adjoined to the first integrated bevel gear portion in such a way that when the first distal elbow bevel gear is driven by the first distal motor drive portion of the first distal motor, the first integrated bevel gear portion and the first integrated spur gear portion are driven to rotate along a same axis of rotation and same rate of rotation. The distal elbow joint subassembly may also include a second distal elbow integrated gear assembly. The second distal elbow integrated gear assembly may include a second integrated spur gear portion. The second integrated spur gear portion may be configured to be driven by the first integrated spur gear portion when the first integrated gear portion is driven by the first distal elbow bevel gear. The second distal elbow integrated gear assembly may also include a second integrated bevel gear portion. The second integrated bevel gear portion may be adjoined to the second integrated spur gear portion in such a way that when the first distal elbow bevel gear is driven by the first distal motor drive portion of the first distal motor, the second integrated spur gear portion and the second integrated bevel gear portion are driven to rotate along a same axis of rotation and same rate of rotation. The distal elbow joint subassembly may also include a second distal elbow bevel gear configured to be driven by the second integrated bevel gear portion of the second distal elbow integrated gear assembly to rotate relative to the distal main elbow axis. The distal elbow joint subassembly may also include a distal elbow planetary gear assembly. The distal elbow planetary gear assembly may include a distal elbow sun gear. The distal elbow sun gear may be configured to be driven by the second distal elbow bevel gear to rotate relative to the distal main elbow axis. The distal elbow planetary gear assembly may also include a distal elbow ring gear configured to not rotate relative to the distal main elbow axis. The distal elbow planetary gear assembly may also include a plurality of distal elbow planetary gears drivable by the distal elbow sun gear. The distal elbow planetary gear assembly may also include a distal elbow planetary gear carrier connected at one end to the plurality of distal elbow planetary gears in such a way that when the distal elbow sun gear rotates relative to the distal main elbow axis, the distal elbow planetary gear carrier rotates relative to the distal main elbow axis. The distal elbow planetary gear carrier may be connected at another end to the proximal end of the forearm segment in such a way that when the distal elbow sun gear is driven to rotate relative to the distal main elbow axis, the distal elbow planetary gear carrier drives the forearm segment to pivotally rotate relative to the distal main elbow axis. The proximal elbow joint subassembly may connect the distal end of the upper arm segment to the distal elbow joint subassembly. The proximal elbow joint subassembly may be configurable to be driven in such a way as to pivotally rotate the forearm segment relative to the proximal main elbow axis.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 1A is illustration of a perspective view of an example embodiment of an external anchor;

FIG. 4B is an illustration of a side view of an example embodiment of a port assembly;

FIG. 4C is an illustration of a cross-sectional view of an example embodiment of a port assembly with a first or second gate assembly in the open position;

FIG. 4D is an illustration of a cross-sectional view of an example embodiment of a port assembly with a first or second gate assembly in the closed position;

FIG. 5C is an illustration of a perspective view of an example embodiment of an instrument arm assembly;

FIG. 5D is an illustration of a side view of an example embodiment of an end-effector assembly secured to an arm assembly;

FIG. 5E is an illustration of a side cross-sectional view of an example embodiment of an end-effector assembly secured to an arm assembly;

FIG. 5F is an illustration of a side view of an example embodiment of an end-effector assembly unsecured from an arm assembly;

FIG. 5G is an illustration of a side cross-sectional view of an example embodiment of an end-effector assembly unsecured from an arm assembly;

FIG. 5L is an illustration of a side view of an example embodiment of an instrument arm assembly;

FIG. 5M is an illustration of a side cross-sectional view of an example embodiment of an instrument arm assembly;

FIG. 5N is an illustration of a top cross-sectional view of an example embodiment of a second arm assembly;

FIG. 5O is an illustration of a transparent perspective partial view of an example embodiment of an instrument arm assembly;

FIG. 5P is another illustration of a side view of an example embodiment of an instrument arm assembly;

FIG. 5Q is another illustration of a side view of an example embodiment of an instrument arm assembly;

FIG. 5S is another illustration of a side view of an example embodiment of an instrument arm assembly;

FIG. 5T is another illustration of a side cross-sectional view of an example embodiment of an instrument arm assembly;

FIG. 6A is an illustration of a perspective view of an example embodiment of an image capturing assembly;

FIG. 6B is an illustration of a cross sectional view of another example embodiment of an image capturing assembly having an internal temperature control assembly;

FIG. 6C is an illustration of perspective views of another example embodiment of an image capturing assembly having internal temperature control assemblies;

FIGS. 8F-K are illustrations of a side view of an example embodiment of a method of configuring a surgical device in a reverse-directed position;

FIG. 10B is an illustration of a perspective view of another example embodiment of an external anchor;

FIG. 12D is an illustration of a perspective view of an example embodiment of an elbow coupling joint assembly;

Although similar reference numbers may be used to refer to similar elements in the figures for convenience, it can be appreciated that each of the various example embodiments may be considered to be distinct variations.

Figure 1B:
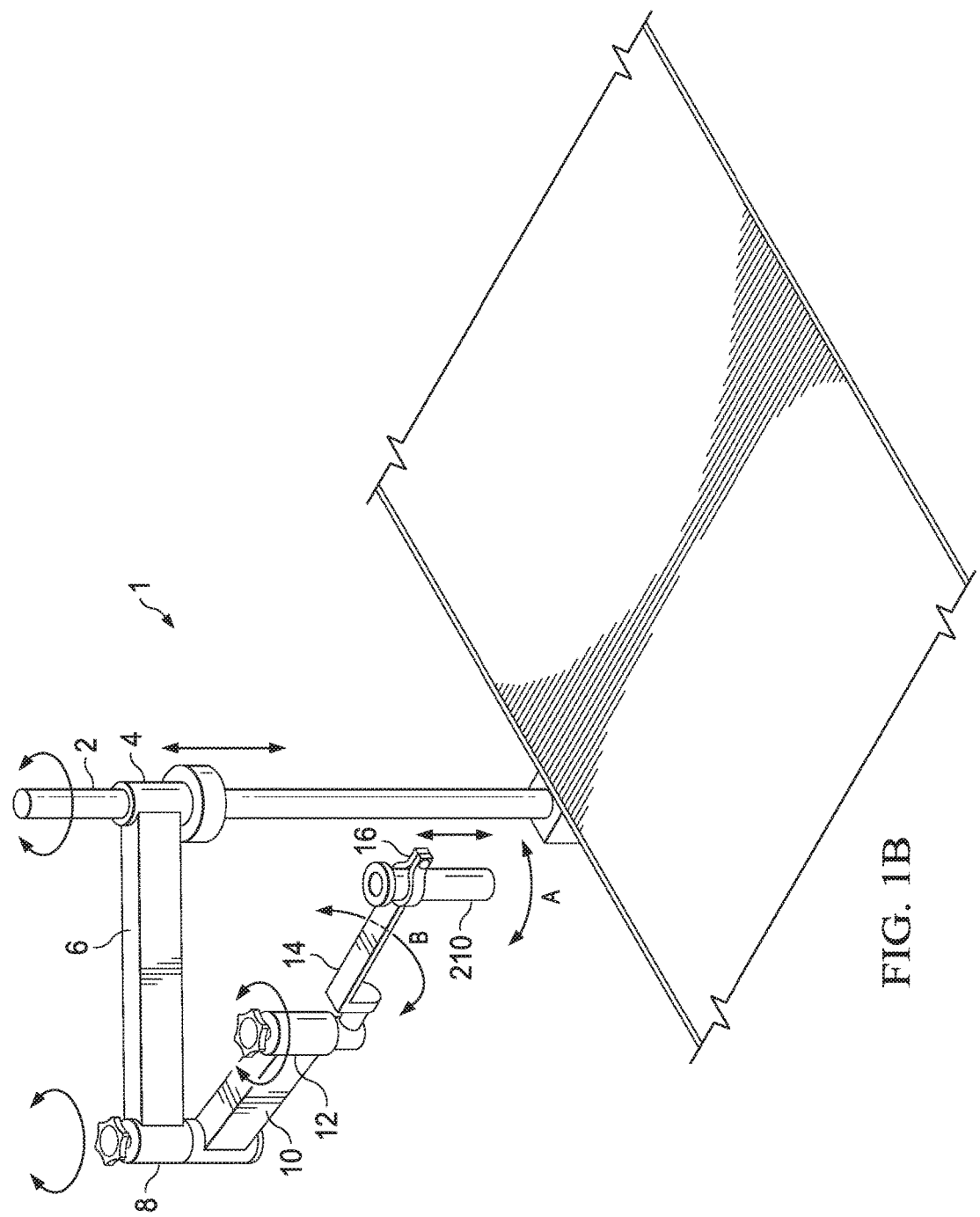
FIG. 1B is another illustration of a perspective view of an example embodiment of an external anchor attached to an example embodiment of a port assembly.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

It is recognized in the present disclosure that, despite recent developments in medical science and technology, one or more problems are encountered in modern surgical technology and methodology, including MIS. For example, a typical MIS procedure requires multiple incisions to a patient in order to allow access via the incisions for the insertion of a camera and various other laparoscopic instruments into the body cavity of the patient.

In addition to the aforementioned disadvantages pertaining to the multiple and rather large incisions, it is recognized in the present disclosure that surgical robotic systems, including surgical robotic arms (and those instruments attached to them), developed for performing robotic-assisted MIS surgical procedures also suffer from one or more problems. For example, it is recognized herein that a major technical challenge for a surgical robotic system is the difficulty in providing sufficient anchoring and/or reactive forces to stabilize against forces that are desired and/or necessary to be applied to the patient by the surgical robotic system during a surgical action. In this regard, certain surgical actions for known surgical robotic systems may require tremendous effort and time, and may not be performed properly or at all as a result of the problem of insufficient anchoring and/or reactive forces.

Another example of a problem recognized in the present disclosure as being encountered by surgical robotic systems is the difficulty in providing an instrument, such as a cutting and/or gripping instrument attached to the end of a surgical robotic arm, with access to all or even most parts, areas, and quadrants of an abdominal cavity of a patient after the surgical robotic system has been set up (or installed) and is ready to perform a surgery. That is, after the surgical robotic arm of the system has been inserted, attached, and properly set up in the abdominal cavity of the patient and is ready to perform a surgical action, the instrument attached to the end of the surgical robotic arm is typically limited to access only certain parts, areas, and quadrants of the abdominal cavity of the patient. It is recognized in the present disclosure that such problems result in large from the limited number of possible degrees of freedom that can be provided by known surgical robotic systems and arms, and more specifically, the limited number of in vivo degrees of freedom (i.e. the degrees of freedom provided within an abdominal cavity of a patient) of known surgical robotic systems and arms. In this regard, surgical robotic systems typically provide only between 2 to 4 in vivo degrees of freedom for each surgical robotic arm.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as trans-vaginal gynecological procedures in women and trans-rectal urological procedures in men. Such systems may encounter one or more problems, such as the inability to access certain organs, tissues, or other surgical sites upon insertion into the natural orifice.

Surgical systems, devices, and methods, including those for use in MIS and natural orifice transluminal endoscopic surgery (or NOTES), are described in the present disclosure for addressing one or more problems of known surgical systems, devices, and methods, including those described above and in the present disclosure. It is to be understood that the principles described in the present disclosure can be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical Device 200).

An illustration of an example embodiment of a surgical device or system (e.g., surgical device or system 200) operable to be inserted into an abdominal cavity of a patient through a single access or opening (e.g., a single incision (such as an incision in or around the umbilical area) or through a natural orifice (such as a rectum or vagina, for performing natural orifice transluminal endoscopic surgery (or NOTES), hereinafter referred to as an "opening") of the patient is depicted in FIG. 2A, FIG. 2B, FIG. 2C, and FIG. 2D. The surgical device may then be anchored so as to position the surgical device 200 in the opening. The surgical device 200 may comprise a port assembly 210 and an instrument arm assembly 230. The surgical device 200 may also comprise other elements, such as one or more other instrument arm assemblies (e.g., instrument arm assembly 240), one or more image capturing assemblies, one or more assistant arm assemblies, etc.

Figure 10A:
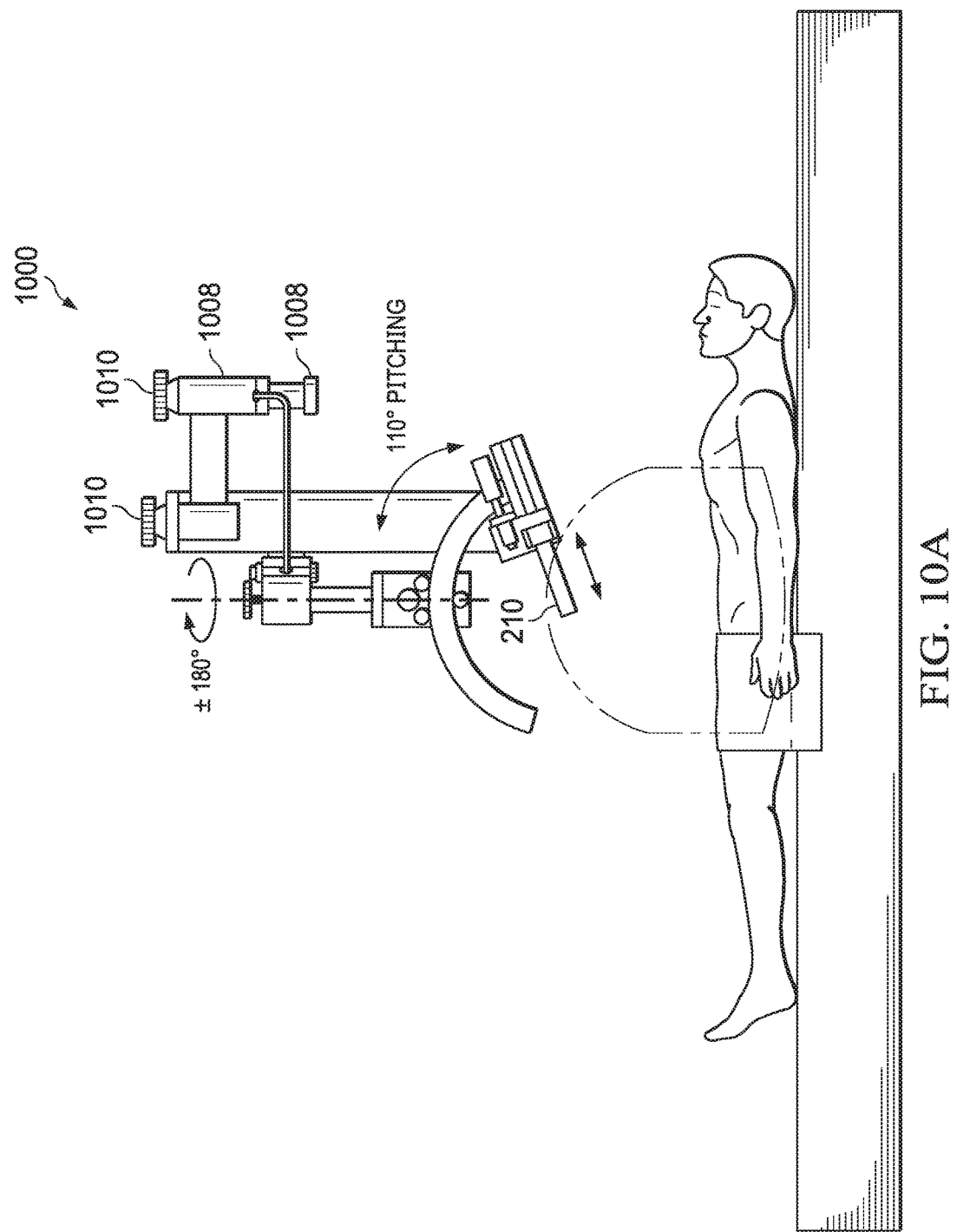
FIG. 10A is an illustration of a perspective view of an example embodiment of an external anchor.

As illustrated in FIG. 1A and FIG. 1B, the surgical device 200 may be provided with an external anchor 1 attachable to the port assembly 210. The external anchor 1 may comprise a configurable assembly of segments 2, 6, 10, and 14 in communication with one another via joints or connecting portions 4, 8, and 12, and external anchor connector 16. The external anchor 1 may be operable to securely fix the position and/or orientation (hereinafter "position") of the port assembly 210 in or about the single opening of the patient, and may also be operable to provide sufficient anchoring and/or reactive forces to stabilize against forces desired and/or necessary to be applied by at least one or more elements of the surgical device 200, including the instrument arm assembly 230, during a surgical action or procedure. The external anchor 1, which may also be in the form of the controllable swivel assembly 1000 illustrated in FIG. 10A and FIG. 10B, may be operable to cooperate with the port assembly 210 to provide one or more in vitro degrees of freedom. For example, the external anchor 1 may be configurable to provide 3 in vitro degrees of freedom. In example embodiments, the one or more in vitro degrees of freedom may include a torsional movement, pivotal movement, telescopic movement, and/or other movements of the port assembly 210 relative to the external anchor 1. For example, a torsional movement of the port assembly 210, as illustrated by arrow A in FIG. 1B, may allow one or more attached instruments, including an instrument arm assembly 230, to re-position during a surgical procedure (i.e. after set up or installation) so as to access other parts, areas, and/or all quadrants of the abdominal cavity of the patient. As another example, a pivotal movement of the port assembly 210, as illustrated by arrow B in FIG. 1B, may allow the port assembly 210 to be positioned in one of a plurality of angles with respect to opening of the patient, and may also allow attached instruments, including the instrument arm assembly 230, to re-position during a surgical procedure (i.e. after set up or installation) so as to access distal areas of the abdominal cavity of the patient. The other joint portions of the external anchor 1 may also be operable to cooperate and/or assist in desired movements of the port assembly 210. The external anchor 1 may be anchored to one or more stationary or fixedly positioned objects, such as a side rail 300 of a surgical table/bed illustrated in FIG. 1A. FIGS. 10A and 10B illustrate other example movements that provide for additional in vitro degrees of freedom via an example embodiment of the external anchor (controllable swivel assembly) 1000. The controllable swivel assembly 1000 will be further described below in at least the section "(1) Providing the external anchor and installing the port assembly."

The surgical device 200 may further comprise one or more additional instrument arm assemblies, such as a second instrument arm assembly 240 illustrated in FIG. 3A, FIG. 3B, FIG. 3C, and FIG. 3D, attachable to the port assembly 210. One or more of the instrument arm assemblies, including the first instrument arm assembly 230, the second instrument arm assembly 240, a third instrument arm assembly (not shown), a fourth instrument arm assembly (not shown), etc., may be attachable or securable to the port assembly 210. Such instrument arm assemblies may be operable to access and perform one or more surgical actions in/on any and all parts, areas, and/or quadrants within a cavity of the patient. For example, surgical device 200 may be configurable to perform surgical actions in a forward direction (or "forward-directed position" or "forward position") (e.g., as illustrated in FIGS. 2B, 2D, 3B, and 3D). As another example, surgical device 200 may be configurable to perform surgical actions in a reverse direction (or "reverse-directed position" or "reverse position") (e.g., as illustrated in FIGS. 2A, 2C, 3A, and 3C).

The surgical device 200 may also comprise one or more image capturing assemblies, such as image capturing assembly 220. The surgical device 200 may further comprise one or more assistant arm assemblies, such as a retractor arm assembly 260, as illustrated in FIGS. 2A, 2B, 3A, and 3B. Furthermore, the surgical device 200 may comprise one or more other instrument arm assemblies, such as suction/irrigation assembly 250, illustrated in FIGS. 2A, 2B, 3A, and 3B, that can be inserted into the opening of the patient via the port assembly 210 before, during, and/or after performing a surgical action or procedure. It is to be understood in the present disclosure that the surgical device 200 may be configurable in a plurality of configurations and arrangements, including having more or less than two instrument arm assemblies (such as third, fourth, fifth, etc. instrument arm assemblies), more than one image capturing assembly (such as second, third, etc. image capturing assemblies), more or less than one assistant arm assembly (such as second, third, etc. assistant arm assemblies), and/or more or less than one other laparoscopic tool in example embodiments without departing from the teachings of the present disclosure.

The Port Assembly (e.g., Port Assembly 210).

An example embodiment of the port assembly (e.g., port assembly 210) is illustrated in FIGS. 2A-D, 3A-D, FIG. 4A, FIG. 4B, FIG. 4C, and FIG. 4D. The port assembly 210 may be configurable to be inserted in or about a single opening of the patient (such as a single incision or a natural orifice) and fixed in position by at least the external anchor (such as the external anchor 1 illustrated in FIGS. 1A and 1B and the controllable swivel assembly 1000 illustrated in FIGS. 10A and 10B).

Figure 2A:
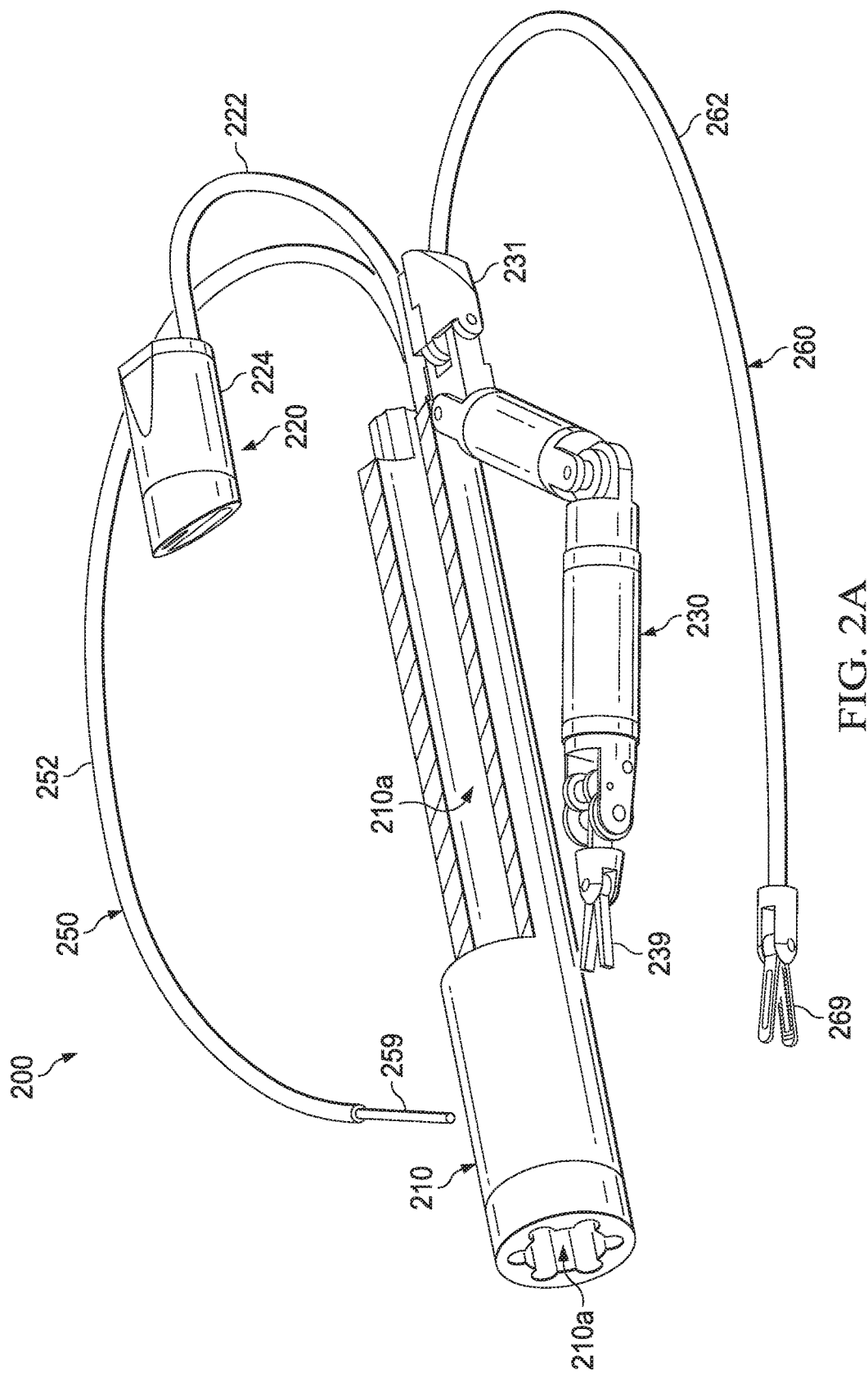
FIG. 2A is an illustration of a perspective view of an example embodiment of a surgical device configured in a reverse-directed position.
Figure 3A:
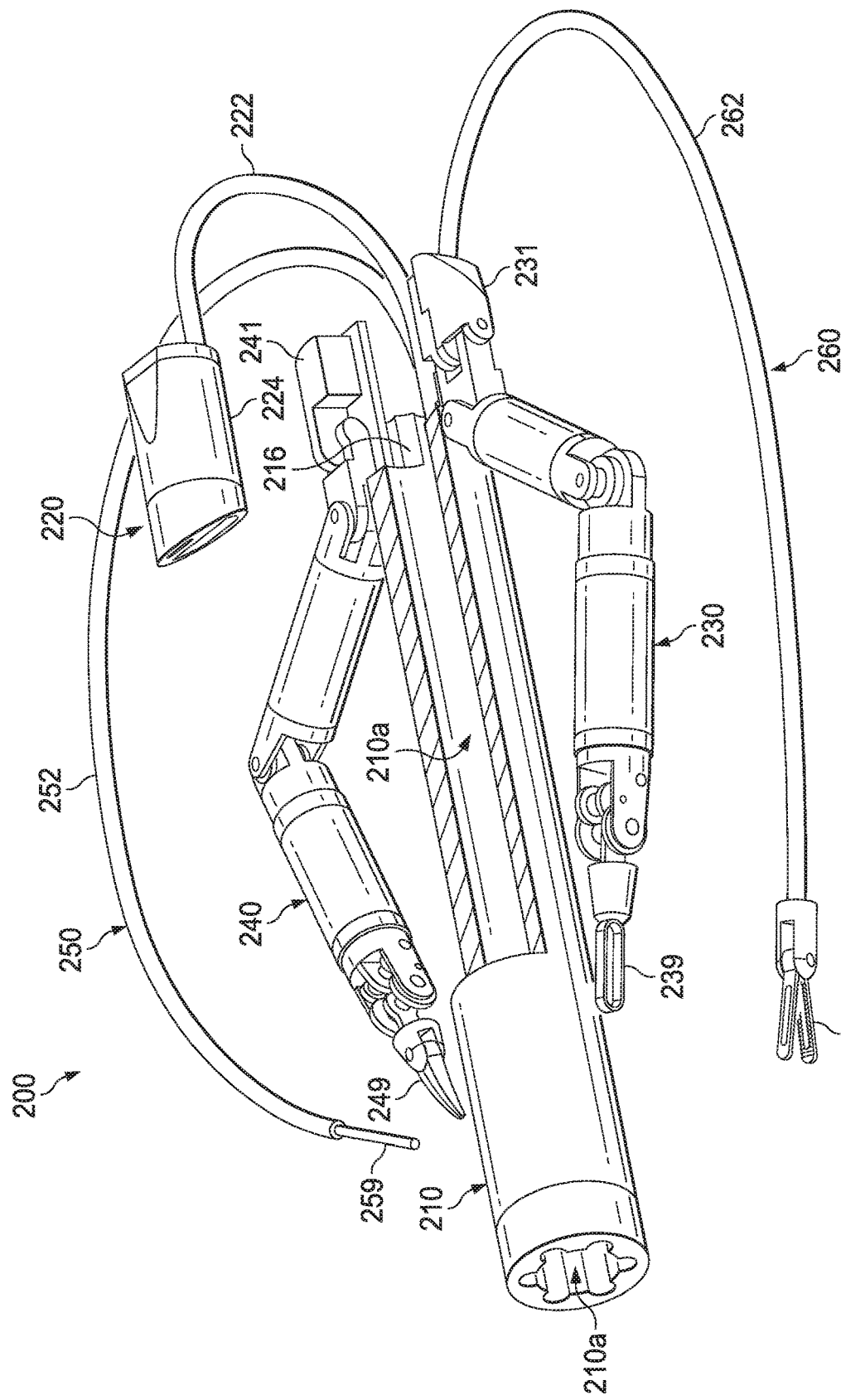
FIG. 3A is another illustration of a perspective view of an example embodiment of a surgical device configured in a reverse-directed position.
Figure 3B:
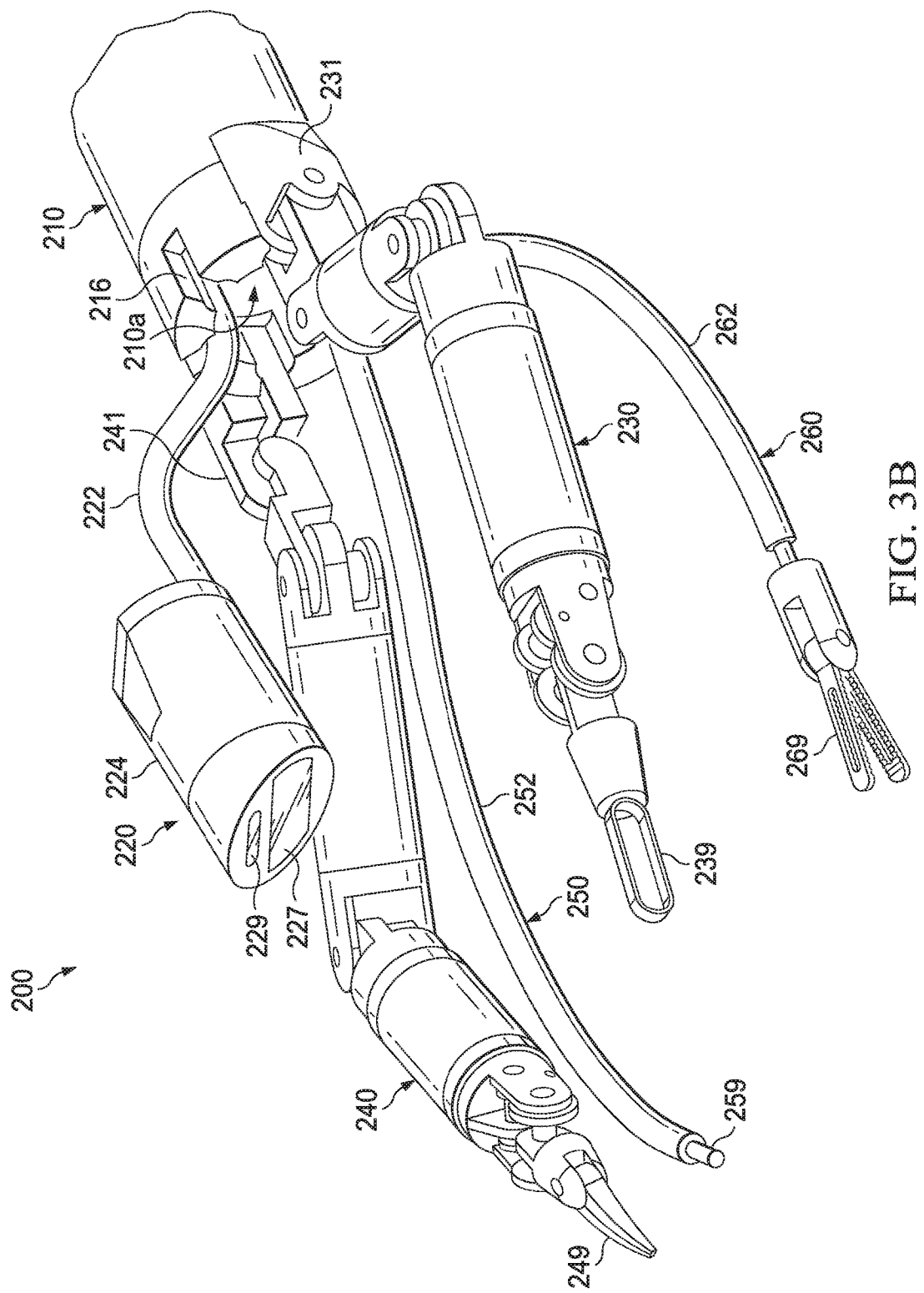
FIG. 3B is another illustration of a perspective view of an example embodiment of a surgical device configured in a forward-directed position.
Figure 3C:
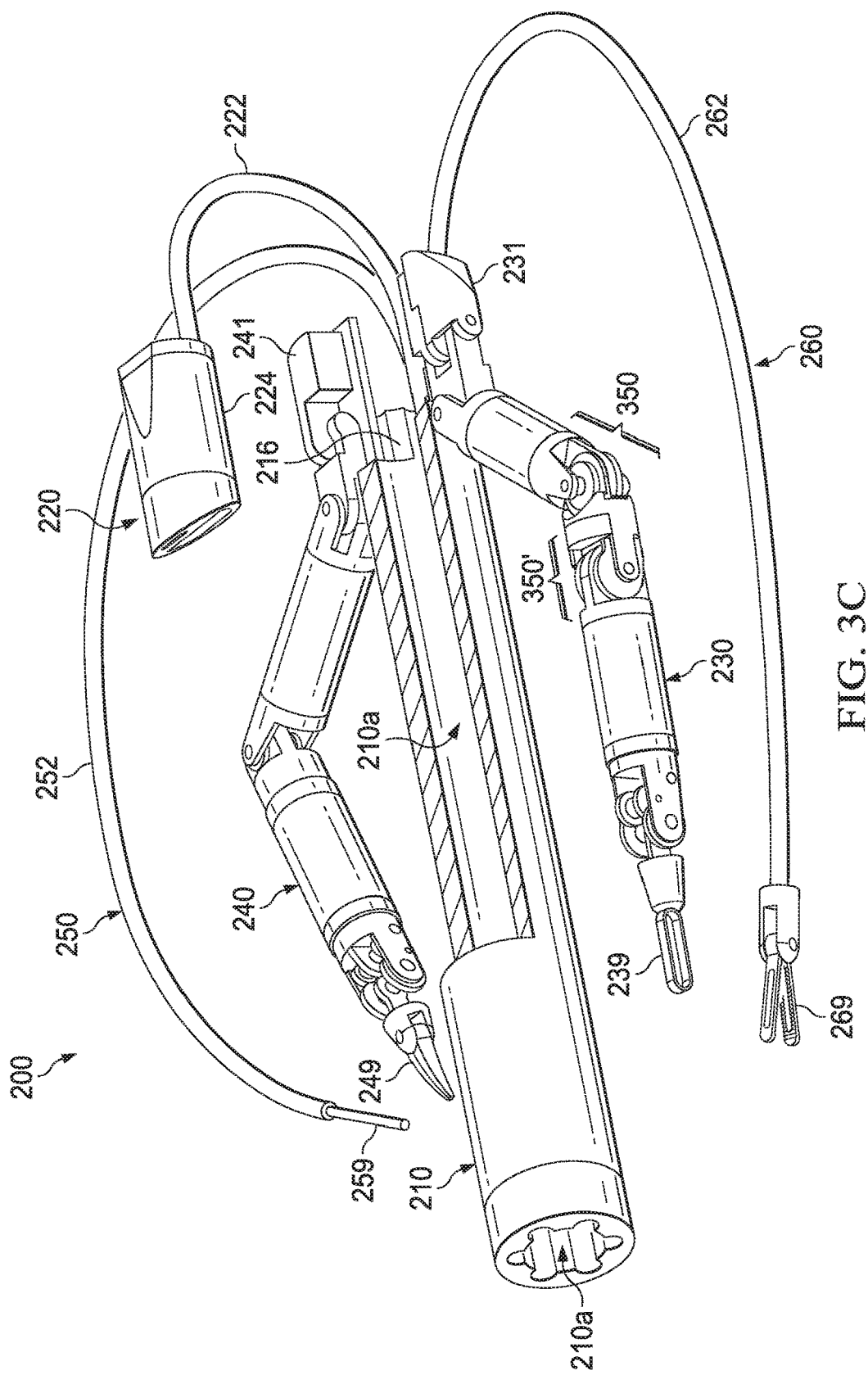
FIG. 3C is another illustration of a perspective view of an example embodiment of a surgical device configured in a reverse-directed position.
Figure 3D:
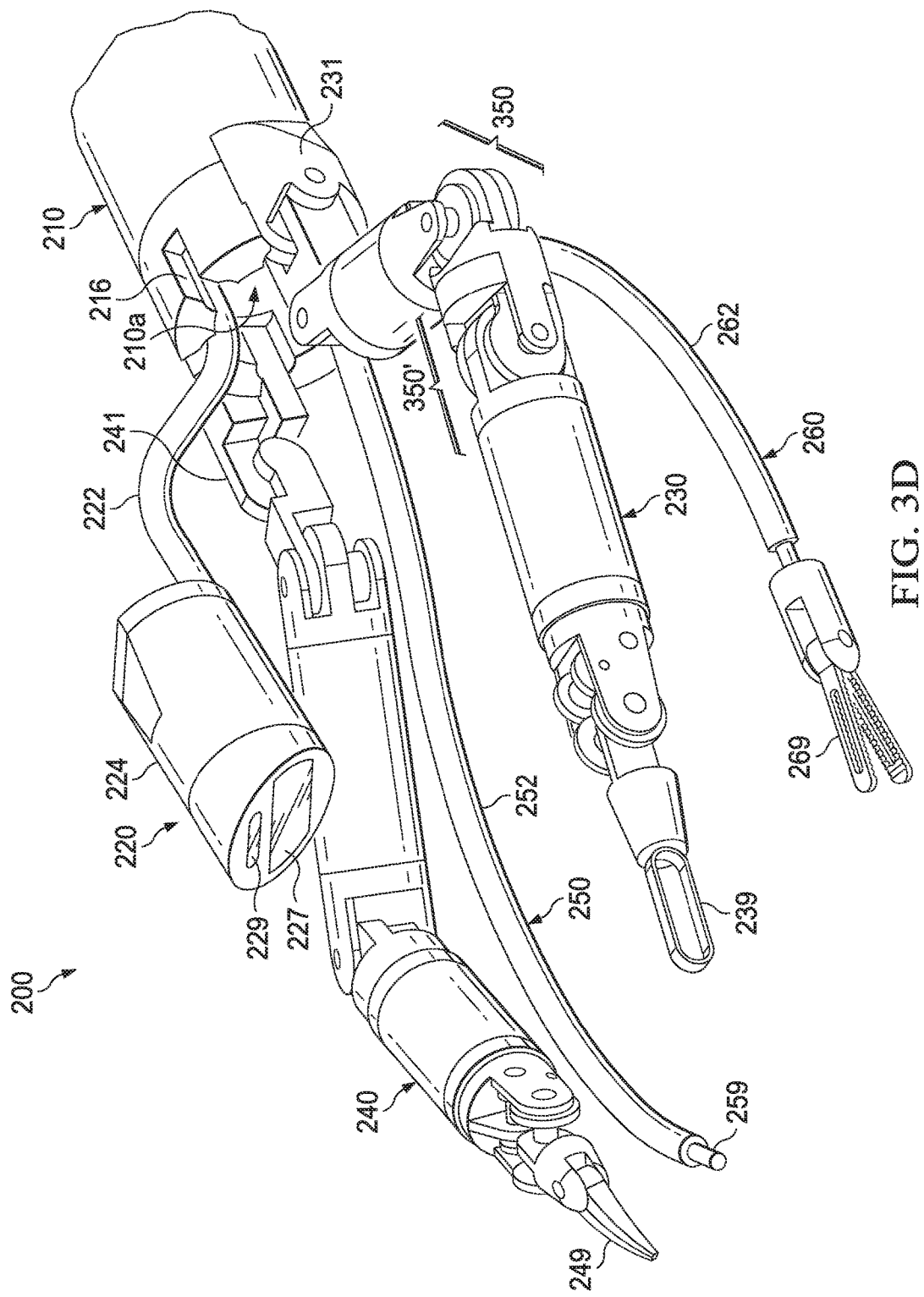
FIG. 3D is another illustration of a perspective view of an example embodiment of a surgical device configured in a forward-directed position.
Figure 4A:
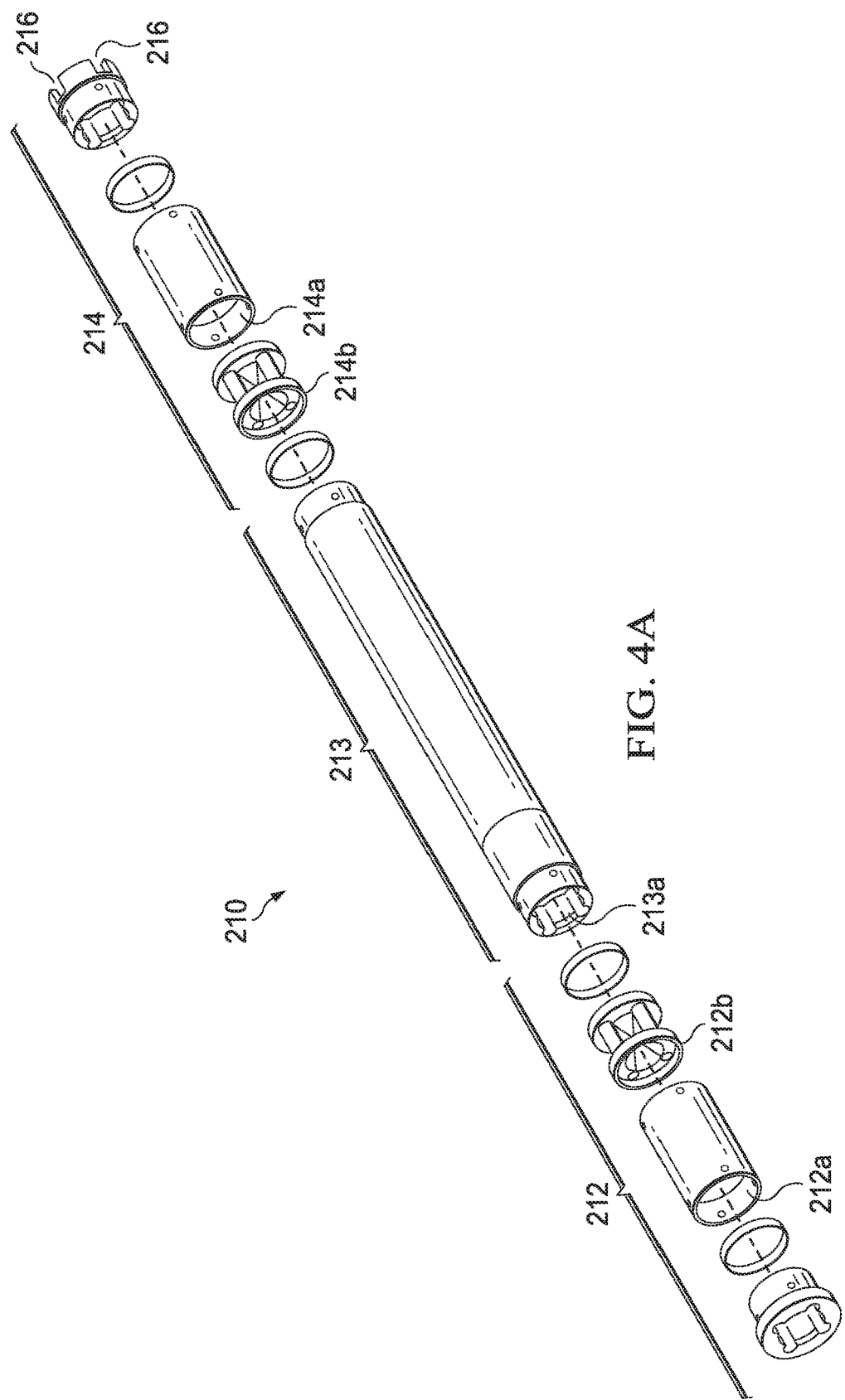
FIG. 4A is an illustration of a perspective exploded view of an example embodiment of a port assembly.

The port assembly 210 may be an elongated structure having a central access channel 210a formed through the port assembly 210. The central access channel 210a may be for use in inserting and removing instruments, such as one or more instrument arm assemblies 230, 240, one or more image capturing assemblies 220, one or more assistant arm assemblies 250, 260, etc. In an example embodiment, the port assembly 210 may include a first end section 212 and a second end section 214. The first end section 212 and second end section 214 may be fixably attachable to one another or formed as a unitary article. The port assembly 210 may also include a mid section 213 between the first end section 212 and the second end section 214. The first end section 212, second end section 214, and mid section 213 may be fixably attachable to one another, as illustrated in FIGS. 4A and 4B, or two or more of these sections may be formed as a unitary article. In an example embodiment, the first end section 212 may be the portion of the port assembly 210 that is secured to the external anchor 1, and the port assembly 210 may be fixed in position at an angle θ relative to the single opening of the patient of between about 0 to +/−90 degrees. These and other elements of the port assembly 210 will now be described below and with reference to FIGS. 2A-D, 3A-D, and 4A-D.

As illustrated in at least FIGS. 4A and 4B, the port assembly 210 may comprise a first end section 212. The first end section 212 may have a first end channel 212a formed through the first end section 212. The first end channel 212a may be considered as a part of the central access channel 210a. The first end section 212 may also include a portion operable to be secured to the external anchor 1, such as a portion on an exterior portion of the first end section 212.

The first end section 212 may also include a first gate assembly 212b, as illustrated in FIGS. 4A, 4C, and 4D. The first gate assembly 212 may be configurable to control access through the first end channel 212a. For example, the first gate assembly 212b may be configurable to be in an open position, as illustrated in FIG. 4C, so as to allow access through the first end channel 212a. The first gate assembly 212b may also be configurable to be in a closed position, as illustrated in FIG. 4D, so as to prevent or restrict access through the first end channel 212a. The first gate assembly 212b may also be configurable to be in a partially closed (or partially opened) position (not shown). The first gate assembly 212b may also be configurable to transition between the closed position and the open position.

In an example embodiment, the first gate assembly 212b may be provided within the first end section 212 in such a way that, when the first gate assembly 212b is configured to be in the open position, as illustrated in FIG. 4C, the first end channel 212a is substantially or completely unobstructed by the first gate assembly 212b. The first gate assembly 212b may be configured to be in the open position when a surgeon desires to insert (or remove) an instrument into (or out of) the cavity of the patient via the first end channel 212a (and the rest of the central access channel 210a).

Similarly, the first gate assembly 212b may be provided within the first end section 212 in such a way that, when the first gate assembly 212b is configured to be in the closed position, as illustrated in FIG. 4D, the first end channel 212a is substantially or completely obstructed by the first gate assembly 212b. The first gate assembly 212b may be configured to be in the closed position when a surgeon desires to maintain an insufflation of the cavity of the patient and/or when the surgeon does not need to insert (or remove) an instrument into (or out of) the cavity of the patient via the first end channel 212a.

The first gate assembly 212b may include a first expandable portion 212b configurable to expand when the first gate assembly 212b is configured to the closed position, as illustrated in FIG. 4D. When the first gate assembly 212b is configured to the closed position, the first expandable portion 212b may be operable to substantially or completely block, among other things, a gas medium (and/or other medium) from passing through the first end channel 212a. For example, if the cavity of the patient is being insufflated using a gas, such as carbon dioxide ($CO_2$), the first gate assembly 212b (i.e., the first expandable portion 212b) may be configurable to substantially prevent the carbon dioxide gas from leaving the cavity of the patient through the first end channel 212a.

The first expandable portion 212b may include one or more first expandable members. For example, the first expandable portion 212b may include six expandable members, as illustrated in FIGS. 4C and 4D. It is to be understood that the first expandable portion 212b may include more or less than six expandable members without departing from the teachings of the present disclosure. Some or all of the first expandable members may be integrated together and/or in communication with one another, such as in a manner where some or all of the first expandable members are operable to receive pressure (i.e., gas medium) from a common or same first source 212b'. For example, when the first gate assembly 212b is configured to the closed position, the first source 212b' may be configurable to provide a positive pressure (i.e., a supply of gas) so as to cause some or all of the first expandable members to expand and block the first end channel 212a (e.g., hermetically block the first end channel 212a). Similarly, when the first gate assembly 212b is configured to the open position, the first source 212b' may be configurable to provide a negative pressure (i.e., remove gas) so as to cause one or more (or all) of the first expandable members to not expand (and/or contract) and unblock the first end channel 212a. It is to be understood that more than one first sources 212b' may provide the positive pressure and negative pressure to the one or more expandable members without departing from the teachings of the present disclosure.

It is recognized in the present disclosure that the first gate assembly 212b may also include a valve (not shown), or the like, in addition to or in replacement of the first expandable portion 212b. The valve may be configurable to perform substantially the same actions of blocking the first end channel 212a when the first gate assembly 212b is configured to the closed position and unblocking the first end channel 212a when the first gate assembly 212b is configured to the open position. The valve may be any type of valve configurable to perform the actions described above and in the present disclosure. The valve may include, but is not limited to including, a ball valve, gate valve, etc., so long as the valve is configurable to substantially block/unblock the first end channel 212a and prevent a gas medium from passing through the first end channel 212a.

The port assembly 210 may also include the second end section 214, as illustrated in at least FIGS. 4A and 4B. The second end section 214 may have a second end channel 214a formed through the second end section 214. The second end channel 214a may be substantially or completely aligned with the first end channel 212a. The second end channel 214a, as well as the first end channel 212a, may be considered as a part of the central access channel 210a in example embodiments. The second end section 214 may also include an insufflation port (not shown) for use in providing insufflation to the cavity of the patient.

The second end section 214 may also include a second gate assembly 214, as illustrated in FIGS. 4A, 4C, and 4D. The second gate assembly 214 may be configurable to control access through the second end channel 214a. For example, the second gate assembly 214b may be configurable to be in an open position, as illustrated in FIG. 4C, so as to allow access through the second end channel 214a. The second gate assembly 214b may also be configurable to be in a closed position, as illustrated in FIG. 4D, so as to prevent or restrict access through the second end channel 214a. The second gate assembly 214b may also be configurable to be in a partially closed (or partially opened) position (not shown). The second gate assembly 214b may also be configurable to transition between the closed position and the open position.

In an example embodiment, the second gate assembly 214b may be provided within the second end section 212 in such a way that, when the second gate assembly 214b is configured to be in the open position, as illustrated in FIG. 4C, the second end channel 214a is substantially or completely unobstructed by the second gate assembly 214b. The second gate assembly 214b may be configured to be in the open position when a surgeon desires to insert (or remove) an instrument into (or out of) the cavity of the patient via the second end channel 214a (and the rest of the central access channel 210a).

Similarly, the second gate assembly 214b may be provided within the second end section 214 in such a way that, when the second gate assembly 214b is configured to be in the closed position, as illustrated in FIG. 4D, the second end channel 214a is substantially or completely obstructed by the second gate assembly 214b. The second gate assembly 214b may be configured to be in the closed position when a surgeon desires to maintain an insufflation of the cavity of the patient and/or when the surgeon does not need to insert (or remove) an instrument into (or out of) the cavity of the patient via the second end channel 214a.

The second gate assembly 214b may include a second expandable portion 214b configurable to expand when the second gate assembly 214b is configured to the closed position, as illustrated in FIG. 4D. When the second gate assembly 214b is configured to the closed position, the second expandable portion 214b may be operable to substantially or completely block, among other things, a gas medium (and/or other medium) from passing through the second end channel 214a. For example, if the cavity of the patient is being insufflated using a gas, such as carbon dioxide ($CO_2$), the second gate assembly 214b (i.e., the second expandable portion 214b) may be configurable to substantially prevent the carbon dioxide gas from leaving the cavity of the patient through the second end channel 214a.

The second expandable portion 214b may include one or more second expandable members. For example, the second expandable portion may include six expandable members, as illustrated in FIGS. 4C and 4D. It is to be understood that the second expandable portion 214b may include more or less than six expandable members without departing from the teachings of the present disclosure. Some or all of the second expandable members may be integrated together and/or in communication with one another, such as in a manner where some or all of the second expandable members are operable to receive pressure (i.e., gas medium) from a common or same second source 214b'. For example, when the second gate assembly 214b is configured to the closed position, the second source 214b' may be configurable to provide a positive pressure (i.e., a supply of gas) so as to cause some or all of the second expandable members to expand and block the second end channel 214a (e.g., hermetically block the second end channel 214a). Similarly, when the second gate assembly 214b is configured to the open position, the second source 214b' may be configurable to provide a negative pressure (i.e., remove gas) so as to cause some or all of the second expandable members to not expand (and/or contract) and unblock the second end channel 214a. It is to be understood that more than one second sources 214b' may provide the positive pressure and negative pressure to the one or more expandable members without departing from the teachings of the present disclosure. It is also to be understood in the present disclosure that one or more of the first sources 212b' and one or more of the second sources 214b' may be the same or different sources.

It is recognized in the present disclosure that the second gate assembly 214b may also include a valve (not shown), or the like, in addition to or in replacement of the second expandable portion 214b. The valve may be configurable to perform substantially the same actions of blocking the second end channel 214a when the second gate assembly 214b is configured to the closed position and unblocking the second end channel 214a when the second gate assembly 214b is configured to the open position. The valve may be any type of valve configurable to perform the actions described above and in the present disclosure. The valve may include, but is not limited to including, a ball valve, gate valve, etc., so long as the valve is configurable to substantially block/unblock the second end channel 214a and prevent a gas medium from passing through the second end channel 214a.

The second end section 214 may also include one or more anchor ports 216, as illustrated in FIGS. 4A and 4B. Each of the anchor ports 216 may be operable to enable an instrument arm assembly 230 or 240, image capturing assembly 220, and/or assistant arm assemblies 250 or 260 to be secured to and unsecured from the port assembly 210. Each of the anchor ports 216 may be formed in any one or more of a plurality of shapes, holes, slots, indentations, protrusions, hooks, fasteners, magnets, buckles, or the like, including those described above and in the present disclosure. For example, as illustrated in FIGS. 4A and 4B, one or more of the anchor ports 216 may include one or more slots, or the like, operable to allow a shoulder section 231 of an instrument arm assembly 230 or 240 to be inserted into and attached.

In example embodiments, the port assembly 210 may also include the mid section 213, as illustrated in at least FIGS. 4A and 4B. The mid section 213 may have a mid section channel 213a formed through the mid section 213. The mid section channel 213a may be substantially or completely aligned with the first end channel 212a and/or the second end channel 214a. In this regard, the mid section channel 213a, as well as the first end channel 212a and/or the second end channel 214a, may be considered as a part of the central access channel 210a in example embodiments. The mid section 213 may also include an insufflation port (not shown) in addition to or in replacement of the insufflation port (not shown) of the second end section 214. In some example embodiments, the mid section 213 may also include a mid section gate assembly (not shown) similar to that of the first gate assembly 212 and second gate assembly 214 described above and in the present disclosure.

In example embodiments, the mid section channel 213a may be operable to cooperate with the first gate assembly 212b and the second gate assembly 214b to function as or like an isolation chamber for instruments, such as the instrument arm assembly 230 or 240, image capturing assembly 220, assistant arm assembly 250 or 260, etc. For example, when an instrument, such as the instrument arm assembly 230, needs to be inserted into the cavity of the patient via the port assembly 210 (or central access channel 210a) and an insufflation of the cavity of the patient needs to be maintained, the first gate assembly 212b may be configured to the open position to allow the instrument to be inserted into the mid section channel 213a. After the instrument (or most of it) passes through the first gate assembly 212b, the first gate assembly 212b may be configured to the closed position. The second gate assembly 214b may then be configured to the open position to allow the instrument to be further inserted through the port assembly 210. After the instrument (or most of it) passes through the second gate assembly 214b, the second gate assembly 214b may be configured to the closed position.

In respect to the central access channel 210a, the central access channel 210a may include or be formed by the first end channel 212a, the second end channel 214a, and/or the mid section channel 213a. The central access channel 210a may be operable to provide an access port (i.e. a passageway or channel) to allow an insertion (or removal) of one or more instruments, such as one or more instrument arm assemblies 230 or 240, one or more image capturing assemblies 220, one or more assistant arm assemblies 250 or 260, etc.

In an example embodiment, the first end section 212, the second end 214, and/or the mid section 213 may be substantially cylindrical in shape. The first end section 212, the second end section 214, and/or the mid section 213 may also be formed in any one of a plurality of other shapes, sizes, and/or dimensions without departing from the teachings of the present disclosure.

In example embodiments, an outer diameter of the first end section 212, the second end 214, and/or the mid section 213 may be between about 28 to 35 mm and an inner diameter (unblocked) of the first end section 212, the second end 214, and/or the mid section 213 may be between about 16 to 21 mm. In an example embodiment, the outer diameter of the first end section 212, the second end 214, and/or the mid section 213 may be about 33 mm and the inner diameter (unblocked) of the first end section 212, the second end 214, and/or the mid section 213 may be about 19 mm. The length of the first end section 212 may be between about 80 to 100 mm, the length of the second end section 214 may be between about 80 to 200 mm, and the length of the mid section 213 may be between about 60 to 80 mm. The overall length of the port assembly 210 may be between about 320 to 380 mm. It is to be understood in the present disclosure that the above dimensions are merely an illustration of example embodiments, and as such the dimensions may be smaller or larger than those recited above without departing from the teachings of the present disclosure.

The port assembly 210, including the first end section 212, the second end section 214, the mid section 213, and/or the anchor ports 216, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. The first gate assembly 212b and the second gate assembly 214b may be formed using any one or more of a plurality of materials, such as bio-compatible materials (such as silicone rubber and polyurethane). It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Image Capturing Assembly (e.g., Image Capturing Assembly 220).

In an example embodiment, the surgical device 200 may comprise one or more image capturing assemblies (e.g., image capturing assembly 220) configurable to be inserted into and attach to the port assembly 210. One or more of the image capturing assemblies 220 may comprise at an image capturing body 224, a multi-curvable body 222, and an anchoring portion 220a.

Figure 9A:
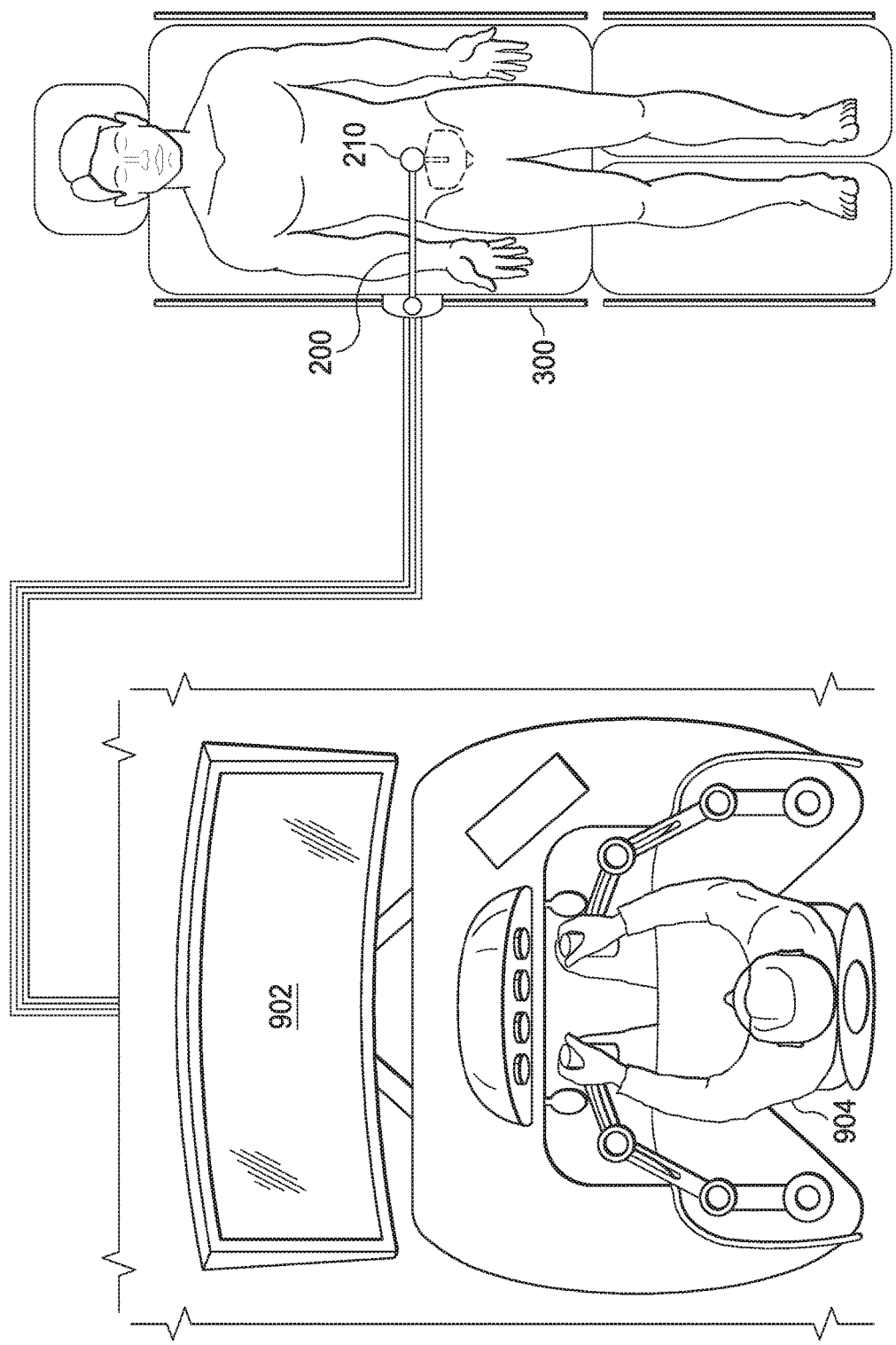
FIG. 9A is an illustration of a perspective view of an example embodiment of a surgical device system.
Figure 9B:
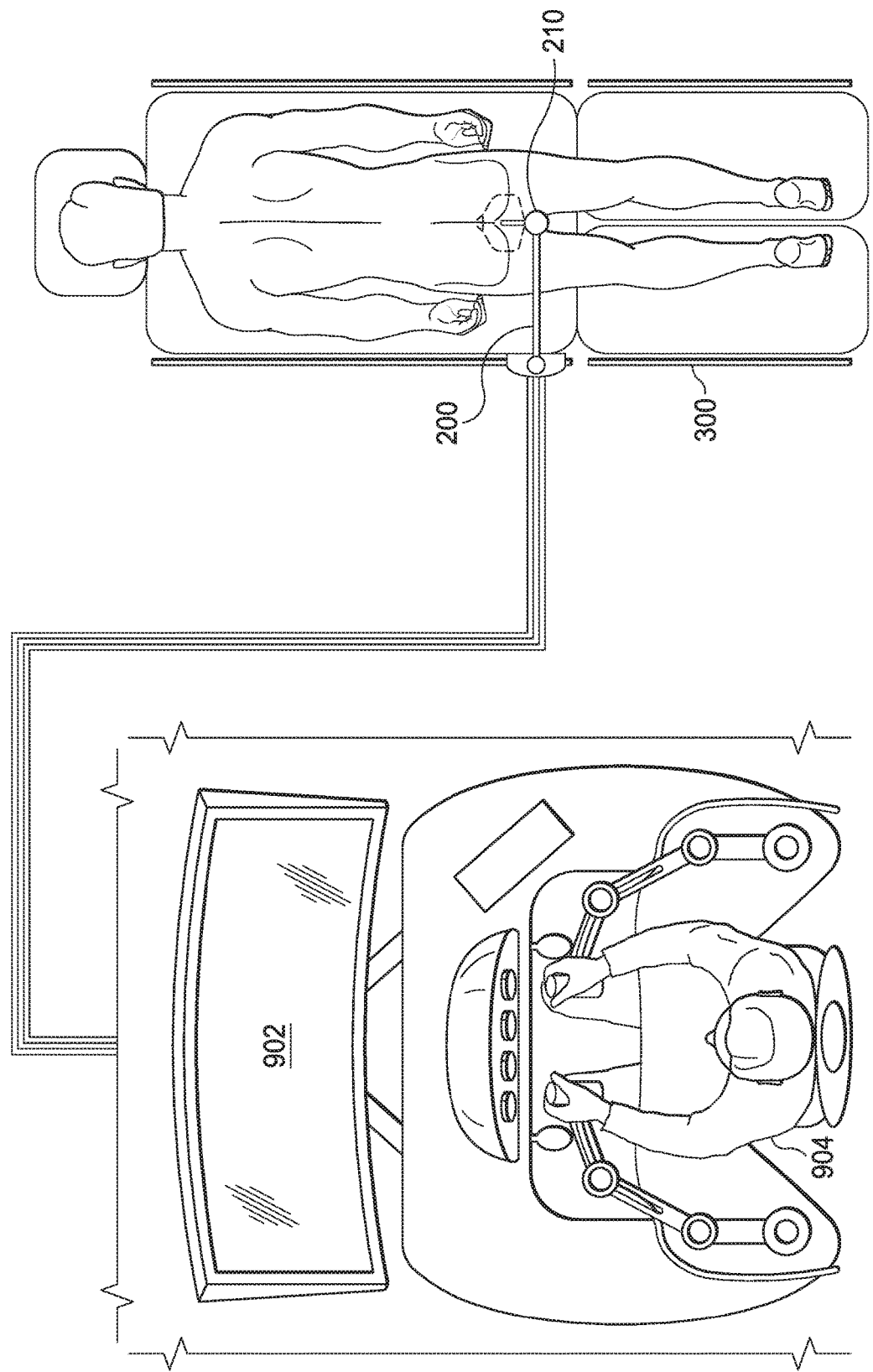
FIG. 9B is an illustration of a perspective view of another example embodiment of a surgical device system.

As illustrated in FIG. 6A, the image capturing body 224 may include one or more cameras 227. Each camera 227 may include a standard and/or high definition 2-dimensional (2D) and/or 3-dimensional (3D) camera operable to capture imaging, such as 2D and/or stereoscopic and/or autostereoscopic 3D imaging, including images, video, and/or audio, and provide in real-time via wired and/or wireless communication the captured imaging, including images, video, and/or audio, to the computing device (or controller or system) of one or more nearby and/or remotely located surgical teams 904, as described above and in the present disclosure. The computing device (or controller or system) may comprise one or more processors, one or more computer-human interfaces, one or more graphical displays (such as computer screens, television screens, portable devices, wearable devices such as glasses, etc.), and/or other devices and/or systems, an example of which is illustrated in FIGS. 9A and 9B. The one or more nearby and/or remotely located surgical teams 904 may be operable to view, hear, sense, analyze, and control (such as pan, zoom, process, adapt, mark, change resolution, etc.) the imaging displayed or represented on one or more standard and/or high definition 2D and/or 3D graphical displays 902, such as shown in the illustration of FIGS. 9A and 9B, and/or portable and/or wearable devices adapted to receive 2D and/or 3D imaging (not shown). The image capturing body 224 may also comprise one or more illumination sources 229, such as an LED, or the like, operable to illuminate or sense at least one or more parts, sections, and/or quadrants of the cavity of the patient, including instruments provided in the cavity of the patient. The image capturing body 224 may further comprise one or more internal temperature control assemblies operable to control (such as reduce) the temperature of one or more components of the image capturing body 224.

As illustrated in the example embodiment of FIG. 6A, one or more of the image capturing assemblies 220 may comprise a multi-curvable body 222 attached to the image capturing body 224. The multi-curvable body 222 may be any elongated multi-curvable, multi-bendable, multi-articulable, and/or snake-like (hereinafter "multi-curvable") body that can be controlled/configured by the surgical team (such as via the computing device/controller) to, among other things, straighten and/or curve (and hold such a straightness and/or curvature) at one or more of a plurality of locations along the multi-curvable body 222, curve (and hold such a curvature) in one or more of a plurality of curvatures, and/or straighten and/or curve (and hold such a straightness and/or curvature) in one or more of a plurality of directions. For example, as illustrated in FIG. 8H, the multi-curvable body 222 may be controllable/configurable by the surgical team (such as via the computing device/controller) to curve at two different locations 222a and 222b along the multi-curvable body 222, and each of the curves may include any curvature and in any direction. It is to be understood that the multi-curvable body 222 may be configurable to curve in more or less than two locations along the multi-curvable body 222 without departing from the teachings of the present disclosure. It is also to be understood that, when the multi-curvable body 222 is configured to curve at any location along the multi-curvable body 222, the curve may be held and/or released (or configured to uncurve, curve less, or straighten) by the surgical team (such as via the computing device/controller).

The multi-curvable body 222 may be formed in any one or more ways known in the art including. For example, the multi-curvable body 222 may include a plurality of segments, each segment linked to an adjacent segment in such a way that the segment may be controlled/configured to be pivotally positioned in a plurality of positions relative to the adjacent segment. As another example, the multi-curvable body 222 may include a plurality of wires, cables, or the like, distributed throughout the multi-curvable body 222 in such a way that a pulling/releasing, shortening/lengthening, tightening/loosening, etc. of one or a combination of cables enables the above-mentioned curving of one or more locations of the multi-curvable body 222 in one or more curvatures and in one or more directions. As another example, the multi-curvable body 222 may include a plurality of springs, gears, motors, etc. for achieving the above-mentioned curving. It is to be understood in the present disclosure that the multi-curvable body 222 may also include a combination of one or more of the above-mentioned approaches.

One or more internal temperature control assemblies (not shown) may be provided for each image capturing assembly 220. Each internal temperature control assembly may be operable to control (such as reduce) the temperature and/or heat emission of the aforementioned camera(s) 227, illumination source(s) 229, and/or multi-curvable body 222. In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well as any solids (if used), may be provided through an interior of the image capturing assembly 220 without increasing dimensions (such as diameter) of the image capturing assembly 220 and/or affecting the controllability/configurability of the multi-curvable body 222.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the cavity of the patient during a surgical procedure. When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the image capturing assembly 220. In example embodiments, the internal temperature control assembly may utilize a combination of gases, liquids, solids, and/or the like without departing from the teachings of the present disclosure.

The image capturing assembly 220 may be secured to the port assembly 210 in one or more of a plurality of ways, including those described above and in the present disclosure for the instrument arm assemblies 230 or 240 and/or the assistant arm assemblies 250 or 260. For example, the image capturing assembly 220 may also comprise an anchoring portion 220a (e.g., similar to the securing portion 231a of the instrument arm assembly 220) operable to attach (or secure) the image capturing assembly 220 to one or more anchor ports 216 of the port assembly 210.

In an example embodiment, the image capturing body 224 and the multi-curvable body 222 may each be substantially cylindrical in shape. The image capturing body 224 and the multi-curvable body 222 may also be formed in any one of a plurality of other shapes, sizes, and/or dimensions without departing from the teachings of the present disclosure.

In an example embodiment, the length of the multi-curvable body 222 may be between about 50 to 150 mm. In example embodiments, a length of multi-curvable body 222 may also be adjustable by the surgical team 904 before, during, and/or after insertion of the camera arm assembly into the cavity of the patient. The outer diameter of the multi-curvable body 222 may be between about 5 to 7 mm. It is to be understood in the present disclosure that the above dimensions are merely an illustration of example embodiments, and as such the dimensions may be smaller or larger than those recited above without departing from the teachings of the present disclosure.

The multi-curvable body 222 may be formed using any one or more of a plurality of materials, such as stainless steel, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

As illustrated in FIG. 6B and FIG. 6C, the image capturing assembly 220 may further comprise a gas shield 228 located nearby one or more lenses of the camera 227. The image capturing assembly 220 may further comprise a gas shield 228 located nearby one or more of the illumination sources 229 and/or any other sensors (such as temperature sensors, pressure sensors, humidity sensors, etc.) provided by the image capturing assembly 220. The gas shield 228 may comprise one or more openings or the like, one or more external gas sources 228, and one or more tubes, channels, or the like, between the one or more external gas sources and the one or more openings of the gas shield 228. In operation, the gas shield 228 may be operable to provide pressurized gases (and/or liquids), such as carbon dioxide, oxygen, other gases or liquids, or combinations thereof, via the one or more openings of the gas shield 228 to an area in front of the camera 227 (as well as in front of the illumination sources 229 and/or other sensors).

Figure 6D:
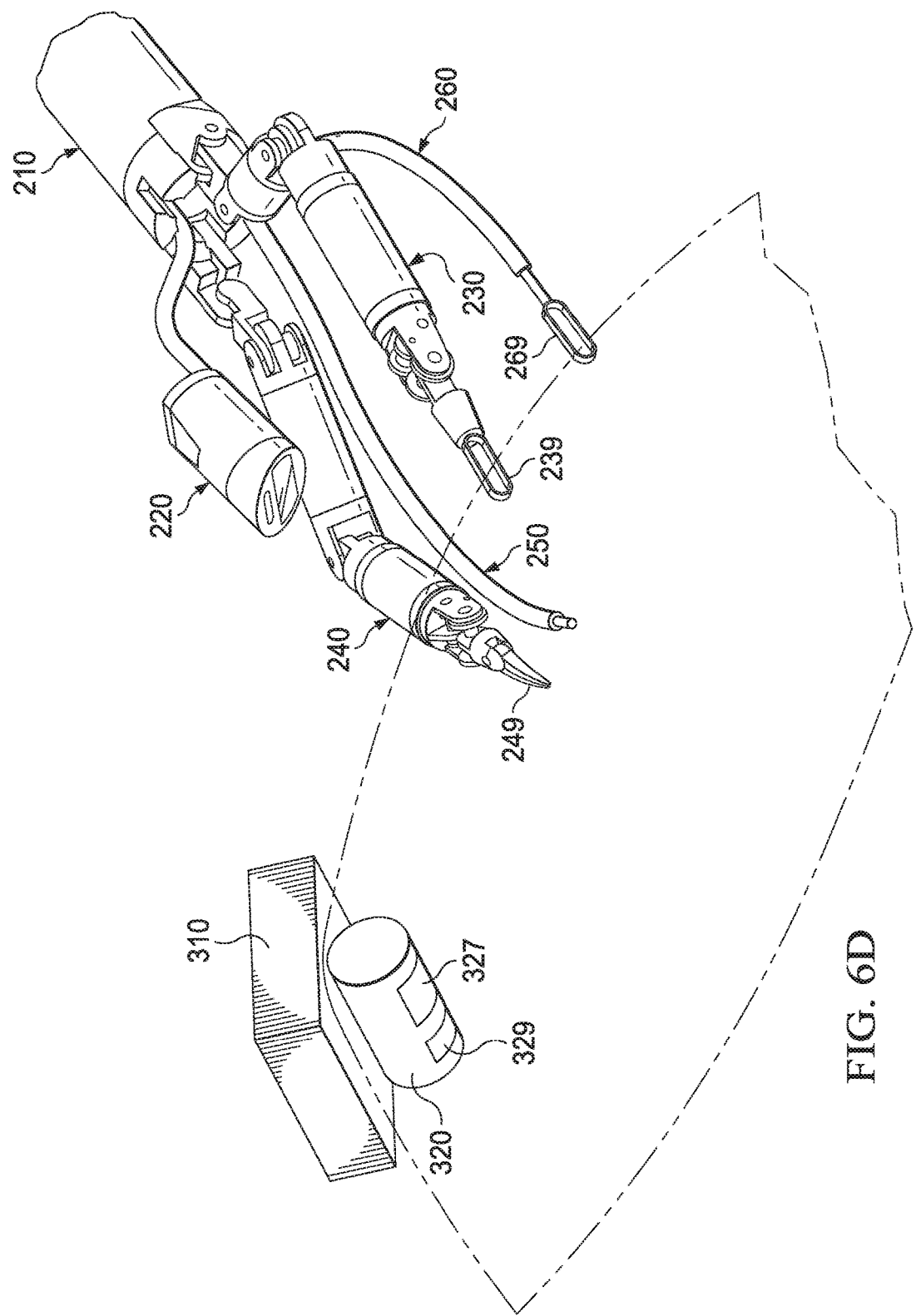
FIG. 6D is an illustration of a perspective view of the system in operation in a cavity of a patient, including a second image capturing assembly.
Figure 7:
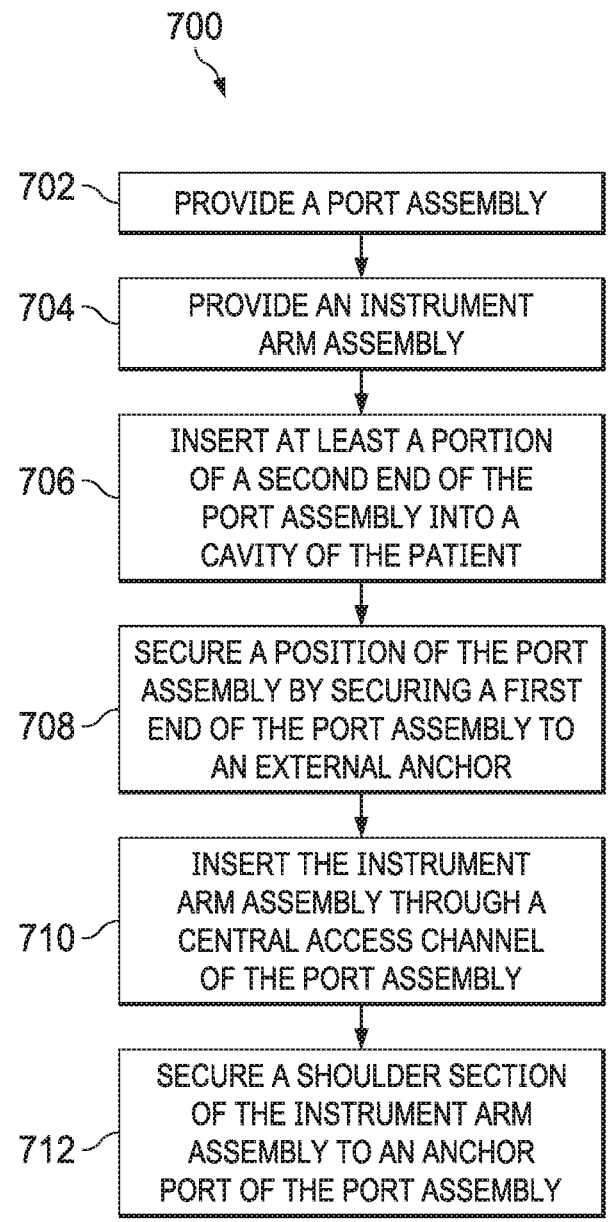
FIG. 7 is a flow diagram of an exemplary method for configuring a surgical device.

The overall system may also include one or more separate image capturing assemblies, such as the separate image capturing assembly 320 illustrated in FIG. 6D. The separate image capturing assembly 320 may be magnetically anchored by a magnetic anchor 310 to an internal wall of the cavity of the patient, such as via a permanent magnet, electromagnet, or the like. In some example embodiments, the magnetic anchor 310 may also be secured/held in position via an external anchor (not shown). The separate image capturing assembly 320 may include one or more cameras 327, and may also include one or more illumination sources 329.

The separate image capturing assembly 320 may be operable to provide one or more of a variety of views, including, but not limited to, a normal view, zoomed view, wide-angled view, and/or panoramic view of the cavity of the patient. The separate image capturing assembly 320 may be positioned in such a way as to provide the surgical team 904 with an unobstructed view of areas of interest within the cavity of the patient. In respect to positioning and securing the separate image capturing assembly 320 in place, as illustrated in FIG. 6D, the separate image capturing assembly 320 may be inserted through the central access channel 210a of the port assembly 210 and to the desired location of the interior wall of the cavity of the patient in one or more of a plurality of ways, including using a surgical tool (not shown), attaching the separate image capturing assembly 320 to a multi-curvable body (not shown) similar to that of the image capturing assembly 220 (as illustrated in FIGS. 2A, 2B, 3A, 3B, and 6D), etc.

The Instrument Arm Assembly (e.g., Instrument Arm Assembly 230, 240).

In an example embodiment, the surgical device 200 may comprise one or more instrument arm assemblies (e.g., first instrument arm assembly 230, second instrument arm assembly 240, third instrument arm assembly (not shown), fourth instrument arm assembly (not shown), etc.), each configurable to attach to the port assembly 210. Although certain figures and/or descriptions provided in the present disclosure may be directed to the first instrument arm assembly 230 and its elements, it is to be understood in the present disclosure that such figures and/or descriptions may also apply to other instrument arm assemblies, including second instrument arm assembly 240, third instrument arm assembly (not shown), fourth instrument arm assembly (not shown), etc.

Figure 5A:
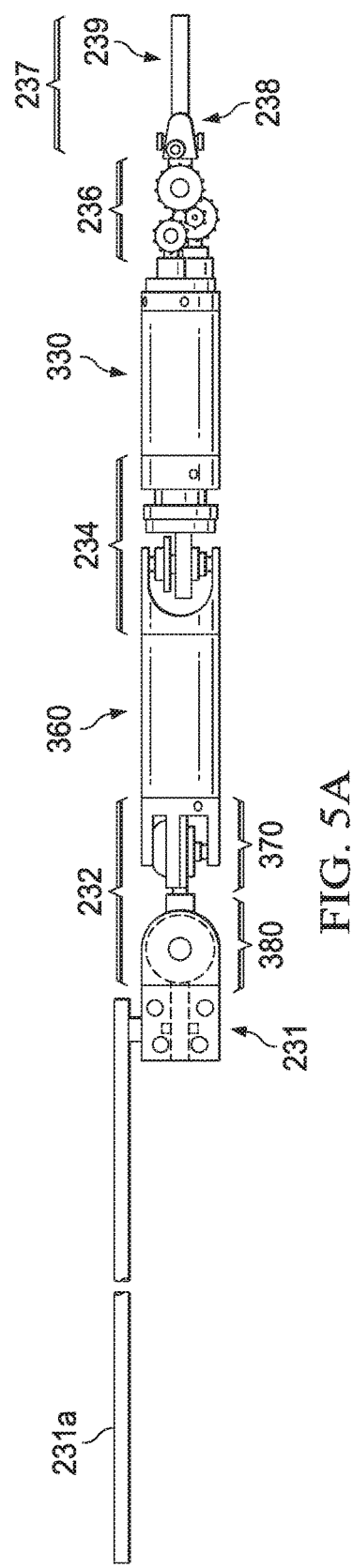
FIG. 5A is an illustration of a side view of an example embodiment of an instrument arm assembly.
Figure 5B:
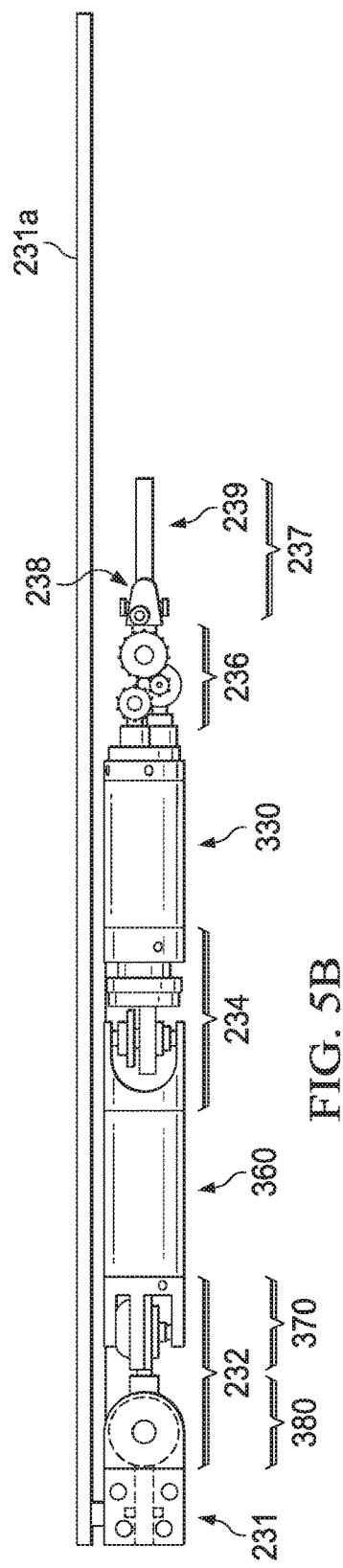
FIG. 5B is another illustration of a side view of an example embodiment of an instrument arm assembly.
Figure 5H:
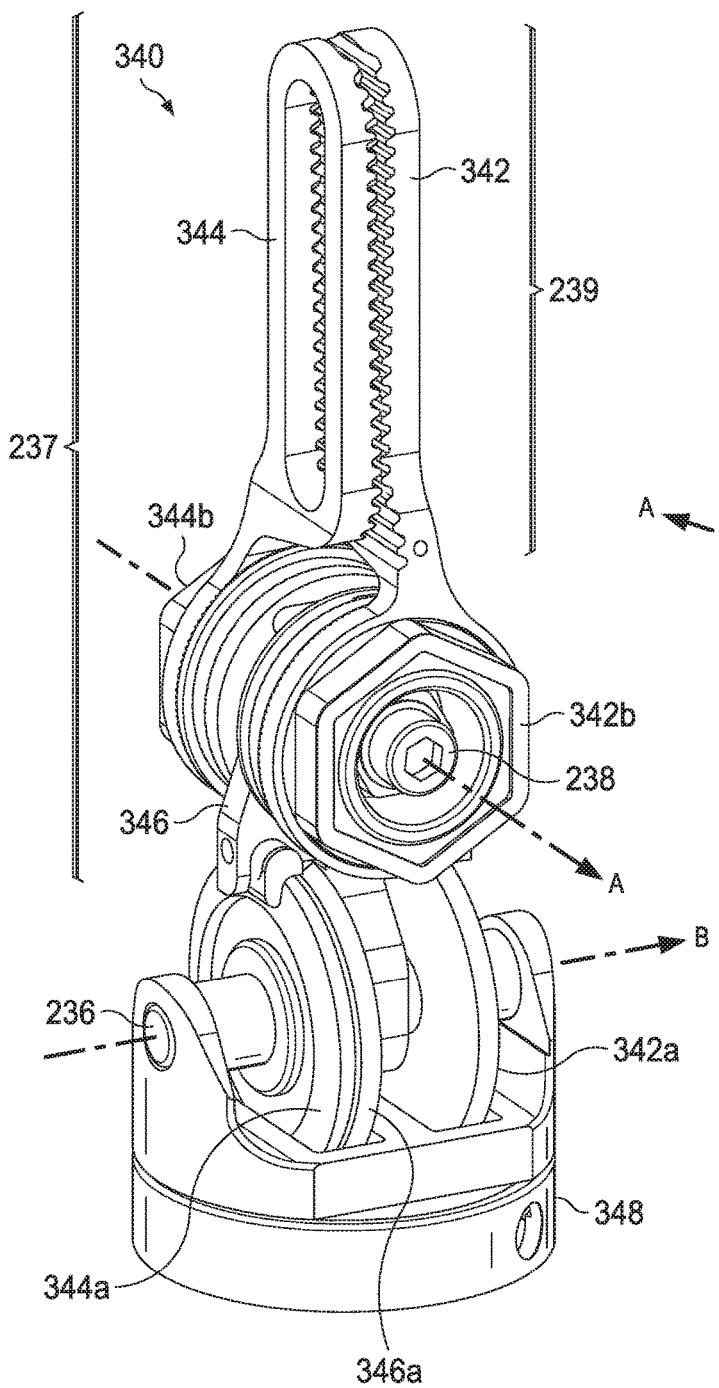
FIG. 5H is an illustration of a perspective view of an example embodiment of an end-effector assembly.
Figure 5I:
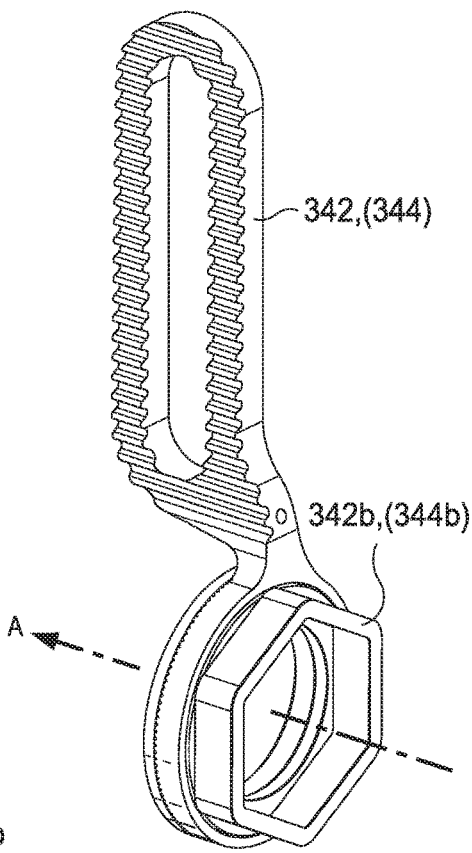
FIG. 5I is an illustration of a perspective view of an example embodiment of an instrument with an insulative portion.
Figures 5J, 5K:
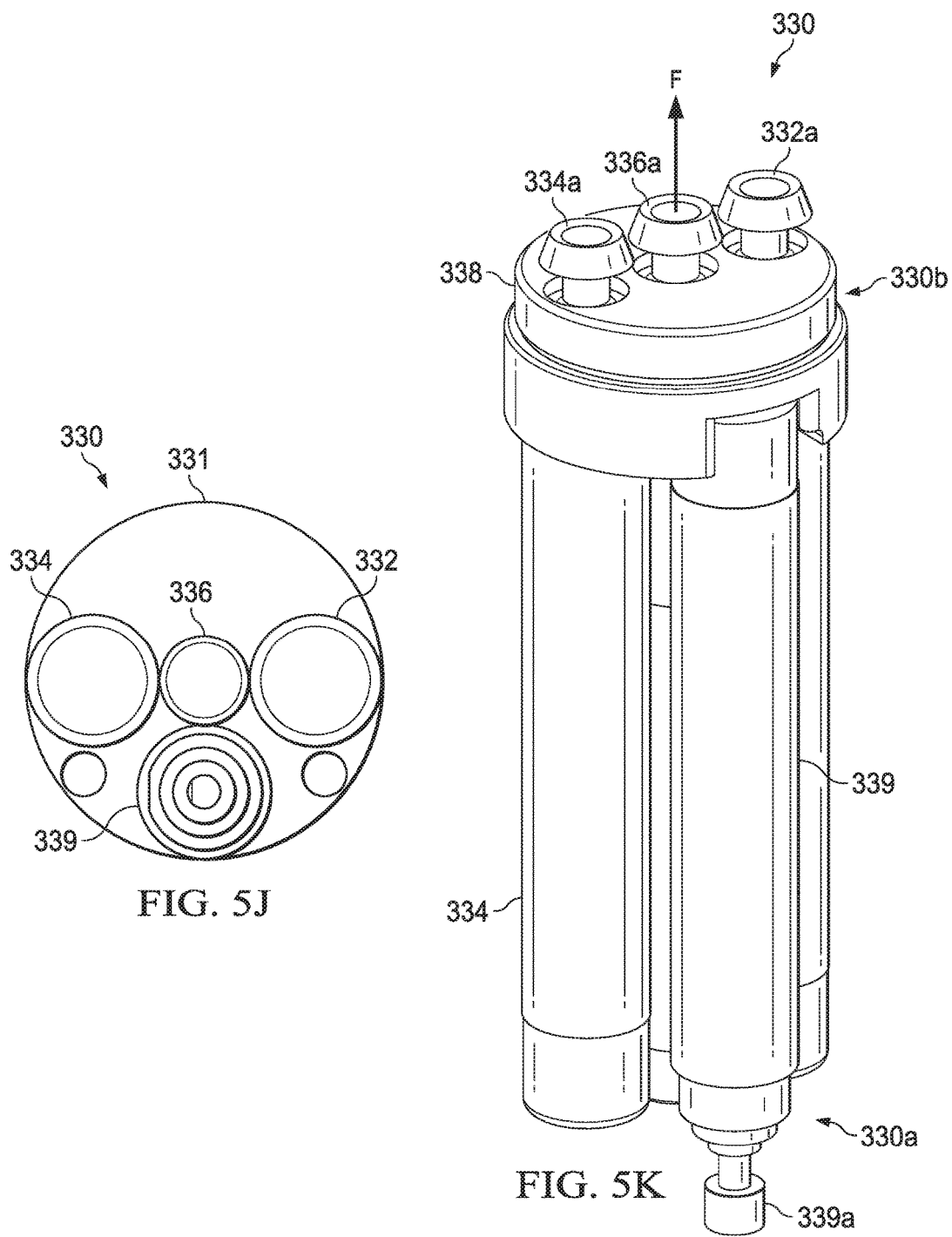
FIG. 5J is an illustration of a top cross-sectional view of an example embodiment of an arm assembly.
FIG. 5K is an illustration of a perspective view of an example embodiment of an arm assembly.
Figure 5R:
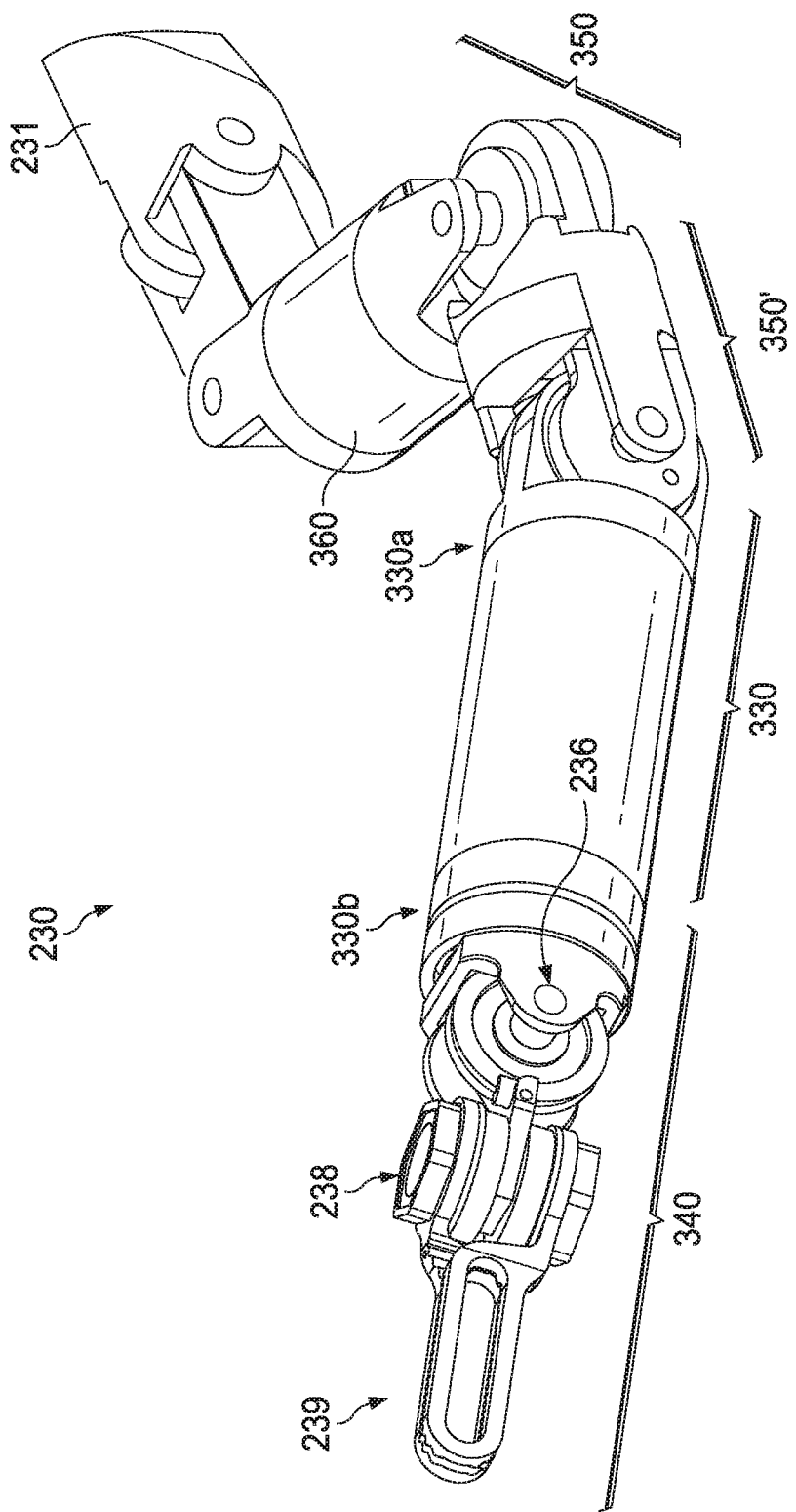
FIG. 5R is another illustration of a perspective view of an example embodiment of an instrument arm assembly.
Figures 5U, 5V:
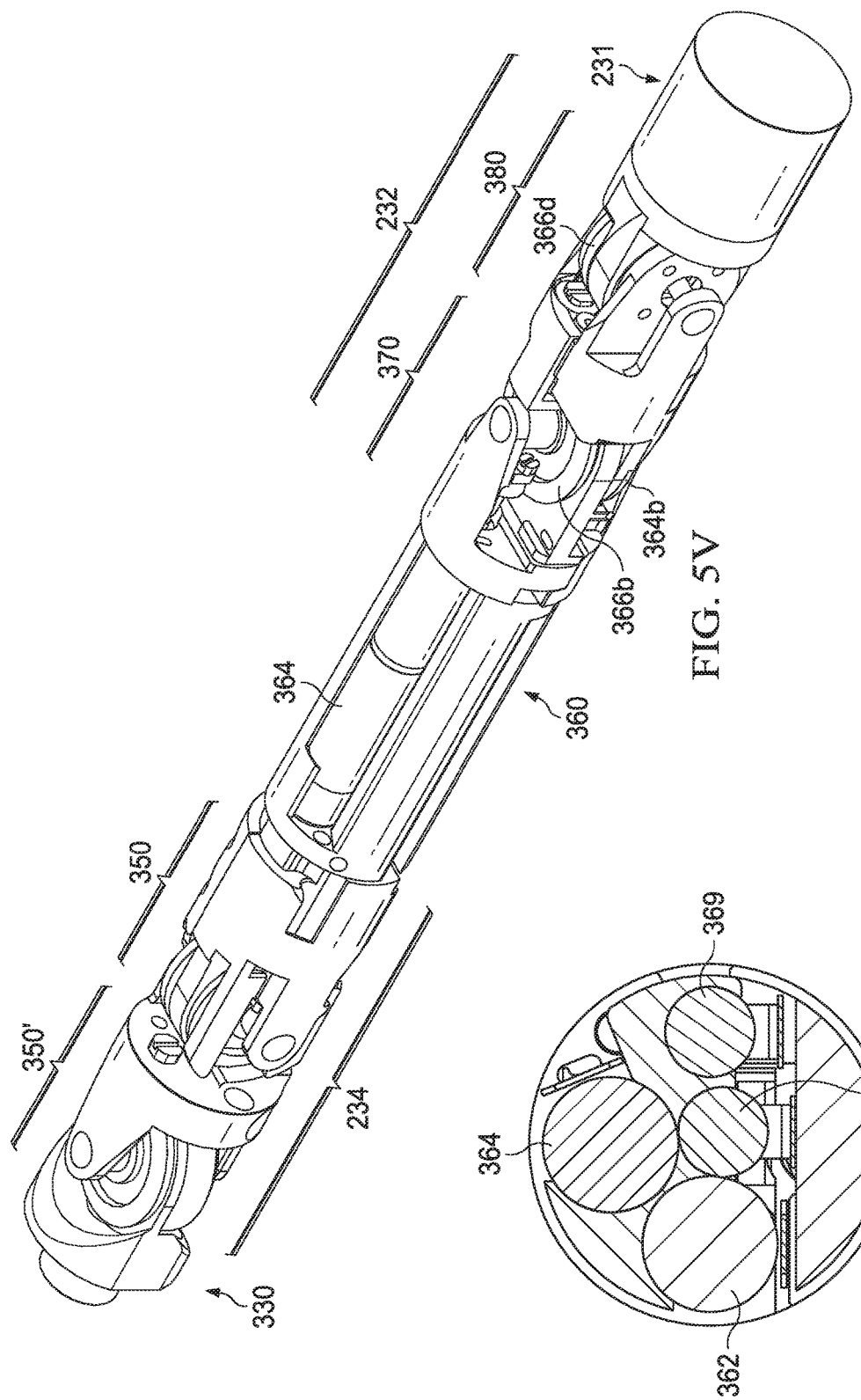
FIG. 5U is another illustration of a top cross-sectional view of an example embodiment of a second arm assembly.
FIG. 5V is another illustration of a transparent perspective partial view of an example embodiment of an instrument arm assembly.

One or more of the instrument arm assemblies (such as 230, 240) may comprise a configurable or configured serially (or linearly) connected arrangement of a plurality of instrument arm segments (or arm assemblies, such as a first arm assembly 330, second arm assembly 360, and shoulder section (e.g., shoulder assembly 231) illustrated in at least FIG. 5C and FIG. 5R) and a plurality of joint portions (such as an elbow joint assembly 234, and shoulder joint assembly 232 illustrated in at least FIG. 5L, FIG. 5M, FIG. 5S, and FIG. 5T), and an end effector assembly 340 (having at least a wrist assembly and an instrument assembly 237, which includes instrument(s) 239 having instrument 342 and/or instrument 344) integrated into and/or connected to one or more of the instrument arm segments and/or joint portions. Although certain figures and description in the present disclosure may be directed to an instrument arm assembly 230, 240 having a serially connected arrangement of an end effector assembly 340 at a distal end, followed by a first arm assembly 330, followed by an elbow joint assembly 234 (having an elbow pitch joint portion 350' followed by an elbow sway joint portion 350), followed by a second arm assembly 360, followed by a shoulder joint assembly 232 (having a shoulder pitch joint portion 370 followed by a shoulder sway joint portion 380), and followed by a shoulder section 231 at a proximal end, it is to be understood in the present disclosure that the serially connected arrangement for the instrument arm assembly 230, 240 may also be in other sequences and include (or not include) other elements. For example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder pitch joint portion 370, followed by a shoulder sway joint portion 380, and followed by a shoulder section 231 at a proximal end. As another example, the serially connected arrangement may include an end-effector assembly 340 at a distal end, followed by a first arm assembly 330, followed by an elbow sway joint portion 350, followed by an elbow pitch joint portion 350', followed by a second arm assembly 360, followed by a shoulder sway joint portion 380, followed by a shoulder pitch joint portion 370, and followed by a shoulder section 231 at a proximal end. In yet another example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder sway joint portion 380, followed by a shoulder pitch joint portion 370, and followed by a shoulder section 231 at a proximal end. As another example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder pitch joint portion 370, and followed by a shoulder section 231 at a proximal end. As another example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder sway joint portion 380, and followed by a shoulder section 231 at a proximal end. As another example, the serially connected arrangement may include an end-effector assembly 340 at a distal end, followed by a first arm assembly 330, followed by an elbow sway joint portion 350, followed by an elbow pitch joint portion 350', followed by a second arm assembly 360, followed by a shoulder pitch joint portion 370, and followed by a shoulder section 231 at a proximal end. As another example, the serially connected arrangement may include an end-effector assembly 340 at a distal end, followed by a first arm assembly 330, followed by an elbow sway joint portion 350, followed by an elbow pitch joint portion 350', followed by a second arm assembly 360, followed by a shoulder sway joint portion 380, and followed by a shoulder section 231 at a proximal end. In yet another example, the serially connected arrangement may include an end-effector assembly 340 at a distal end, followed by a first arm assembly 330, followed by an elbow sway joint portion 350, followed by a second arm assembly 360, followed by a shoulder pitch joint portion 370, followed by a shoulder sway joint portion 380, and followed by a shoulder section 231 at a proximal end. As another example, the serially connected arrangement may include an end-effector assembly 340 at a distal end, followed by a first arm assembly 330, followed by an elbow sway joint portion 350, followed by a second arm assembly 360, followed by a shoulder sway joint portion 380, followed by a shoulder pitch joint portion 370, and followed by a shoulder section 231 at a proximal end. Other serially connected arrangements with more or less elements are also contemplated without departing from the teachings of the present disclosure.

The end effector or instrument 239, 342, 344 may be any instrument suitable for use in surgical procedures, such as a cutting and/or gripping instrument. One or more of the instrument arm assemblies (such as 230, 240) may also comprise one or more illumination sources (not shown), such as an LED, or the like, operable to illuminate one or more parts of the end effector or instrument 239, 342, 344, instrument arm assemblies, and/or parts, sections, and/or quadrants of the abdominal cavity of the patient.

One or more of the instrument arm assemblies (such as 230, 240) may also comprise one or more integrated motors (e.g., integrated motors 332, 334, 336, and/or 339 illustrated in at least FIG. 5E, FIG. 5G, FIG. 5J, and FIG. 5K and integrated motors 362, 364, 366, and/or 369 illustrated in at least Figure M, FIG. 5N, FIG. 5O, FIG. 5T, FIG. 5U, and FIG. 5V), each integrated motor operable to provide at least one degree of freedom for the instrument arm assembly. Each integrated motor (e.g., integrated motors 332, 334, 336, 339, 362, 364, 366, and/or 369) may be fully and independently functioning motors that are housed entirely (with the exception of, for example, power and/or control cables, which may be fed via the port assembly) in an instrument arm segment (or arm assembly, such as the first arm assembly 330, second arm assembly 360, and/or shoulder assembly 231), such as in housing 331 and/or 360'. One or more of the instrument arm assemblies may also include an integrated haptic and/or force feedback subsystem (not shown) in communication with one or more of the integrated motors and/or other sensors and/or instruments operable to provide to the surgical team (such as via computing device/controller) with one or more of a plurality of feedback responses and/or measurements, including those pertaining to position (including orientation), applied force, proximity, temperature, pressure, humidity, etc., of, by, and/or nearby to the instrument arm assembly. For example, the surgical team 904 may be provided with a master input device having manipulators, or the like, having haptic and/or force feedback and designed to map and sense the surgical team's 904 delicate finger-twisting, wrist-bending, and/or other arm/shoulder movements into movements of the instrument arm (such as 230, 240) with high precision, high dexterity, and minimum burden, while also providing feedback of contact resistance (such as tissue resistance).

When an instrument arm assembly (such as 230, 240) comprises one or more illumination sources, cameras, haptic and/or force feedback instruments, and/or other sensors and/or instruments, as described above and in the present disclosure, the instrument arm assembly may also comprise a gas shield, such as the gas shield described above for the image capturing assembly 220. One or more of the instrument arm assemblies (such as 230, 240) may further comprise one or more internal temperature control assemblies operable to control (such as reduce or increase) the temperature of one or more components of the instrument arm assembly.

As illustrated in the example embodiment of FIGS. 2A-D, 3A-D, FIG. 5A, FIG. 5B, FIG. 5P, and FIG. 5Q, each of the instrument arm assemblies, including the first instrument arm assembly 230, may comprise shoulder section 231, second arm assembly 360, 360, first arm assembly 330, and end-effector assembly 340. The instrument arm assembly 230 may also comprise a shoulder joint assembly 232 having a shoulder sway joint section 380 and/or shoulder pitch joint section 370; an elbow joint assembly 234 having an elbow sway joint section 350 and/or elbow pitch joint section 350'; a third joint portion (or wrist section) 236 pivotally moveable relative to an axis B (as illustrated in at least FIGS. 5D-H); and an end effector joint portion 238 pivotally moveable relative to an axis A (as illustrated in at least FIGS. 5D-H). Each of the aforementioned joint portions may be configurable, either manually and/or via the computing device (or system), to provide an attached instrument arm segment (and the end effector 239, 342, 344) with one or more in vivo degrees of freedom when the instrument arm assembly is provided in the abdominal cavity of the patient. For example, the shoulder joint assembly 232 may be operable to provide the second arm assembly 360 with one or more degrees of freedom (e.g., resembling the one or more degrees of freedom of the human shoulder). Specifically, the shoulder joint assembly 232 may include a shoulder sway joint section 380 operable to provide the second arm assembly 360 with a movement (e.g., rotation or pivotal movement) relative to an axis E (as illustrated in at least FIGS. 5L, 5M, 5S, and 5T). The shoulder joint assembly 232 may include a shoulder pitch joint section 370 operable to provide the second arm assembly 360 with a movement (e.g., rotation or pivotal movement) relative to an axis D (as illustrated in at least FIGS. 5L, 5M, 5S, and 5T). Axis E may be different from axis D (e.g., axis E may be substantially orthogonal to axis D). As another example, the elbow joint assembly 234 may be operable to provide the first arm assembly 330 with one or more degrees of freedom. Specifically, the elbow joint assembly 234 may include an elbow sway joint assembly 350 operable to provide the first arm assembly 330 with a movement (e.g., rotation or pivotal movement) relative to an axis C (as illustrated in at least FIGS. 5L, 5M, 5S, and 5T). The elbow joint assembly 234 may include an elbow pitch joint section 350' operable to provide the first arm assembly 330 with a movement (e.g., rotation or pivotal movement) relative to an axis C' (as illustrated in at least FIGS. 5S and 5T). Axis C may be different from axis C' (e.g., axis C may be substantially orthogonal to axis C'). As another example, the third joint portion (or wrist section) 236 may be operable to provide the instrument assembly 237 with one or more degrees of freedom resembling the one or more degrees of freedom of the human wrist. Specifically, the third joint portion (or wrist section) 236 may be operable to provide the instrument assembly 237 with a movement (e.g., rotation or pivotal movement) relative to an axis B (as illustrated in at least FIGS. 5L, 5M, 5S, and 5T). As another example, the end effector joint portion 238 (as illustrated in at least FIGS. 5A-B, 5P-Q, 5H) may be operable to provide the end effector or instrument 239, 342, 344 with one or more degrees of freedom. Specifically, the end effector joint portion 238 may be operable to provide the end effector or instrument 239, 342, 344 with a movement (e.g., rotation or pivotal movement) relative to an axis A (as illustrated in at least FIGS. 5D-I, 5L-M, 5S-T). Axis B may be different form axis A (e.g., axis B may be substantially orthogonal to axis A). Accordingly, one or more of the instrument arm assemblies may be configurable, either manually and/or via the computing device/controller, to provide seven or more in vivo degrees of freedom and, together with the at least one to three or more in vitro degree of freedom provided by the port assembly 210 and the controllable swivel assembly 1000 (see FIGS. 10A and 10B), the one or more of the instrument arm assemblies may be configurable, either manually and/or via the computing device/controller, to provide a total of eight to ten or more degrees of freedom. It is recognized herein that the aforementioned at least seven in vivo degrees of freedom for the instrument arm assembly enables at least the full range of natural movements by a surgeon's arm (via a controller/computer-human interface/manipulator/master input device, such as the example illustrated in FIGS. 9A and 9B) to be substantially directly mapped and/or translated to the instrument arm assembly.

Each joint portion, including joint portions 232, 370, 380, 234, 350, 350', 236, and/or 238 may comprise any one or more configurations of gears and/or gear assemblies, including straight gear configurations, planetary gear configurations, beveled gear configurations, spiral beveled gear configurations, hypoid gear configurations, helical gear configurations, worm gear configurations, and/or any other gear configuration without departing from the teachings of the present disclosure. In example embodiments, each instrument arm assembly may also comprise one or more internal integrated motors 332, 334, 336, 339, 362, 364, 366, 369, or the like, operable to actuate (e.g., via first instrument drive portion 332a, second instrument drive portion 334a, wrist drive portion 336a, first arm assembly drive assembly 339a (which is configurable to drive the first arm assembly 330 relative to an axis F, as illustrated in at least FIG. 5K), elbow sway drive portion 362a, elbow pitch drive portion 362a', shoulder pitch drive portion 364a, shoulder sway drive portion 366a) the gears of each joint portion (e.g., first instrument driven portion 342a, second instrument driven portion 344a, wrist driven portion 346a, first arm assembly driven assembly 347 (which is configurable to be driven by the first arm assembly drive assembly 339a to drive the first arm assembly 330 relative to an axis F, as illustrated in at least FIG. 5K), elbow sway driven portion 352, elbow pitch driven portion 352', shoulder pitch driven portion 364b, shoulder sway driven portion 366b, 366c (if needed), 366d (if needed)) and joint portions 232, 370, 380, 234, 350, 350', 236, and 238 and/or the segments 231, 360, 330, and 340. In this regard, each of the integrated motors, joint portions, and/or segments described above and in the present disclosure may be operable to communicate, such as receive control commands and/or transmit information, from and/or to the computing device/controller of one or more nearby and/or remotely located surgical teams 904 via wired and/or wireless communication in example embodiments. Furthermore, each of the integrated motors, joint portions, and/or instrument arm segments described above and in the present disclosure may be operable to receive power and/or control signals from an external power source and/or the computing device/controller via wired and/or wireless transmissions in example embodiments.

End-Effector Assembly (e.g., End-Effector Assembly 340).

An example embodiment of the end-effector assembly (e.g., end-effector assembly 340) may comprise an instrument assembly 237. The end-effector assembly 340 may also include a wrist assembly. The instrument assembly 237 may include a first instrument assembly and a second instrument assembly. Although the figures illustrate an end-effector assembly having a first instrument and a second instrument, it is to be understood in the present disclosure that the end-effector assembly may have more other instruments or may only have a first instrument or a second instrument without departing from the teachings of the present disclosure. The wrist assembly may include wrist joint portion 236, and may also include wrist connector 348.

(i) First Instrument Assembly.

An example embodiment of the first instrument assembly may comprise a first instrument (e.g., first instrument 342) for use in performing a surgical action. The first instrument 342 may be any surgical instrument without departing from the teachings of the present disclosure.

In an example embodiment, the first instrument 342 may be configurable to receive an electric current (e.g., first electric current) applied from a first energy source (not shown) so as to perform actions of an electrosurgical instrument. Although the first instrument may be described above and in the present disclosure to receive an electric current, it is to be understood that the first instrument may also be configurable to receive a voltage potential, thermal energy, heat, cold temperature application, radiation, etc. to perform the said surgical action without departing from the teachings of the present disclosure.

The first instrument assembly may also comprise a first instrument driven portion (e.g., first instrument driven portion 342a). The first instrument driven portion 342a may be configurable to be driven by the first instrument drive portion 332a of the integrated motor 332. The first instrument driven portion 342a may be driven by the first instrument drive portion 332a in such a way as to move the first instrument 342. For example, the first instrument driven portion 342a may be driven to move the first instrument 342 relative to a first axis (e.g., axis A). In this regard, such movement of the first instrument 342 may be a rotation of a distal end of the first instrument 342 relative to a proximal end of the first instrument 342, and such proximal end may serve as a pivot for such movement.

The first instrument driven portion 342a may be any mechanism, device, or the like, configurable to be driven by the first instrument drive portion 332a. For example, the first instrument driven portion 342a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one first instrument driven portion, it is to be understood in the present disclosure that the end-effector assembly may have more than one first instrument driven portions without departing from the teachings of the present disclosure.

In example embodiments wherein the end-effector assembly 340 is detachable (i.e., unsecurable) from the arm assembly 330, it is to be understood that the first instrument drive portion 332a of the integrated motor 332 may be operable to drive the first instrument driven portion 342a when the end-effector assembly 340 is secured (i.e., attached) to the arm assembly 330. Specifically, the first instrument drive portion 332a of the integrated motor 332 may be operable to drive the first instrument driven portion 342a when the wrist connector portion 338 is secured (i.e., attached) to the wrist assembly (as further described below and in the present disclosure) of the end-effector assembly (and more specifically, the connector 348 of the end-effector assembly 340).

In example embodiments wherein the end-effector assembly 340 is detachable (i.e., unsecurable) from the arm assembly 330, it is to be understood that one or more connectable and unconnectable electric wires, cables, or the like, may be provided to enable the first instrument 342 to receive the electric current from the energy source to perform the actions of an electrosurgical instrument.

The first instrument assembly may also comprise a first instrument insulative portion (e.g., first instrument insulative portion 342b). The first instrument insulative portion 342b may be providable between the first instrument 342 and one or more portions of the end-effector assembly 340 so as to electrically isolate (or electrically insulate, thermally isolate, thermally insulate, and the like) the first instrument 342 from the one or more portions of the end-effector assembly 340. In an example embodiment, the first instrument insulative portion 342b may be providable between the first instrument 342 and the first instrument driven portion 342a so as to electrically isolate (or electrically insulate, thermally isolate, thermally insulate, and the like) the first instrument 342 from the first instrument driven portion 342a. Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the second instrument 344 via the first instrument driven portion 342a and/or other component/portion of the surgical arm assembly.

The first instrument insulative portion 342b may be formed using any one or more of a plurality of materials, such as electrically insulative materials, thermally insulative materials, plastics, elastomers, ceramics, glasses, and minerals. It is to be understood in the present disclosure that other materials may also be used without departing from the teachings of the present disclosure.

The first instrument 342 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the first instrument 342 may include an opening, or the like, for use in receiving and housing at least a portion of the first instrument insulative portion 342b. The first axis (e.g., axis A) may be formed through a center of the opening of the first instrument 342 in example embodiments. Although the opening may be depicted in the figures to be circular in shape and the corresponding exterior portion of the first instrument insulative portion 342b being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(ii) Second Instrument Assembly.

An example embodiment of the second instrument assembly may comprise a second instrument (e.g., second instrument 344) for use in performing a surgical action. The second instrument 344 may be any surgical instrument without departing from the teachings of the present disclosure.

In an example embodiment, the second instrument 344 may be configurable to receive an electric current (e.g., second electric current) applied from a second energy source (not shown) so as to perform actions of an electrosurgical instrument. Although the second instrument may be described above and in the present disclosure to receive an electric current, it is to be understood that the second instrument may also be configurable to receive a voltage potential, thermal energy, heat, cold temperature application, radiation, etc. to perform the said surgical action without departing from the teachings of the present disclosure.

The second instrument assembly may also comprise a second instrument driven portion (e.g., second instrument driven portion 344a). The second instrument driven portion 344a may be configurable to be driven by the second instrument drive portion 334a of the integrated motor 334. The second instrument driven portion 344a may be driven by the second instrument drive portion 334a in such a way as to move the second instrument 344. For example, the second instrument driven portion 344a may be driven to move the second instrument 344 relative to the first axis (e.g., axis A). In this regard, such movement of the second instrument 344 may be a rotation of a distal end of the second instrument 344 relative to a proximal end of the second instrument 344, and such proximal end may serve as a pivot for such movement.

The second instrument driven portion 344a may be any mechanism, device, or the like, configurable to be driven by the second instrument drive portion 334a. For example, the second instrument driven portion 344a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one second instrument driven portion, it is to be understood in the present disclosure that the end-effector assembly may have more than one second instrument driven portions without departing from the teachings of the present disclosure.

In example embodiments wherein the end-effector assembly 340 is detachable (i.e., unsecurable) from the arm assembly 330, it is to be understood that the second instrument drive portion 334a of the integrated motor 334 may be operable to drive the second instrument driven portion 344a when the end-effector assembly 340 is secured (i.e., attached) to the arm assembly 330. Specifically, the second instrument drive portion 334a of the integrated motor 334 may be operable to drive the second instrument driven portion 344a when the wrist connector portion 338 is secured (i.e., attached) to the wrist assembly (as further described below and in the present disclosure) of the end-effector assembly (and more specifically, the connector 348 of the end-effector assembly 340).

In example embodiments wherein the end-effector assembly 340 is detachable (i.e., unsecurable) from the arm assembly 330, it is to be understood that one or more connectable and unconnectable electric wires, cables, or the like, may be provided to enable the second instrument 344 to receive the electric current from the energy source to perform the actions of an electrosurgical instrument.

The second instrument assembly may also comprise a second instrument insulative portion (e.g., second instrument insulative portion 344b). The second instrument insulative portion 344b may be providable between the second instrument 344 and one or more portions of the end-effector assembly 340 so as to electrically isolate (or electrically insulate, thermally isolate, thermally insulate, and the like) the second instrument 344 from the one or more portions of the end-effector assembly 340. In an example embodiment, the second instrument insulative portion 344b may be providable between the second instrument 344 and the second instrument driven portion 344a so as to electrically isolate (or electrically insulate, thermally isolate, thermally insulate, and the like) the second instrument 344 from the second instrument driven portion 344a. Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the first instrument 342 via the second instrument driven portion 344a and/or other component/portion of the surgical arm assembly.

The second instrument insulative portion 344b may be formed using any one or more of a plurality of materials, such as electrically insulative materials, thermally insulative materials, plastics, elastomers, ceramics, glasses, and minerals. It is to be understood in the present disclosure that other materials may also be used without departing from the teachings of the present disclosure.

The second instrument 344 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the second instrument 344 may include an opening, or the like, for use in receiving and housing at least a portion of the second instrument insulative portion 344b. The first axis (e.g., axis A) may be formed through a center of the opening of the second instrument 344 in example embodiments. Although the opening may be depicted in the figures to be circular in shape and the corresponding exterior portion of the second instrument insulative portion 344b being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(iii) Cooperation of the First Instrument Assembly and Second Instrument Assembly.

In example embodiments, the first instrument (e.g., first instrument 342) and second instrument (e.g., second instrument 344) may be selectively moveable/drivable independently from one another. In example embodiments, the first instrument 342 and the second instrument 344 may be selectively moveable/drivable in a similar or same manner, such as being moveable/driveable at the same time, for the same duration, and/or with the same output energy. Although the figures illustrate end-effector assembly having a first instrument and a second instrument, it is to be understood in the present disclosure that the end-effector assembly may have more other instruments or may only have a first instrument or a second instrument without departing from the teachings of the present disclosure. For example, the first instrument 342 and the second instrument 344 may cooperate to form a grasper. As another example, the first instrument 342 and the second instrument 344 may cooperate to form scissors. As another example, the first instrument 342 and the second instrument 344 may cooperate to form a Maryland grasper. Other forms and types of first instruments and/or second instruments are contemplated in the present disclosure in addition to or in replacement of the first instrument and/or second instrument described above and herein without departing from the teachings of the present disclosure.

For example, as described above, the first instrument 342 may be configurable to receive an electric current (e.g., first electric current) applied from a first energy source (not shown) so as to perform actions of an electrosurgical instrument. In addition to or in replacement, the second instrument 344 may be configurable to receive an electric current (e.g., second electric current) applied from a second energy source (not shown). The first current may be the same in magnitude as but opposite in direction to the second current in example embodiments, and the first energy source may be the same as or different from the second energy source in example embodiments. In such embodiments where the first instrument and second instrument collectively cooperate to form a monopolar electrosurgical instrument, or the like, when a mass (e.g., a tissue mass) is provided between the first instrument 342 and second instrument 344 and an electric current is applied to the first instrument 342 or the second instrument 344, the mass will serve to enable the applied electric current to pass through and aid in cutting, coagulating, desiccating, and/or fulgurating the mass. Similarly, in embodiments where the first instrument and second instrument collectively cooperate to form a bipolar electrosurgical instrument, or the like, when a mass (e.g., a tissue mass) is provided between the first instrument 342 and second instrument 344 and an electric current is applied to the first instrument 342 and the second instrument 344, the mass will serve to enable the applied electric current to pass through and aid in performing a surgical action, including cutting, coagulating, desiccating, cauterizing, and/or fulgurating the mass. Although the first instrument and/or second instrument may be described above and in the present disclosure to receive an electric current, it is to be understood that the first instrument and/or second instrument may also be configurable to receive a voltage potential, thermal energy, heat, cold temperature application, radiation, etc. to perform the said surgical action without departing from the teachings of the present disclosure.

(iv) Wrist Assembly.

The wrist assembly may be securable or secured to the instrument assembly 237 in example embodiments. The wrist assembly may comprise a wrist driven portion (e.g., wrist driven portion 346a). The wrist assembly may further comprise a connector (e.g., connector 348).

The wrist driven portion 346a may be configurable to be driven by the wrist drive portion 336a via the integrated motor 336. The wrist driven portion 346a may be driven by the wrist drive portion 336a in such a way as to move the instrument assembly 237, including the first instrument 342 and/or second instrument 344. For example, the wrist driven portion 346a may be driven to pivotally move the first instrument 342 relative to a second axis (e.g., axis B). In this regard, such movement of the first instrument 342 may be a rotation (or pivotal movement) of a distal end of the first instrument 342 relative to a point on the second axis (e.g., axis B), and such point may serve as a pivot for such movement. In addition to or in replacement, the wrist driven portion 346a may be driven by the wrist drive portion 336a in such a way as to move the second instrument 344. For example, the wrist driven portion 346a may be driven to pivotally move the second instrument 344 relative to the second axis (e.g., axis B). In this regard, such movement of the second instrument 344 may be a rotation (or pivotal movement) of a distal end of the second instrument 344 relative to a point on the second axis (e.g., axis B), and such point may serve as a pivot for such movement. In example embodiments, the wrist driven portion 346a may be driven by the wrist drive portion 336a in such a way as to collectively move the first instrument 342 and the second instrument 344. For example, the wrist driven portion 346a may be driven to collectively move the first instrument 342 and the second instrument 344 relative to the second axis (e.g., axis B). In this regard, such movement of the first instrument 342 and the second instrument 344 may be a collective rotation (or pivotal movement) of a distal end of the first instrument 342 and distal end of the second instrument 344 relative to a point on the second axis (e.g., axis B), and such point may serve as a pivot for such movement. Axis B may be different from axis A (e.g., axis B may be substantially orthogonal to axis A).

The wrist driven portion 346a may be any mechanism, device, or the like, configurable to be driven by the wrist drive portion 336a. For example, the wrist driven portion 346a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one wrist driven portion, it is to be understood in the present disclosure that the end-effector assembly may have more than one wrist driven portions without departing from the teachings of the present disclosure.

Arm Assemblies (e.g., First Arm Assembly 330, Second Arm Assembly 360).

(i) First Arm Assembly (e.g., First Arm Assembly 330).

An example embodiment of the first arm assembly 330 is illustrated in at least FIGS. 5A-C, 5L-M, and 5S-T. The arm assembly 330 may be securable to the end-effector assembly 340. In an example embodiment, the arm assembly 330 may be securable to and unsecurable from (e.g., detached) the end-effector assembly 340. As illustrated in FIGS. 5C and 5J, the arm assembly 330 may include an arm assembly body (e.g., arm assembly body 331), a first end 330a (or proximal end), and a second end 330b (or distal end) opposite to the first end 330a. The elbow pitch joint portion 350' may be secured to the first end 330a and the end-effector assembly 340 may be secured to the second end 330b. The wrist connector portion 338 may be provided at the second end 330*b*. The arm assembly body 331 may securely house one or more of a plurality of drive assemblies.

In an example embodiment, the arm assembly body 331 may securely house a first instrument drive assembly. The first instrument drive assembly may include a first integrated motor (e.g., first integrated motor 332), and may also include a first instrument drive portion (e.g., first instrument drive portion 332*a*). The first instrument drive portion 332*a* may be provided at the second end 330*b* of the arm assembly body 331. The first instrument drive portion 332*a* may be controllable by the first integrated motor 332 to drive the first instrument driven portion 342*a* when the wrist connector portion 338 is secured to the wrist assembly. The first instrument drive portion 332*a* may be any mechanism, device, or the like, configurable to drive the first instrument driven portion 342*a*. For example, the first instrument drive portion 332*a* may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first instrument drive portion 332*a*, it is to be understood in the present disclosure that the arm assembly may have more than one first instrument drive portions 332*a* without departing from the teachings of the present disclosure.

The arm assembly body 331 may also securely house a second instrument drive assembly in example embodiments. The second instrument drive assembly may include a second integrated motor (e.g., second integrated motor 334), and may also include a second instrument drive portion (e.g., second instrument drive portion 334*a*). The second instrument drive portion 334*a* may be provided at the second end 330*b* of the arm assembly body 331. The second instrument drive portion 334*a* may be controllable by the second integrated motor 334 to drive the second instrument driven portion 344*a* when the wrist connector portion 338 is secured to the wrist assembly. The second instrument drive portion 334*a* may be any mechanism, device, or the like, configurable to drive the second instrument driven portion 344*a*. For example, the second instrument drive portion 334*a* may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one second instrument drive portion 334*a*, it is to be understood in the present disclosure that the arm assembly may have more than one second instrument drive portions 334*a* without departing from the teachings of the present disclosure.

The arm assembly body 331 may also securely house a wrist drive assembly in example embodiments. The wrist drive assembly may include a third integrated motor (e.g., third integrated motor 336), and may also include a wrist drive portion (e.g., wrist drive portion 336*a*). The wrist drive portion 336*a* may be provided at the second end 330*b* of the arm assembly body 331. The wrist drive portion 336*a* may be controllable by the third integrated motor 336 to drive the wrist driven portion 346*a* when the wrist connector portion 338 is secured to the wrist assembly. The wrist drive portion 336*a* may be any mechanism, device, or the like, configurable to drive the wrist driven portion 346*a*. For example, the wrist drive portion 336*a* may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one wrist drive portion 336*a*, it is to be understood in the present disclosure that the arm assembly may have more than one wrist drive portions 336*a* without departing from the teachings of the present disclosure.

The arm assembly body 331 may also securely house a first arm assembly drive assembly in example embodiments. The first arm assembly drive assembly may include a fourth integrated motor (e.g., fourth integrated motor 339), and may also include a first arm assembly drive portion (e.g., first arm assembly drive portion 339*a*). The first arm assembly drive portion 339*a* may be provided at the first end 330*a* of the arm assembly body 331. The first arm assembly drive portion 339*a* may be controllable by the fourth integrated motor 339 to drive the first arm assembly driven portion 347 to drive the first arm assembly body 331 to move relative to an axis (e.g., axis F illustrated in FIG. 5K). Axis F may be formed by the first arm assembly 330 (e.g., axis F may be formed by a center line drawn through the first arm assembly body 331). The first arm assembly drive portion 339*a* may be any mechanism, device, or the like, configurable to drive the first arm assembly body 331 to move relative to the first arm assembly joint portion 350. For example, the first arm assembly drive portion 339*a* may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first arm assembly drive portion 339*a*, it is to be understood in the present disclosure that the arm assembly may have more than first arm assembly drive portions 339*a* without departing from the teachings of the present disclosure.

Although the figures illustrate the first arm assembly 330 having the first integrated motor 332, second integrated motor 334, third integrated motor 336, fourth integrated motor 339, first instrument drive portion 332*a*, second instrument drive portion 334*a*, wrist drive portion 336*a*, and first arm assembly drive portion 339*a*, it is to be understood that the first arm assembly 330 may (or may not) include the first integrated motor 332, second integrated motor 334, third integrated motor 336, fourth integrated 339, first instrument drive portion 332*a*, second instrument drive portion 334*a*, wrist drive portion 336*a*, and/or first arm assembly drive portion 339*a*, and/or may also include other integrated motor(s) and/or other drive portions, without departing from the teachings of the present disclosure. It is also to be understood that the first integrated motor 332, second integrated motor 334, third integrated motor 336, fourth integrated motor 339, first instrument drive portion 332*a*, second instrument drive portion 334*a*, wrist drive portion 336*a*, and/or first arm assembly drive portion 339a may be located, in part or in whole, in the first arm assembly 330, second arm assembly 360, and/or any other location or element of the arm assembly 230 without departing from the teachings of the present disclosure.

(ii) Second Arm Assembly (e.g., Second Arm Assembly 360)

An example embodiment of the second arm assembly 360 is illustrated in at least FIGS. 5A-C, 5L-M, and 5S-T. The second arm assembly 360 may be securable to the first arm assembly 330 on one end (via the elbow sway joint portion 350 and/or elbow pitch joint portion 350') and securable to the shoulder section 231 on another end (via the shoulder sway joint portion 380 and/or shoulder pitch joint portion 370). When secured to the shoulder section 231, the second arm assembly 360 may be configurable to move in one or more of a plurality of ways relative to the shoulder section 231, including, but not limited to, pitch, yaw, and/or roll relative to the shoulder section 231. In an example embodiment, the second arm assembly 360 may be securable to and unsecurable from (e.g., detached) the first arm assembly 330. As illustrated in at least FIGS. 5L-N and 5S-U, the second arm assembly 360 may include a second arm assembly body or housing (e.g., second arm assembly body 360'), a first end 360a (or proximal end), and a second end 360b (or distal end) opposite to the first end 360a. The elbow sway joint portion 350 or elbow pitch joint portion 350' may be secured to the second end 360b. The shoulder pitch joint portion 370 or shoulder sway joint portion 380 may be secured to the first end 360a. As illustrated in at least FIGS. 5S and 5T, in an example embodiment, an end of the elbow sway joint portion 350 (e.g., proximal end) may be secured to the second arm assembly 360 (e.g., distal end, such as second end 360b), another end of the elbow sway joint portion 350 (e.g., distal end) may be secured to the elbow pitch joint portion 350' (e.g., proximal end), an end of the elbow pitch joint portion 350' (e.g., distal end) may be secured to the first arm assembly 330 (e.g., proximal end, such as first end 330a), an end of the shoulder pitch joint portion 370 (e.g., distal end) may be secured to the second arm assembly 360 (e.g., proximal end, such as first end 360a), another end of the shoulder pitch joint portion 370 (e.g., proximal end) may be secured to the shoulder sway joint portion 380 (e.g., distal end), and an end of the shoulder sway joint portion 380 (e.g., proximal end) may be secured to the shoulder section 231 (e.g., distal end). The second arm assembly body 360' may securely house one or more of a plurality of drive assemblies.

In an example embodiment, the second arm assembly body 360' may securely house an elbow pitch drive assembly. The elbow pitch drive assembly may include a fifth integrated motor (e.g., fifth integrated motor 362), and may also include an elbow pitch drive portion (e.g., elbow pitch drive portion 362a'). The elbow pitch drive portion 362a' may be provided at the second end 360b (e.g., distal end) of the second arm assembly 360. The elbow pitch drive portion 362a' may be controllable by the fifth integrated motor 362 to drive the elbow pitch driven portion 352'. The elbow pitch drive portion 362a' may be any mechanism, device, or the like, configurable to drive the elbow pitch driven portion 352'. In an example embodiment, the elbow pitch drive portion 362a' may be configurable to drive the elbow pitch driven portion 352' so as to cause the first arm assembly 330 to pivotally move or rotate relative to an axis (e.g., axis C'). Put differently, the fifth integrated motor 362 may be configurable to pivotally move or rotate the first arm assembly 330 relative to the second arm assembly 360 and/or elbow sway joint portion 350 (and with respect to axis C'). For example, the elbow pitch drive portion 362a' may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one elbow pitch drive portion 362a', it is to be understood in the present disclosure that the second arm assembly may have more than one elbow drive portions 362a without departing from the teachings of the present disclosure.

The second arm assembly body 360' may also securely house an elbow sway drive assembly. The elbow sway drive assembly may include a sixth integrated motor (e.g., sixth integrated motor 369), and may also include an elbow sway drive portion (e.g., elbow sway drive portion 362a). The elbow sway drive portion 362a may be provided at the second end 360b (e.g., distal end) of the second arm assembly 360. The elbow sway drive portion 362a may be controllable by the sixth integrated motor 369 to drive the elbow sway driven portion 352. The elbow sway drive portion 362a may be any mechanism, device, or the like, configurable to drive the elbow sway driven portion 352. In an example embodiment, the elbow sway drive portion 362a may be configurable to drive the elbow sway driven portion 352 so as to cause the first arm assembly 330 to pivotally move or rotate relative to an axis (e.g., axis C). Put differently, the sixth integrated motor 369 may be configurable to pivotally move or rotate the elbow pitch joint portion 350' (and consequently the first arm assembly 330) relative to the second arm assembly 360 (and with respect to axis C). The axis C may be different from axis C'. In an example embodiment, axis C may be substantially orthogonal to axis C'. The elbow sway drive portion 362a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one elbow sway drive portion 362a, it is to be understood in the present disclosure that the second arm assembly may have more than one elbow sway drive portions 362a without departing from the teachings of the present disclosure.

The second arm assembly body 360' may also securely house a shoulder pitch drive assembly in example embodiments. The shoulder pitch drive assembly may include a seventh integrated motor (e.g., seventh integrated motor 364) and a shoulder pitch drive portion (e.g., shoulder pitch drive portion 364a). The shoulder pitch drive portion 364a may be provided at the first end 360a (e.g., proximal end) of the second arm assembly 360. The shoulder pitch drive portion 364a may be controllable by the seventh integrated motor 364 to drive the shoulder pitch driven portion 364b. The shoulder pitch drive portion 364a may be any mechanism, device, or the like, configurable to drive the shoulder pitch driven portion 364b. In an example embodiment, the shoulder pitch drive portion 364a may be configurable to drive the shoulder pitch driven portion 364b so as to cause the second arm assembly 360 to pivotally move or rotate relative to an axis (e.g., axis D). Put differently, the seventh integrated motor 364 may be configurable to pivotally move or rotate the second arm assembly 360 relative to the shoulder sway joint portion 380 (and/or shoulder section 231) (and with respect to axis D). For example, the shoulder pitch drive portion 364a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one shoulder pitch drive portion 364a, it is to be understood in the present disclosure that the second arm assembly may have more than one shoulder pitch drive portions 364a without departing from the teachings of the present disclosure.

The second arm assembly body 360' may also securely house a shoulder sway drive assembly in example embodiments. The shoulder sway drive assembly may include an eighth integrated motor (e.g., eighth integrated motor 366) and a shoulder sway drive portion (e.g., shoulder sway drive portion 366a). The shoulder sway drive portion 366a may be provided at the first end 360a (e.g. proximal end) of the second arm assembly 360. The shoulder sway drive portion 366a may be controllable by the eighth integrated motor 366 to drive the shoulder sway driven portion 366b, 366c, and/or 366d. The shoulder sway drive portion 366a may be any mechanism, device, or the like, configurable to drive the first shoulder sway driven portion 366b. In an example embodiment, the shoulder sway drive portion 366a may be configurable to drive the shoulder sway driven portion 366b, 366c, and/or 366d so as to cause the second arm assembly 360 to pivotally move or rotate relative to an axis (e.g., axis E). Put differently, the eighth integrated motor 366 may be configurable to pivotally move or rotate the shoulder pitch joint portion 370 (and/or the second arm assembly 360) relative to the shoulder section 231 (and with respect to axis E). The axis E may be different from axis D. In an example embodiment, axis E may be substantially orthogonal to axis D. One or more of the shoulder sway drive portion 366a, first shoulder sway driven portion 366b, second shoulder sway driven portion 366c, and third shoulder sway driven portion 366d may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one shoulder sway drive portion 366a, one first shoulder sway driven portion 366b, one second shoulder sway driven portion 366c, one third shoulder sway driven portion 366d, it is to be understood in the present disclosure that the second arm assembly may have more than one shoulder sway drive portions 366a, more than one first shoulder sway driven portion 366b, more than one second shoulder sway driven portions 366c, and/or more than one third shoulder sway driven portions 366d without departing from the teachings of the present disclosure. Furthermore, it is to be understood in the present disclosure that the second arm assembly may or may not have second shoulder sway driven portion 366c, and/or may or may not have one or more additional or other intermediate shoulder sway driven portions between the shoulder sway drive portion 366a and the third shoulder sway driven portion 366d without departing from the teachings of the present disclosure.

Although the figures illustrate the second arm assembly 360 having the fifth integrated motor 362, sixth integrated motor 369, seventh integrated motor 364, eighth integrated motor 366, elbow pitch drive portion 362a', elbow sway drive portion 362a, shoulder pitch drive portion 364a, and shoulder sway drive portion 366a, it is to be understood that the second arm assembly 360 may or may not include the fifth integrated motor 362, sixth integrated motor 369, seventh integrated motor 364, eighth integrated motor 366, elbow pitch drive portion 362a', elbow sway drive portion 362a, shoulder pitch drive portion 364a, and/or shoulder sway drive portion 366a, and/or may also include other integrated motor(s) and/or other drive portions, without departing from the teachings of the present disclosure. It is also to be understood that the fifth integrated motor 362, sixth integrated motor 369, seventh integrated motor 364, eighth integrated motor 366, elbow pitch drive portion 362a', elbow sway drive portion 362a, shoulder pitch drive portion 364a, and/or shoulder sway drive portion 366a may be located, in part or in whole, in the first arm assembly 330, second arm assembly 360, and/or any other location or element of the arm assembly 230 without departing from the teachings of the present disclosure.

Each of the instrument arm assemblies may be securable to (and unsecured from) the anchor ports 216 of the port assembly 210 via a securing portion 231a of the shoulder section 231. It is recognized in the present disclosure that the instrument arm assembly 230, 240 may be secured to the anchor port 216 of the port assembly 210 in the forward-directed position (e.g., as illustrated in FIGS. 2B, 2D, 3B, and 3D) and/or the reverse-directed position (e.g., as illustrated in FIGS. 2A, 2C, 3A, and 3C). Furthermore, in example embodiments, the instrument arm assembly 230, 240 may or may not be transitionable between the forward-directed position and the reverse-directed position. In example embodiments where the instrument arm assembly 230, 240 is transitionable between the forward-directed position and the reverse-directed position, such transition may be performable before, during, and/or after the securing of the shoulder section 231 to the anchor port 216 of the port assembly 210. For example, in such embodiments, the securing portion 231a may be adjustably changed in position relative to the shoulder section 231, such as from the forward-directed position illustrated in FIGS. 5A and 5P to the reverse-directed position illustrated in FIGS. 5B and 5Q, and vice versa.

One or more internal temperature control assemblies (not shown) may be provided for each of the one or more instrument arm assemblies 230, 240. Each internal temperature control assembly may be operable to control (such as reduce) the temperature and/or heat emission of the aforementioned gears and/or gear assemblies, motors, instrument joint portions (such as 232, 370, 380, 234, 236, and/or 238), and/or instrument arm segments (such as 231, 360, 330, and/or 340). The one or more internal temperature control assemblies may also be operable to control (such as increase or decrease) the temperature of the end effector 239, 342, 344 (which may be desirable when the end effector 239, 342, 344 is a cutting tool, or the like). In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well any solids (if used), may be provided through an interior of the instrument arm assembly without increasing dimensions (such as diameter) of the instrument arm assembly.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the body cavity, such as via an opening (not shown). When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the instrument arm assembly 230, 240.

In example embodiments, the internal temperature control assembly may utilize a combination of gases, liquids, solids, and/or the like without departing from the teachings of the present disclosure.

After the instrument arm assembly 230, 240 has been inserted and attached (or secured) to the port assembly 210, the end effector or instrument 239, 342, 344 may be configurable, either manually and/or via the computing device (or system), to apply between about 0 to 20 N of force via the integrated motors 332, 334 when performing surgical actions and procedures, such as clipping and/or grasping actions. Furthermore, the end effector or instrument 239, 342, 344 may be configurable, either manually and/or via the computing device/controller, to apply between about 0 to 10 N of force via the integrated motors 332, 334, 336, 339 when performing other surgical actions and procedures, such as translational, twisting, pulling, and/or pushing actions. It is to be understood in the present disclosure that the above range of applicable force are merely an illustration of example embodiments, and as such the range of applicable force may be smaller or larger than those recited above without departing from the teachings of the present disclosure.

In an example embodiment, the instrument arm segments, including the shoulder section 231, the second arm assembly 360, the first arm assembly 330, and/or the end-effector assembly 340, may be substantially cylindrical in shape. The instrument arm segments, including the shoulder section 231, the second arm assembly 360, the first arm assembly 330, and/or the end-effector assembly 340, may also be formed in any one of a plurality of other shapes, sizes, and/or dimensions without departing from the teachings of the present disclosure.

As described above, the instrument arm assembly 230, 240 may also include one or more securing portions 231a. The securing portion 231a may be attachable or attached to the first instrument arm segment 231, a part of the first instrument arm segment 231, and/or formed as a unitary article with the first instrument arm segment 231. Such securing portions 231a may be for use in securing the instrument arm assembly 230, 240 to the anchor ports 216. Such securing portions 231a may also be for use in performing or assisting in performing the process of inserting the instrument arm assembly 230, 240 into and securing onto the port assembly 210 in example embodiments.

After the instrument arm assembly 230 is inserted through the port assembly 210 and into the cavity of a patient (such as a vagina or rectum), the securing portion 231a of the first instrument arm segment (or shoulder section) 231 may be securely received by the anchor port 216 of the port assembly 210.

In an example embodiment, the length of the securing portion 231a may be between about 350 to 450 mm, the length of the shoulder section 231 may be between about 15 to 40 mm, the length of the second arm assembly 360 may be between about 80 to 105 mm, the length of the first arm assembly 330 may be between about 65 to 90 mm, the length of the end-effector assembly 340 may be between about 5 to 30 mm, and the overall length of the collective instrument arm may be between about 165 to 265 mm. In example embodiments, the length of the securing portion 231a may be between about 340 to 400 mm, the length of the shoulder section 231 may be between about 15 to 25 mm, the length of the second arm assembly 360 may be between about 90 to 100 mm, the length of the first arm assembly 330 may be between about 75 to 85 mm, the length of the end-effector assembly 340 may be between about 15 to 25 mm, and the overall length of the collective instrument arm may be between about 195 to 235 mm. In example embodiments, a length of one or more of the instrument arm segments, the securing portion 231a, and/or the end effector or instrument 239, 342, 344 may also be adjustable by the computing device (or system) of one or more nearby and/or remotely located surgical teams 904 before, during, and/or after insertion of the instrument arm assembly into the cavity of the patient. The outer diameter of one or more of the instrument arm segments may be about 10 to 16 mm. In an example embodiment, the outer diameter of one or more of the instrument arm segments may be about 16 mm.

Each of the instrument arm assemblies, including the securing portion 231a, the shoulder section 231, the second arm assembly 360, the first arm assembly 330, the instrument assembly 237, the end effector or instrument 239, 342, 344, the shoulder sway joint portion 380 (or joint portion along axis E), the shoulder pitch joint portion 370 (or joint portion along axis D), the elbow pitch joint portion 350' (or joint portion along axis C), the elbow sway joint portion 350 (or joint portion along axis C'), the third joint portion 236 (or joint portion along axis B), and/or the instrument joint 238 (or joint portion along axis A), may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. It is to be understood in the present disclosure that other materials may also be used without departing from the teachings of the present disclosure.

Other Example Embodiments of the Instrument Arm Assembly (e.g., Instrument Arm Assembly 230, 240).

As illustrated in at least FIGS. 11-14, an example embodiment of the surgical device 200 may include one or more arm assemblies (e.g., first instrument arm assembly 230, second instrument arm assembly 240, third instrument arm assembly (not shown), fourth instrument arm assembly (not shown), etc.). Each arm assembly 230, 240 may be configurable to attach (or anchor or secure) to an example embodiment of the port assembly 210 (as described above and in the present disclosure). Although some figures and/or descriptions provided in the present disclosure may be directed to the first instrument arm assembly 230 and its elements, it is to be understood that such figures and/or descriptions may also apply to other arm assemblies illustrated and/or described above and in the present disclosure, including second instrument arm assembly 240, third instrument arm assembly (not shown), fourth instrument arm assembly (not shown), etc. without departing from the teachings of the present disclosure.

The arm assembly 230, 240 may include a serially (or linearly) connected arrangement of arm segments. For example, as illustrated in at least the perspective view of FIG. 11A, the arm assembly 230, 240 may include a forearm segment (e.g., forearm segment 1100), an upper arm segment (e.g., upper arm segment 1140), and a shoulder segment (e.g., shoulder segment 231).

The arm assembly 230, 240 may also include joint portions. For example, as illustrated in at least the perspective view of FIG. 11A and the cross-sectional views of FIG. 11B (which is a cross-sectional view of the arm assembly 230, 240 along the Line A illustrated in FIG. 11A) and FIG. 11C (which is a cross-sectional view of the arm assembly 230, 240 along the Line B illustrated in FIG. 11A), the arm assembly 230, 240 may include an elbow coupling joint assembly (e.g., elbow coupling joint assembly 1120). The elbow coupling joint assembly 1120 may include a distal elbow joint (e.g., distal elbow joint 1120a) and a proximal elbow joint (e.g., proximal elbow joint 1120b). The elbow coupling joint assembly 1120 may also include a distal elbow joint subassembly comprising one or more gears for driving the forearm segment 1100 to rotate (e.g., pivotally rotate relative to axis C', as illustrated by Direction C' in FIG. 11C) relative to the distal elbow joint 1120a. The elbow coupling joint assembly 1120 may also include a proximal elbow joint subassembly comprising one or more gears for driving the distal elbow joint 1120a (and the forearm segment 1100 attached to the distal elbow joint 1120a) to rotate (e.g., pivotally rotate relative to axis C, as illustrated by Direction C in FIG. 11B) relative to the proximal elbow joint 1120b.

In addition to or alternatively, the arm assembly 230, 240 may include a shoulder coupling joint assembly (e.g., shoulder coupling joint assembly 1160). The shoulder coupling joint assembly 1160 may include a distal shoulder joint (e.g., distal shoulder joint 1160a) and a proximal shoulder joint (e.g., proximal shoulder joint 1160b). The shoulder coupling joint assembly 1160 may also include a distal shoulder joint subassembly comprising one or more gears for driving the upper arm segment 1140 to rotate (e.g., pivotally rotate relative to axis D, as illustrated by Direction D in FIG. 11C) relative to the distal shoulder joint 1160a. The shoulder coupling joint assembly 1160 may also include a proximal shoulder joint subassembly comprising one or more gears for driving the distal shoulder joint 1160a (and the upper arm segment 1140 attached to the distal shoulder joint 1160a) to rotate (e.g., pivotally rotate relative to axis E, as illustrated by Direction E in FIG. 11B) relative to the proximal shoulder joint 1160b.

The arm assembly 230, 240 may also include an end effector assembly (e.g., end effector assembly 340 as described above and in the present disclosure having a wrist assembly and an instrument assembly 237; which may include instrument(s) 239 having instrument 342 and/or instrument 344) integrated into and/or connected to one or more of the arm segments and/or joint portions. The end effector or instrument 239, 342, 344 may be any instrument suitable for use in surgical procedures, such as a cutting and/or gripping instrument.

The arm assembly 230, 240 may also include one or more integrated motors, including those described above and in the present disclosure. For example, the arm assembly 230, 240 may include integrated motors 332, 334, 336, and/or 339 illustrated in at least FIGS. 5E, 5G, 5J, and 5K. In addition to or alternatively, the arm assembly 230, 240 may include integrated motors 362, 364, 366, and/or 369 illustrated in at least FIGS. 5M-O, and 5T-V. In addition to or alternatively, the arm assembly 230, 240 may include integrated motors 1142, 1144, 1146, and/or 1148 illustrated in at least FIGS. 11B-C, the perspective view of the elbow coupling joint assembly 1120 of FIG. 12A, the perspective view of the elbow coupling joint assembly 1120 of FIG. 12D, the perspective view of the shoulder coupling joint assembly 1160 of FIG. 13A, the perspective view of the shoulder coupling joint assembly 1160 of FIG. 13D, and the cross-sectional side view of the elbow coupling joint assembly 1120 FIG. 14D.

Figure 11A:
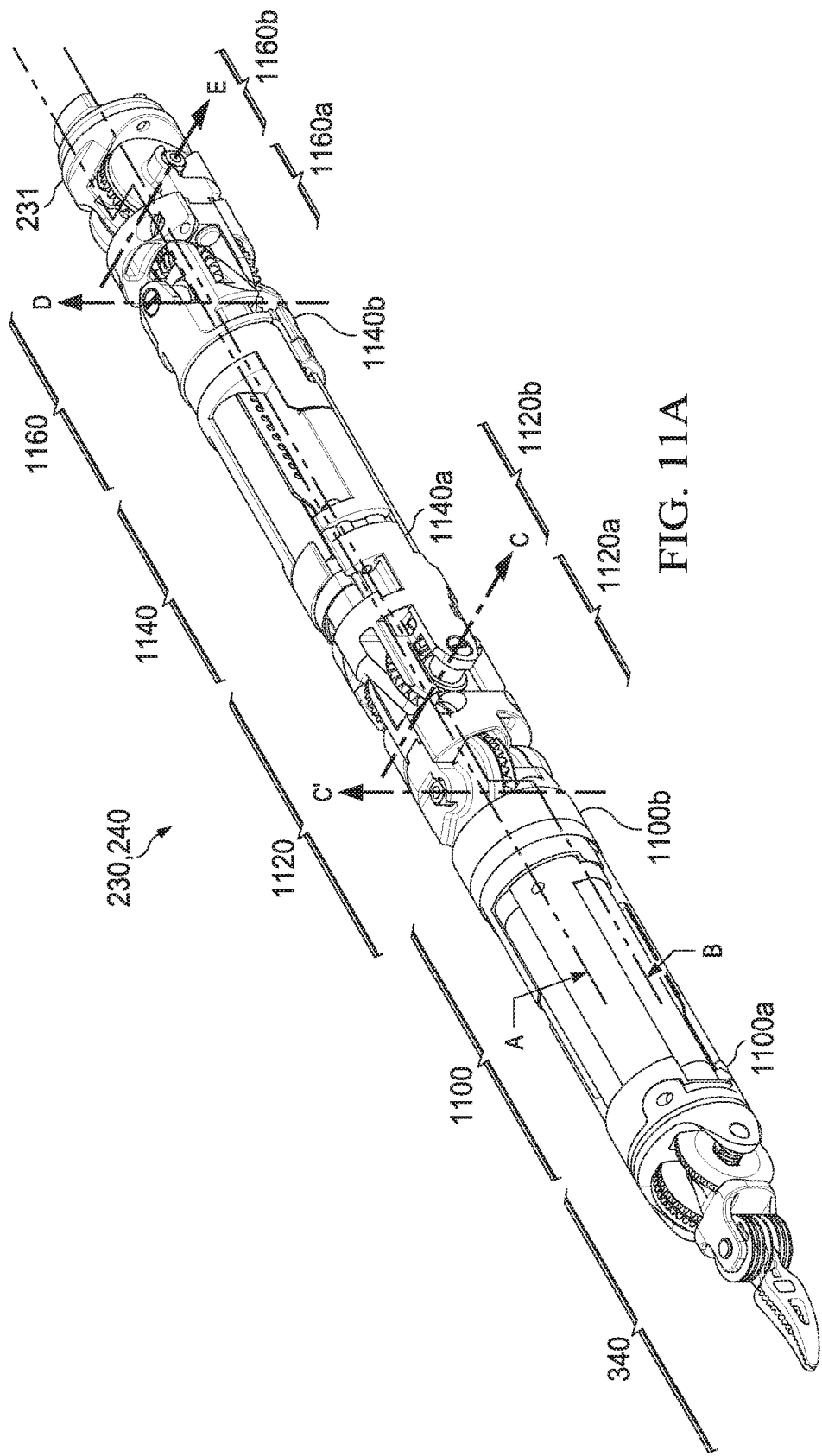
FIG. 11A is an illustration of a perspective view of an example embodiment of an arm assembly.
Figure 11B:
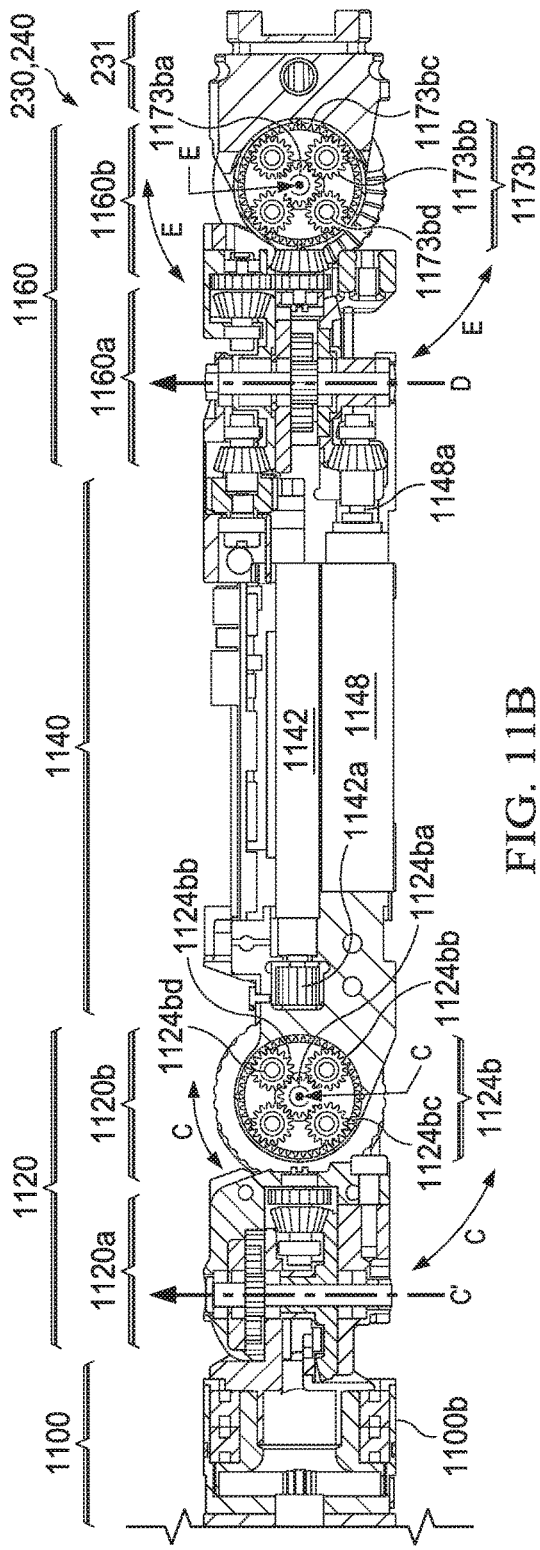
FIG. 11B is an illustration of a cross-sectional side view of an example embodiment of an arm assembly.
Figure 11C:
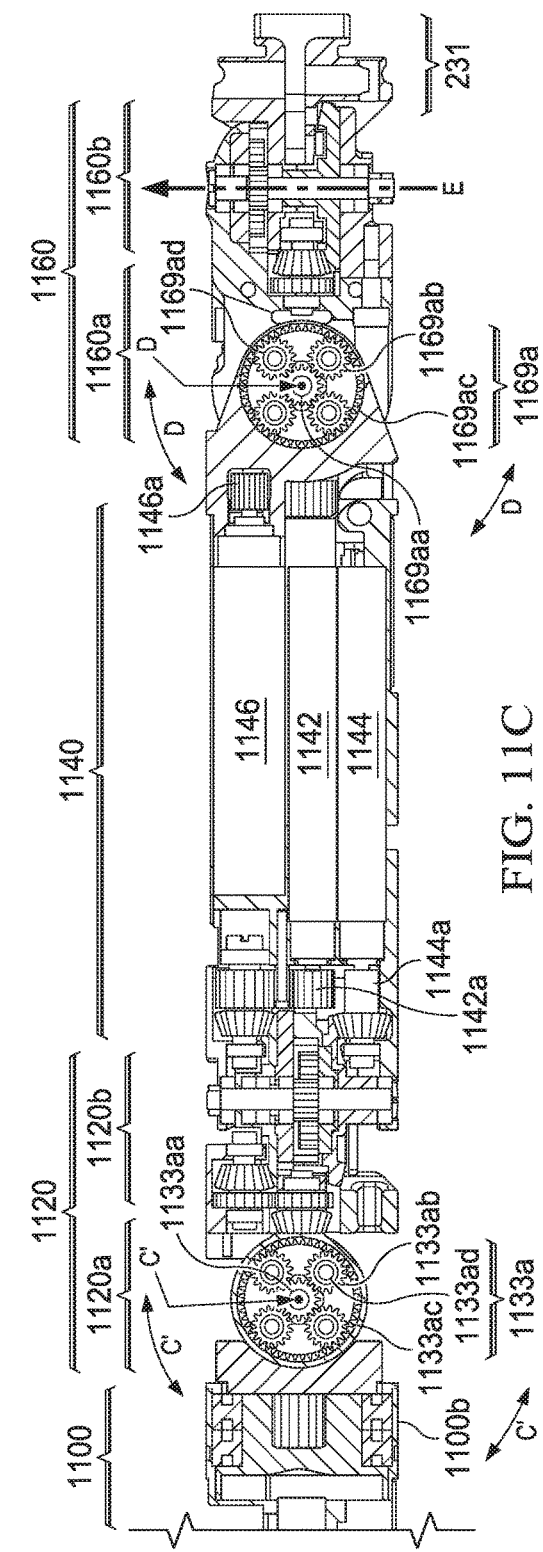
FIG. 11C is an illustration of a cross-sectional side view of an example embodiment of an arm assembly.

As illustrated in at least FIGS. 11B and 11C and described above and in the present disclosure, each integrated motor may include a drive portion or the like (e.g., drive portion 1142a for first distal motor 1142, drive portion 1144a for second distal motor 1144, drive portion 1146a for first proximal motor 1146, and drive portion 1148a for second proximal motor 1148) configurable to rotate so as to drive one or more gears (as further described in the present disclosure) and provide for at least one degree of freedom for the arm assembly 230, 240. Each integrated motor may be fully and independently functioning motors that are housed entirely (with the exception of, for example, power and/or control cables, which may be fed via the port assembly) in an arm segment (e.g., arm segments 1100, 1140, and/or 231).

In the example embodiments illustrated in at least FIGS. 11B and 11C, integrated motors 1142 and 1144 are housed in upper arm segment 1140, and are used to drive the elbow coupling joint assembly 1120. In particular, first distal motor 1142 is configurable to drive the distal elbow joint 1120a via the distal elbow joint subassembly (as further described in the present disclosure). Furthermore, second distal motor 1144 is configurable to drive the proximal elbow joint 1120b via the proximal elbow joint subassembly (as further described in the present disclosure).

Furthermore, integrated motors 1146 and 1148 are housed in upper arm segment 1140, and are used to drive the shoulder coupling joint assembly 1160. In particular, second proximal motor 1148 is configurable to drive the proximal shoulder joint 1160b via the proximal shoulder joint subassembly (as further described in the present disclosure). Furthermore, first proximal motor 1146 is configurable to drive the distal shoulder joint 1160a via the distal shoulder joint subassembly (as further described in the present disclosure).

One or more of the arm assemblies 230, 240 may also include an integrated haptic and/or force feedback subsystem (not shown) in communication with one or more of the integrated motors and/or other sensors and/or instruments operable to provide to the surgical team (such as via computing device/controller) with one or more of a plurality of feedback responses and/or measurements, including those pertaining to position (including orientation), applied force, proximity, temperature, pressure, humidity, etc., of, by, and/or nearby to the instrument arm assembly. For example, the surgical team 904 may be provided with a master input device having manipulators, or the like, having haptic and/or force feedback and designed to map and sense the surgical team's 904 delicate finger-twisting, wrist-bending, and/or other arm/shoulder movements into movements of the instrument arm (such as 230, 240) with high precision, high dexterity, and minimum burden, while also providing feedback of contact resistance (such as tissue resistance).

These and other elements of the arm assembly 230, 240 will now be further described with reference to the figures.

End Effector Assembly (e.g., End Effector Assembly 340).

In an example embodiment, the arm assembly 230, 240 may include an end effector assembly (e.g., end effector assembly 340). As described above and in the present disclosure, the end effector assembly 340 may include a wrist assembly and an instrument assembly 237. The instrument assembly 237 may include one or more instruments 239. As illustrated in at least FIGS. 5D-H, each instrument 239 may include instrument 342 and/or instrument 344. The end effector or instrument 239, 342, 344 may be any instrument suitable for use in surgical procedures, such as a cutting and/or gripping instrument.

Forearm Segment (e.g., Forearm Segment 1100).

An example embodiment of the forearm segment 1100 is illustrated in at least FIGS. 11A-C. The forearm segment 1100 may be securable to the end-effector assembly 340. In an example embodiment, the arm assembly 230 may be securable to and unsecurable from (e.g., detached) the end-effector assembly 340. The forearm segment 1100 may include a distal end 1100a and a proximal end 1100b. The distal elbow joint 1120a may be secured to the proximal end 1100a and the end-effector assembly 340 may be secured to the distal end 1100b.

In an example embodiment, the forearm segment 1100 may be similar to or the same as the first arm assembly 330 described above and in the present disclosure. For example, the forearm segment 1100 may include the first integrated motor 332, second integrated motor 334, third integrated motor 336, fourth integrated motor 339, first instrument drive portion 332a, second instrument drive portion 334a, wrist drive portion 336a, and/or first arm assembly drive portion 339a. It is to be understood that the forearm segment 1100 may (or may not) include the first integrated motor 332, second integrated motor 334, third integrated motor 336, fourth integrated 339, first instrument drive portion 332a, second instrument drive portion 334a, wrist drive portion 336a, and/or first arm assembly drive portion 339a, and/or may also include other integrated motor(s) and/or other drive portions, without departing from the teachings of the present disclosure.

Upper Arm Segment (e.g., Upper Arm Segment 1140).

An example embodiment of the upper arm segment 1140 is illustrated in at least FIGS. 11A-C. The upper arm assembly 1140 may include a distal end 1140a and a proximal end 1140b. The proximal elbow joint 1120b may be secured to the proximal end 1140a and the distal shoulder joint 1160a may be secured to the distal end 1140b.

In an example embodiment, the upper arm segment 1140 may securely house the first distal motor (e.g., first distal motor 1142). The first distal motor 1142 may include a first distal motor drive portion (e.g., first distal motor drive portion 1142a). The first distal motor drive portion 1142a may be provided at or near the distal end 1140a of the upper arm segment 1140. The first distal motor drive portion 1142a may be controllable by the first distal motor 1142 to drive the distal elbow joint subassembly (as further described in the present disclosure, which may include first distal elbow bevel gear 1124a, second distal elbow bevel gear 1125a, third distal elbow bevel gear 1126a, first distal elbow spur gear 1128a, second distal elbow spur gear 1129a, fourth distal elbow bevel gear 1131a, fifth distal elbow bevel gear 1132a, and/or distal elbow planetary gear assembly 1133a) so as to rotate the forearm segment 1100 relative to the distal elbow joint 1120a (e.g., rotate in Direction C' relative to axis C', as illustrated in at least FIG. 11C).

The upper arm segment 1140 may also securely house the second distal motor (e.g., second distal motor 1144). The second distal motor 1144 may include a second distal motor drive portion (e.g., second distal motor drive portion 1144a). The second distal motor drive portion 1144a may be provided at or near the distal end 1140a of the upper arm segment 1140. The second distal motor drive portion 1144a may be controllable by the second distal motor 1144 to drive the proximal elbow joint subassembly (as further described in the present disclosure, which may include first proximal elbow bevel gear 1122b, second proximal elbow bevel gear 1123b, and/or proximal elbow planetary gear assembly 1124b) so as to rotate the distal elbow joint 1120a (and the forearm segment 1100 attached to the distal elbow joint 1120a) relative to the proximal elbow joint 1120b (e.g., rotate in Direction C relative to axis C, as illustrated in at least FIG. 11B).

The upper arm segment 1140 may also securely house the first proximal motor (e.g., first proximal motor 1146). The first proximal motor 1146 may include a first proximal motor drive portion (e.g., first proximal motor drive portion 1146a). The first proximal motor drive portion 1146a may be provided at or near the proximal end 1140b of the upper arm segment 1140. The first proximal motor drive portion 1146a may be controllable by the first proximal motor 1146 to drive the distal shoulder joint subassembly (as further described in the present disclosure, which may include first distal shoulder bevel gear 1168a, second distal shoulder bevel gear 1169a, and/or distal shoulder planetary gear assembly 1170a) so as to rotate the upper arm segment 1140 relative to the distal shoulder joint 1160a (e.g., rotate in Direction D relative to axis D, as illustrated in at least FIG. 11C).

The upper arm segment 1140 may also securely house the second proximal motor (e.g., second proximal motor 1148). The second proximal motor 1148 may include a second proximal motor drive portion (e.g., second proximal motor drive portion 1148a). The second proximal motor drive portion 1148a may be provided at or near the proximal end 1140b of the upper arm segment 1140. The second proximal motor drive portion 1148a may be controllable by the second proximal motor 1148 to drive the proximal shoulder joint subassembly (as further described in the present disclosure, which may include first proximal shoulder bevel gear 1163b, second proximal shoulder bevel gear 1164b, third proximal shoulder bevel gear 1165b, first proximal shoulder spur gear 1167b, third proximal shoulder spur gear 1169b, fourth proximal shoulder bevel gear 1171b, fifth proximal shoulder bevel gear 1172b, and/or proximal shoulder planetary gear assembly 1173b) so as to rotate the distal shoulder joint 1160a (and the upper arm segment 1140 attached to the distal shoulder joint 1160a) relative to the proximal shoulder joint 1160b (e.g., rotate in Direction E relative to axis E, as illustrated in at least FIG. 11B).

Although the figures illustrate the upper arm assembly 1140 having the first distal motor 1142, second distal motor 1144, first proximal motor 1146, second proximal motor 1148, first distal motor drive portion 1142a, second distal motor drive portion 1144a, first proximal motor drive portion 1146*a*, and second proximal motor drive portion 1148*a*, it is to be understood that the upper arm assembly 1140 may (or may not) include the first distal motor 1142, second distal motor 1144, first proximal motor 1146, second proximal motor 1148, first distal motor drive portion 1142*a*, second distal motor drive portion 1144*a*, first proximal motor drive portion 1146*a*, and/or second proximal motor drive portion 1148*a*, and/or may also include other integrated motor(s) and/or other drive portions, without departing from the teachings of the present disclosure. It is also to be understood that the first distal motor 1142, second distal motor 1144, first proximal motor 1146, second proximal motor 1148, first distal motor drive portion 1142*a*, second distal motor drive portion 1144*a*, first proximal motor drive portion 1146*a*, and second proximal motor drive portion 1148*a* may be located, in part or in whole, in the upper arm assembly 1140, forearm assembly 1100, and/or any other location or element of the arm assembly 230, 240 without departing from the teachings of the present disclosure.

Elbow Coupling Joint Assembly (e.g., Elbow Coupling Joint Assembly 1120).

Figure 12A:
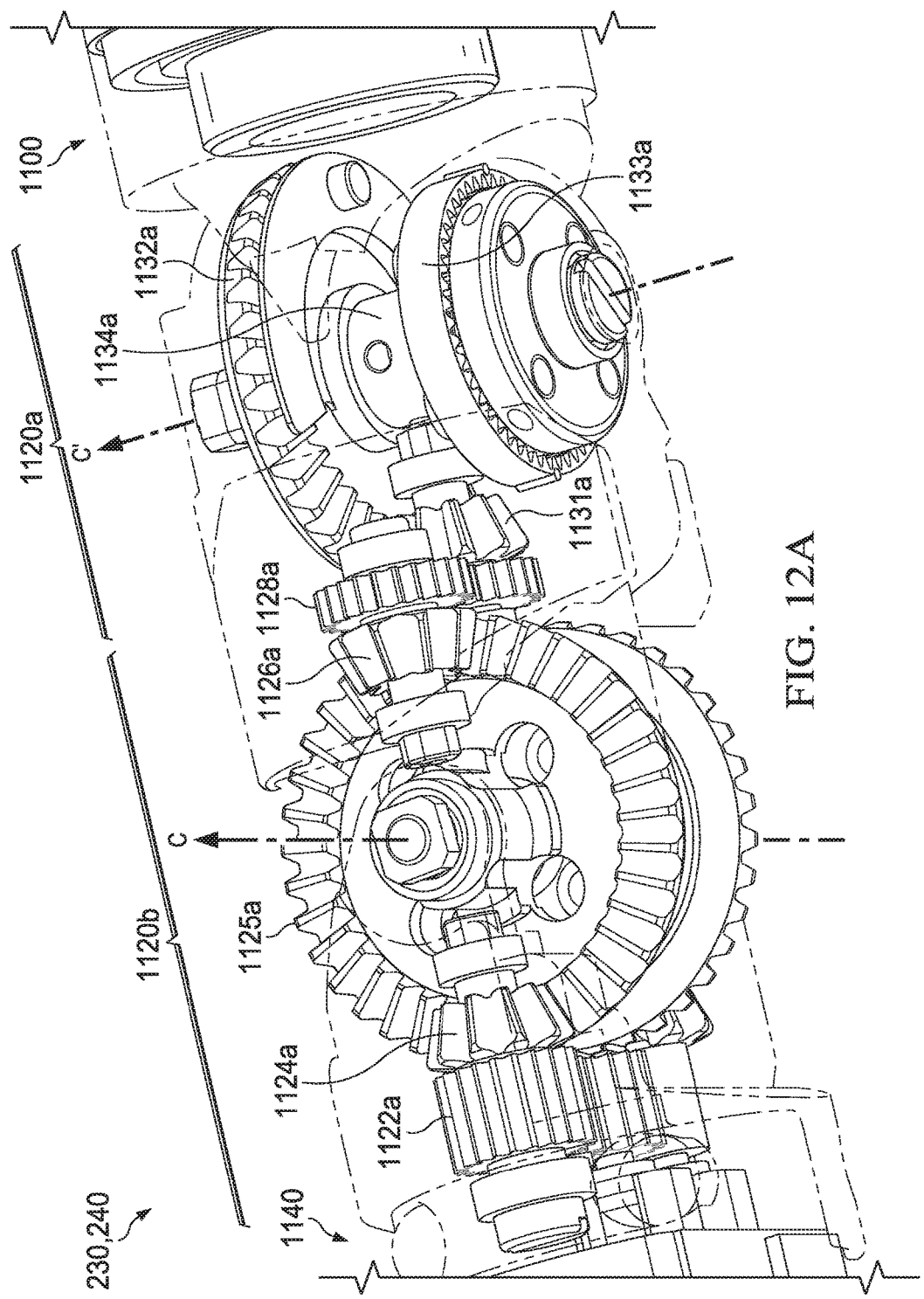
FIG. 12A is an illustration of a perspective view of an example embodiment of an elbow coupling joint assembly.
Figure 14A:
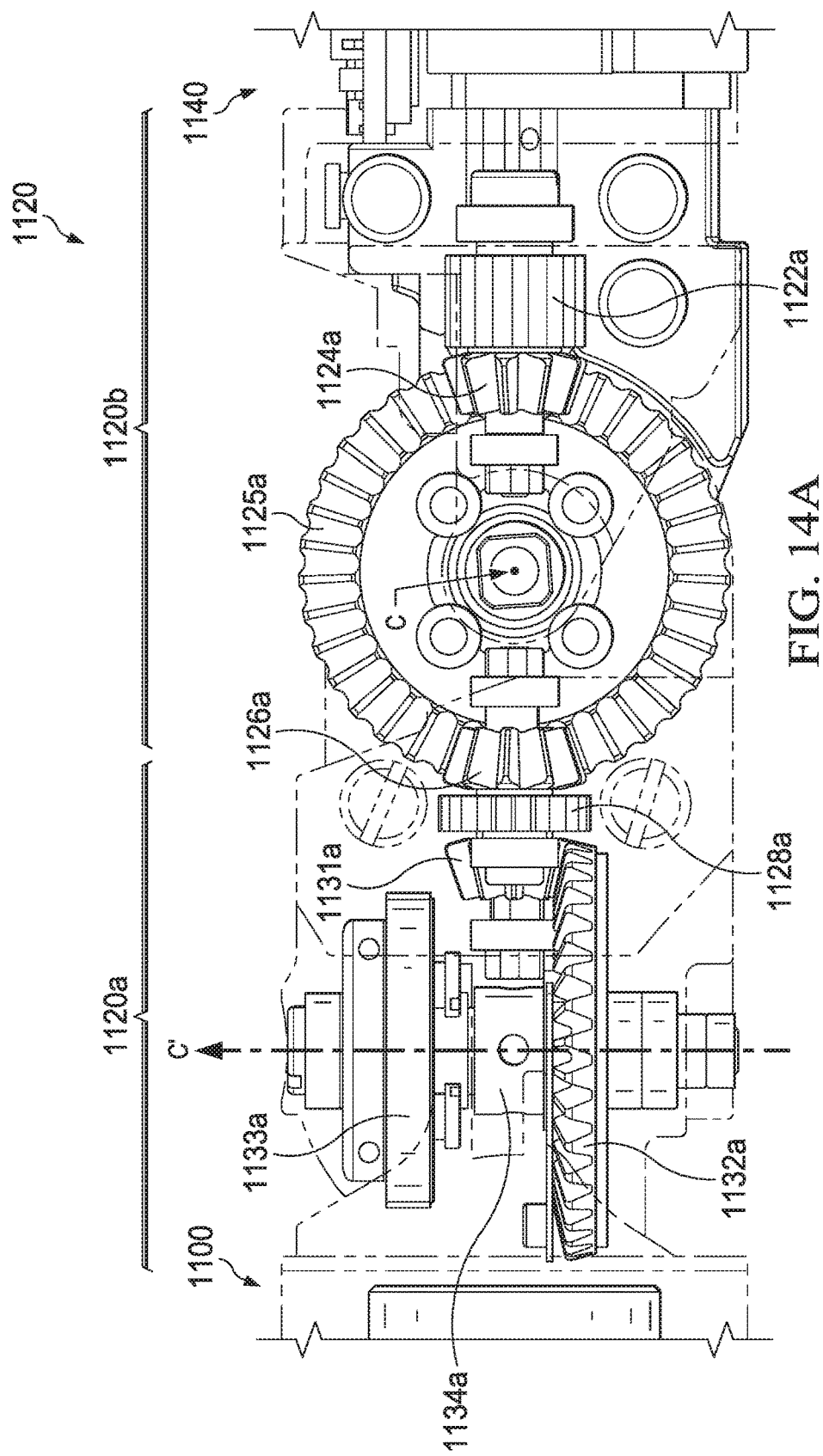
FIG. 14A is an illustration of a side view of an example embodiment of an elbow coupling joint assembly.
Figure 14B:
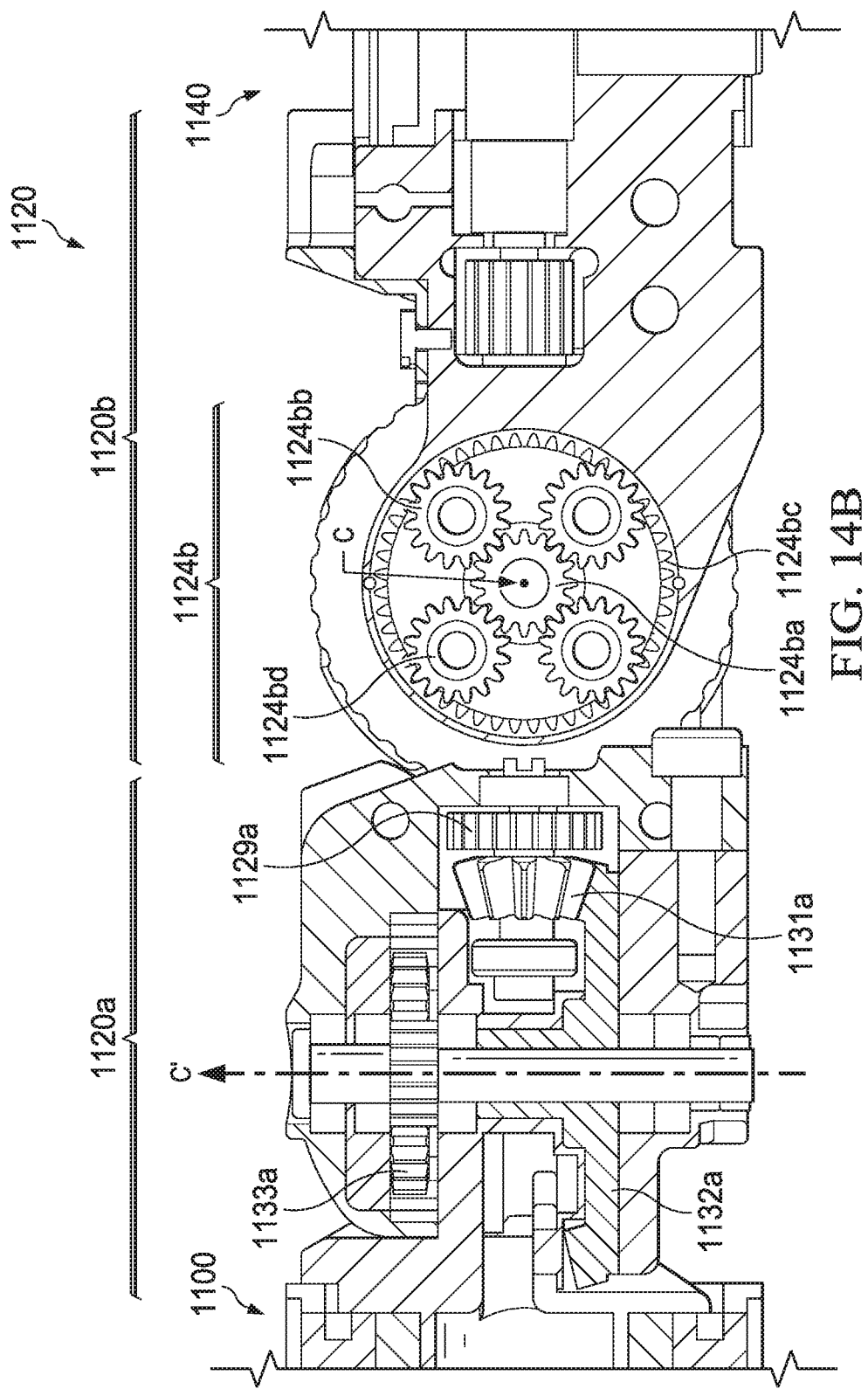
FIG. 14B is an illustration of a cross-sectional side view of an example embodiment of an elbow coupling joint assembly.
Figure 14C:
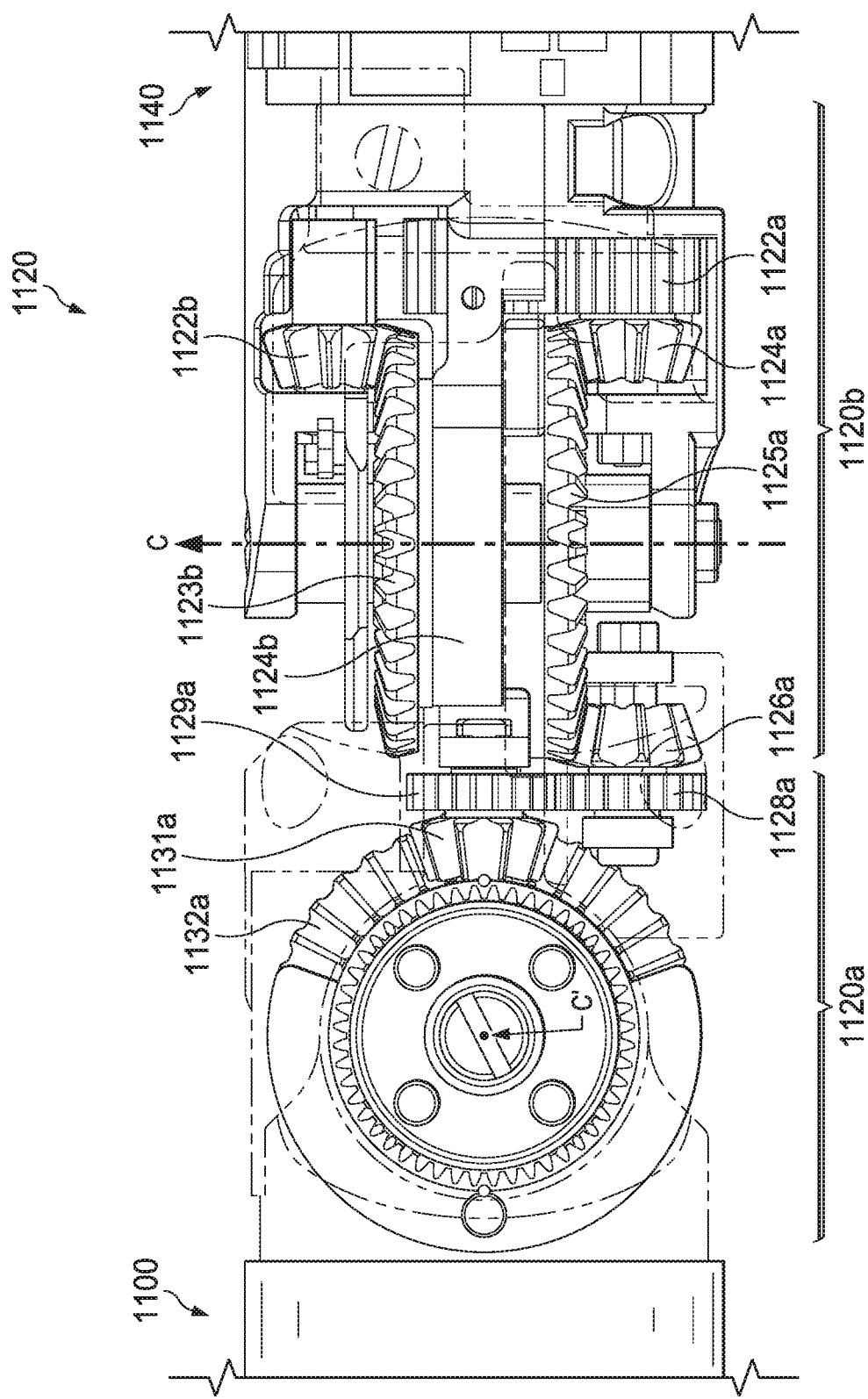
FIG. 14C is an illustration of is another side view of an example embodiment of an elbow coupling joint assembly.
Figure 14D:
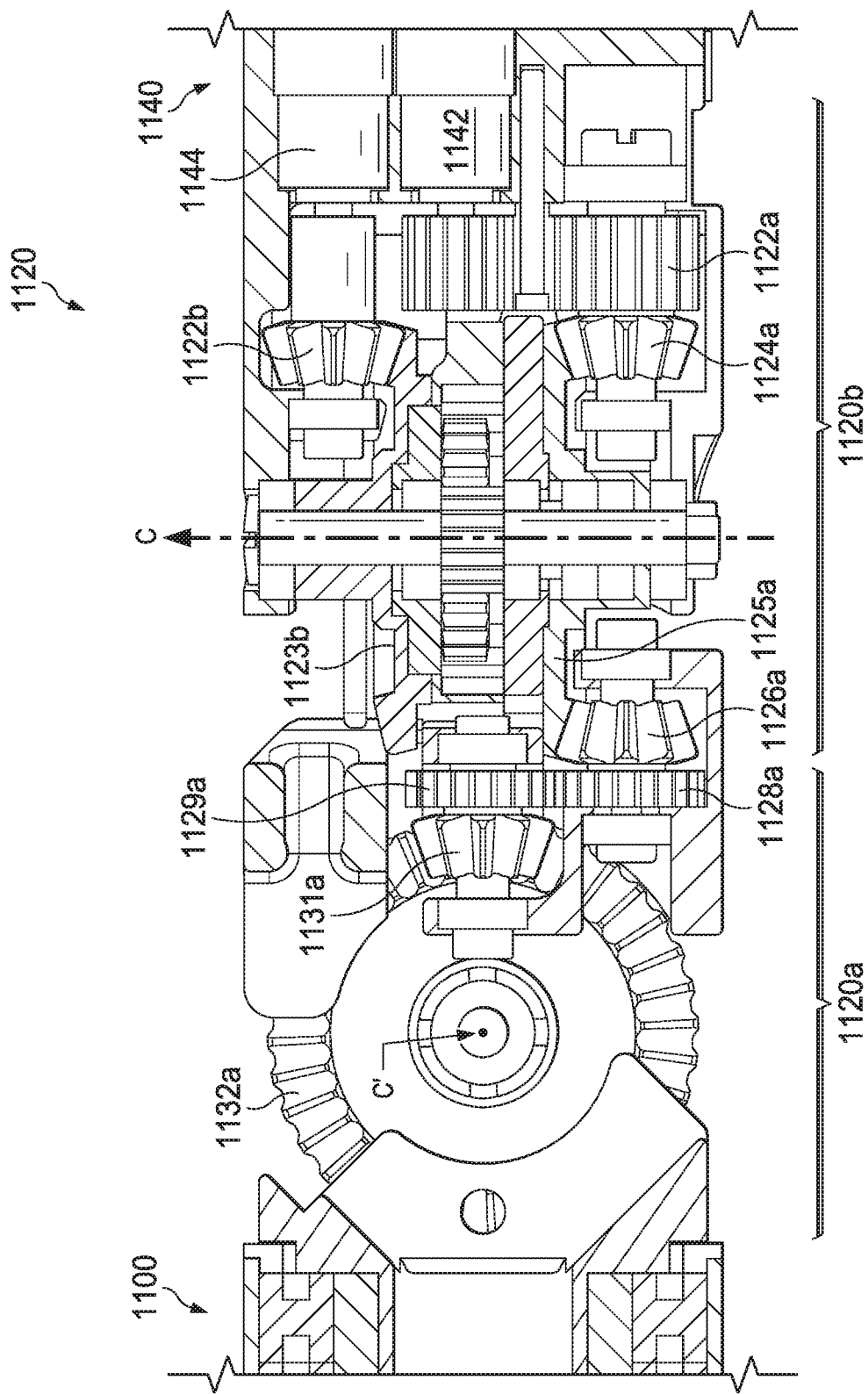
FIG. 14D is an illustration of another cross-sectional side view of an example embodiment of an elbow coupling joint assembly.

As illustrated in FIGS. 12A and 12D, the side views of FIG. 14A and FIG. 14C, and the cross-sectional side views of FIG. 14B and FIG. 14D, an example embodiment of the arm assembly 230, 240 may include an elbow coupling joint assembly (e.g., elbow coupling joint assembly 1120). The elbow coupling joint assembly 1120 may include a distal elbow joint 1120*a* and a proximal elbow joint 1120*b*.

The distal elbow joint 1120*a* may have an axis of rotation C', as illustrated in at least FIGS. 11B, 11C, 12A, 12D, and 14A-D. The distal elbow joint 1120*a* may be configured to enable the forearm segment 1100 to rotate (or pivotally rotate) relative to axis C'. Put differently, the distal elbow joint 1120*a* may be configured to enable the forearm segment 1100 to rotate (or pivotally rotate) relative to the distal elbow joint 1120*a*. As further described below and in the present disclosure, such rotation relative to axis C' may be driven by the first distal motor 1142 and distal elbow joint subassembly.

The proximal elbow joint 1120*b* may have an axis of rotation C, as illustrated in at least FIGS. 11B, 11C, 12A, 12D, and 14A-D. The proximal elbow joint 1120*b* may be configured to enable the distal elbow joint 1120*a* (and the forearm segment 1100 attached to the distal elbow joint 1120*a*) to rotate (or pivotally rotate) relative to axis C. Put differently, the proximal elbow joint 1120*b* may be configured to enable the distal elbow joint 1120*a* (and the forearm segment 1100 attached to the distal elbow joint 1120*a*) to rotate (or pivotally rotate) relative to the proximal elbow joint 1120*b*.

Put differently, the proximal elbow joint 1120*b* may be configured to enable the forearm segment 1100 to rotate (or pivotally rotate) relative to the proximal elbow joint 1120*b*. The rotational axis C of proximal elbow joint 1120*b* may not be parallel to the rotational axis C' of the distal elbow joint 1120*a*. For example, the rotational axis C of proximal elbow joint 1120*b* may be orthogonal to the rotational axis C' of the distal elbow joint 1120*a*. As further described below and in the present disclosure, such rotation relative to axis C may be driven by the second distal motor 1144 and proximal elbow joint subassembly.

(i) The Distal Elbow Joint Subassembly.

In an example embodiment, the first distal motor 1142 may drive the distal elbow joint subassembly so as to cause the forearm segment 1100 to rotate (or pivotally rotate) relative to the distal elbow joint 1120*a* (or relative to axis C', as depicted by the Direction C' illustrated in FIG. 11C). As illustrated in at least FIGS. 11B, 11C, 12A, 12D, and 14A-D, the distal elbow joint subassembly includes a plurality of gears. More specifically, the distal elbow joint subassembly includes a gear train system having a plurality of gear stages.

The distal elbow joint subassembly may include a first distal elbow gear stage. The first distal elbow gear stage may include a first distal elbow bevel gear (e.g., first distal elbow bevel gear 1124*a*, as illustrated in at least FIGS. 12A, 12D, 14A, 14C, and 14D). The distal elbow joint subassembly may also include one or more gears between the first distal motor drive portion 1142*a* and the first distal elbow bevel gear 1124*a*, such as one or more spur gears 1121*a*, 1122*a* (as illustrated in FIGS. 12A and 12D). The distal elbow joint subassembly may also include one or more connectors or the like between the first distal motor drive portion 1142*a* and the first distal elbow bevel gear 1124*a*, such as connector 1123*a* (as illustrated in at least FIGS. 12A and 12D).

Alternatively, as illustrated in at least FIGS. 14A and 14C, the first distal elbow bevel gear 1124*a* may be configured so as to be driven directly by the first distal motor drive portion 1142*a* in example embodiments (e.g., without the one or more spur gears 1121*a*, 1122*a*), which is recognized in the present disclosure to enable a reduction in total length of the arm assembly 230, 240.

The first distal elbow gear stage may also include a second distal elbow bevel gear (e.g., second distal elbow bevel gear 1125*a*, as illustrated in at least FIGS. 12A, 12D, 14A, 14C, and 14D). The second distal elbow bevel gear 1125*a* may be drivable by the first distal elbow bevel gear 1124*a* so as to rotate relative to axis C (the second distal elbow bevel gear 1125*a* may have a central axis of rotation corresponding to axis C).

A gear ratio between the first distal elbow bevel gear 1124*a* and the second distal elbow bevel gear 1125*a* may be between about 1:2 to 1:5 (e.g., 1:3).

The first distal elbow gear stage may also include a third distal elbow bevel gear (e.g., third distal elbow bevel gear 1126*a*, as illustrated in at least FIGS. 12A, 12D, 14A, 14C, and 14D). The third distal elbow bevel gear 1126*a* may be drivable by the second distal elbow bevel gear 1125*a* so as to rotate.

A gear ratio between the second distal elbow bevel gear 1125*a* and the third distal elbow bevel gear 1126*a* may be between about 2:1 to 5:1 (e.g., 3:1).

The distal elbow joint subassembly may include a second distal elbow gear stage. The second distal elbow gear stage may include a first distal elbow spur gear (e.g., first distal elbow spur gear 1128*a*, as illustrated in at least FIGS. 12A, 12D, 14A, 14C, and 14D). The distal elbow joint subassembly may also include one or more connectors between the third distal elbow bevel gear 1126*a* and the first distal elbow spur gear 1128*a*, such as connector 1127*a* (as illustrated in at least FIGS. 12A and 12D).

Alternatively, as illustrated in at least FIGS. 14A and 14C, the first distal elbow spur gear 1128*a* may be directly coupled (or connected or secured) to the third distal elbow bevel gear 1126*a* in example embodiments, which is recognized in the present disclosure to enable a reduction in total length of the arm assembly 230, 240.

The second distal elbow gear stage may also include a second distal elbow spur gear (e.g., second distal elbow spur gear 1129*a*, as illustrated in at least FIGS. 12A, 14C, and 14D). The second distal elbow spur gear 1129*a* may be drivable by the first distal elbow spur gear 1128*a* so as to rotate.

A gear ratio between the first distal elbow spur gear 1128a and the second distal elbow spur gear 1129a may be between about 1:1 to 1:4 (e.g., 1:2).

The distal elbow joint subassembly may include a third distal elbow gear stage. The third distal elbow gear stage may include a fourth distal elbow bevel gear (e.g., fourth distal elbow bevel gear 1131a, as illustrated in at least FIGS. 12A, 14A, 14B, 14C, and 14D). The distal elbow joint subassembly may also include one or more connectors or the like between the second distal elbow spur gear 1129a and the fourth distal elbow bevel gear 1131a, such as connector 1130a (as illustrated in at least FIG. 12A).

Alternatively, as illustrated in at least FIGS. 14B-D, the fourth distal elbow bevel gear 1131a may be directly coupled (or connected or secured) to the second distal elbow spur gear 1129a in example embodiments, which is recognized in the present disclosure to enable a reduction in total length of the arm assembly 230, 240.

The third distal elbow gear stage may also include a fifth distal elbow bevel gear (e.g., fifth distal elbow bevel gear 1132a, as illustrated in at least FIGS. 12A and 14A-D). The fifth distal elbow bevel gear 1132a may be drivable by the fourth distal elbow bevel gear 1131a so as to rotate relative to axis C' (the fifth distal elbow bevel gear 1132a may have a central axis of rotation corresponding to axis C').

A gear ratio between the fourth distal elbow bevel gear 1131a and the fifth distal elbow bevel gear 1132a may be between about 1:2 to 1:5 (e.g., 1:3).

The distal elbow joint subassembly may include a fourth distal elbow gear stage. The fourth distal elbow gear stage may include a distal elbow planetary gear assembly (e.g., distal elbow planetary gear assembly 1133a, as illustrated in at least FIGS. 11C, 12A, and 14A). The distal elbow joint subassembly may also include one or more connectors or the like (e.g., connector portion 1134a) and/or the fifth distal elbow bevel gear 1132a and/or distal elbow sun gear 1133aa may have an extended portion between the fifth distal elbow bevel gear 1132a and the distal elbow planetary gear assembly 1133a, which is recognized in the present disclosure to enable improved spacing for cabling to pass through the elbow coupling joint assembly 1120 (e.g., pass through between the fifth distal elbow bevel gear 1132a and the distal elbow planetary gear assembly 1133a).

Alternatively, as illustrated in at least FIGS. 11B and 12A, the fifth distal elbow bevel gear 1132a may be directly coupled (or connected or secured) to the distal elbow planetary gear assembly 1133a (i.e., the fifth distal elbow bevel gear 1132a directly coupled or connected or secured to distal elbow sun gear 1133aa) in example embodiments.

Figure 12B:
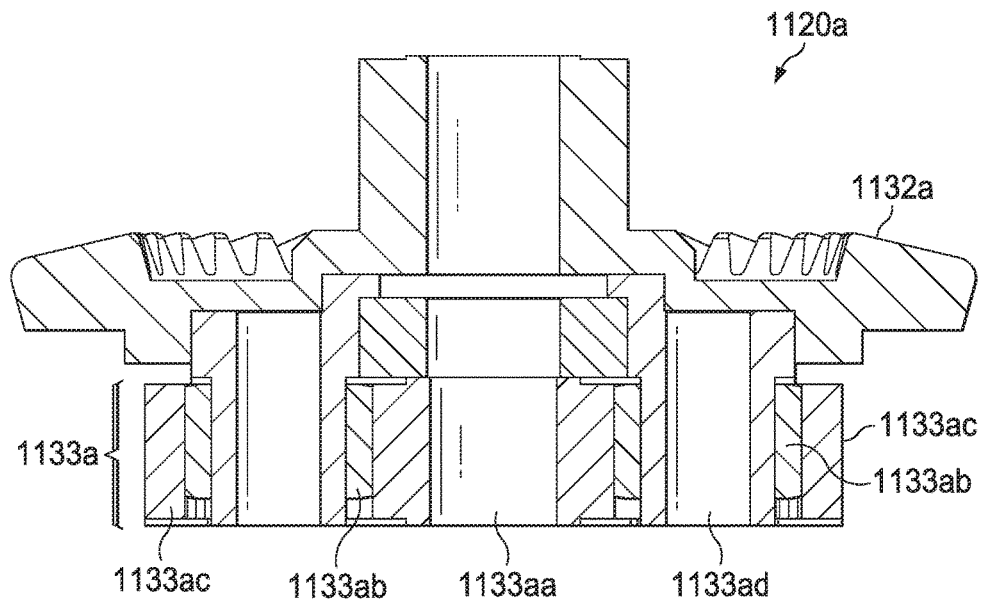
FIG. 12B is an illustration of a side view of an example embodiment of a distal elbow planetary gear assembly.
Figure 12C:
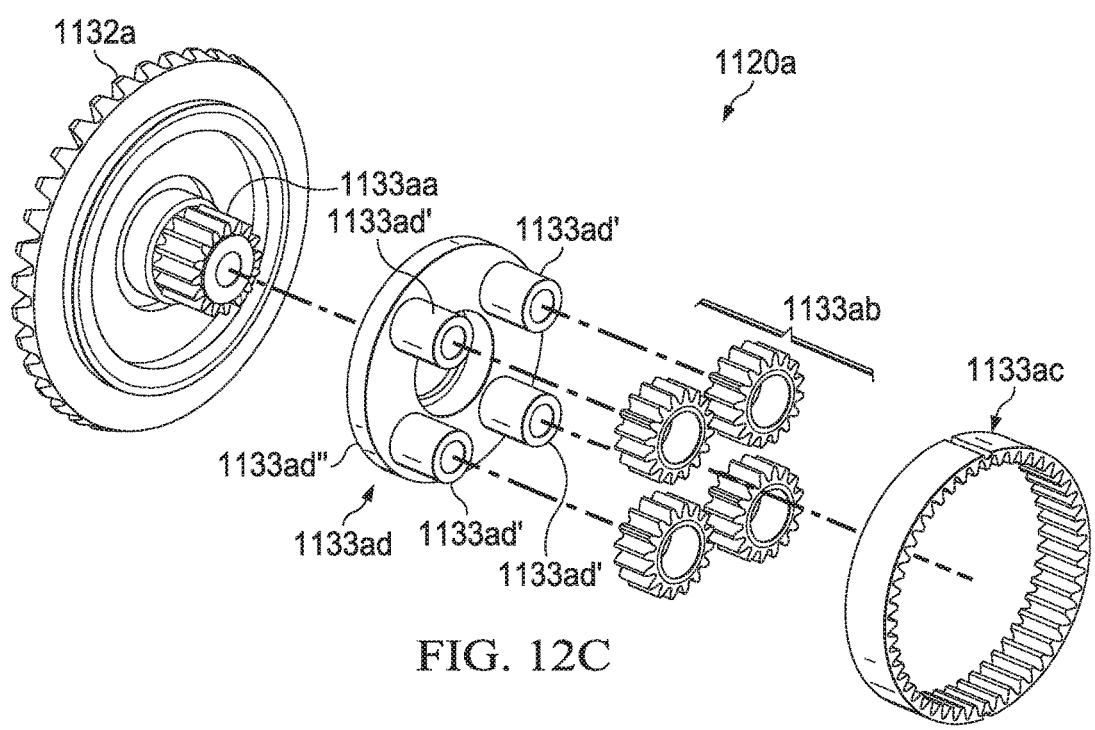
FIG. 12C is an illustration of an exploded perspective view of an example embodiment of a distal elbow planetary gear assembly.

FIG. 12B illustrates a side view and FIG. 12C illustrates an exploded perspective view of an example embodiment of the distal elbow planetary gear assembly 1133a. The distal elbow planetary gear assembly 1133a may have a central axis corresponding to axis C'. The distal elbow planetary gear assembly 1133a may include a distal elbow sun gear 1133aa. The distal elbow sun gear 1133aa may be drivable by the fifth distal elbow bevel gear 1132a so as to rotate relative to axis C'. The distal elbow sun gear 1133aa and/or the fifth distal elbow bevel gear 1132a may include an extended portion (not shown) so as to enable a spacing between the each other and allow for cabling to run through such spacing.

The distal elbow planetary gear assembly 1133a may also include a plurality of distal elbow planetary (or planet) gears 1133ab. For example, the distal elbow planetary gear assembly 1133a may include 4 or more distal elbow planetary gears 1133ab. Each of the distal elbow planetary gears 1133ab may be configured to rotate relative to its central axis. The distal elbow planetary gears 1133ab may be drivable by the distal elbow sun gear 1133aa to collectively rotate around axis C'.

The distal elbow planetary gear assembly 1133a may also include a distal elbow ring gear 1133ac. The distal elbow ring gear 1133ac may be fixed or locked from rotating relative to axis C' in example embodiments so as to enable the plurality of distal elbow planetary gears 1133ab to collectively rotate around axis C'.

The distal elbow planetary gear assembly 1133a may also include a distal elbow planetary gear carrier 1133ad. The distal elbow planetary gear carrier 1133ad may have a plurality of first ends 1133ad' connected to plurality of distal elbow planetary gears 1133ab. The distal elbow planetary gear carrier 1133ad may also have a second end 1133ad" connected to a portion of the distal end 1100b of the forearm segment 1100.

In this regard, when the distal elbow sun gear 1133aa is driven by the fifth distal elbow bevel gear 1132a to rotate relative to axis C', the distal elbow sun gear 1133aa in turn drives the plurality of distal elbow planetary gears 1133ab to collectively rotate relative to axis C'. Such collective rotation of the plurality of distal elbow planetary gears 1133ab around axis C' in turn drives the distal elbow planetary gear carrier 1133ad to rotate relative to axis C' (via the connection between the first ends 1133ad' of the distal elbow planetary gear carrier 1133ad and the plurality of distal elbow planetary gears 1133ab). Such rotation of the distal elbow planetary gear carrier 1133ad around axis C' in turn drives the forearm segment 1100 to rotate (or pivotally rotate) relative to axis C' (e.g., in the Direction C', as illustrated in at least FIG. 11C) (via the connection between the second end 1133ad" of the distal elbow planetary gear carrier 1133ad and the distal end 1100b of the forearm segment 1100).

A gear ratio between the fifth distal elbow bevel gear 1132a and the distal elbow planetary gear assembly 1133a may be between about 1:2 to 1:8 (e.g., 1:5).

Accordingly, the forearm segment 1100 may be driven to rotate (or pivotally rotate) relative to axis C' (or rotate relative to the distal elbow joint 1120a) by driving the first distal motor 1142, which in turn drives the first distal elbow gear stage (which includes the first distal elbow bevel gear 1124a, the second distal elbow bevel gear 1125a, the third distal elbow bevel gear 1126a), which in turn drives the second distal elbow gear stage (which includes the first distal elbow spur gear 1128a and the second distal elbow spur gear 1129a), which in turn drives the third distal elbow gear stage (which includes the fourth distal elbow bevel gear 1131a and the fifth distal elbow bevel gear 1132a), which in turn drives the fourth distal elbow gear stage (which includes the distal elbow planetary gear assembly 1133a having the distal elbow sun gear 1133aa, the distal elbow planetary gears 1133ab, the distal elbow ring gear 1133ac, and the distal elbow planetary gear carrier 1133ad), which in turn drives the forearm segment 1100 to rotate relative to axis C'.

A gear or magnification ratio for the distal elbow joint assembly may be between about 1:20 to 1:50 (e.g., 1:30).

The distal elbow joint assembly may be or include any other gear configuration for driving the forearm segment 1100, including those described in the present disclosure. For example, the distal elbow joint assembly may include any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure.

(ii) The Proximal Elbow Joint Subassembly.

In an example embodiment, the second distal motor 1144 may drive the proximal elbow joint subassembly so as to cause the distal elbow joint 1120*a* (and the forearm segment 1100 attached to the distal elbow joint 1120*a*) to rotate (or pivotally rotate) relative to the proximal elbow joint 1120*b* (or relative to axis C, as depicted by the Direction C illustrated in FIG. 11B).

Put differently, the second distal motor 1144 may drive the proximal elbow joint subassembly so as to cause the forearm segment 1100 (which is attached to the distal elbow joint 1120*a*) to rotate (or pivotally rotate) relative to the proximal elbow joint 1120*b* (or relative to axis C, as depicted by the Direction C illustrated in FIG. 11B). As illustrated in at least FIGS. 11B, 11C, 12A, 12D, and 14A-D, the proximal elbow joint subassembly includes a plurality of gears. More specifically, the proximal elbow joint subassembly includes a gear train system having a plurality of gear stages.

The proximal elbow joint subassembly may include a first proximal elbow gear stage. The first proximal elbow gear stage may include a first proximal elbow bevel gear (e.g., first proximal elbow bevel gear 1122*b*, as illustrated in at least FIGS. 12D, 14C, and 14D). The proximal elbow joint subassembly may also include one or more gears between the second distal motor drive portion 1144*a* and the first proximal elbow bevel gear 1122*b*, such as one or more spur gears (not shown). The proximal elbow joint subassembly may also include one or more connectors or the like between the second distal motor drive portion 1144*a* and the first proximal elbow bevel gear 1122*b*, such as connector 1121*b* (as illustrated in at least FIG. 12D).

Alternatively, as illustrated in at least FIGS. 14C and 14D, the first proximal elbow bevel gear 1122*b* may be configured so as to be driven directly by the second distal motor drive portion 1144*a* in example embodiments (as shown in at least FIGS. 14C and 14D), which is recognized in the present disclosure to enable a reduction in total length of the arm assembly 230, 240.

The first proximal elbow gear stage may also include a second proximal elbow bevel gear (e.g., second proximal elbow bevel gear 1123*b*, as illustrated in at least FIGS. 12D, 14C, and 14D). The second proximal elbow bevel gear 1123*b* may be drivable by the first proximal elbow bevel gear 1122*b* so as to rotate relative to axis C (the second proximal elbow bevel gear 1123*b* may have a central axis of rotation corresponding to axis C).

A gear ratio between the first proximal elbow bevel gear 1122*b* and the second proximal elbow bevel gear 1123*b* may be between about 1:2 to 1:5 (e.g., 1:3).

The proximal elbow joint subassembly may include a second proximal elbow gear stage. The second proximal elbow gear stage may include a proximal elbow planetary gear assembly (e.g., proximal elbow planetary gear assembly 1124*b*, as illustrated in at least FIGS. 11B, 12D, and 14C). The proximal elbow joint subassembly may also include one or more connectors (not shown) and/or the second proximal elbow bevel gear 1123*b* and/or proximal elbow sun gear 1124*ba* may have an extended portion between the second proximal elbow bevel gear 1123*b* and the proximal elbow planetary gear assembly 1124*b* (not shown), which is recognized in the present disclosure to enable improved spacing for cabling to pass through the elbow coupling joint assembly 1120 (e.g., pass through between the second proximal elbow bevel gear 1123*b* and the proximal elbow planetary gear assembly 1124*b*).

Alternatively, as illustrated in at least FIGS. 11C, 12D, and 14C, the second proximal elbow bevel gear 1123*b* may be directly coupled (or connected or secured) to the proximal elbow planetary gear assembly 1124*b* (i.e., the second proximal elbow bevel gear 1123*b* directly coupled or connected or secured to proximal elbow sun gear 1124*ba*) in example embodiments.

Figure 12E:
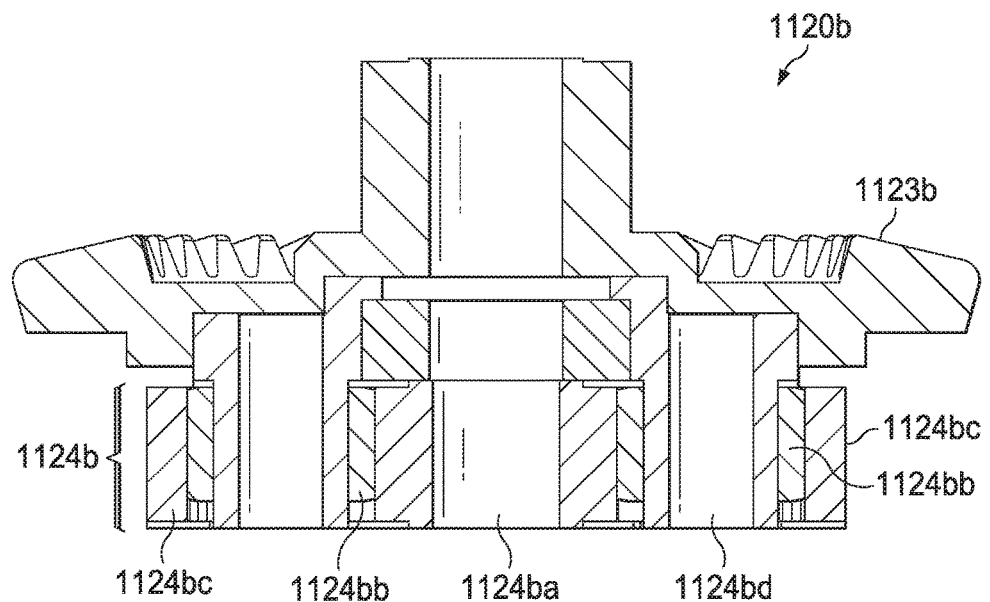
FIG. 12E is an illustration of a side view of an example embodiment of a proximal elbow planetary gear assembly.
Figure 12F:
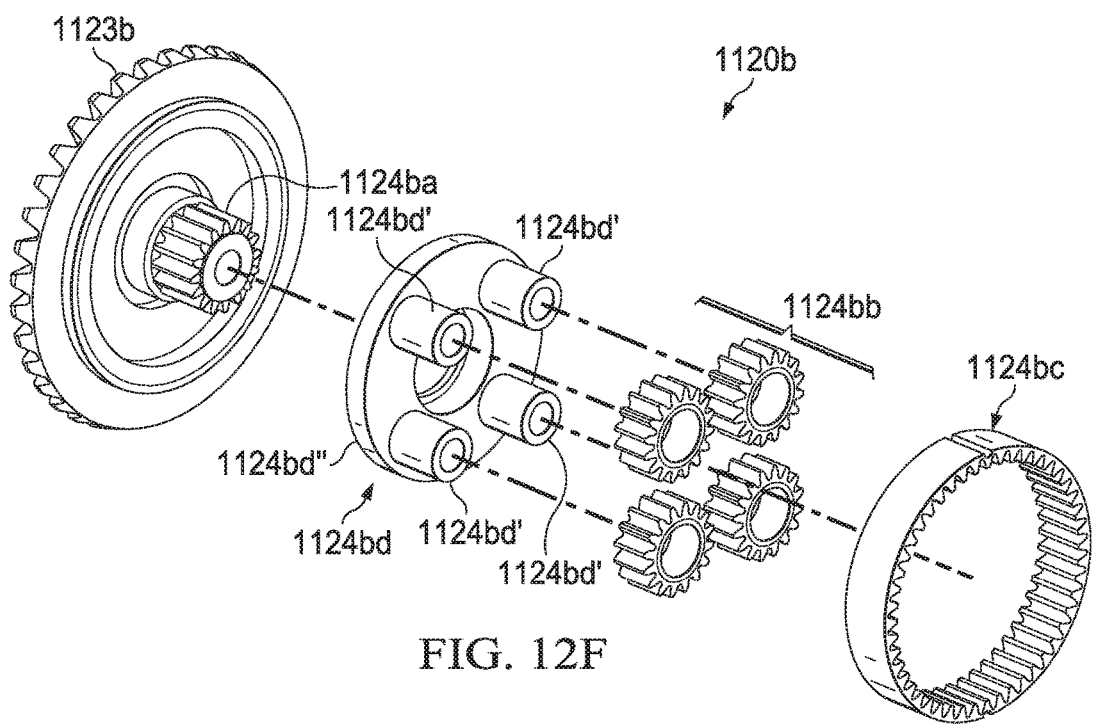
FIG. 12F is an illustration of an exploded perspective view of an example embodiment of a proximal elbow planetary gear assembly.

FIG. 12E illustrates a side view and FIG. 12F illustrates an exploded perspective view of an example embodiment of the proximal elbow planetary gear assembly 1124*b*. The proximal elbow planetary gear assembly 1124*b* may have a central axis corresponding to axis C. The proximal elbow planetary gear assembly 1124*b* may include a proximal elbow sun gear 1124*ba*. The proximal elbow sun gear 1124*ba* may be drivable by the second proximal elbow bevel gear 1123*b* so as to rotate relative to axis C. The proximal elbow sun gear 1124*ba* and/or the second proximal elbow bevel gear 1123*b* may include an extended portion so as to enable a spacing between the each other and allow for cabling to run through such spacing.

The proximal elbow planetary gear assembly 1124*b* may also include a plurality of proximal elbow planetary (or planet) gears 1124*bb*. For example, the proximal elbow planetary gear assembly 1124*b* may include 4 or more proximal elbow planetary gears 1124*bb*. Each of the proximal elbow planetary gears 1124*bb* may be configured to rotate relative to its central axis. The proximal elbow planetary gears 1124*bb* may be drivable by the proximal elbow sun gear 1124*ba* to collectively rotate around axis C.

The proximal elbow planetary gear assembly 1124*b* may also include a proximal elbow ring gear 1124*bc*. The proximal elbow ring gear 1124*bc* may be fixed or locked from rotating relative to axis C in example embodiments so as to enable the plurality of proximal elbow planetary gears 1124*bb* to collectively rotate around axis C.

The proximal elbow planetary gear assembly 1124*b* may also include a proximal elbow planetary gear carrier 1124*bd*. The proximal elbow planetary gear carrier 1124*bd* may have a plurality of first ends 1124*bd'* connected to the plurality of proximal elbow planetary gears 1124*bb*. The proximal elbow planetary gear carrier 1124*bd* may also have a second end 1124*bd''* connected to a portion of a proximal end of the distal elbow joint 1120*a*.

In this regard, when the proximal elbow sun gear 1124*ba* is driven by the second proximal elbow bevel gear 1123*b* to rotate relative to axis C, the proximal elbow sun gear 1124*ba* in turn drives the plurality of proximal elbow planetary gears 1124*bb* to collectively rotate relative to axis C. Such collective rotation of the plurality of proximal elbow planetary gears 1124*bb* around axis C in turn drives the proximal elbow planetary gear carrier 1124*bd* to rotate relative to axis C (via the connection between the first ends 1124*bd'* of the proximal elbow planetary gear carrier 1124*bd* and the plurality of proximal elbow planetary gears 1124*bb*). Such rotation of the proximal elbow planetary gear carrier 1124*bd* around axis C in turn drives the distal elbow joint 1120*a* to rotate (or pivotally rotate) relative to axis C (e.g., in the Direction C, as illustrated in at least FIG. 11B) (via the connection between the second end 1124*bd''* of the proximal elbow planetary gear carrier 1124*bd* and the proximal end of the distal elbow joint 1120*a*).

A gear ratio between the second proximal elbow bevel gear 1123*b* and the proximal elbow planetary gear assembly 1124*b* may be between about 1:2 to 1:8 (e.g., 1:5).

Accordingly, distal elbow joint 1120*a* (and the forearm segment 1100 attached to the distal elbow joint 1120*a*) may be driven to rotate (or pivotally rotate) relative to axis C (or rotate relative to the proximal elbow joint 1120*b*) by driving the second distal motor 1144, which in turn drives the first proximal elbow gear stage (which includes the first proximal elbow bevel gear 1122*b* and the second proximal elbow bevel gear 1123*b*), which in turn drives the second proximal elbow gear stage (which includes the proximal elbow planetary gear assembly 1124*b* having the proximal elbow sun gear 1124*ba*, the proximal elbow planetary gears 1124*bb*, the proximal elbow ring gear 1124*bc*, and the proximal elbow planetary gear carrier 1124*bd*), which in turn drives the distal elbow joint 1120*a* (and the forearm segment 1100 attached to the distal elbow joint 1120*a*) to rotate relative to axis C.

Put differently, the forearm segment 1100 (which is attached to the distal elbow joint 1120*a*) may be driven to rotate (or pivotally rotate) relative to axis C (or rotate relative to the proximal elbow joint 1120*b*) by driving the second distal motor 1144, which in turn drives the first proximal elbow gear stage (which includes the first proximal elbow bevel gear 1122*b* and the second proximal elbow bevel gear 1123*b*), which in turn drives the second proximal elbow gear stage (which includes the proximal elbow planetary gear assembly 1124*b* having the proximal elbow sun gear 1124*ba*, the proximal elbow planetary gears 1124*bb*, the proximal elbow ring gear 1124*bc*, and the proximal elbow planetary gear carrier 1124*bd*), which in turn drives the forearm segment 1100 (which is attached to the distal elbow joint 1120*a*) to rotate relative to axis C.

A gear or magnification ratio for the proximal elbow joint assembly may be between about 1:10 to 1:30 (e.g., 1:20).

The proximal elbow joint assembly may be or include any other gear configuration for driving the forearm segment 1100, including those described in the present disclosure. For example, the proximal elbow joint assembly may include any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure.

Shoulder Coupling Joint Assembly (e.g., Shoulder Coupling Joint Assembly 1160).

Figure 13A:
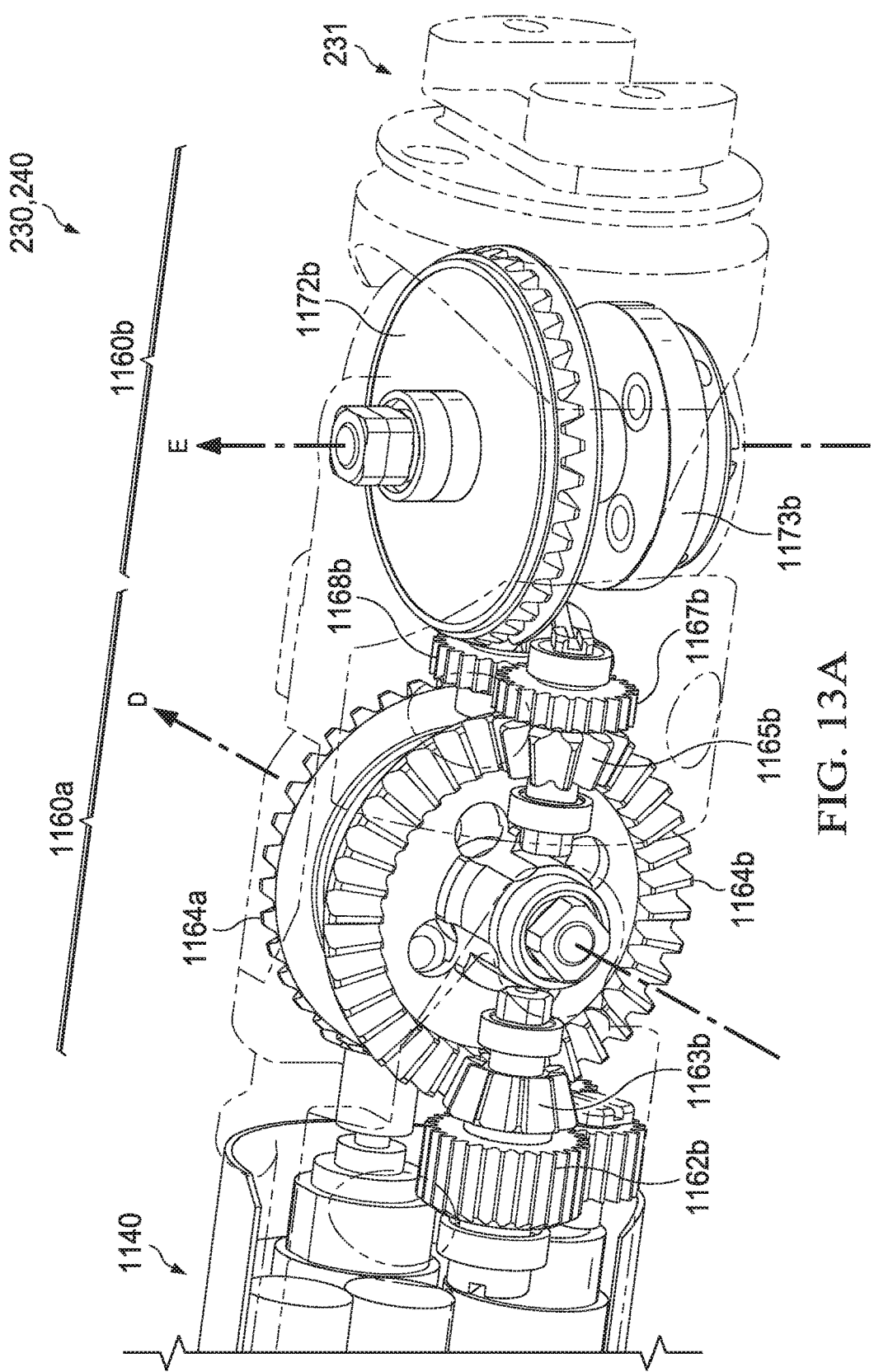
FIG. 13A is an illustration of a perspective view of an example embodiment of a shoulder coupling joint assembly.
Figure 13B:
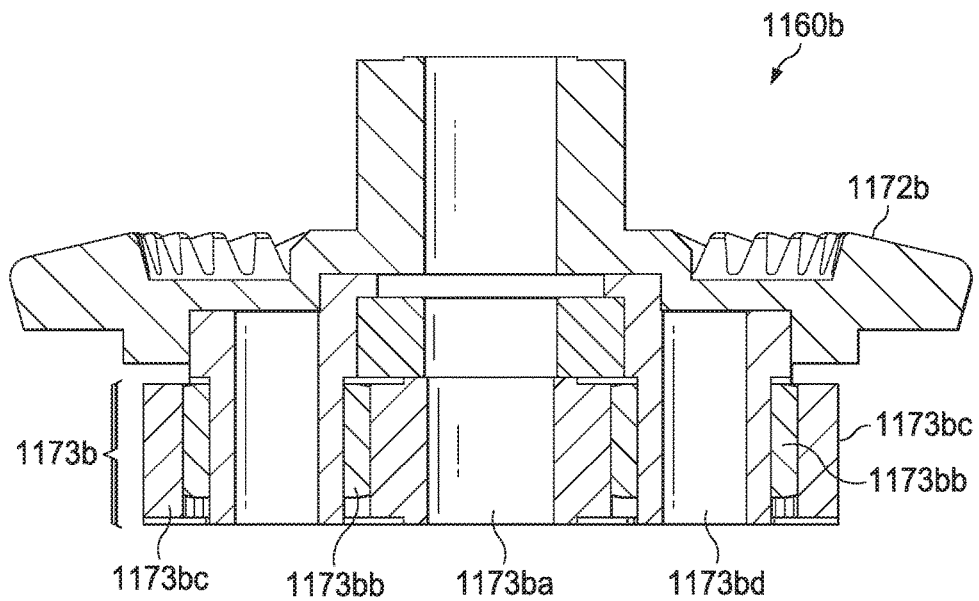
FIG. 13B is an illustration of a side view of an example embodiment of a distal shoulder planetary gear assembly.
Figure 13C:
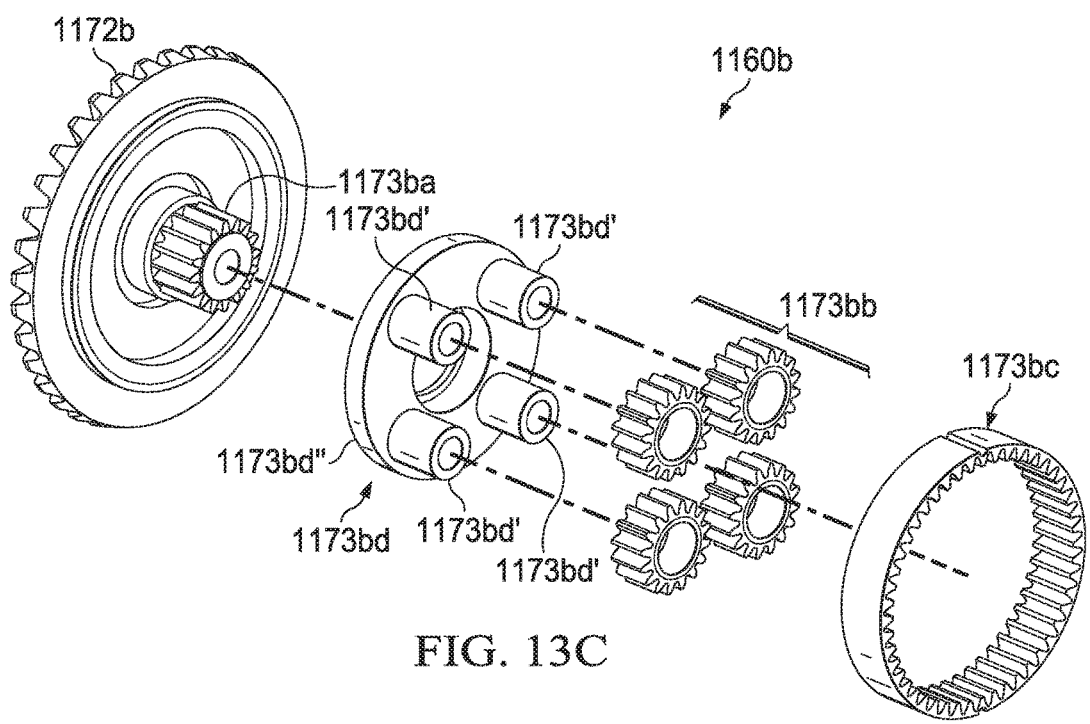
FIG. 13C is an illustration of an exploded perspective view of an example embodiment of a distal shoulder planetary gear assembly.
Figure 13D:
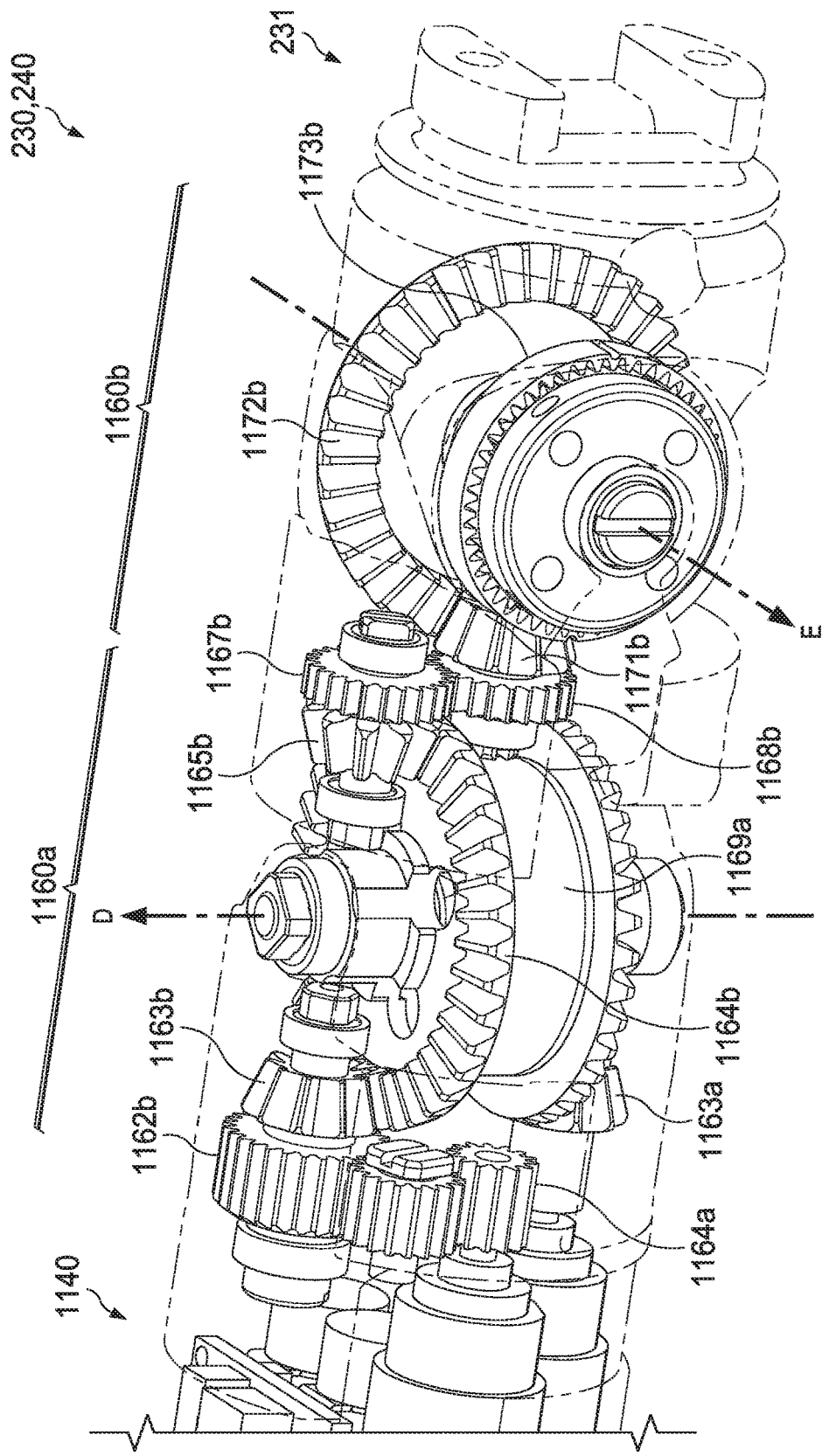
FIG. 13D is an illustration of a perspective view of an example embodiment of a shoulder coupling joint assembly.
Figure 15A:
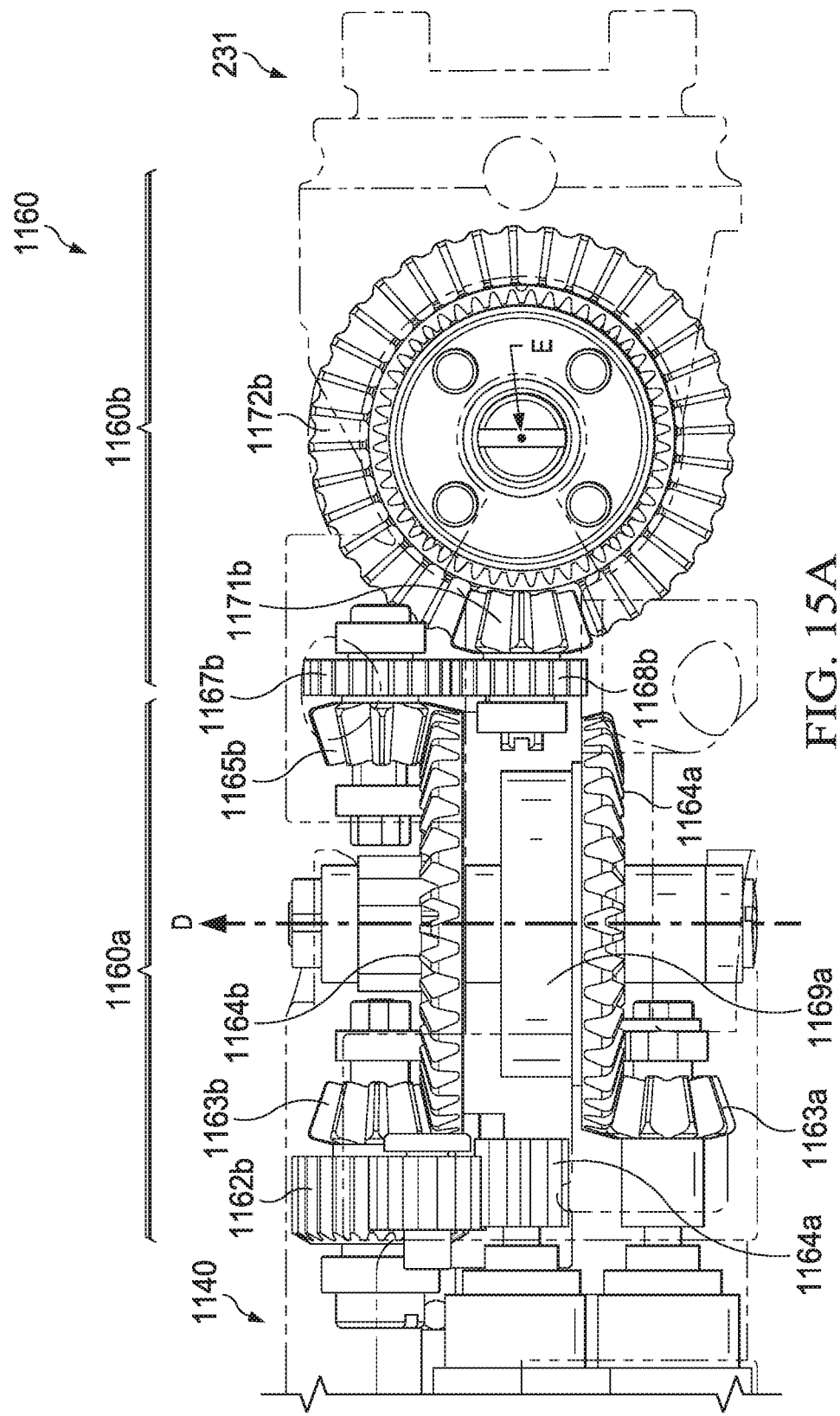
FIG. 15A is an illustration of a side view of an example embodiment of a shoulder coupling joint assembly.
Figure 15B:
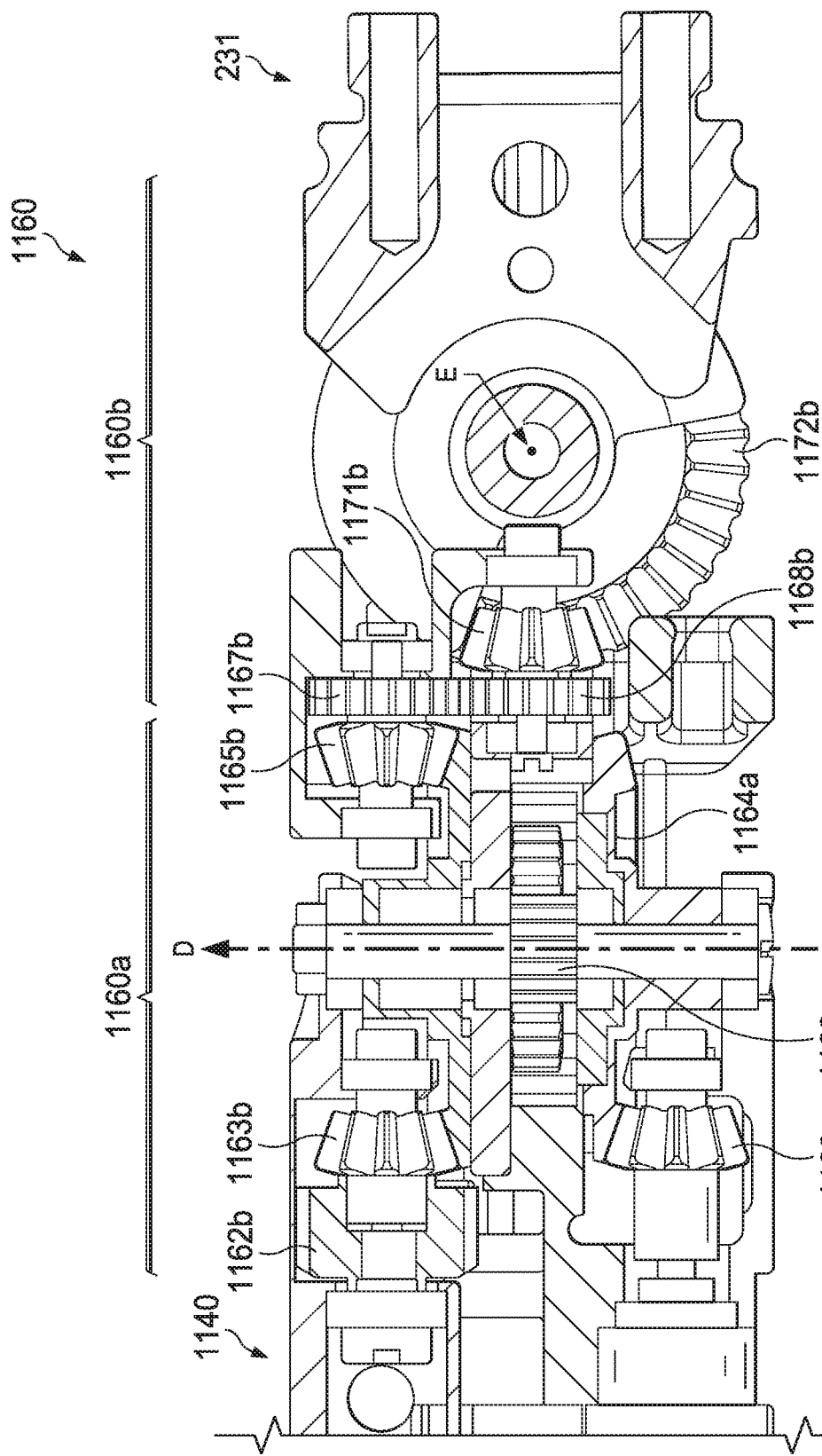
FIG. 15B is an illustration of a cross-sectional side view of an example embodiment of a shoulder coupling joint assembly.
Figure 15C:
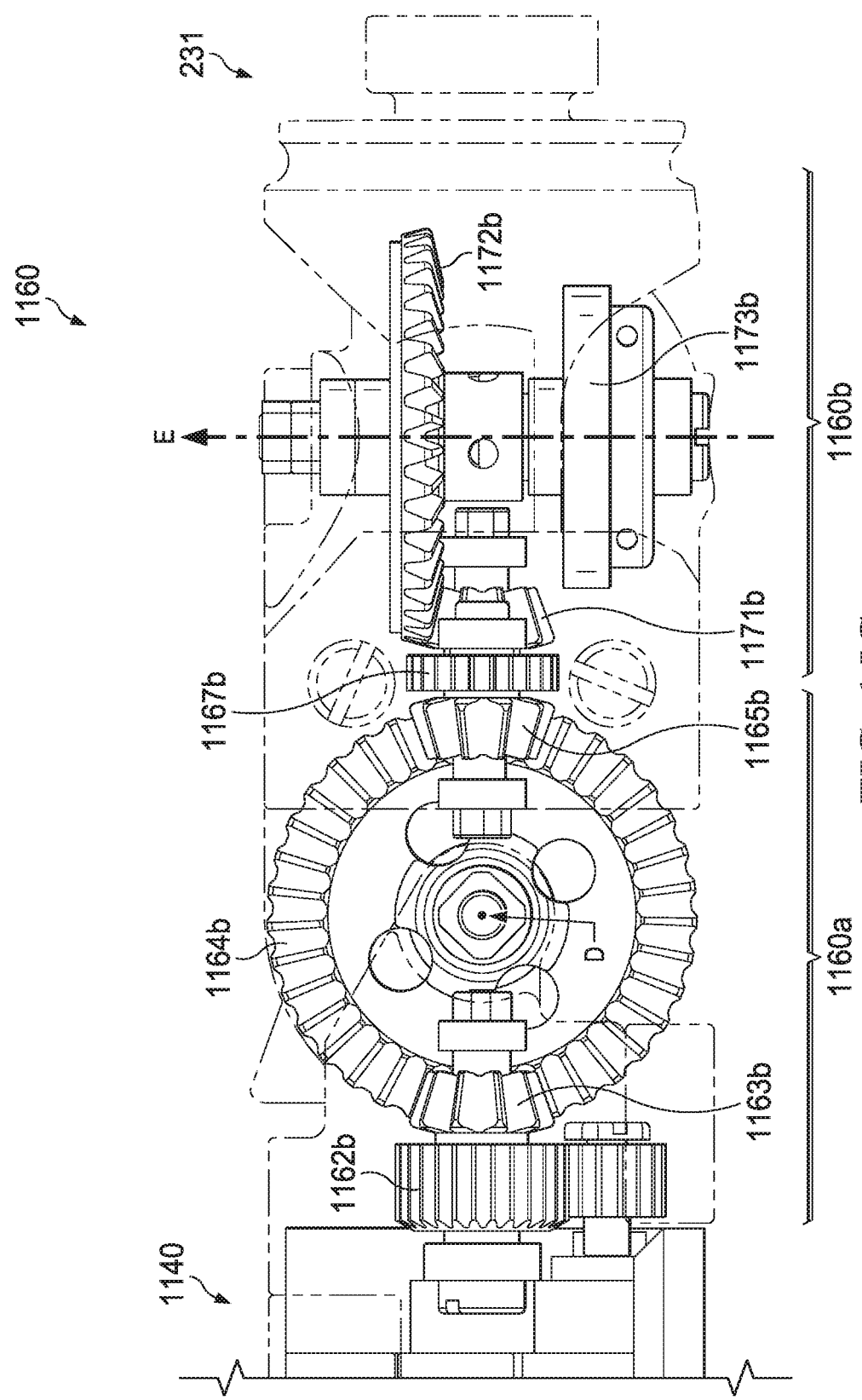
FIG. 15C is an illustration of is another side view of an example embodiment of a shoulder coupling joint assembly.
Figure 15D:
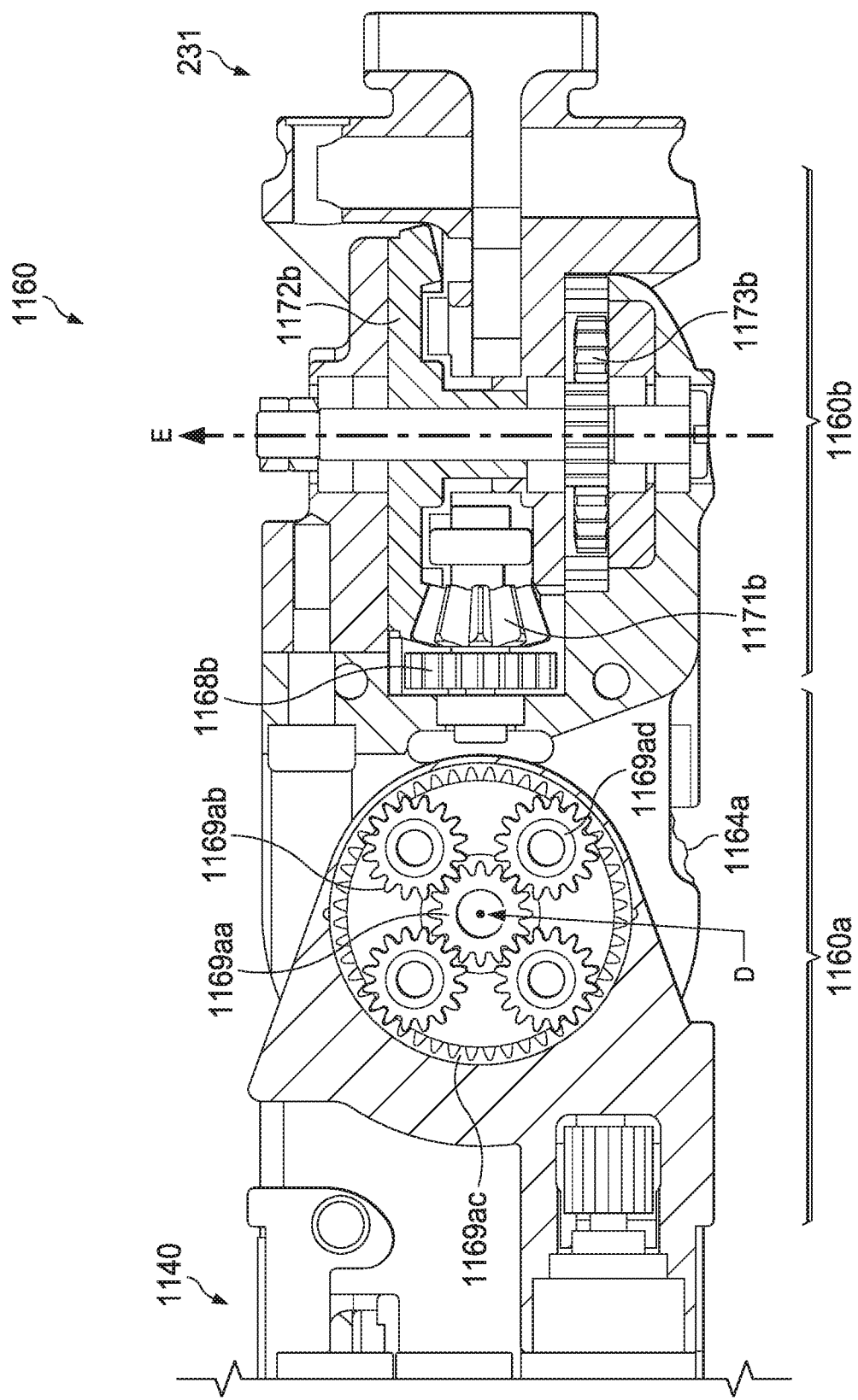
FIG. 15D is an illustration of another cross-sectional side view of an example embodiment of a shoulder coupling joint assembly.

As illustrated in FIGS. 13A and 13D, the side views of FIG. 15A and FIG. 15C, and the cross-sectional side views of FIG. 15B and FIG. 15D, an example embodiment of the arm assembly 230, 240 may include a shoulder coupling joint assembly (e.g., shoulder coupling joint assembly 1160). The shoulder coupling joint assembly 1160 may include a distal shoulder joint 1160*a* and a proximal shoulder joint 1160*b*.

The distal shoulder joint 1160*a* may have an axis of rotation D, as illustrated in at least FIGS. 11B, 11C, 13A, 13D, and 15A-D. The distal shoulder joint 1160*a* may be configured to enable the upper arm segment 1140 to rotate (or pivotally rotate) relative to axis D. Put differently, the distal shoulder joint 1160*a* may be configured to enable the upper arm segment 1140 to rotate (or pivotally rotate) relative to the distal shoulder joint 1160*a*. As further described below and in the present disclosure, such rotation relative to axis D may be driven by the first proximal motor 1146 and distal shoulder joint subassembly.

The proximal shoulder joint 1160*b* may have an axis of rotation E, as illustrated in at least FIGS. 11B, 11C, 13A, 13D, and 15A-D. The proximal shoulder joint 1160*b* may be configured to enable the distal shoulder joint 1160*a* (and the upper arm segment 1140 attached to the distal shoulder joint 1160*a*) to rotate (or pivotally rotate) relative to axis E. Put differently, the proximal shoulder joint 1160*b* may be configured to enable the distal shoulder joint 1160*a* (and the upper arm segment 1140 attached to the distal shoulder joint 1160*a*) to rotate (or pivotally rotate) relative to the proximal shoulder joint 1160*b*.

Put differently, the proximal shoulder joint 1160*b* may be configured to enable the upper arm segment 1140 to rotate (or pivotally rotate) relative to the proximal shoulder joint 1160*b*. The rotational axis E of proximal shoulder joint 1160*b* may not be parallel to the rotational axis D of the distal shoulder joint 1160*a*. For example, the rotational axis E of proximal shoulder joint 1160*b* may be orthogonal to the rotational axis D of the distal shoulder joint 1160*a*. As further described below and in the present disclosure, such rotation relative to axis E may be driven by the second proximal motor 1148 and proximal shoulder joint subassembly.

(i) The Distal Shoulder Joint Subassembly.

In an example embodiment, the first proximal motor 1146 may drive the distal shoulder joint subassembly so as to cause the upper arm segment 1140 to rotate (or pivotally rotate) relative to the distal shoulder joint 1160*a* (or relative to axis D, as depicted by the Direction D illustrated in FIG. 11C). As illustrated in at least FIGS. 11B, 11C, 13A, 13D, and 15A-D, the distal shoulder joint subassembly includes a plurality of gears. More specifically, the distal shoulder joint subassembly includes a gear train system having a plurality of gear stages.

The distal shoulder joint subassembly may include a first distal shoulder gear stage. The first distal shoulder gear stage may include a first distal shoulder bevel gear (e.g., first distal shoulder bevel gear 1168*a*, as illustrated in at least FIGS. 13A, 13D, 15C, and 15D). The distal shoulder joint subassembly may also include one or more gears between the first proximal motor drive portion 1146*a* and the first distal shoulder bevel gear 1168*a*, such as one or more spur gears 1164*a*, 1165*a*, 1166*a*. Alternatively, the distal shoulder joint subassembly may be configured in such a way that the first proximal motor drive portion 1146*a* directly drives the first distal shoulder bevel gear 1168*a* (e.g., without the one or more spur gears 1164*a*, 1165*a*, and 1166*a*). The distal shoulder joint subassembly may also include one or more connectors or the like between the first proximal motor drive portion 1146*a* and the first distal shoulder bevel gear 1168*a*, such as connector 1162*a*, 1163*a*, 1167*a* (as illustrated in at least FIG. 13D).

Alternatively, as illustrated in at least FIGS. 15C and 15D, the first distal shoulder bevel gear 1168*a* may be configured so as to be driven more directly by the first proximal motor drive portion 1146*a* in example embodiments, which is recognized in the present disclosure to enable a reduction in total length of the arm assembly 230, 240. For example, spur gear 1166*a* may be directly coupled to first distal shoulder bevel gear 1168*a* (e.g., without connector 1167*a*), as illustrated in at least FIG. 15C.

The first distal shoulder gear stage may also include a second distal shoulder bevel gear (e.g., second distal shoulder bevel gear 1169*a*, as illustrated in at least FIGS. 13D, 15C, and 15D). The second distal shoulder bevel gear 1169*a* may be drivable by the first distal shoulder bevel gear 1168*a* so as to rotate relative to axis D (the second distal shoulder bevel gear 1169a may have a central axis of rotation corresponding to axis D).

A gear ratio between the first distal shoulder bevel gear 1168a and the second distal shoulder bevel gear 1169a may be between about 1:2 to 1:5 (e.g., 1:3).

The distal shoulder joint subassembly may include a second distal shoulder gear stage. The second distal shoulder gear stage may include a distal shoulder planetary gear assembly (e.g., distal shoulder planetary gear assembly 1170a, as illustrated in at least FIGS. 11C, 13D, and 15C). The distal shoulder joint subassembly may also include one or more connectors (not shown) and/or the second distal shoulder bevel gear 1169a and/or distal shoulder sun gear 1170aa may have an extended portion (not shown) between the second distal shoulder bevel gear 1169a and the distal shoulder planetary gear assembly 1170a, which is recognized in the present disclosure to enable improved spacing for cabling to pass through the shoulder coupling joint assembly 1160 (e.g., pass through between the second distal shoulder bevel gear 1169a and the distal shoulder planetary gear assembly 1170a).

Alternatively, as illustrated in at least FIGS. 11B, 13D, and 15C, the second distal shoulder bevel gear 1169a may be directly coupled (or connected or secured) to the distal shoulder planetary gear assembly 1170a (i.e., the second distal shoulder bevel gear 1169a directly coupled or connected or secured to distal shoulder sun gear 1170aa) in example embodiments.

Figure 13E:
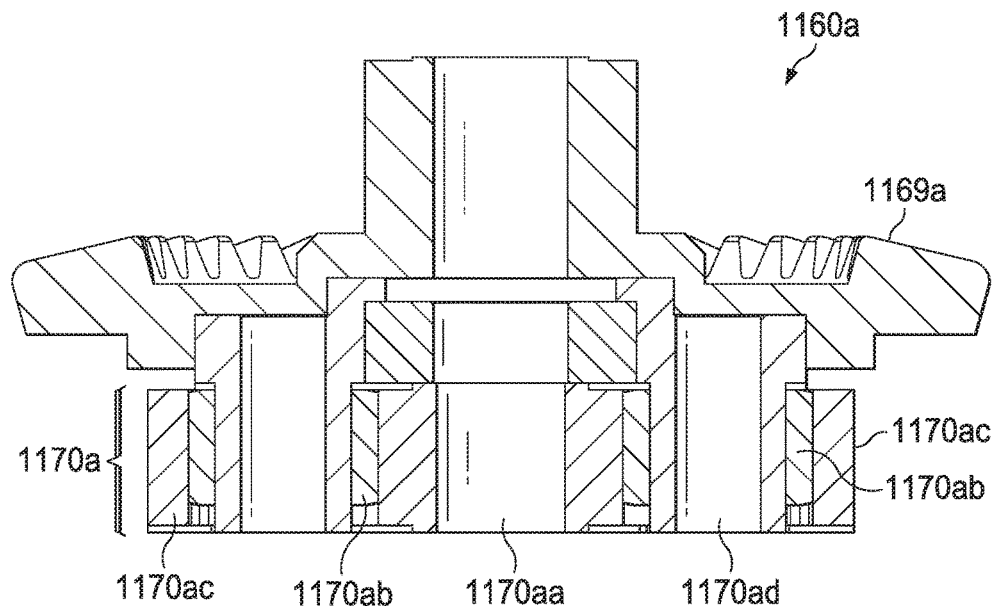
FIG. 13E is an illustration of a side view of an example embodiment of a proximal shoulder planetary gear assembly.
Figure 13F:
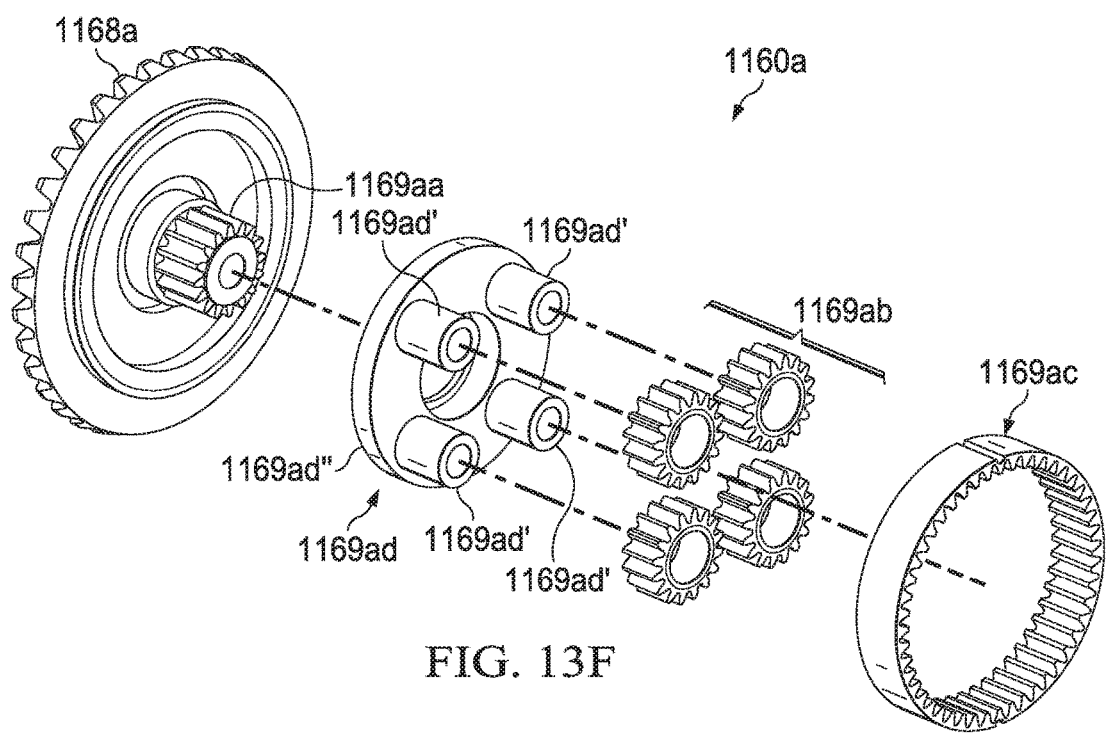
FIG. 13F is an illustration of an exploded perspective view of an example embodiment of a proximal shoulder planetary gear assembly.

FIG. 13E illustrates a side view and FIG. 13F illustrates an exploded perspective view of an example embodiment of the distal shoulder planetary gear assembly 1170a. The distal shoulder planetary gear assembly 1170a may have a central axis corresponding to axis D. The distal shoulder planetary gear assembly 1170a may include a distal shoulder sun gear 1170aa. The distal shoulder sun gear 1170aa may be drivable by the second distal shoulder bevel gear 1170a so as to rotate relative to axis D. The distal shoulder sun gear 1170aa and/or the second distal shoulder bevel gear 1169a may include an extended portion (not shown) so as to enable a spacing between the each other and allow for cabling to run through such spacing.

The distal shoulder planetary gear assembly 1170a may also include a plurality of distal shoulder planetary (or planet) gears 1170ab. For example, the distal shoulder planetary gear assembly 1170a may include 4 or more distal shoulder planetary gears 1170ab. Each of the distal shoulder planetary gears 1170ab may be configured to rotate relative to its central axis. The distal shoulder planetary gears 1170ab may be drivable by the distal shoulder sun gear 1170aa to collectively rotate around axis D.

The distal shoulder planetary gear assembly 1170a may also include a distal shoulder ring gear 1170ac. The distal shoulder ring gear 1170ac may be fixed or locked from rotating relative to axis D in example embodiments so as to enable the plurality of distal shoulder planetary gears 1170ab to collectively rotate around axis D.

The distal shoulder planetary gear assembly 1170a may also include a distal shoulder planetary gear carrier 1170ad. The distal shoulder planetary gear carrier 1170ad may have a plurality of first ends 1170ad' connected to the plurality of proximal elbow planetary gears 1170ab. The distal shoulder planetary gear carrier 1170ad may also have a second end 1170ad'' connected to a portion of a proximal end 1140b of the upper arm segment 1140.

In this regard, when the distal shoulder sun gear 1170aa is driven by the second distal shoulder bevel gear 1169a to rotate relative to axis D, the distal shoulder sun gear 1170aa in turn drives the plurality of distal shoulder planetary gears 1170ab to collectively rotate relative to axis D. Such collective rotation of the plurality of distal shoulder planetary gears 1170ab around axis D in turn drives the distal shoulder planetary gear carrier 1170ad to rotate relative to axis D (via the connection between the first ends 1170ad' of the distal shoulder planetary gear carrier 1170ad and the plurality of distal shoulder planetary gears 1170ab). Such rotation of the distal shoulder planetary gear carrier 1170ad around axis C in turn drives the upper arm segment 1140 to rotate (or pivotally rotate) relative to axis D (e.g., in the Direction D, as illustrated in at least FIG. 11C) (via the connection between the second end 1170ad'' of the distal shoulder planetary gear carrier 1170ad and the proximal end 1140b of the upper arm segment 1140).

A gear ratio between the second distal shoulder bevel gear 1169a and the distal shoulder planetary gear assembly 1170a may be between about 1:2 to 1:8 (e.g., 1:5).

Accordingly, the upper arm segment 1140 may be driven to rotate (or pivotally rotate) relative to axis D (or relative to the distal shoulder joint 1160b) by driving the first proximal motor 1146, which in turn drives the first distal shoulder gear stage (which includes the first distal shoulder bevel gear 1168a and the second distal shoulder bevel gear 1169a), which in turn drives the second distal shoulder gear stage (which includes the distal shoulder planetary gear assembly 1170a having the distal shoulder sun gear 1170aa, the distal shoulder planetary gears 1170ab, the distal shoulder ring gear 1170ac, and the distal shoulder planetary gear carrier 1170ad), which in turn drives the upper arm segment 1140 to rotate relative to axis D.

A gear or magnification ratio for the distal shoulder joint assembly may be between about 1:20 to 1:50 (e.g., 1:30).

The distal shoulder joint assembly may be or include any other gear configuration for driving the upper arm segment 1140, including those described in the present disclosure. For example, the distal shoulder joint assembly may include any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure.

(ii) The Proximal Shoulder Joint Subassembly.

In an example embodiment, the second proximal motor 1148 may drive the proximal shoulder joint subassembly so as to cause the distal shoulder joint 1160a (and the upper arm segment 1140 attached to the distal shoulder joint 1160a) to rotate (or pivotally rotate) relative to the proximal shoulder joint 1160b (or relative to axis E, as depicted by the Direction E illustrated in FIG. 11B).

Put differently, the second proximal motor 1148 may drive the proximal shoulder joint subassembly so as to cause the upper arm segment 1140 (which is attached to the distal shoulder joint 1160a) to rotate (or pivotally rotate) relative to the proximal shoulder joint 1160b (or relative to axis E, as depicted by the Direction E illustrated in FIG. 11B). As illustrated in at least FIGS. 11B, 11C, 13A, 13D, and 15A-D, the proximal shoulder joint subassembly includes a plurality of gears. More specifically, the proximal shoulder joint subassembly includes a gear train system having a plurality of gear stages.

The proximal shoulder joint subassembly may include a first proximal shoulder gear stage. The first proximal shoulder gear stage may include a first proximal shoulder bevel gear (e.g., first proximal shoulder bevel gear 1163*b*, as illustrated in at least FIGS. 13A, 15A, 15C, and 15D). The proximal shoulder joint subassembly may also include one or more gears between the second proximal motor drive portion 1148*a* and the first proximal shoulder bevel gear 1163*ba*, such as one or more spur gears (not shown). The proximal shoulder joint subassembly may also include one or more connectors or the like between the second proximal motor drive portion 1148*a* and the first proximal shoulder bevel gear 1163*b*, such as connector 1161*b*, 1162*b* (as illustrated in at least FIG. 13A).

Alternatively, as illustrated in at least FIGS. 15A and 15C, the first proximal shoulder bevel gear 1163*a* may be configured so as to be driven directly by the second proximal motor drive portion 1148*a* in example embodiments (e.g., as illustrated in at least FIGS. 15C and 15D), which is recognized in the present disclosure to enable a reduction in total length of the arm assembly 230, 240.

The first proximal shoulder gear stage may also include a second proximal shoulder bevel gear (e.g., second proximal shoulder bevel gear 1164*b*, as illustrated in at least FIGS. 13A, 13D, 15A, 15C, and 15D). The second proximal shoulder bevel gear 1164*b* may be drivable by the first proximal shoulder bevel gear 1163*b* so as to rotate relative to axis D (the second proximal shoulder bevel gear 1164*b* may have a central axis of rotation corresponding to axis D).

A gear ratio between the first proximal shoulder bevel gear 1163*b* and the second proximal shoulder bevel gear 1164*b* may be between about 1:2 to 1:5 (e.g., 1:3).

The first proximal shoulder gear stage may also include a third proximal shoulder bevel gear (e.g., proximal shoulder elbow bevel gear 1165*b*, as illustrated in at least FIGS. 13A, 15A, 15C, and 15D). The third proximal shoulder bevel gear 1165*b* may be drivable by the second proximal shoulder bevel gear 1164*b* so as to rotate.

A gear ratio between the second proximal shoulder bevel gear 1164*b* and the third proximal shoulder bevel gear 1165*b* may be between about 2:1 to 5:1 (e.g., 3:1).

The proximal shoulder joint subassembly may include a second proximal shoulder gear stage. The second proximal shoulder gear stage may include a first proximal shoulder spur gear (e.g., first proximal shoulder spur gear 1167*b*, as illustrated in at least FIGS. 13A, 15A, 15C, and 15D). The proximal shoulder joint subassembly may also include one or more connectors between the third proximal shoulder bevel gear 1165*b* and the first proximal shoulder spur gear 1167*b*, such as connector 1166*b* (as illustrated in at least FIG. 13A).

Alternatively, as illustrated in at least FIGS. 15A and 15C, the first proximal shoulder spur gear 1167*b* may be directly coupled (or connected or secured) to the third proximal shoulder bevel gear 1165*b* in example embodiments, which is recognized in the present disclosure to enable a reduction in total length of the arm assembly 230, 240.

The second proximal shoulder gear stage may also include a second proximal shoulder spur gear (e.g., second proximal shoulder spur gear 1168*b*, as illustrated in at least FIGS. 13A, 15C, and 15D). The second proximal shoulder spur gear 1168*b* may be drivable by the first proximal shoulder spur gear 1167*b* so as to rotate.

A gear ratio between the first proximal shoulder spur gear 1167*b* and the second proximal shoulder spur gear 1168*b* may be between about 1:1 to 1:4 (e.g., 1:2).

The second proximal shoulder gear stage may also include a third proximal shoulder spur gear (e.g., third proximal shoulder spur gear 1169*b*, as illustrated in at least FIG. 13A). The third proximal shoulder spur gear 1169*b* may be drivable by the second proximal shoulder spur gear 1168*b* so as to rotate.

A gear ratio between the second proximal shoulder spur gear 1168*b* and the third proximal shoulder spur gear 1169*b* may be between about 1:1 to 1:4 (e.g., 1:2).

The proximal shoulder joint subassembly may include a third proximal shoulder gear stage. The third proximal shoulder gear stage may include a fourth proximal shoulder bevel gear (e.g., fourth proximal shoulder bevel gear 1171*b*, as illustrated in at least FIGS. 13A, 15A, 15B, 15C, and 15D). The proximal shoulder joint subassembly may also include one or more connectors or the like between the third proximal shoulder spur gear 1169*b* and the fourth proximal shoulder bevel gear 1171*b*, such as connector 1170*b* (as illustrated in at least FIG. 13A).

Alternatively, as illustrated in at least FIGS. 15B-D, the fourth proximal shoulder bevel gear 1171*b* may be directly coupled (or connected or secured) to the third proximal shoulder spur gear 1169*b* in example embodiments, which is recognized in the present disclosure to enable a reduction in total length of the arm assembly 230, 240.

The third proximal shoulder gear stage may also include a fifth proximal shoulder bevel gear (e.g., fifth proximal shoulder bevel gear 1172*b*, as illustrated in at least FIGS. 13A and 15A-D). The fifth proximal shoulder bevel gear 1172*b* may be drivable by the fourth proximal shoulder bevel gear 1171*b* so as to rotate relative to axis E (the fifth proximal shoulder bevel gear 1172*b* may have a central axis of rotation corresponding to axis E).

A gear ratio between the fourth proximal shoulder bevel gear 1171*b* and the fifth proximal shoulder bevel gear 1172*b* may be between about 1:2 to 1:5 (e.g., 1:3).

The proximal shoulder joint subassembly may include a fourth proximal shoulder gear stage. The fourth proximal shoulder gear stage may include a proximal shoulder planetary gear assembly (e.g., proximal shoulder planetary gear assembly 1173*b*, as illustrated in at least FIGS. 11B, 13A, and 15A). The proximal shoulder joint subassembly may also include one or more connectors or the like (not shown) and/or the fifth proximal shoulder bevel gear 1172*b* and/or proximal shoulder sun gear 1173*ba* may have an extended portion (not shown) between the fifth proximal shoulder bevel gear 1172*b* and the proximal shoulder planetary gear assembly 1173*b*, which is recognized in the present disclosure to enable improved spacing for cabling to pass through the shoulder coupling joint assembly 1160 (e.g., pass through between the fifth proximal shoulder bevel gear 1172*b* and the proximal shoulder planetary gear assembly 1173*b*).

Alternatively, as illustrated in at least FIGS. 11C and 13A, the fifth proximal shoulder bevel gear 1172*b* may be directly coupled (or connected or secured) to the proximal shoulder planetary gear assembly 1173*b* (i.e., the fifth proximal shoulder bevel gear 1172*b* directly coupled or connected or secured to the proximal shoulder sun gear 1173*ba*) in example embodiments.

FIG. 13B illustrates a side view and FIG. 13C illustrates an exploded perspective view of an example embodiment of the proximal shoulder planetary gear assembly 1173*b*. The proximal shoulder planetary gear assembly 1173*b* may have a central axis corresponding to axis E. The proximal shoulder planetary gear assembly 1173*b* may include a proximal shoulder sun gear 1173*ba*. The proximal shoulder sun gear 1173*ba* may be drivable by the fifth proximal shoulder bevel gear 1172*b* so as to rotate relative to axis E. The proximal shoulder sun gear 1173*ba* and/or the fifth proximal shoulder bevel gear 1172*b* may include an extended portion (not shown) so as to enable a spacing between the each other and allow for cabling to run through such spacing.

The proximal shoulder planetary gear assembly 1173*b* may also include a plurality of proximal shoulder planetary (or planet) gears 1173*bb*. For example, the proximal shoulder planetary gear assembly 1173*b* may include 4 or more proximal shoulder planetary gears 1173*bb*. Each of the proximal shoulder planetary gears 1173*bb* may be configured to rotate relative to its central axis. The proximal shoulder planetary gears 1173*bb* may be drivable by the proximal shoulder sun gear 1173*ba* to collectively rotate around axis E.

The proximal shoulder planetary gear assembly 1173*b* may also include a proximal shoulder ring gear 1173*bc*. The proximal shoulder ring gear 1173*bc* may be fixed or locked from rotating relative to axis E in example embodiments so as to enable the plurality of proximal shoulder planetary gears 1173*bb* to collectively rotate around axis E.

The proximal shoulder planetary gear assembly 1173*b* may also include a proximal shoulder planetary gear carrier 1173*bd*. The proximal shoulder planetary gear carrier 1173*bd* may have a plurality of first ends 1173*bd'* connected to plurality of proximal shoulder planetary gears 1173*bb*. The proximal shoulder planetary gear carrier 1173*bd* may also have a second end 1173*bd"* connected to a portion of a proximal end of the distal shoulder joint 1160*a*.

In this regard, when the proximal shoulder sun gear 1173*ba* is driven by the fifth proximal shoulder bevel gear 1172*b* to rotate relative to axis E, the proximal shoulder sun gear 1173*ba* in turn drives the plurality of proximal shoulder planetary gears 1173*bb* to collectively rotate relative to axis E. Such collective rotation of the plurality of proximal shoulder planetary gears 1173*bb* around axis E in turn drives the proximal shoulder planetary gear carrier 1173*bd* to rotate relative to axis E (via the connection between the first ends 1173*bd'* of the proximal shoulder planetary gear carrier 1173*bd* and the plurality of proximal shoulder planetary gears 1173*bb*). Such rotation of the proximal shoulder planetary gear carrier 1173*bd* around axis E in turn drives the distal shoulder joint 1160*a* (and the upper arm segment 1140 attached to the distal shoulder joint 1160*a*) to rotate (or pivotally rotate) relative to axis E (e.g., in the Direction E, as illustrated in at least FIG. 11B) (via the connection between the second end 1173*bd"* of the proximal shoulder planetary gear carrier 1173*bd* and the proximal end of the distal shoulder joint 1140).

A gear ratio between the fifth proximal shoulder bevel gear 1172*b* and the proximal shoulder planetary gear assembly 1173*b* may be between about 1:2 to 1:8 (e.g., 1:5).

Accordingly, the distal shoulder joint 1160*a* (and the upper arm segment 1140 attached to the distal shoulder joint 1160*a*) may be driven to rotate (or pivotally rotate) relative to axis E (or relative to the proximal shoulder joint 1160*b*) by driving the second proximal motor 1148, which in turn drives the first proximal shoulder gear stage (which includes the first proximal shoulder bevel gear 1163*b*, the second proximal shoulder bevel gear 1164*b*, the third proximal shoulder bevel gear 1165*b*), which in turn drives the second proximal shoulder gear stage (which includes the first proximal shoulder spur gear 1167*b*, the second proximal shoulder spur gear 1168*b*, and the third proximal shoulder spur gear 1169*b*), which in turn drives the third proximal shoulder gear stage (which includes the fourth proximal shoulder bevel gear 1171*b* and the fifth proximal shoulder bevel gear 1172*b*), which in turn drives the fourth proximal shoulder gear stage (which includes the proximal shoulder planetary gear assembly 1173*b* having the proximal shoulder sun gear 1173*ba*, the proximal shoulder planetary gears 1173*bb*, the proximal shoulder ring gear 1173*bc*, and the proximal shoulder planetary gear carrier 1173*bd*), which in turn drives the distal shoulder joint 1160*a* (and the upper arm segment 1140 attached to the distal shoulder joint 1160*a*) to rotate relative to axis E.

Put differently, the upper arm segment 1140 (which is attached to the distal shoulder joint 1160*a*) may be driven to rotate (or pivotally rotate) relative to axis E (or relative to the proximal shoulder joint 1160*b*) by driving the second proximal motor 1148, which in turn drives the first proximal shoulder gear stage (which includes the first proximal shoulder bevel gear 1163*b*, the second proximal shoulder bevel gear 1164*b*, the third proximal shoulder bevel gear 1165*b*), which in turn drives the second proximal shoulder gear stage (which includes the first proximal shoulder spur gear 1167*b*, the second proximal shoulder spur gear 1168*b*, and the third proximal shoulder spur gear 1169*b*), which in turn drives the third proximal shoulder gear stage (which includes the fourth proximal shoulder bevel gear 1171*b* and the fifth proximal shoulder bevel gear 1172*b*), which in turn drives the fourth proximal shoulder gear stage (which includes the proximal shoulder planetary gear assembly 1173*b* having the proximal shoulder sun gear 1173*ba*, the proximal shoulder planetary gears 1173*bb*, the proximal shoulder ring gear 1173*bc*, and the proximal shoulder planetary gear carrier 1173*bd*), which in turn drives the the upper arm segment 1140 (which is attached to the distal shoulder joint 1160*a*) to rotate relative to axis E.

A gear or magnification ratio for the proximal shoulder joint assembly may be between about 1:20 to 1:50 (e.g., 1:30).

The proximal shoulder joint assembly may be or include any other gear configuration for driving the upper arm segment 1140, including those described in the present disclosure. For example, the proximal shoulder joint assembly may include any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure.

Shoulder Segment (e.g., Shoulder Segment 231).

An example embodiment of the shoulder segment 231 is illustrated in at least FIGS. 11A-C. A distal end of the shoulder segment 231 may be securable to the shoulder coupling joint assembly 1160. A proximal end of the shoulder segment 231 may be securable to the port assembly 210. In an example embodiment, the shoulder segment 231 may be securable to and unsecurable from (e.g., detached) the port assembly 210.

In an example embodiment, the shoulder segment 231 may be similar to or the same as the shoulder segment 231 described above and in the present disclosure.

The Assistant Arm Assemblies (e.g., Assistant Arm Assembly 250, 260)

In an example embodiment, the surgical device 200 may comprise one or more assistant arm assemblies (e.g., assistant arm assembly 250 or 260) configurable to be inserted into and attach to the port assembly 210. As illustrated in FIGS. 2A, 2B, 3A, and 3B, one or more of the assistant arm assemblies may be a suction/irrigation assembly 250 or an assistant instrument arm assembly such as a retractor arm assembly 260, and each of them may include a multi-curvable body 252 or 262, respectively, and an anchoring portion, respectively (e.g., similar to the multi-curvable body 222 and anchoring portion 220a of the image capturing assembly 220).

As illustrated in FIGS. 2A, 2B, 3A, and 3B, the suction/irrigation assembly 250 may include an end having a suction port 259 for applying a suction or negative pressure, which may be for use in removing liquids (e.g., blood, etc.) from the cavity of the patient. In respect to the assistant instrument arm assembly 260, the assistant instrument arm assembly 260 may include an end having an instrument 269, such as a gripper, retractor, cutter, needle, or the like, which may be for use in assisting the one or more instrument arm assemblies 230 and/or 240 in performing the surgical action.

As illustrated in the example embodiment of FIGS. 2A, 2B, 3A, and 3B, the assistant arm assemblies 250 and/or 260 may comprise a multi-curvable body 252 and/or 262, respectively, attached to their ends (suction port or instrument, respectively). The multi-curvable body 252 or 262 may be any elongated multi-curvable body similar to that of the image capturing assembly 220 described above and in the present disclosure that can be controlled/configured by the surgical team 904 (such as via the computing device/controller/manipulator/master input device) to, among other things, straighten and/or curve (and hold such a straightness and/or curvature) at one or more of a plurality of locations along the multi-curvable body 252 or 262, curve (and hold such a curvature) in one or more of a plurality of curvatures, and/or straighten and/or curve (and hold such a straightness and/or curvature) in one or more of a plurality of directions. It is to be understood that, when the multi-curvable body 252 or 262 is configured to curve at any location along the multi-curvable body 252 or 262, the curve may be held and/or released (or configured to uncurve, curve less, or straighten) by the surgical team 904 (such as via the computing device/controller/manipulator/master input device).

The multi-curvable body 252 or 262 may be formed in any one or more ways known in the art. For example, the multi-curvable body 252 or 262 may be a unitary or substantially unitary elongated body having a plurality of wires, cables, or the like, distributed/run throughout the multi-curvable body 252 or 262 in such a way that a manipulating, such as a pulling/releasing, shortening/lengthening, tightening/loosening, etc., of one or a combination of such wires, cables, or the like enables the above-mentioned curving of one or more locations of the multi-curvable body 252 or 262 in one or more curvatures and in one or more directions. As another example, the multi-curvable body 252 or 262 may include a plurality of segments, each segment linked to an adjacent segment in such a way that the segment may be controlled/configured to be pivotly positioned in a plurality of positions relative to the adjacent segment. As another example, the multi-curvable body 252 or 262 may include a plurality of springs, gears, motors, etc. for achieving the above-mentioned curving of one or more locations of the multi-curvable body 252 or 262 in one or more curvatures and in one or more directions. It is to be understood in the present disclosure that the multi-curvable body 252 or 262 may also include a combination of one or more of the above-mentioned approaches.

The assistant arm assembly 250 or 260 may be secured to the port assembly 210 in one or more of a plurality of ways, including those described above and in the present disclosure for the instrument arm assemblies 230, 240 and/or the image capturing assembly 220. For example, the assistant arm assembly 250 or 260 may also comprise an anchoring portion (e.g., similar to the anchoring portion 220a of the image capturing assembly 220 and/or the securing portion 231a of the instrument arm assembly 220), respectively, operable to attach (or secure) the assistant arm assembly 250 or 260 to one or more anchor ports 216 of the port assembly 210.

In an example embodiment, the multi-curvable body 252 or 262 may each be substantially cylindrical in shape. The multi-curvable body 252 or 262 may also be formed in any one of a plurality of other shapes, sizes, and/or dimensions without departing from the teachings of the present disclosure.

In an example embodiment, the length of the multi-curvable body 252 or 262 may be between about 170 to 270 mm. In example embodiments, a length of multi-curvable body 252 or 262 may also be adjustable by the surgical team 904 before, during, and/or after insertion of the camera arm assembly into the cavity of the patient. The outer diameter of the multi-curvable body 252 or 262 may be between about 5 to 7 mm. It is to be understood in the present disclosure that the above dimensions are merely an illustration of example embodiments, and as such the dimensions may be smaller or larger than those recited above without departing from the teachings of the present disclosure.

Controller

In example embodiments, the surgical system may include a controller (or computing device, manipulator, and/or master input device). The controller may be configurable to perform one or more of a plurality of operations in and on the surgical system 200. For example, the controller may be configurable to communicate with and/or control one or more elements of the surgical system 200, such as the external anchor 1 or 1000, the port assembly 210, the instrument arm assemblies 230 or 240, the image capturing assembly 220, and/or the assistant arm assemblies 250 or 260. The controller may be accessible and/or controllable by the surgical team 904, and the surgical team may be able to communicate with and/or control the configuring and/or operation of the one or more elements of the surgical system 200. For example, the controller may be configurable to control a movement and action of some or all parts of the instrument arm assemblies 230 or 240, the first gate assembly 212b, the second gate assembly 214b, the movement and action of some or all parts of the image capturing assembly 220 (including the image capturing, temperature control, etc.), the movement and action of some or all parts of the multi-curvable body 222 of the image capturing assembly 220, the movement and action of some or all parts of the multi-curvable body 252 or 262 of the assistant arm assemblies, the movement and action of some or all parts of the assistant arm assemblies 250 or 260, and the like.

Method of Setting Up the Surgical Device 200 in a Forward-Directed Position (e.g., Method 700)

As illustrated in FIG. 7 and FIGS. 8A-E, example embodiments of the surgical device 200 may be configurable to perform a forward-directed surgical action or procedure in one of a plurality of ways. In an example embodiment, the external anchor 1 may be provided and installed/anchored to the stationary object. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210*a*, secured to the anchor ports 216, and configured in the cavity of the patient. A surgical action or procedure may then be performed in any part, area, and/or quadrant of the cavity of the patient using the surgical device 200. These processes will now be described below with references to at least FIGS. 7, 8A-E, 9B, and 10B.

(1) Providing the External Anchor and Installing the Port Assembly.

In an example embodiment, the external anchor 1 may be provided and installed/anchored to one or more stationary objects, such as a side rail 300 of a surgical table/bed, as illustrated in FIGS. 1A and 1B. One or more segments 2, 6, 10, and 14 of the external anchor 1 may cooperate using one or more joints 4, 8, 12, and 16 of the external anchor 1 to fix the position (including orientation) of the port assembly 210 in or about the opening of the patient.

In an example embodiment, as illustrated in FIGS. 10A and 10B, the external anchor 1 may comprise a controllable swivel assembly 1000 operable to provide one or more additional in vitro degrees of freedom, such as via a first swivel portion 1002, second swivel portion 1004, and/or third swivel portion 1006. The controllable swivel assembly 1000 may further comprise a motor 1002*a* for the first swivel portion 1002, a motor 1004*a* for the second swivel portion 1004, a motor 1006*a* for the third swivel portion 1006, one or more supporting arms 1008, and one or more locks 1010.

The first swivel portion 1002 may be operable to provide, as one of the in vitro degrees of freedom, a translational movement of the port assembly 210 along an axis defined by the elongated length of the port assembly 210, as illustrated by the arrow A. In example embodiments, the translational movement, as illustrated by arrow A, provided by the first swivel portion 1002 may be between about 0 to 50 mm.

The controllable swivel assembly 1000 may further comprise a second swivel portion 1004 operable to provide, as another one of the in vitro degrees of freedom, a torsional or rotational movement of the port assembly 210 about an axis depicted by axis Y. In example embodiments, the torsional or rotational movement, as illustrated by the arrow B, provided by the second swivel portion 1004 may be between about +/−180 degrees.

The controllable swivel assembly 1000 may further comprise a third swivel portion 1006 operable to provide, as another one of the in vitro degrees of freedom, a pivotal or rotational movement of the port assembly 210 about an axis perpendicular to the Y-axis, such as the axis depicted by axis Z (which comes out of the page). In example embodiments, the Z-axis or the center of rotation may be located at about opening of the patient, such as at the mid-point of the abdominal wall. In example embodiments, the pivotal or rotational movement, as illustrated by the arrow C, provided by the third swivel portion 1006 may be between about +/−80 degrees.

It is recognized in the present disclosure that the controllable swivel assembly 1000 may comprise the first swivel portion 1002, second swivel portion 1004, and/or third swivel portion 1006 in example embodiments. The controllable swivel assembly 1000 may further comprise other swivel portions (not shown) when more than three in vitro degrees of freedom and/or movements/rotations other than those providable by the first swivel portion 1002, second swivel portion 1004, and third swivel portion 1006 are desired and/or required.

The controllable swivel assembly 1000, including the first swivel portion 1002, the second swivel portion 1004, and/or the third swivel portion 1006, may be controllable either locally or remotely by the surgical team.

In an example embodiment, the port assembly 210 may be installed and secured to the external anchor 1 or 1000. As illustrated in FIGS. 8A-E, the second end 214 of the port assembly 210 may be inserted into the opening of the patient and into the cavity of the patient and the first end 212 of the port assembly 210 may be secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212*b* and the second gate assembly 214*b* may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 2B:
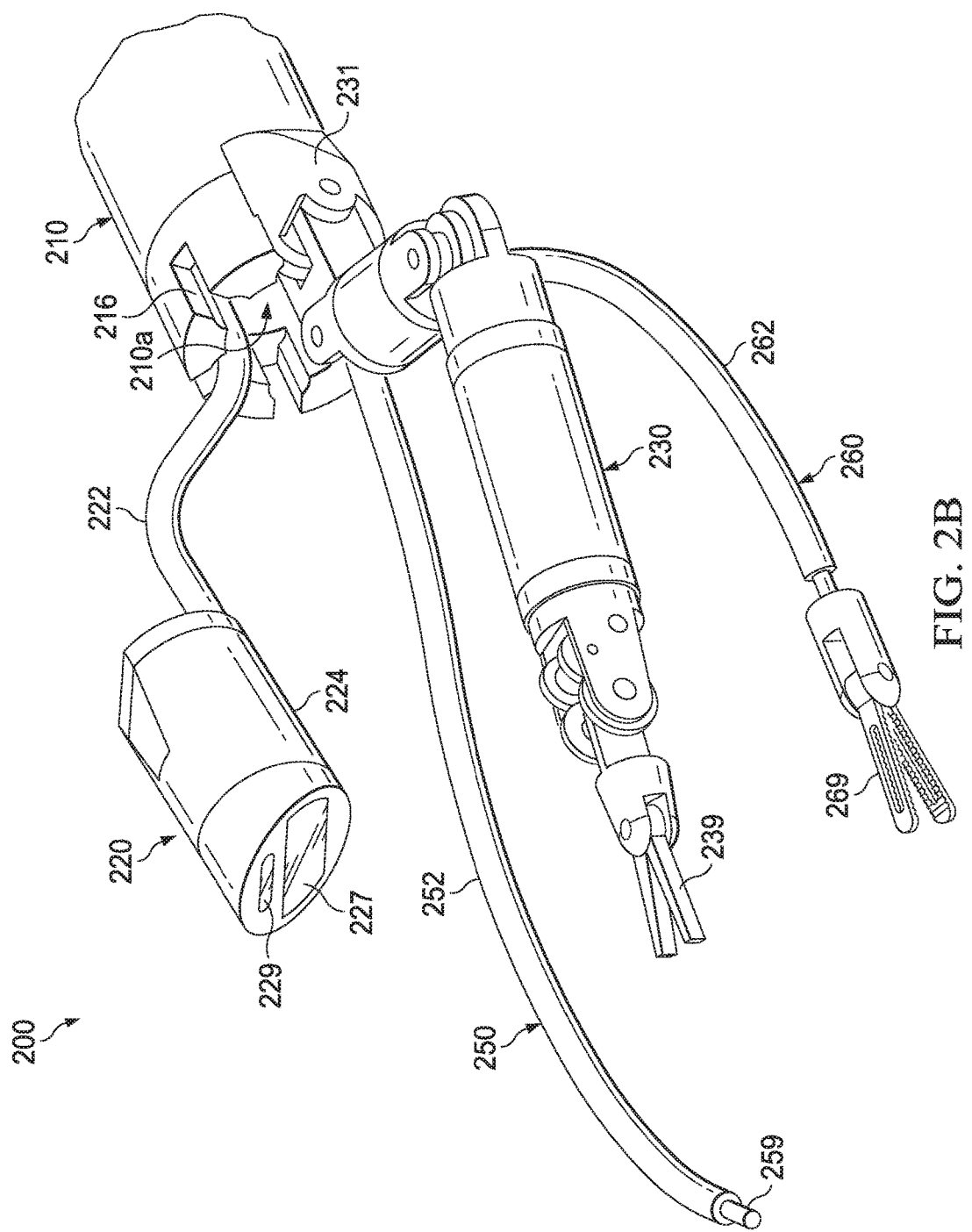
FIG. 2B is an illustration of a perspective view of an example embodiment of a surgical device configured in a forward-directed position.
Figure 2C:
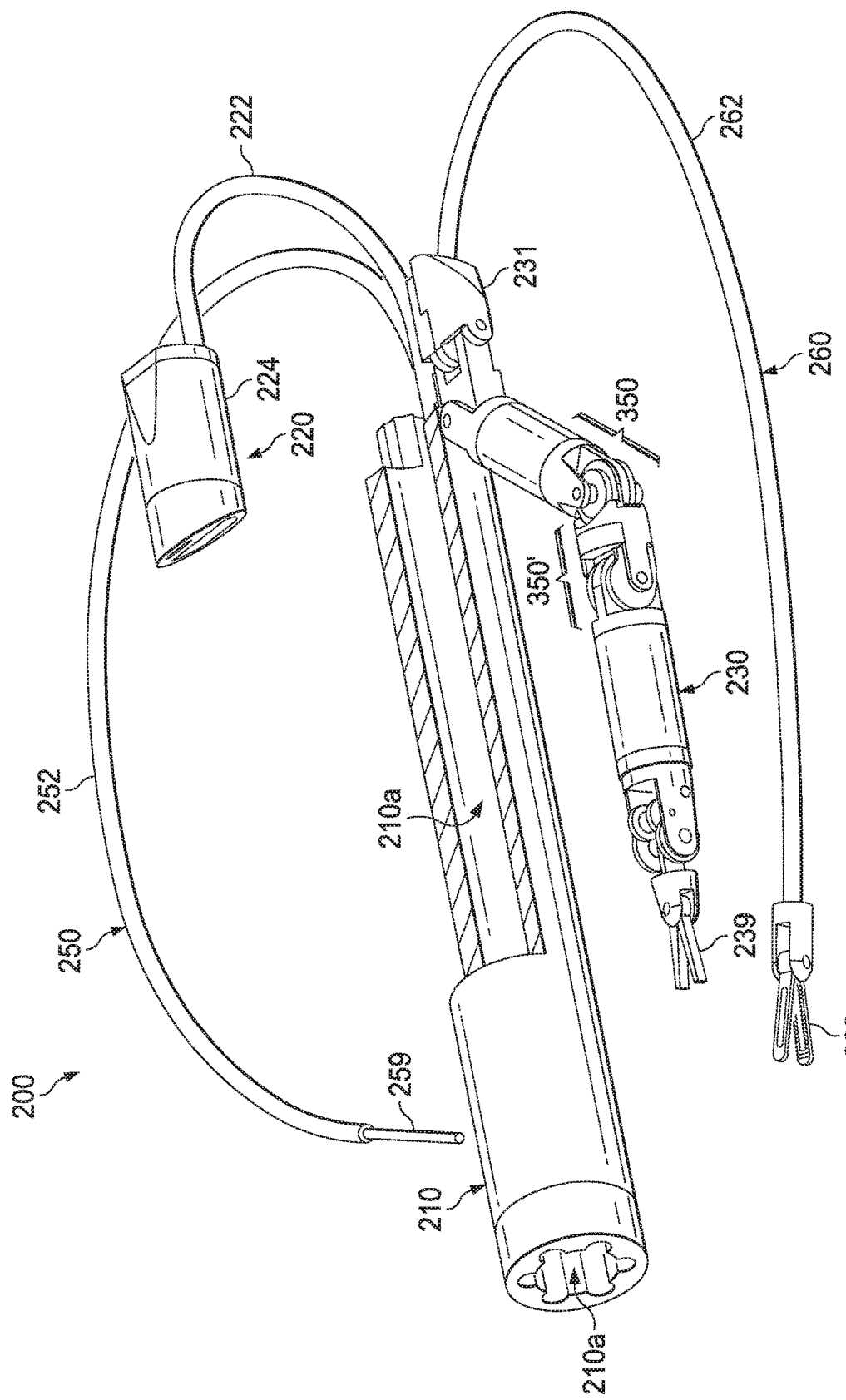
FIG. 2C is another illustration of a perspective view of an example embodiment of a surgical device configured in a reverse-directed position.
Figure 2D:
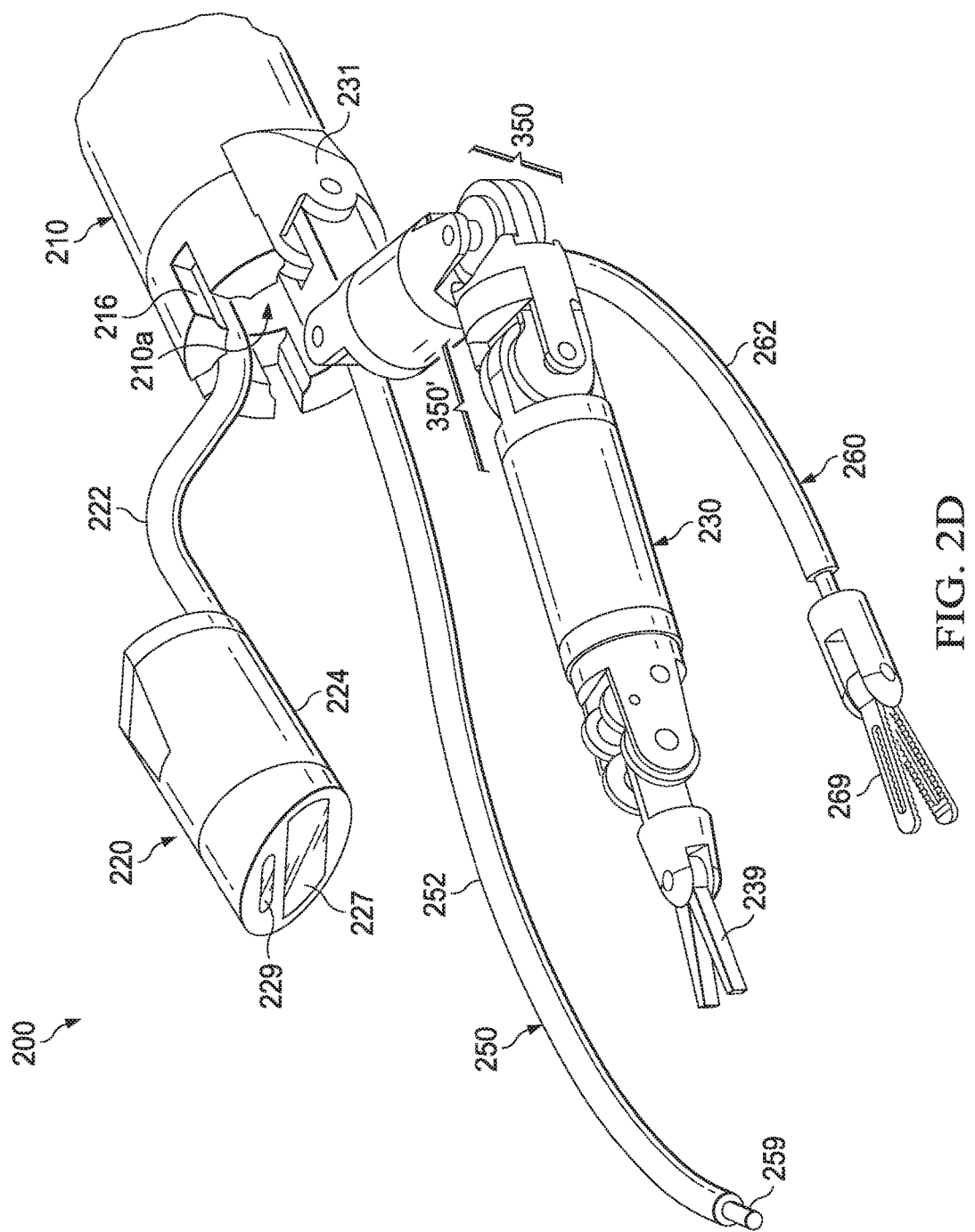
FIG. 2D is another illustration of a perspective view of an example embodiment of a surgical device configured in a forward-directed position.
Figure 8A:
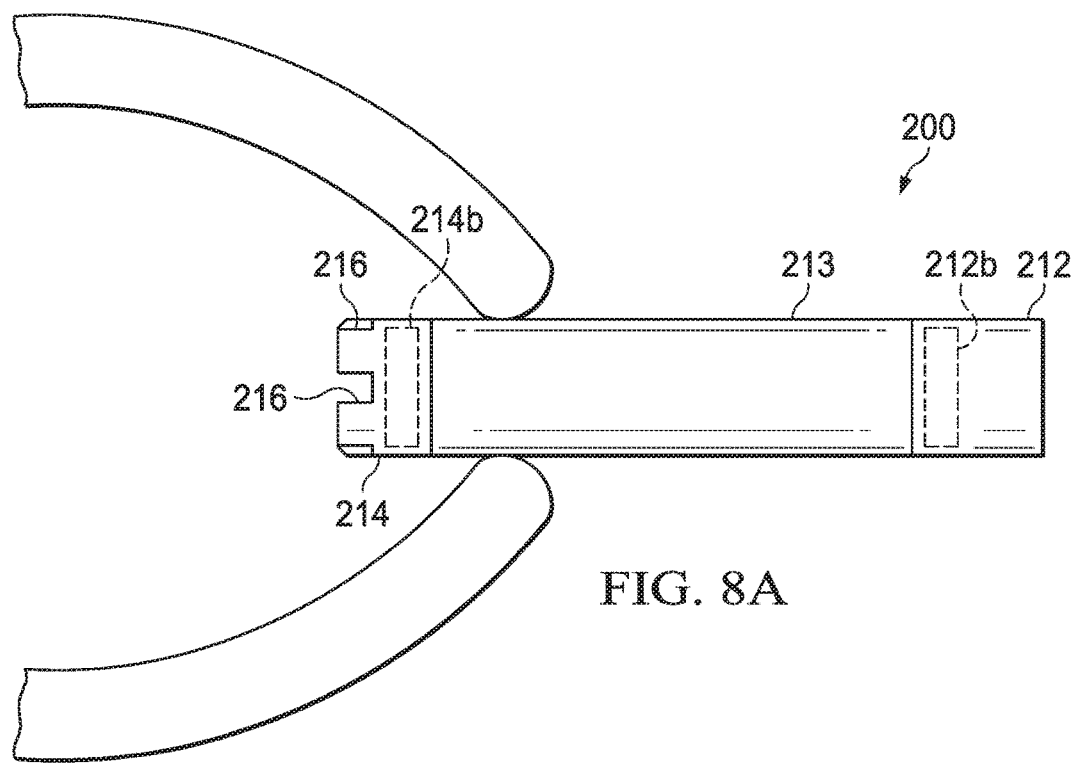
FIGS. 8A-E are illustrations of a side view of an example embodiment of a method of configuring a surgical device in a forward-directed position.

After the workable volume/space in the cavity has been formed and the port assembly 210 is secured in position, as illustrated in FIG. 8A, the image capturing assembly 220 may be inserted through the central access channel 210*a* and secured to the anchor port 216 of the port assembly 210. To do so while maintaining the workable volume/space, the first gate assembly 212*b* may be configured to the open position while the second gate assembly 214*b* is configured to the closed position. Once the first gate assembly 212*b* is in the open position, the image capturing assembly 220 may be inserted into the mid section 213. The first gate assembly 212*b* may then be configured to the closed position after the image capturing assembly 220 passes through the first gate assembly 212*b*. The second gate assembly 214*b* may then be configured to the open position. It is recognized in the present disclosure that the workable volume/space in the cavity is maintained via the insufflation since the first gate assembly 212*b* is configured to the closed position. Once the second gate assembly 214*b* is in the open position, the image capturing assembly 220 may be inserted into the cavity of the patient and the anchor portion 220*a* secured to an anchor port 216. The second gate assembly 214*b* may then be configured to the closed position after the image capturing assembly 220 passes through the second gate assembly 214*b*. The multi-curvable body 222 of the image capturing assembly 220 may then be configured/controlled to curve in one or more locations along the multi-curvable body 222 so that the image capturing assembly 220 can be directed in a forward-directed position (as illustrated in FIGS. 2B and 3B).

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8B:
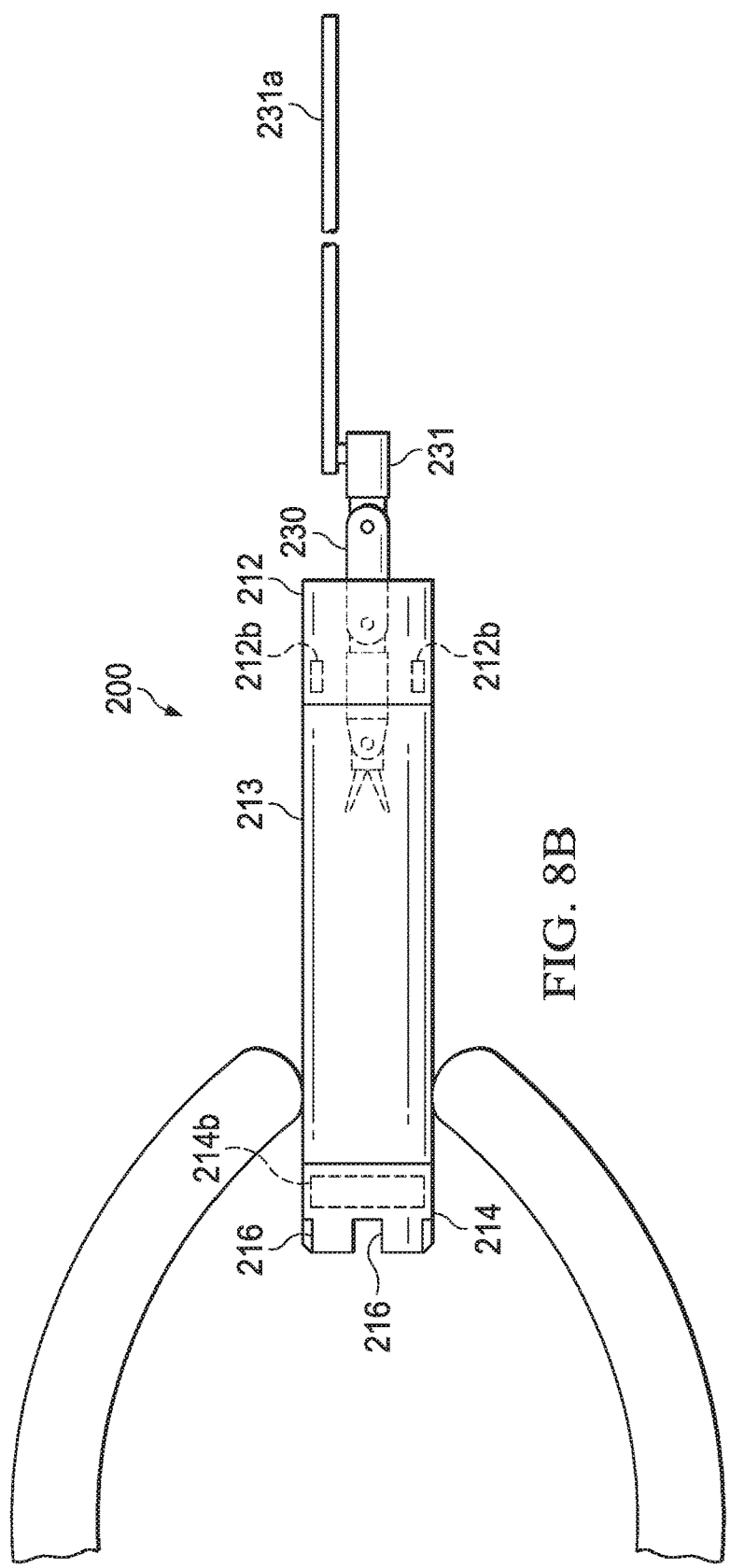
Figure 8C:
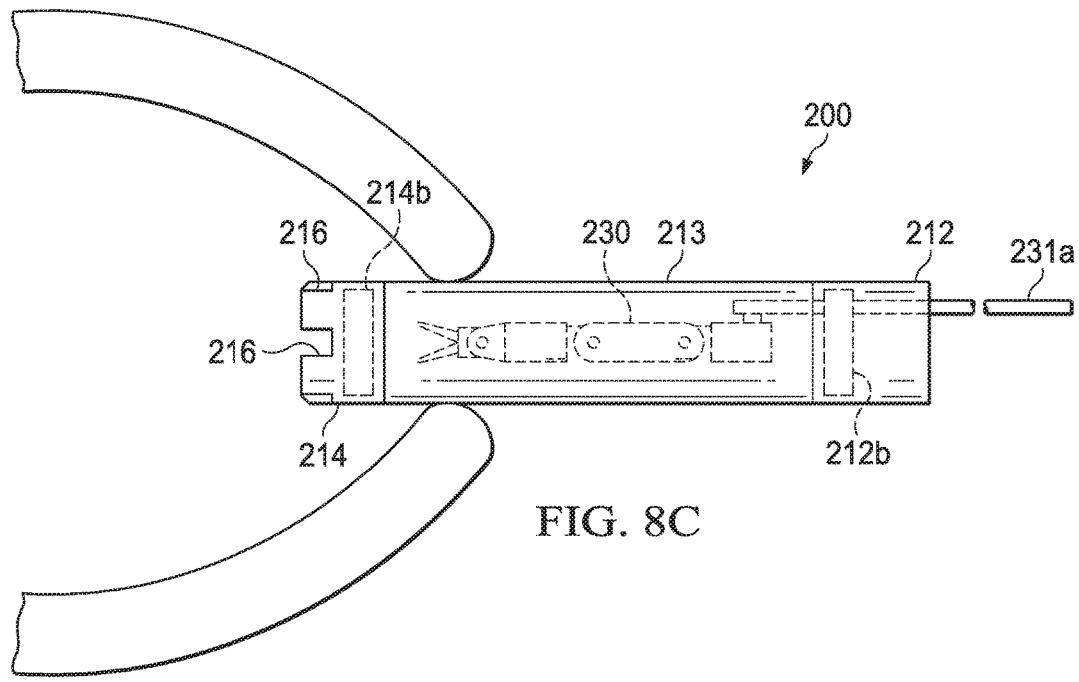
Figure 8D:
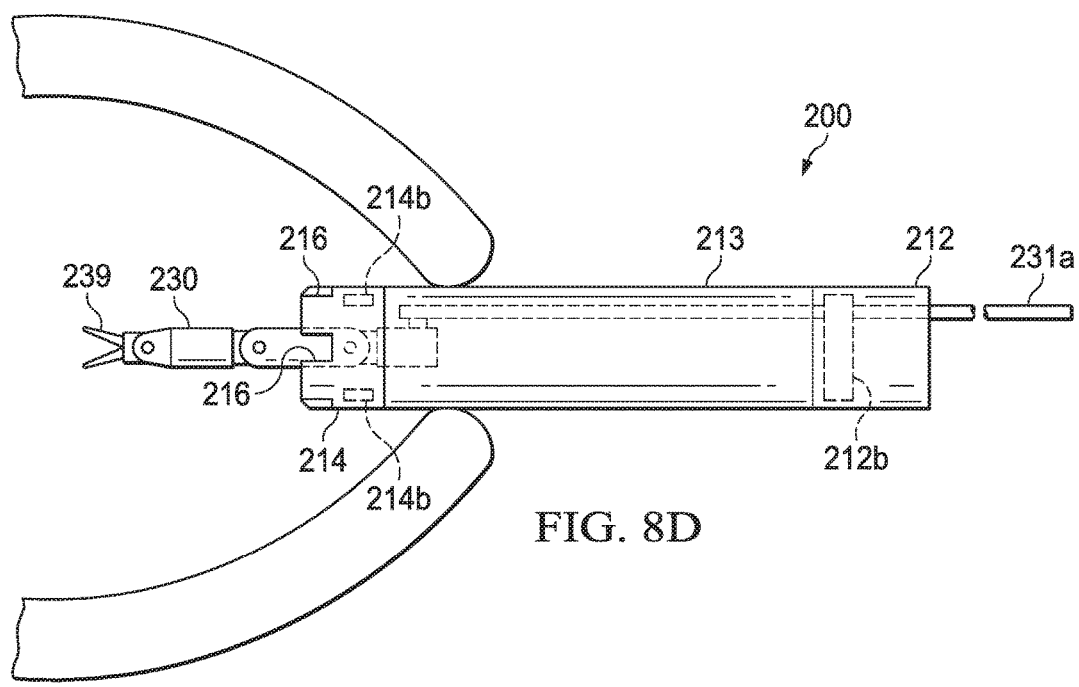
Figure 8E:
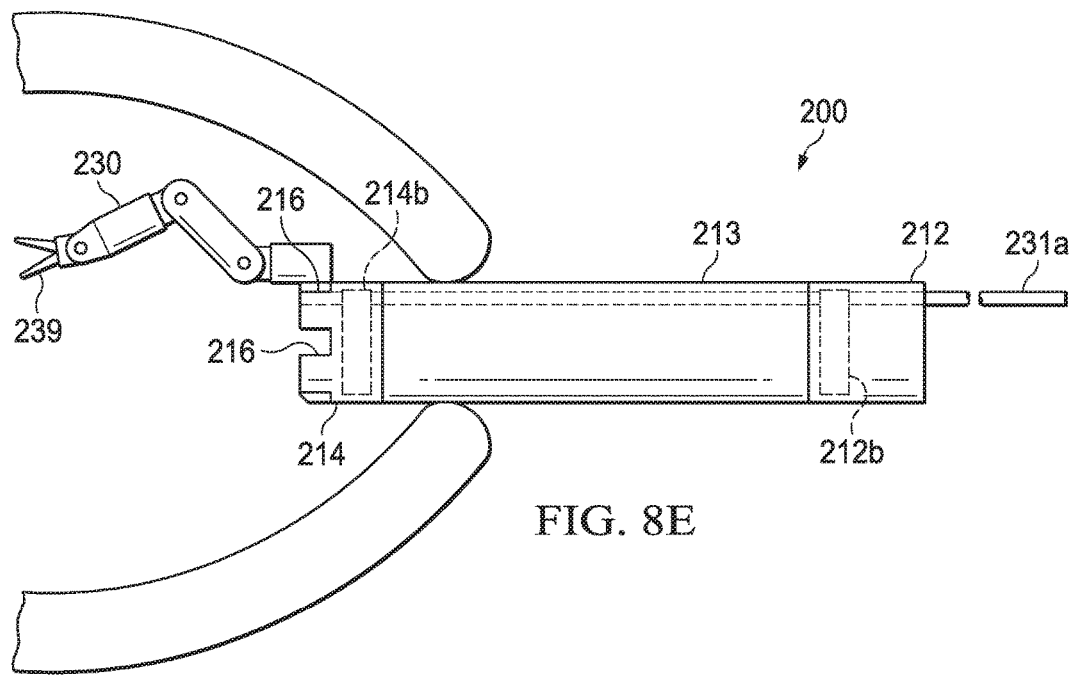

The instrument arm assembly 230 may be inserted through the central access channel 210*a* and secured to the anchor port 216 of the port assembly 210. To do so while maintaining the workable volume/space, the first gate assembly 212b may again be configured to the open position while the second gate assembly 214b is configured to the closed position. Once the first gate assembly 212b is in the open position, the instrument arm assembly 230 may be inserted into the mid section 213, as illustrated in FIG. 8B. The first gate assembly 212b may then be configured to the closed position after the instrument arm assembly 230 passes through the first gate assembly 212b and into the mid section 213, as illustrated in FIG. 8C. The second gate assembly 214b may then be configured to the open position, as illustrated in FIG. 8D. Once the second gate assembly 214b is in the open position, the instrument arm assembly 230 may be inserted into the cavity of the patient and the securing portion 231a secured to an anchor port 216, as illustrated in FIG. 8E. The second gate assembly 214b may then be configured to the closed position after the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted into the port assembly 210 via the central access channel 210a in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching.

Method of Setting Up the Surgical Device 200 in a Reverse-Directed Position (e.g., Method 700)

As illustrated in FIGS. 7 and 8F-K, example embodiments of the surgical device 200 may be configurable to perform a reverse-directed surgical action or procedure in one of a plurality of ways. In an example embodiment, the external anchor 1 may be provided and installed/anchored to the stationary object in a similar manner as described above and in the present disclosure. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210a, secured to the anchor ports 216, and configured in the cavity of the patient. For the inserting, each of the image capturing assemblies 220, instrument arm assemblies 230 and/or 240, and assistant arm assemblies 250 and/or 260 are inserted in reverse orientation as compared to the forward-directed position described above and in the present disclosure. A surgical action or procedure may then be performed in any part, area, and/or quadrant of the cavity of the patient using the surgical device 200. These processes will now be described below with references to at least FIGS. 7, 8F-K, 9B, and 10B.

(1) Providing the External Anchor and Installing the Port Assembly.

In an example embodiment, the port assembly 210 may be installed and secured to the external anchor 1 or 1000. As illustrated in FIGS. 8A-E, the second end 214 of the port assembly 210 is inserted into the opening of the patient and into the cavity of the patient and the first end 212 of the port assembly 210 is secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212b and the second gate assembly 214b may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 8F:
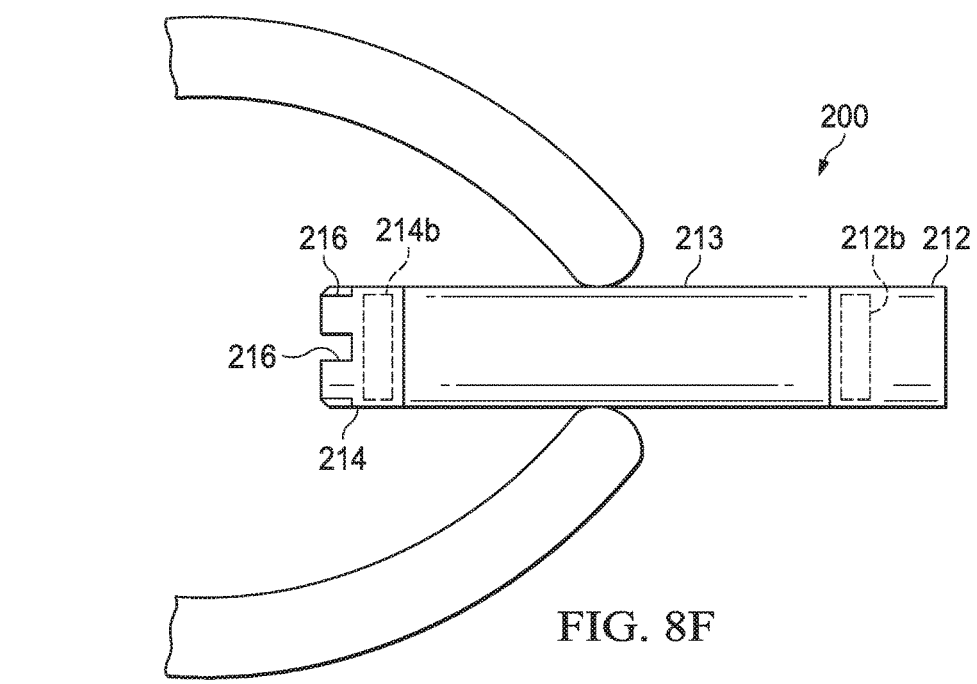

After the workable volume/space in the cavity has been formed and the port assembly 210 is secured in position, as illustrated in FIG. 8F, the image capturing assembly 220 may be inserted with the image capturing body 224 inserted last through the central access channel 210a and secured to the anchor port 216 of the port assembly 210. To do so while maintaining the workable volume/space, the first gate assembly 212b may be configured to the open position while the second gate assembly 214b is configured to the closed position. Once the first gate assembly 212b is in the open position, the image capturing assembly 220 may be inserted into the mid section 213. The first gate assembly 212b may then be configured to the closed position after the image capturing assembly 220 passes through the first gate assembly 212b. The second gate assembly 214b may then be configured to the open position. It is recognized in the present disclosure that the workable volume/space in the cavity is maintained via the insufflation since the first gate assembly 212b is configured to the closed position. Once the second gate assembly 214b is in the open position, the image capturing assembly 220 may be inserted completely into the cavity of the patient with the image capturing body 224 being closest to the anchor port 216. The multi-curvable body 222 of the image capturing assembly 220 may then be configured/controlled to curve in one or more locations along the multi-curvable body 222 so that the image capturing assembly 220 can be directed in a reverse-directed position next to the outer surface of the port assembly 210 (as illustrated in FIGS. 2A and 3A). The image capturing assembly 220 may then be provided adjacent to the outer surface of the port assembly 210 so that the anchoring portion 220a of the image capturing assembly 220 is adjacent to the anchor port 216. The anchoring portion 220a of the image capturing assembly 220 may then be secured to the anchor port 216. The second gate assembly 214b may be configured to the closed position after the image capturing assembly 220 passes through the second gate assembly 214b.

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8G:
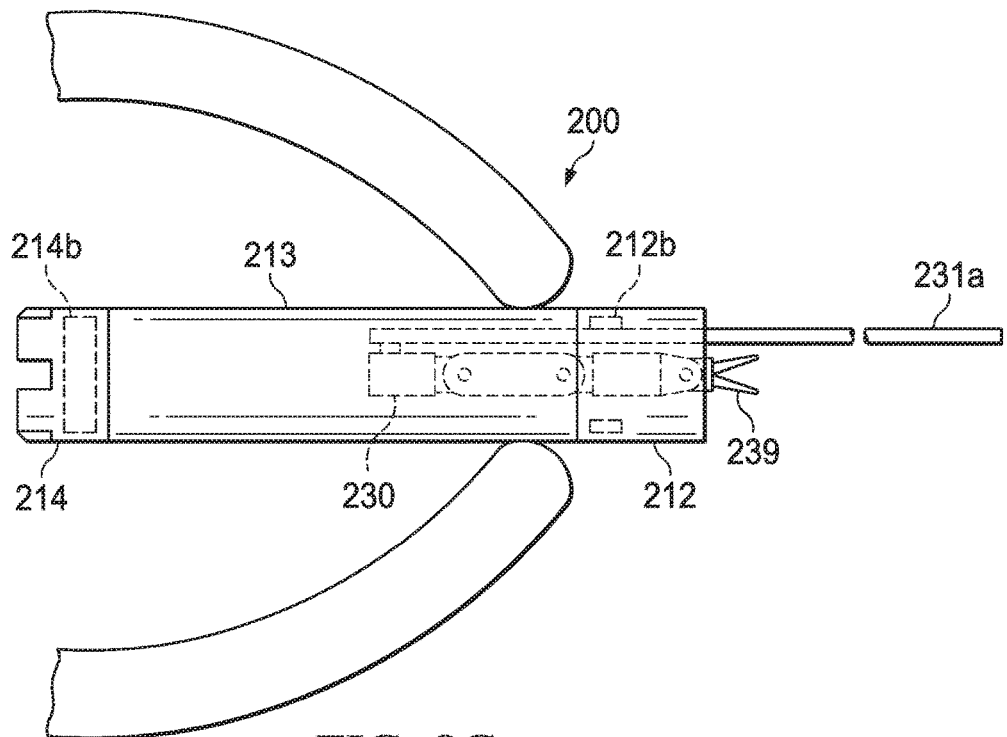
Figure 8H:
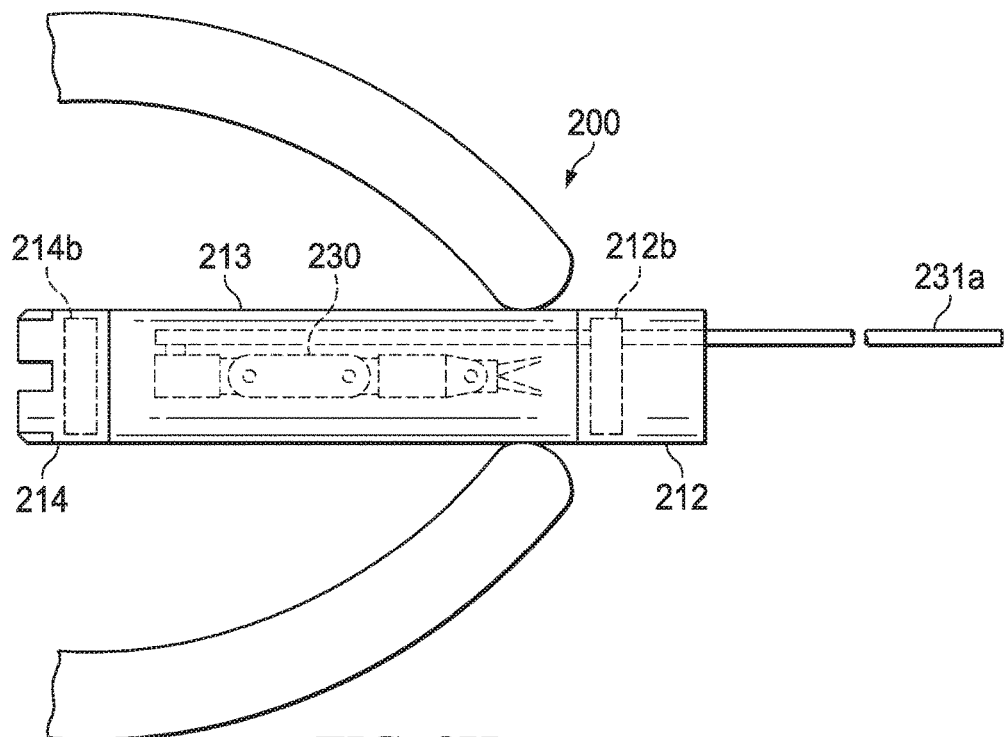
Figure 8I:
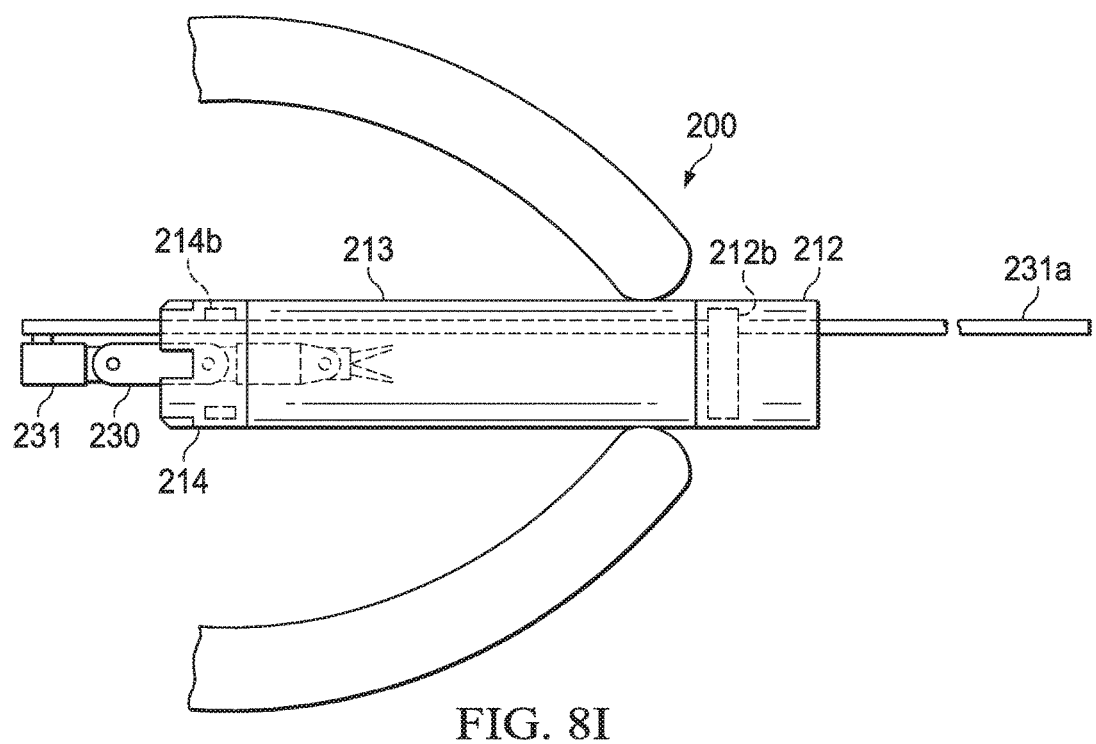
Figure 8K:
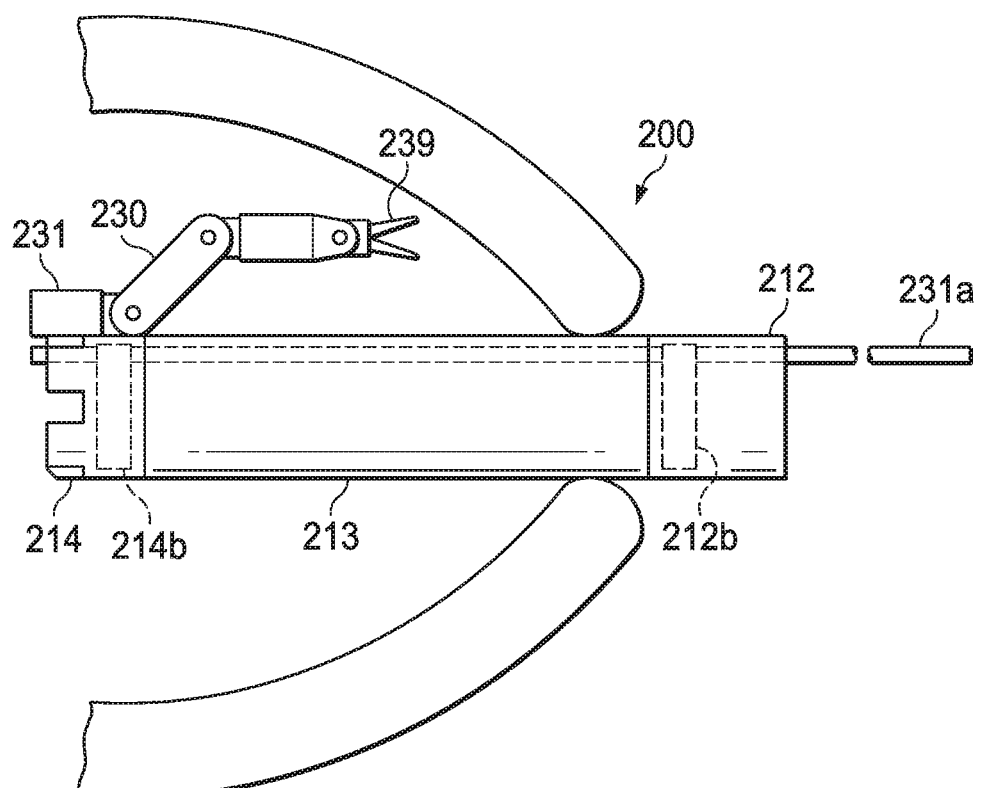

To insert the instrument arm assembly 230 through the central access channel 210a and secure it to the anchor port 216 of the port assembly 210 while maintaining the workable volume/space, the first gate assembly 212b may again be configured to the open position while the second gate assembly 214b is configured to the closed position. Once the first gate assembly 212b is in the open position, the instrument arm assembly 230 may be inserted with the end effector 239, 342, 344 inserted last into the mid section 213, as illustrated in FIG. 8G. The first gate assembly 212b may then be configured to the closed position after the instrument arm assembly 230 passes through the first gate assembly 212b and into the mid section 213, as illustrated in FIG. 8H. The second gate assembly 214b may then be configured to the open position, as illustrated in FIG. 8I. Once the second gate assembly 214b is in the open position, the instrument arm assembly 230 may be inserted completely into the cavity of the patient with the end effector 239, 342, 344 being closest to the anchor port 216, as illustrated in FIG. 8J. The instrument arm assembly 230 may then be turned 180 degrees (if needed) and/or moved so that the instrument arm assembly 230 can be brought next to the outer surface of the port assembly 210. The instrument arm assembly 230 may then be pulled adjacent to the outer surface of the port assembly 210 so that the securing portion 231a of the shoulder section 231 of the instrument arm assembly 230 is adjacent to the anchor port 216. The securing portion 231a of the instrument arm assembly 230 may then be secured to the anchor port 216, as illustrated in FIG. 8K. The second gate assembly 214b may be configured to the closed position at any time after at least the end effector 230 of the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted and installed in a reverse-directed manner via the central access channel 210a of the port assembly 210 in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching in the reverse-directed manner.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A robotic arm assembly, the robotic arm assembly comprising:
   a forearm segment, the forearm segment formed as an elongated structure with a proximal end and a distal end;
   an upper arm segment, the upper arm segment formed as an elongated structure with a proximal end and a distal end, the upper arm segment having:
      a first distal motor, the first distal motor having a first distal motor drive portion at the distal end of the upper arm segment, the first distal motor drive portion configured to rotate relative to a first axis, the first axis being parallel to a central axis of the upper arm segment; and
   an elbow coupling joint assembly, the elbow coupling joint assembly connecting the proximal end of the forearm segment to the distal end of the upper arm segment, the elbow coupling joint assembly having:
      a distal elbow joint subassembly connected at a distal end to the proximal end of the forearm segment, the distal elbow joint subassembly including a gear train system having a plurality of gear stages including:
         a first distal elbow gear stage, the first distal elbow gear stage having:
            a first distal elbow bevel gear configured to be driven by the first distal motor drive portion of the first distal motor to rotate relative to the first axis;
            a second distal elbow bevel gear drivable by the first distal elbow bevel gear, the second distal elbow bevel gear configured to rotate relative to a first main elbow axis when driven by the first distal elbow bevel gear, the first main elbow axis being orthogonal to the first axis; and
            a third distal elbow bevel gear drivable by the second distal elbow bevel gear, the third distal elbow bevel gear configured to rotate relative to an axis orthogonal to the first main elbow axis when the first distal elbow bevel gear drives the second distal elbow bevel gear to rotate relative to the first main elbow axis;
         a second distal elbow gear stage, the second distal elbow gear stage having:
            a first distal elbow spur gear connected to the third distal elbow bevel gear, the first distal elbow spur gear configured to rotate relative to a same axis of rotation as the third distal elbow bevel gear when the third distal elbow bevel gear is driven to rotate; and
            a second distal elbow spur gear drivable by the first distal elbow spur gear, the second distal elbow spur gear configured to rotate relative to an axis of rotation that is parallel to the axis of rotation of the first distal elbow spur gear when the second distal elbow spur gear is driven by the first distal elbow spur gear;
         a third distal elbow gear stage, the third distal elbow gear stage having:
            a fourth distal elbow bevel gear connected to the second distal elbow spur gear, the fourth distal elbow bevel gear configured to be driven by the second distal elbow spur gear to rotate relative to the same axis of rotation as that of the second distal elbow spur gear; and
            a fifth distal elbow bevel gear drivable by the fourth distal elbow bevel gear, the fifth distal elbow bevel gear configured to rotate relative to a second main elbow axis when driven by the fourth distal elbow bevel gear, the second main elbow axis being orthogonal to the first main elbow axis; and
         a fourth distal elbow gear stage, the fourth distal elbow gear stage having a distal elbow planetary gear assembly, the distal elbow planetary gear assembly having:
            a distal elbow sun gear configured to be driven by the fifth distal elbow bevel gear to rotate relative to the second main elbow axis;
            a distal elbow ring gear configured to not rotate relative to the second main elbow axis;
            a plurality of distal elbow planetary gears drivable by the distal elbow sun gear; and
            a distal elbow planetary gear carrier connected at one end to the plurality of distal elbow planetary gears in such a way that when the distal elbow sun gear rotates relative to the second main elbow axis, the distal elbow planetary gear carrier rotates relative to the second main elbow axis, wherein the distal elbow planetary gear carrier is connected at another end to the proximal end of the forearm segment in such a way that when the distal elbow sun gear is driven to rotate relative to the second main elbow axis, the distal elbow planetary gear carrier drives the forearm segment to pivotally rotate relative to the second main elbow axis;
      a proximal elbow joint subassembly connecting the distal end of the upper arm segment to the distal elbow joint subassembly, the proximal elbow joint subassembly configurable to be driven in such a way as to pivotally rotate the forearm segment relative to the first main elbow axis.

2. The robotic arm assembly of claim 1, wherein the upper arm segment further comprises:
   a second distal motor, the second distal motor having a second distal motor drive portion at the distal end of the upper arm segment, the second distal motor drive portion configured to rotate relative to a second axis, the second axis being parallel to the first axis.

3. The robotic arm assembly of claim 2, wherein the proximal elbow joint subassembly includes a gear train system having a plurality of gear stages including:
- a first proximal elbow stage, the first proximal elbow stage having:
  - a first proximal elbow bevel gear configured to be driven by the second distal motor drive portion of the second distal motor to rotate relative to the second axis; and
  - a second proximal elbow bevel gear drivable by the first proximal elbow bevel gear, the second proximal elbow bevel gear configured to rotate relative to the first main elbow axis when driven by the first proximal elbow bevel gear; and
- a second proximal elbow stage, the second proximal elbow stage having a proximal elbow planetary gear assembly, the proximal elbow planetary gear assembly having:
  - a proximal elbow sun gear configured to be driven by the second proximal elbow bevel gear to rotate relative to the first main elbow axis;
  - a proximal elbow ring gear configured to not rotate relative to the first main elbow axis;
  - a plurality of proximal elbow planetary gears drivable by the proximal elbow sun gear; and
  - a proximal elbow planetary gear carrier connected at one end to the plurality of proximal elbow planetary gears in such a way that when the proximal elbow sun gear rotates relative to the first main elbow axis, the proximal elbow planetary gear carrier rotates relative to the first main elbow axis, wherein the proximal elbow planetary gear carrier is connected at another end to the distal end of the upper arm segment in such a way that when the proximal elbow sun gear is driven to rotate relative to the first main elbow axis, the proximal elbow planetary gear carrier drives the forearm segment to pivotally rotate relative to the first main elbow axis.

4. The robotic arm assembly of claim 1, wherein the distal end of the forearm segment is securable to an end effector assembly via a wrist joint.

5. The robotic arm assembly of claim 1, further comprising a shoulder segment, the shoulder segment having a proximal end and a distal end.

6. The robotic arm assembly of claim 5, further comprising:
- a shoulder coupling joint assembly, the shoulder coupling joint assembly connecting the proximal end of the upper arm segment to the distal end of the shoulder segment;
- wherein the upper arm segment further includes one or more of the following:
  - a first proximal motor, the first proximal motor having a first proximal motor drive portion at the proximal end of the upper arm segment, the first proximal motor drive portion configured to rotate relative to a third axis, the third axis being parallel to the first axis; and/or
  - a second proximal motor, the second proximal motor having a second proximal motor drive portion at the upper end of the proximal arm segment, the second proximal motor drive portion configured to rotate relative to a fourth axis, the fourth axis being parallel to the first axis.

7. The robotic arm assembly of claim 6, wherein the shoulder coupling joint assembly includes:
- a distal shoulder joint subassembly connected at a distal end to the proximal end of the upper arm segment, the distal shoulder joint subassembly including a gear train system having a plurality of gear stages including:
  - a first distal shoulder stage, the first distal shoulder stage having:
    - a first distal shoulder bevel gear configured to be driven by the first proximal motor drive portion of the first proximal motor to rotate relative to the third axis; and
    - a second distal shoulder bevel gear drivable by the first distal shoulder bevel gear, the second distal shoulder bevel gear configured to rotate relative to a first main shoulder axis when driven by the first distal shoulder bevel gear, the first main shoulder axis being orthogonal to the third axis; and
  - a second distal shoulder stage, the second distal shoulder stage having a distal shoulder planetary gear assembly, the distal shoulder planetary gear assembly having:
    - a distal shoulder sun gear configured to be driven by the second distal shoulder bevel gear to rotate relative to the first main shoulder axis;
    - a distal shoulder ring gear configured to not rotate relative to the first main shoulder axis;
    - a plurality of distal shoulder planetary gears drivable by the distal shoulder sun gear; and
    - a distal shoulder planetary gear carrier connected at one end to the plurality of distal shoulder planetary gears in such a way that when the distal shoulder sun gear rotates relative to the first main shoulder axis, the distal shoulder planetary gear carrier rotates relative to the first main shoulder axis, wherein the distal shoulder planetary gear carrier is connected at another end to the proximal end of the upper arm segment in such a way that when the distal shoulder sun gear is driven to rotate relative to the first main shoulder axis, the distal shoulder planetary gear carrier drives the upper arm segment to pivotally rotate relative to the first main shoulder axis; and
- a proximal shoulder joint subassembly connecting the distal end of the shoulder segment to the distal shoulder joint subassembly.

8. The robotic arm assembly of claim 6, wherein the shoulder coupling joint assembly includes:
- a distal shoulder joint subassembly connected at a distal end to the proximal end of the upper arm segment, the distal shoulder joint subassembly configurable to be driven in such a way as to pivotally rotate the upper arm segment relative to a first main shoulder axis, the first main shoulder axis being orthogonal to the fourth axis;
- a proximal shoulder joint subassembly connecting the distal end of the shoulder segment to the distal shoulder joint subassembly, the proximal shoulder joint subassembly including a gear train system having a plurality of gear stages including:
  - a first proximal shoulder gear stage, the first proximal shoulder gear stage having:
    - a first proximal shoulder bevel gear configured to be driven by the second proximal motor drive portion of the second proximal motor to rotate relative to the fourth axis;
    - a second proximal shoulder bevel gear drivable by the first proximal shoulder bevel gear, the second proximal shoulder bevel gear configured to rotate relative to the first main shoulder axis when driven by the first proximal shoulder bevel gear; and
a third proximal shoulder bevel gear drivable by the second proximal shoulder bevel gear, the third proximal shoulder bevel gear configured to rotate relative to an axis orthogonal to the first main shoulder axis when the first proximal shoulder bevel gear drives the second proximal shoulder bevel gear to rotate relative to the first main shoulder axis;
a second proximal shoulder gear stage, the second proximal shoulder gear stage having:
a first proximal shoulder spur gear connected to the third proximal shoulder bevel gear, the first proximal shoulder spur gear configured to rotate relative to a same axis of rotation as the third proximal shoulder bevel gear when the third proximal shoulder bevel gear is driven to rotate; and
a second proximal shoulder spur gear drivable by the first proximal shoulder spur gear, the second proximal shoulder spur gear configured to rotate relative to an axis of rotation that is parallel to the axis of rotation of the first proximal shoulder spur gear when the second proximal shoulder spur gear is driven by the first proximal shoulder spur gear;
a third proximal shoulder gear stage, the third proximal shoulder gear stage having:
a fourth proximal shoulder bevel gear connected to the second proximal shoulder spur gear, the fourth proximal shoulder bevel gear configured to be driven by the second proximal shoulder spur gear to rotate relative to the same axis of rotation as that of the second proximal shoulder spur gear; and
a fifth proximal shoulder bevel gear drivable by the fourth proximal shoulder bevel gear, the fifth proximal shoulder bevel gear configured to rotate relative to a second main shoulder axis when driven by the fourth proximal shoulder bevel gear, the second main shoulder axis being orthogonal to the first main shoulder axis; and
a fourth proximal shoulder gear stage, the fourth proximal shoulder gear stage having a proximal shoulder planetary gear assembly, the proximal shoulder planetary gear assembly having:
a proximal shoulder sun gear connected to the fifth proximal shoulder bevel gear, the proximal shoulder sun gear configured to be driven by the fifth proximal shoulder bevel gear to rotate relative to the second main shoulder axis;
a proximal shoulder ring gear configured to not rotate relative to the second main shoulder axis;
a plurality of proximal shoulder planetary gears drivable by the proximal shoulder sun gear; and
a proximal shoulder planetary gear carrier connected at one end to the plurality of proximal shoulder planetary gears in such a way that when the proximal shoulder sun gear rotates relative to the second main shoulder axis, the proximal shoulder planetary gear carrier rotates relative to the second main shoulder axis, wherein the proximal shoulder planetary gear carrier is connected at another end to the distal end of the shoulder segment in such a way that when the proximal shoulder sun gear is driven to rotate relative to the second main shoulder axis, the proximal shoulder planetary gear carrier drives the upper arm segment to pivotally rotate relative to the second main shoulder axis.

9. The robotic arm assembly of claim 1, wherein one or more of the following apply:
the first distal elbow spur gear and the third distal elbow bevel gear are directly connected to one another in such a way that a portion of the first distal elbow spur gear is secured to a portion of the third distal elbow bevel gear; and/or
the second distal elbow spur gear and the fourth distal elbow bevel gear are directly connected to one another in such a way that a portion of the second distal elbow spur gear is directly secured to a portion of the fourth distal elbow bevel gear; and/or
the distal elbow sun gear and the fifth distal elbow bevel gear are directly connected to one another in such a way that a portion of the distal elbow sun gear is secured to a portion of the fifth distal elbow bevel gear; and/or
the first distal elbow bevel gear is driven by the first distal motor drive portion of the first distal motor to rotate relative to the first axis via one or more spur gears provided between the first distal elbow bevel gear and the first distal motor drive portion of the first distal motor.

10. The robotic arm assembly of claim 1, wherein one or more of the following apply:
the first distal elbow spur gear and the third distal elbow bevel gear are connected to one another via a first common elongated member connected at one end to the first distal elbow spur gear and at another end to the third distal elbow bevel gear, the first distal elbow spur gear, the third distal elbow bevel gear, and the first common elongated member having a common central axis of rotation; and/or
the second distal elbow spur gear and the fourth distal elbow bevel gear are connected to one another via a second common elongated member connected at one end to the second distal elbow spur gear and at another end to the fourth distal elbow bevel gear, the second distal elbow spur gear, the fourth distal elbow bevel gear, and the second common elongated member having a common central axis of rotation; and/or
the distal elbow sun gear and the fifth distal elbow bevel gear are connected to one another via a third common elongated member connected at one end to the distal elbow sun gear and at another end to the fifth distal elbow bevel gear, the distal elbow sun gear, the fifth distal elbow bevel gear, and the third common elongated member having a common central axis of rotation.

11. A robotic arm assembly, the robotic arm assembly comprising:
a forearm segment, the forearm segment formed as an elongated structure with a proximal end and a distal end;
an upper arm segment, the upper arm segment formed as an elongated structure with a proximal end and a distal end, the upper arm segment having:
a first distal motor, the first distal motor having a first distal motor drive portion at the distal end of the upper arm segment, the first distal motor drive portion configured to rotate relative to a first axis, the first axis being parallel to a central axis of the upper arm segment;
an elbow coupling joint assembly, the elbow coupling joint assembly connecting the proximal end of the forearm segment to the distal end of the upper arm segment, the elbow coupling joint assembly having:

a proximal elbow joint subassembly connected at a proximal end to the distal end of the upper arm segment, the proximal elbow joint subassembly including a gear train system having a plurality of gear stages including:
   a first proximal elbow gear stage, the first proximal elbow gear stage having:
      a first proximal elbow bevel gear configured to be driven by the first distal motor drive portion of the first distal motor to rotate relative to the first axis; and
      a second proximal elbow bevel gear drivable by the first proximal elbow bevel gear, the second proximal elbow bevel gear configured to rotate relative to a first main elbow axis when driven by the first proximal elbow bevel gear, the first main elbow axis being orthogonal to the first axis; and
   a second proximal elbow gear stage, the second proximal elbow gear stage having a proximal elbow planetary gear assembly, the proximal elbow planetary gear assembly having:
      a proximal elbow sun gear connected to the second proximal elbow bevel gear, the proximal elbow sun gear configured to be driven by the second proximal elbow bevel gear to rotate relative to the first main elbow axis;
      a proximal elbow ring gear configured to not rotate relative to the first main elbow axis;
      a plurality of proximal elbow planetary gears drivable by the proximal elbow sun gear; and
      a proximal elbow planetary gear carrier connected at one end to the plurality of proximal elbow planetary gears in such a way that when the proximal elbow sun gear rotates relative to the first main elbow axis, the proximal elbow planetary gear carrier rotates relative to the first main elbow axis; and
   a distal elbow joint subassembly connected at a distal end to the proximal end of the forearm segment, the distal elbow joint subassembly configurable to be driven in such a way as to pivotally rotate the forearm segment relative to a second main elbow axis, the second main elbow axis being orthogonal to the first main elbow axis;
   wherein the proximal elbow planetary gear carrier is connected at another end to the distal end of the upper arm segment, and wherein when the proximal elbow sun gear is driven to rotate relative to the first main elbow axis, the proximal elbow planetary gear carrier drives the forearm segment to pivotally rotate relative to the first main elbow axis.

12. The robotic arm assembly of claim 11, wherein the upper arm segment further comprises:
   a second distal motor, the second distal motor having a second distal motor drive portion at the distal end of the upper arm segment, the second distal motor drive portion configured to rotate relative to a second axis, the second axis being parallel to the first axis.

13. The robotic arm assembly of claim 12, wherein the distal elbow joint subassembly includes a gear train system having a plurality of gear stages including:
   a first distal elbow gear stage, the first distal elbow gear stage having:
      a first distal elbow bevel gear configured to be driven by the second distal motor drive portion of the second distal motor to rotate relative to the second axis;
      a second distal elbow bevel gear drivable by the first distal elbow bevel gear, the second distal elbow bevel gear configured to rotate relative to the first main elbow axis when driven by the first distal elbow bevel gear; and
      a third distal elbow bevel gear drivable by the second distal elbow bevel gear, the third distal elbow bevel gear configured to rotate relative to an axis orthogonal to the first main elbow axis when the first distal elbow bevel gear drives the second distal elbow bevel gear to rotate relative to the first main elbow axis;
   a second distal elbow gear stage, the second distal elbow gear stage having:
      a first distal elbow spur gear connected to the third distal elbow bevel gear, the first distal elbow spur gear configured to rotate relative to a same axis of rotation as the third distal elbow bevel gear when the third distal elbow bevel gear is driven to rotate; and
      a second distal elbow spur gear drivable by the first distal elbow spur gear, the second distal elbow spur gear configured to rotate relative to an axis of rotation that is parallel to the axis of rotation of the first distal elbow spur gear when the second distal elbow spur gear is driven by the first distal elbow spur gear;
   a third distal elbow gear stage, the third distal elbow gear stage having:
      a fourth distal elbow bevel gear connected to the second distal elbow spur gear, the fourth distal elbow bevel gear configured to be driven by the second distal elbow spur gear to rotate relative to the same axis of rotation as that of the second distal elbow spur gear; and
      a fifth distal elbow bevel gear drivable by the fourth distal elbow bevel gear, the fifth distal elbow bevel gear configured to rotate relative to the second main elbow axis when driven by the fourth distal elbow bevel gear; and
   a fourth distal elbow gear stage, the fourth distal elbow gear stage having a distal elbow planetary gear assembly, the distal elbow planetary gear assembly having:
      a distal elbow sun gear connected to the fifth distal elbow bevel gear, the distal elbow sun gear configured to be driven by the fifth distal elbow bevel gear to rotate relative to the second main elbow axis;
      a distal elbow ring gear configured to not rotate relative to the second main elbow axis;
      a plurality of distal elbow planetary gears drivable by the distal elbow sun gear; and
      a distal elbow planetary gear carrier connected at one end to the plurality of distal elbow planetary gears in such a way that when the distal elbow sun gear rotates relative to the second main elbow axis, the distal elbow planetary gear carrier rotates relative to the second main elbow axis, wherein the distal elbow planetary gear carrier is connected at another end to the proximal end of the forearm segment in such a way that when the distal elbow sun gear is driven to rotate relative to the second main elbow axis, the distal elbow planetary gear carrier drives the forearm segment to pivotally rotate relative to the second main elbow axis.

14. The robotic arm assembly of claim 13, wherein one or more of the following apply:
- the first distal elbow spur gear and the third distal elbow bevel gear are directly connected to one another in such a way that a portion of the first distal elbow spur gear is secured to a portion of the third distal elbow bevel gear; and/or
- the second distal elbow spur gear and the fourth distal elbow bevel gear are directly connected to one another in such a way that a portion of the second distal elbow spur gear is directly secured to a portion of the fourth distal elbow bevel gear; and/or
- the distal elbow sun gear and the fifth distal elbow bevel gear are directly connected to one another in such a way that a portion of the distal elbow sun gear is secured to a portion of the fifth distal elbow bevel gear; and/or
- the first proximal elbow bevel gear is driven by the first distal motor drive portion of the first distal motor to rotate relative to the first axis via one or more spur gears provided between the first proximal elbow bevel gear and the first distal motor drive portion of the first distal motor.

15. The robotic arm assembly of claim 13, wherein one or more of the following apply:
- the first distal elbow spur gear and the third distal elbow bevel gear are connected to one another via a first common elongated member connected at one end to the first distal elbow spur gear and at another end to the third distal elbow bevel gear, the first distal elbow spur gear, the third distal elbow bevel gear, and the first common elongated member having a common central axis of rotation; and/or
- the second distal elbow spur gear and the fourth distal elbow bevel gear are connected to one another via a second common elongated member connected at one end to the second distal elbow spur gear and at another end to the fourth distal elbow bevel gear, the second distal elbow spur gear, the fourth distal elbow bevel gear, and the second common elongated member having a common central axis of rotation; and/or
- the distal elbow sun gear and the fifth distal elbow bevel gear are connected to one another via a third common elongated member connected at one end to the distal elbow sun gear and at another end to the fifth distal elbow bevel gear, the distal elbow sun gear, the fifth distal elbow bevel gear, and the third common elongated member having a common central axis of rotation.

16. The robotic arm assembly of claim 11, wherein the distal end of the forearm segment is securable to an end effector assembly via a wrist joint.

17. The robotic arm assembly of claim 11, further comprising a shoulder segment, the shoulder segment having a proximal end and a distal end.

18. The robotic arm assembly of claim 17, further comprising:
- a shoulder coupling joint assembly, the shoulder coupling joint assembly connecting the proximal end of the upper arm segment to the distal end of the shoulder segment;
- wherein the upper arm segment further includes one or more of the following:
  - a first proximal motor, the first proximal motor having a first proximal motor drive portion at the proximal end of the upper arm segment, the first proximal motor drive portion configured to rotate relative to a third axis, the third axis being parallel to the first axis; and/or
  - a second proximal motor, the second proximal motor having a second proximal motor drive portion at the upper end of the proximal arm segment, the second proximal motor drive portion configured to rotate relative to a fourth axis, the fourth axis being parallel to the first axis.

19. The robotic arm assembly of claim 18, wherein the shoulder coupling joint assembly includes:
- a distal shoulder joint subassembly connected at a distal end to the proximal end of the upper arm segment, the distal shoulder joint subassembly including a gear train system having a plurality of gear stages including:
  - a first distal shoulder stage, the first distal shoulder stage having:
    - a first distal shoulder bevel gear configured to be driven by the first proximal motor drive portion of the first proximal motor to rotate relative to the third axis; and
    - a second distal shoulder bevel gear drivable by the first distal shoulder bevel gear, the second distal shoulder bevel gear configured to rotate relative to a first main shoulder axis when driven by the first distal shoulder bevel gear, the first main shoulder axis being orthogonal to the third axis; and
  - a second distal shoulder stage, the second distal shoulder stage having a distal shoulder planetary gear assembly, the distal shoulder planetary gear assembly having:
    - a distal shoulder sun gear connected to the second distal shoulder bevel gear, the distal shoulder sun gear configured to be driven by the second distal shoulder bevel gear to rotate relative to the first main shoulder axis;
    - a distal shoulder ring gear configured to not rotate relative to the first main shoulder axis;
    - a plurality of distal shoulder planetary gears drivable by the distal shoulder sun gear; and
    - a distal shoulder planetary gear carrier connected at one end to the plurality of distal shoulder planetary gears in such a way that when the distal shoulder sun gear rotates relative to the first main shoulder axis, the distal shoulder planetary gear carrier rotates relative to the first main shoulder axis, wherein the distal shoulder planetary gear carrier is connected at another end to the proximal end of the upper arm segment in such a way that when the distal shoulder sun gear is driven to rotate relative to the first main shoulder axis, the distal shoulder planetary gear carrier drives the upper arm segment to pivotally rotate relative to the first main shoulder axis; and
- a proximal shoulder joint subassembly connecting the distal end of the shoulder segment to the distal shoulder joint subassembly.

20. The robotic arm assembly of claim 18, wherein the shoulder coupling joint assembly includes:
- a distal shoulder joint subassembly connected at a distal end to the proximal end of the upper arm segment, the distal shoulder joint subassembly configurable to be driven in such a way as to pivotally rotate the upper arm segment relative to a first main shoulder axis, the first main shoulder axis being orthogonal to the fourth axis;
- a proximal shoulder joint subassembly connecting the distal end of the shoulder segment to the distal shoulder joint subassembly, the proximal shoulder joint subassembly including a gear train system having a plurality of gear stages including:
a first proximal shoulder gear stage, the first proximal shoulder gear stage having:
a first proximal shoulder bevel gear configured to be driven by the second proximal motor drive portion of the second proximal motor to rotate relative to the fourth axis;
a second proximal shoulder bevel gear drivable by the first proximal shoulder bevel gear, the second proximal shoulder bevel gear configured to rotate relative to the first main shoulder axis when driven by the first proximal shoulder bevel gear; and
a third proximal shoulder bevel gear drivable by the second proximal shoulder bevel gear, the third proximal shoulder bevel gear configured to rotate relative to an axis orthogonal to the first main shoulder axis when the first proximal shoulder bevel gear drives the second proximal shoulder bevel gear to rotate relative to the first main shoulder axis;
a second proximal shoulder gear stage, the second proximal shoulder gear stage having:
a first proximal shoulder spur gear connected to the third proximal shoulder bevel gear, the first proximal shoulder spur gear configured to rotate relative to a same axis of rotation as the third proximal shoulder bevel gear when the third proximal shoulder bevel gear is driven to rotate; and
a second proximal shoulder spur gear drivable by the first proximal shoulder spur gear, the second proximal shoulder spur gear configured to rotate relative to an axis of rotation that is parallel to the axis of rotation of the first proximal shoulder spur gear when the second proximal shoulder spur gear is driven by the first proximal shoulder spur gear;
a third proximal shoulder gear stage, the third proximal shoulder gear stage having:
a fourth proximal shoulder bevel gear connected to the second proximal shoulder spur gear, the fourth proximal shoulder bevel gear configured to be driven by the second proximal shoulder spur gear to rotate relative to the same axis of rotation as that of the second proximal shoulder spur gear; and
a fifth proximal shoulder bevel gear drivable by the fourth proximal shoulder bevel gear, the fifth proximal shoulder bevel gear configured to rotate relative to a second main shoulder axis when driven by the fourth proximal shoulder bevel gear, the second main shoulder axis being orthogonal to the first main shoulder axis; and
a fourth proximal shoulder gear stage, the fourth proximal shoulder gear stage having a proximal shoulder planetary gear assembly, the proximal shoulder planetary gear assembly having:
a proximal shoulder sun gear connected to the fifth proximal shoulder bevel gear, the proximal shoulder sun gear configured to be driven by the fifth proximal shoulder bevel gear to rotate relative to the second main shoulder axis;
a proximal shoulder ring gear configured to not rotate relative to the second main shoulder axis;
a plurality of proximal shoulder planetary gears drivable by the proximal shoulder sun gear; and
a proximal shoulder planetary gear carrier connected at one end to the plurality of proximal shoulder planetary gears in such a way that when the proximal shoulder sun gear rotates relative to the second main shoulder axis, the proximal shoulder planetary gear carrier rotates relative to the second main shoulder axis, wherein the proximal shoulder planetary gear carrier is connected at another end to the distal end of the shoulder segment in such a way that when the proximal shoulder sun gear is driven to rotate relative to the second main shoulder axis, the proximal shoulder planetary gear carrier drives the upper arm segment to pivotally rotate relative to the second main shoulder axis.

21. A robotic arm assembly, the robotic arm assembly comprising:
a forearm segment, the forearm segment formed as an elongated structure with a proximal end and a distal end;
an upper arm segment, the upper arm segment formed as an elongated structure with a proximal end and a distal end, the upper arm segment having:
a first distal motor, the first distal motor having a first distal motor drive portion at the distal end of the upper arm segment, the first distal motor drive portion configured to rotate relative to a first axis of rotation; and
an elbow coupling joint assembly, the elbow coupling joint assembly connecting the proximal end of the forearm segment to the distal end of the upper arm segment via a serial arrangement of a distal elbow joint and a proximal elbow joint, the distal elbow joint forming a distal main elbow axis, the proximal elbow joint forming a proximal main elbow axis, the distal main elbow axis being orthogonal to the proximal main elbow axis, the elbow coupling joint assembly having:
a distal elbow joint subassembly, the distal elbow joint subassembly having:
a first distal elbow bevel gear configured to be driven by the first distal motor drive portion of the first distal motor;
a first distal elbow integrated gear assembly, the first distal elbow integrated gear assembly having:
a first integrated bevel gear portion, the first integrated bevel gear portion configured to be driven by the first distal elbow bevel gear when the first distal elbow bevel gear is driven by the first distal motor drive portion of the first distal motor; and
a first integrated spur gear portion, the first integrated spur gear portion adjoined to the first integrated bevel gear portion in such a way that when the first distal elbow bevel gear is driven by the first distal motor drive portion of the first distal motor, the first integrated bevel gear portion and the first integrated spur gear portion are driven to rotate along a same axis of rotation and same rate of rotation;
a second distal elbow integrated gear assembly, the second distal elbow integrated gear assembly having:
a second integrated spur gear portion, the second integrated spur gear portion configured to be driven by the first integrated spur gear portion when the first integrated gear portion is driven by the first distal elbow bevel gear; and
a second integrated bevel gear portion, the second integrated bevel gear portion adjoined to the second integrated spur gear portion in such a way that when the first distal elbow bevel gear is driven by the first distal motor drive portion of the first distal motor, the second integrated spur gear portion and the second integrated bevel gear portion are driven to rotate along a same axis of rotation and same rate of rotation;

a second distal elbow bevel gear configured to be driven by the second integrated bevel gear portion of the second distal elbow integrated gear assembly to rotate relative to the distal main elbow axis;

a distal elbow planetary gear assembly, the distal elbow planetary gear assembly having:
  a distal elbow sun gear, the distal elbow sun gear configured to be driven by the second distal elbow bevel gear to rotate relative to the distal main elbow axis;
  a distal elbow ring gear configured to not rotate relative to the distal main elbow axis;
  a plurality of distal elbow planetary gears drivable by the distal elbow sun gear; and
  a distal elbow planetary gear carrier connected at one end to the plurality of distal elbow planetary gears in such a way that when the distal elbow sun gear rotates relative to the distal main elbow axis, the distal elbow planetary gear carrier rotates relative to the distal main elbow axis, wherein the distal elbow planetary gear carrier is connected at another end to the proximal end of the forearm segment in such a way that when the distal elbow sun gear is driven to rotate relative to the distal main elbow axis, the distal elbow planetary gear carrier drives the forearm segment to pivotally rotate relative to the distal main elbow axis;

a proximal elbow joint subassembly connecting the distal end of the upper arm segment to the distal elbow joint subassembly, the proximal elbow joint subassembly configurable to be driven in such a way as to pivotally rotate the forearm segment relative to the proximal main elbow axis.

22. The robotic arm assembly of claim 21, wherein the upper arm segment further comprises:
a second distal motor, the second distal motor having a second distal motor drive portion at the distal end of the upper arm segment, the second distal motor drive portion configured to rotate relative to a second axis of rotation, the second axis of rotation being parallel to the first axis of rotation.

23. The robotic arm assembly of claim 22, wherein the proximal elbow joint subassembly includes:
a first proximal elbow stage, the first proximal elbow stage having:
  a first proximal elbow bevel gear configured to be driven by the second distal motor drive portion of the second distal motor to rotate relative to the second axis of rotation; and
  a second proximal elbow bevel gear drivable by the first proximal elbow bevel gear, the second proximal elbow bevel gear configured to rotate relative to the proximal main elbow axis when driven by the first proximal elbow bevel gear; and
a second proximal elbow stage, the second proximal elbow stage having a proximal elbow planetary gear assembly, the proximal elbow planetary gear assembly having:
  a proximal elbow sun gear connected to the second proximal elbow bevel gear, the proximal elbow sun gear configured to be driven by the second proximal elbow bevel gear to rotate relative to the proximal main elbow axis;
  a proximal elbow ring gear configured to not rotate relative to the proximal main elbow axis;
  a plurality of proximal elbow planetary gears drivable by the proximal elbow sun gear; and
  a proximal elbow planetary gear carrier connected at one end to the plurality of proximal elbow planetary gears in such a way that when the proximal elbow sun gear rotates relative to the proximal main elbow axis, the proximal elbow planetary gear carrier rotates relative to the proximal main elbow axis, wherein the proximal elbow planetary gear carrier is connected at another end to the distal end of the upper arm segment in such a way that when the proximal elbow sun gear is driven to rotate relative to the proximal main elbow axis, the proximal elbow planetary gear carrier drives the forearm segment to pivotally rotate relative to the proximal main elbow axis.

24. The robotic arm assembly of claim 21, wherein the distal end of the forearm segment is securable to an end effector assembly via a wrist joint.

25. The robotic arm assembly of claim 21, further comprising a shoulder segment, the shoulder segment having a proximal end and a distal end.

26. The robotic arm assembly of claim 25, further comprising:
a shoulder coupling joint assembly, the shoulder coupling joint assembly connecting the proximal end of the upper arm segment to the distal end of the shoulder segment via a serial arrangement of a distal shoulder joint and a proximal shoulder joint, the distal shoulder joint forming a distal main shoulder axis, the proximal shoulder joint forming a proximal main shoulder axis, the distal main shoulder axis being orthogonal to the proximal main shoulder axis;
wherein the upper arm segment further includes one or more of the following:
  a first proximal motor, the first proximal motor having a first proximal motor drive portion at the proximal end of the upper arm segment, the first proximal motor drive portion configured to rotate relative to a third axis of rotation, the third axis of rotation being parallel to the first axis of rotation; and/or
  a second proximal motor, the second proximal motor having a second proximal motor drive portion at the upper end of the proximal arm segment, the second proximal motor drive portion configured to rotate relative to a fourth axis of rotation, the fourth axis of rotation being parallel to the first axis of rotation.

27. The robotic arm assembly of claim 26, wherein the shoulder coupling joint assembly includes:
a distal shoulder joint subassembly connected at a distal end to the proximal end of the upper arm segment, the distal shoulder joint subassembly including a gear train system having a plurality of gear stages including:
  a first distal shoulder gear stage, the first distal shoulder gear stage having:
    a first distal shoulder bevel gear configured to be driven by the first proximal motor drive portion of the first proximal motor to rotate relative to the third axis of rotation; and
    a second distal shoulder bevel gear drivable by the first distal shoulder bevel gear, the second distal shoulder bevel gear configured to rotate relative to the distal main shoulder axis when driven by the first distal shoulder bevel gear, the distal main shoulder axis being orthogonal to the third axis; and a second distal shoulder gear stage, the second distal shoulder gear stage having a distal shoulder planetary gear assembly, the distal shoulder planetary gear assembly having:

a distal shoulder sun gear connected to the second distal shoulder bevel gear, the distal shoulder sun gear configured to be driven by the second distal shoulder bevel gear to rotate relative to the distal main shoulder axis;

a distal shoulder ring gear configured to not rotate relative to the distal main shoulder axis;

a plurality of distal shoulder planetary gears drivable by the distal shoulder sun gear; and a distal shoulder planetary gear carrier connected at one end to the plurality of distal shoulder planetary gears in such a way that when the distal shoulder sun gear rotates relative to the distal main shoulder axis, the distal shoulder planetary gear carrier rotates relative to the distal main shoulder axis, wherein the distal shoulder planetary gear carrier is connected at another end to the proximal end of the upper arm segment in such a way that when the distal shoulder sun gear is driven to rotate relative to the distal main shoulder axis, the distal shoulder planetary gear carrier drives the upper arm segment to pivotally rotate relative to the distal main shoulder axis; and a proximal shoulder joint subassembly connecting the distal end of the shoulder segment to the distal shoulder joint subassembly.

28. The robotic arm assembly of claim 26, wherein the shoulder coupling joint assembly includes:

a distal shoulder joint subassembly connected at a distal end to the proximal end of the upper arm segment, the distal shoulder joint subassembly configurable to be driven in such a way as to pivotally rotate the upper arm segment relative to the distal main shoulder axis, the distal main shoulder axis being orthogonal to the fourth axis;

a proximal shoulder joint subassembly connecting the distal end of the shoulder segment to the distal shoulder joint subassembly, the proximal shoulder joint subassembly including a gear train system having a plurality of gear stages including:

a first proximal shoulder bevel gear configured to be driven by the second proximal motor drive portion of the second proximal motor;

a first proximal shoulder integrated gear assembly, the first proximal shoulder integrated gear assembly having:

a third integrated bevel gear portion, the third integrated bevel gear portion configured to be driven by the first proximal shoulder bevel gear when the first proximal shoulder bevel gear is driven by the second proximal motor drive portion of the second proximal motor; and a third integrated spur gear portion, the third integrated spur gear portion adjoined to the third integrated bevel gear portion in such a way that when the first proximal shoulder bevel gear is driven by the second proximal motor drive portion of the second proximal motor, the third integrated bevel gear portion and the third integrated spur gear portion are driven to rotate along a same axis of rotation and same rate of rotation;

a second proximal shoulder integrated gear assembly, the second proximal shoulder integrated gear assembly having:

a fourth integrated spur gear portion, the fourth integrated spur gear portion configured to be driven by the third integrated spur gear portion when the third integrated gear portion is driven by the first proximal shoulder bevel gear; and a fourth integrated bevel gear portion, the fourth integrated bevel gear portion adjoined to the fourth integrated spur gear portion in such a way that when the first proximal shoulder bevel gear is driven by the second proximal motor drive portion of the second proximal motor, the fourth integrated spur gear portion and the fourth integrated bevel gear portion are driven to rotate along a same axis of rotation and same rate of rotation;

a second proximal shoulder bevel gear configured to be driven by the fourth integrated bevel gear portion of the second proximal shoulder integrated gear assembly to rotate relative to the proximal main shoulder axis;

a proximal shoulder planetary gear assembly, the proximal shoulder planetary gear assembly having:

a proximal shoulder sun gear, the proximal shoulder sun gear configured to be driven by the second proximal shoulder bevel gear to rotate relative to the proximal main shoulder axis;

a proximal shoulder ring gear configured to not rotate relative to the proximal main shoulder axis;

a plurality of proximal shoulder planetary gears drivable by the proximal shoulder sun gear; and a proximal shoulder planetary gear carrier connected at one end to the plurality of proximal shoulder planetary gears in such a way that when the proximal shoulder sun gear rotates relative to the proximal main shoulder axis, the proximal shoulder planetary gear carrier rotates relative to the proximal main shoulder axis, wherein the proximal shoulder planetary gear carrier is connected at another end to the proximal end of the forearm segment in such a way that when the proximal shoulder sun gear is driven to rotate relative to the proximal main shoulder axis, the proximal shoulder planetary gear carrier drives the upper arm segment to pivotally rotate relative to the proximal main shoulder axis.

* * * * *